US006416959B1

(12) United States Patent
Giuliano et al.

(10) Patent No.: US 6,416,959 B1
(45) Date of Patent: Jul. 9, 2002

(54) SYSTEM FOR CELL-BASED SCREENING

(76) Inventors: Kenneth Giuliano, 351 Hawthorne Rd., Pittsburgh, PA (US) 15209; Ravi Kapur, 2942 E. Bardoneer Rd., Gibsonia, PA (US) 15044

( * ) Notice: Subject to any disclaimer, the term of this patent is extended or adjusted under 35 U.S.C. 154(b) by 0 days.

(21) Appl. No.: 09/513,783

(22) Filed: Feb. 25, 2000

Related U.S. Application Data

(63) Continuation-in-part of application No. 09/430,656, filed on Oct. 29, 1999, and a continuation-in-part of application No. 09/398,965, filed on Sep. 17, 1999, which is a continuation-in-part of application No. 09/352,171, filed on Jul. 12, 1999, which is a continuation-in-part of application No. 09/031,271, filed on Feb. 27, 1998, which is a continuation-in-part of application No. 08/810,983, filed on Feb. 27, 1997, now Pat. No. 5,989,835
(60) Provisional application No. 60/122,152, filed on Feb. 26, 1999, provisional application No. 60/123,399, filed on Mar. 8, 1999, provisional application No. 60/151,797, filed on Aug. 31, 1999, and provisional application No. 60/168,408, filed on Dec. 1, 1999.

(51) Int. Cl.$^7$ ............................................. G01N 33/533

(52) U.S. Cl. ..................... 435/7.2; 435/7.21; 435/29; 435/40.5; 435/40.51; 435/288.3; 435/288.4; 436/546; 436/172; 436/800; 436/809; 356/300; 356/326; 356/328; 382/255; 382/141; 250/201.3; 348/345

(58) Field of Search ................................. 435/7.2, 7.21, 435/29, 40, 5, 40.51, 288.3, 288.4; 436/546, 172, 800, 809; 356/300, 326, 328; 382/255, 141; 250/201.3; 348/345

(56) References Cited

U.S. PATENT DOCUMENTS

| 4,467,531 A | | 8/1984 | Kamentsky ..................... 435/7 |
|---|---|---|---|
| 5,436,128 A | * | 7/1995 | Harpold et al. ................. 435/6 |
| 5,790,710 A | * | 8/1998 | Price et al. .................. 382/255 |
| 5,989,835 A | * | 11/1999 | Dunlay et al. ................ 435/7.2 |

FOREIGN PATENT DOCUMENTS

| WO | WO 97/45730 | 12/1997 | .......... G01N/33/50 |
|---|---|---|---|
| WO | WO 98/38490 | 9/1998 | .......... G01N/15/14 |
| WO | WO 00/03246 | 1/2000 | .......... G01N/33/53 |
| WO | WO 00/17624 | 3/2000 | .......... G01N/15/14 |
| WO | WO 00/26408 | 5/2000 | ............ G12Q/1/68 |

OTHER PUBLICATIONS

Schroder et al., FLIR: A new instrument for accurate, high throughput optical screening., Journal of Biomedical Screening, vol. 1, No. 2, 1996, pp. 75–80.*
Taylor et al., "The new vision of light microscopy"., American Scientis, vol. 80, pp. 322–335, 1992.*
Zaccolo, M. et al., "A genetically encoded, fluorescent indicator for cyclic AMP in living cells", Nature Cell Biology vol. 2, Jan. 2000, pp. 25–29.

Doi, N. et al., "Design of generic biosensors based on green fluorescent proteins with allosteric sites by directed evolution", 1999 Federation of European Biochemical Societies, FEBS Letters 453, 1999 pp. 305–307.
Mizukami, S., et al., "Imaging of caspase–3 activation in HeLa cells stimulated with etoposide using a novel fluorescent probe", FEBS Letter 453, 1999, pp. 356–360.
Pap, E.H.W., et al,. "Ratio–fruorescence microscopy of lipid oxidation in living cells using C11–BODIPY 581/591", FEBS Letters 453 1999, pp. 278–282.
Gryczynski, Zygmunt et al., "Polarizaiton Sensing of Fluorophores in Tissues for Drug Compliance Monitoring", Analytical Biochemistry 273, 1999, pp. 204–211.
Pancrazio, J.J., "Development and Application of Cell–Bases Biosensors", Annals of Biomedical Engineering vol. 27, 1999 pp. 697–711.
Taylor, Laura C. et al., "Application of High–Density Optical Microwell Arrays in a Live–Cell Biosensing System", Analytical Biochemistry vol. 278, 2000, pp. 132–142.
Tolosa, Leah et al., "Glucose Sensor for Low–Cost Lifetime–Based Sensing Using a Genetically Engineered Protein", Analytical Biochemistry 267, 1999, pp. 114–120.
Thompson, Richard B., "Selectivity and Sensitivity of Fluorescent Lifetime–Based Metal Ion Biosensing Using a Carbonic Anhydrase Transducer", Analytical Biochemistry vol. 267, 1999 pp. 185–195.
Xu, Yao et al., "A bioluminescence resonance energy transfer (BRET) system: Application ot interacting circadian clock proteins", Proc. Natl. Acad. Sci. Cell Biology, Jan. 1999 pp 151–156.
Yang, Feng, et al., "High Efficient Green Fluorscent Protein–Based Kinase Substrates", Analytical Biochemistry vol. 266, 1999, pp 167–173.
Manders, Erik M.M. et al., "Direct Imaging of DNA in Living Cells Reveals the dynamics of Chromosome Formation", The Journal of Cells Biology, vol. 144 No. 5, Mar. 8, 1999 pp 813–821.
Farinas, Javier et al., "Receptor–mediated Targetting of Fluorescent Probes in Living Cells", The Journal of Biological Chemistry, vol. 274, No. 12, Mar. 19, 1999 pp 7603–7606.
Lin, Hai–Jui et al., "Lifetime–Based pH Sensors: Indicators for Acidic Environments", Analytical Biochemistry vol. 269 1999 pp 162–167.
Jayaraman, Sujatha et al., Synthesis and characterization dual–wavelength C1 sensitive flourescent indicators for ratio imaging, Ameican Physiological Society 1999 pp C747–C757.

(List continued on next page.)

Primary Examiner—Christopher L. Chin
Assistant Examiner—Lisa V Cook

(57) ABSTRACT

The present invention provides systems, methods, screens, reagents and kits for optical system analysis of cells to rapidly determine the distribution, environment, or activity of fluorescently labeled reporter molecules in cells for the purpose of screening large numbers of compounds for those that specifically affect particular biological functions.

17 Claims, 49 Drawing Sheets

OTHER PUBLICATIONS

Farrar, Sophie J., et al., "Stoichiometry of a Ligand–gated Ion Channel Determined by Fluorescence Energy Transfer", The Journal of Biological Chemistry, vol. 274, No. 15, Apr. 9, 1999 pp 10100–10104.

Heidemann, Steven R., et al., "Direct Observations of the Mechanical Behaviors of the Cytoskeleton in Living Fibroblasts", The Journal of Cell Biology vol. 145, Apr. 5, 1999 109–122.

Lakowicz, Joseph R. et al., "Anisotripy–Based Sensing with Reference Fluorophores", Analytical Biochemistry 267, 1999 pp. 397–405.

Sagot, Isabelle, et al., "Imaging flourescence resonance energy transfer between two green flourescent proteins in living yeast", FEBS Letters 447, 1999 pp 53–57.

Ng, Tony, et al., "Imaging Protein Kinase C$\beta$ Activation in Cells", Science vol. 283 Mar. 26, 1999 pp 2085–2089.

Fujii, Gen., et al., "Analysis of Nuclear Localization Signals Using a Green Fluorescent Protein–Fusion Protein Library", Experimental Cell Research 251, 1999, pp 299–306.

Hug, Hubert et al., Rhodamine 110–Linked Amino Acids and Peptides as Substrates To Measure Caspase Activity upon Apoptosis Indication in Intact Cells, Biochemistry 1999 38, pp 13906–13911.

Ito, Yoichiro et al., "A Novel Mutant of Green Fluorescent Protein with Enhanced Sensitivity of Microanalysis at 488 nm Excitation", Biochemical and Biophysical Research Communications, 164 1999, pp 556–560.

Lee, Chao–Lin, et al., "Localized measurement of kinase activation in oocytes of *Xenopus laevix*", Nature Biotechnology vol. 17 Aug. 1999, pp 759–762.

Dery, Olivier, et al., "Trafficking of Proteinase–activated Peceptor–2 and $\beta$–Arrestin–1 Tagged with Green Fluorescent Protein", The Journal of Biological Chemistry vol. 275 No. 26, Jun. 25, 1999, pp 18524–18535.

Clark, Heather a., et al., "Optical Nanosensors for chemical Analysis inside Single Living Cells. 1. Fabrication, Characterization, and Methods for Intracellular", Anal Chem, 1999, 71 pp 4831–4836.

Li & Glazer, Design, Synthesis, and Spectroscopic Properties of Peptide–Bridged fluorescence Energy–Transfer Cassettes, Bioconjugate Chem, 1999 10, pp 241–245.

Clark, Heather A., et al., "Optical nonosensors for Chemical Analysis inside Single Living Cells. 2. Sensors for pH and Calcium and the Intracellular Application of PEBBLE Sensors", Anal Chem, 1999, 71 pp 4837–4843.

Ruehr, Mary Louise et al., "Cyclic AMP–dependent Protein Kinase Binding to a–kinase Anchoring Proteins in Living Cells by Fluorescence Resonance Energy Transfer of Green Flourescent Protein Fusion Proteins", The Journal of Biological Chemistry vol. 274, No. 46 Nov. 12, 1999 pp 33092–33096.

Pin, Sokhom S., et al., "Analysis of Protein–Peptide Interaction by a Minaturized Fluorescence Polarization Assay using Cyclin–Dependent Kinase 2/Cyclin E as a Model Systems", Analytical Biochemistry vol. 275, 1999, pp 156–161.

De Silva, A. Prasanna et al., "Emerging fluorscence sensing technologies: From photophysical principles to cellular applications", Proc. Natl. Acad. Sci., vol. 96 Jul. 1999 pp 8336–8337.

Gether, Ulrick, Chapter 14 "Fluorescence Spectroscopy Analysis of Conformational Changes in the $\beta$2—Andrenergic Receptor", Structure–Function Analysis of G Protein–Coupled Receptors edited by Jurgen Wess, Wiley–Liss, Inc. 1999 pp 315–334.

Wildt & Deuschle, "cobA, a red fluorescent transcriptional reporter for *Escherichia coli*, yeast, and mammalian cells", Nature Biotechnology vol. 17 Dec. 1999 pp 1175–1178.

Schobel, Uwe, et al., "New Donor–Acceptor Pairfor Fluorescent Immunoassays by Energy Transfer", Institute of Physical and Theoretical Chemistry, Aug. 1999.

Sujatha, Jayaraman et al., "long–wavelength iodide–sensitive fluorescent indicators for measurement of functional CFTR expression in cells", American Physiological Society, 1999 Special Communications.

Kask, Peet et al., "Fluorescence–intensity distribution analysis and its application in biomolecular detection technology", PNAS vol. 96 Nov. 23,1999 pp 13756–13761.

Wang, Qiming J. et al., "Differential Localization of Protein Kinase C$\delta$ by Phorbol Esters and Related Compounds Using a Fusion Protein with Green Fluorescent Protein", The Journal of Biological Chemistry, vol. 274, No. 52, Dec. 24, 1999 pp. 37233–37239.

Gast, Rainer et al., "Method for Determining Protein Kinase Substrate Specificities by the Phosphorylation of Peptide Libraries on Breads, Phosphate–Specific Straining, Automated Sorting, and Sequencing", Analytical Biochemistry vol. 276, 1999 pp 227–241.

Zurgil, Naomi et al., "Fluorescein Fluorescence Hyperpolarization as an Early Kinetic Measure of the Apoptotic Process", Biochemical and Biophysical Research Communications vol. 268, 2000, pp 155–163.

Geoghegan, Kieran F., et al., "Dye–Pair Reporter Systems for Protein–Peptide Molecular Interactions", Pfizer, Inc., Central Research Division Oct. 19, 1999.

* cited by examiner

Figure 2
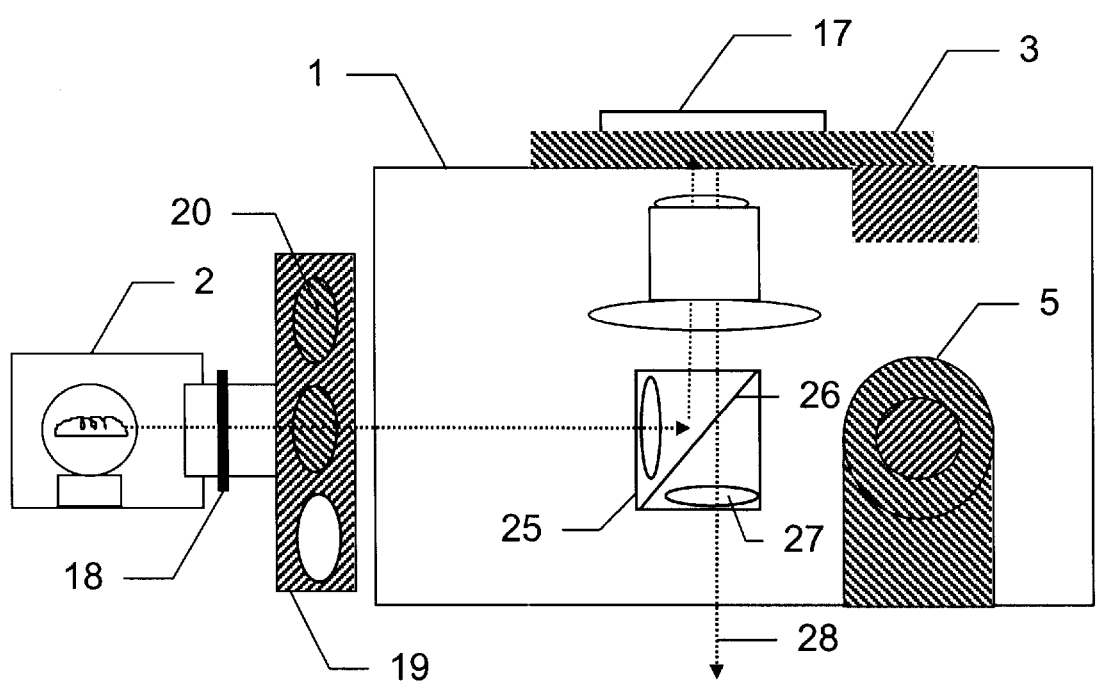
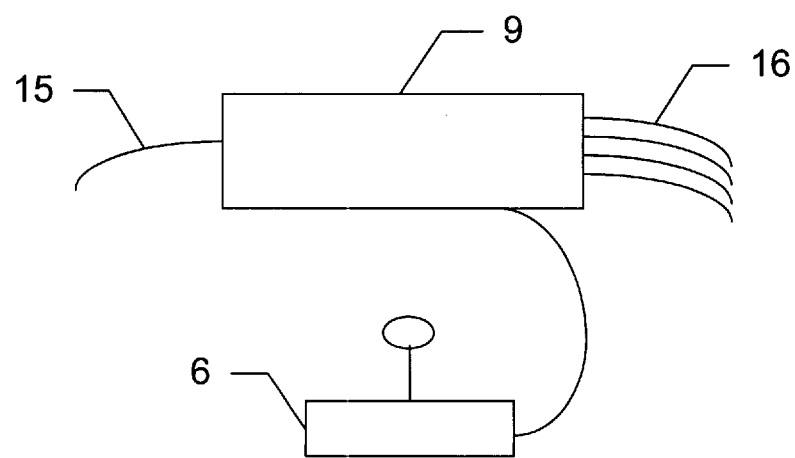

Figure 9
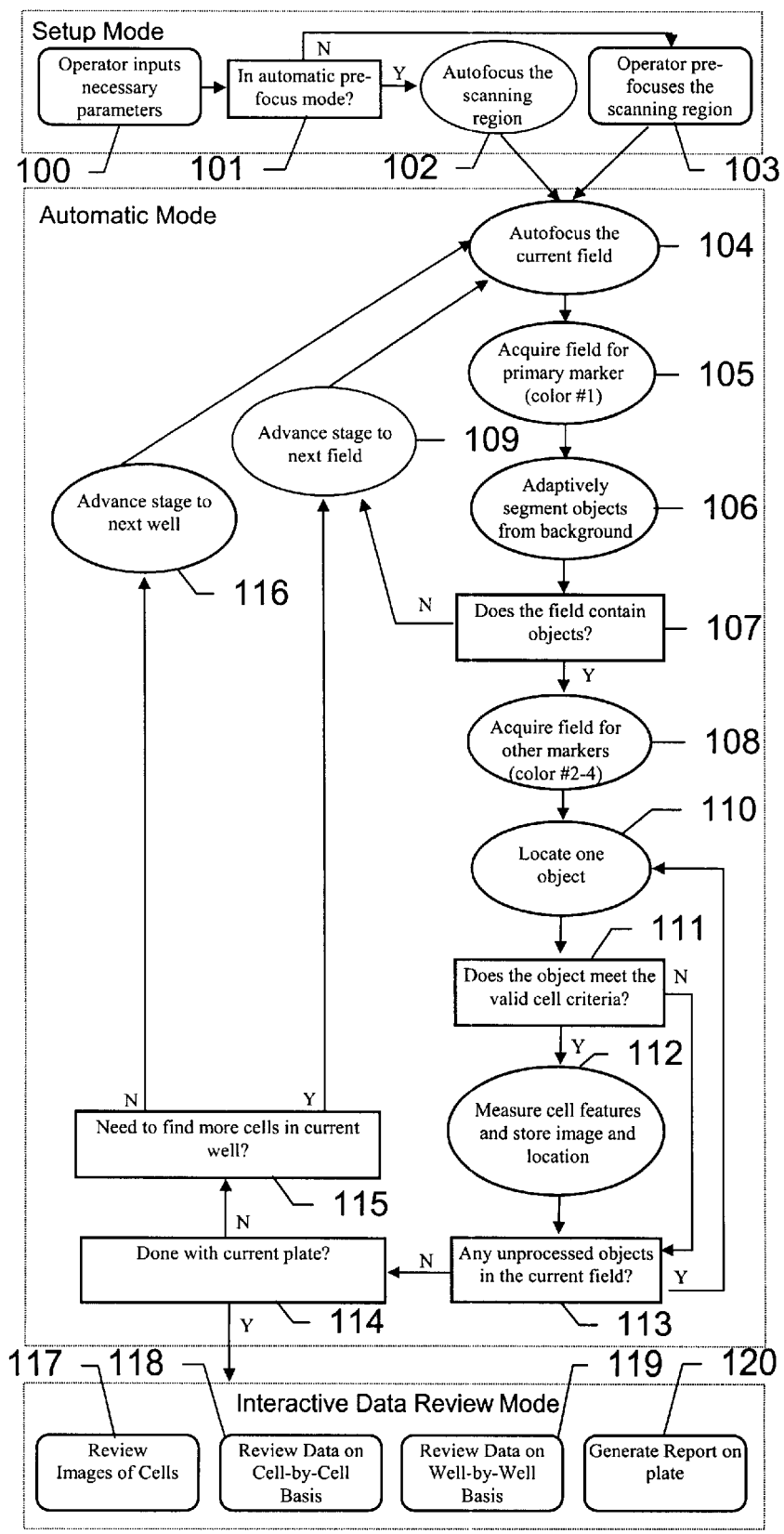
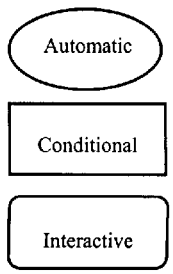

FIGURE 29A-1

1.  SIGNAL SEQUENCES

| EPITOPE | SEQUENCE | SEQ ID NO: | REFERENCE |
|---|---|---|---|
| FLAG epitope | 5'GACTACAAAGACGACG<br><br>AA Seq: ACGACAAA | 35<br><br>36 | Kasir, et al., 1999. J Biol Chem. 274:24873-80. |
| HA epitope | 5'TACCCATACGACGTACCAGACTACGCA<br><br>AA Seq: YPYDVPDYA | 37<br><br>38 | Smith, et al., 1999. J Biol Chem. 274:19894-900. |
| KT3 epitope | 5'CCACCAGAACCAGAAACA<br><br>AA seq: PPEPET | 39<br><br>40 | MacArthur and Walter. 1984. J Virol. 52:483-91. |
| Myc epitope | 5'GCAGAAGAACAAAAATTAATAAGCGAAGAAGACTTA<br><br>AA Seq: AEEQKLISEEDL | 41<br><br>42 | Gosney, et al., 1990. Anticancer Res. 10:623-8. |

EYFP: SEQ ID NO: 43 (Nucleic acid); SEQ ID NO:44 (Amino acid)

```
M   V   S   K       G   E   E   L       F   T   G   V       V   P   I   L       V   E   L   D
ATGGTGAGCAAG        GGCGAGGAGCTG        TTCACCGGGGTG        GTGCCCATCCTG        GTCGAGCTGGAC

G   D   V   N       G   H   K   F       S   V   S   G       E   G   E   G       D   A   T   Y
GGCGACGTAAAC        GGCCACAAGTTC        AGCGTGTCCGGC        GAGGGCGAGGGC        GATGCCACCTAC

G   K   L   T       L   K   F   I       C   T   T   G       K   L   P   V       P   W   P   T
GGCAAGCTGACC        CTGAAGTTCATC        TGCACCACCGGC        AAGCTGCCCGTG        CCCTGGCCCACC

L   V   T   T       F   G   Y   G       L   Q   C   F       A   R   Y   P       D   H   M   K
CTCGTGACCACC        TTCGGCTACGGC        CTGCAGTGCTTC        GCCCGCTACCCC        GACCACATGAAG

Q   H   D   F       F   K   S   A       M   P   E   G       Y   V   Q   E       R   T   I   F
CAGCACGACTTC        TTCAAGTCCGCC        ATGCCCGAAGGC        TACGTCCAGGAG        CGCACCATCTTC

F   K   D   D       G   N   Y   K       T   R   A   E       V   K   F   E       G   D   T   L
TTCAAGGACGAC        GGCAACTACAAG        ACCCGCGCCGAG        GTGAAGTTCGAG        GGCGACACCCTG

V   N   R   I       E   L   K   G       I   D   F   K       E   D   G   N       I   L   G   H
GTGAACCGCATC        GAGCTGAAGGGC        ATCGACTTCAAG        GAGGACGGCAAC        ATCCTGGGGCAC

K   L   E   Y       N   Y   N   S       H   N   V   Y       I   M   A   D       K   Q   K   N
AAGCTGGAGTAC        AACTACAACAGC        CACAACGTCTAT        ATCATGGCCGAC        AAGCAGAAGAAC

G   I   K   V       N   F   K   I       R   H   N   I       E   D   G   S       V   Q   L   A
GGCATCAAGGTG        AACTTCAAGATC        CGCCACAACATC        GAGGACGGCAGC        GTGCAGCTCGCC

D   H   Y   Q       N   T   P       I   G   D   G       P   V   L   L       P   D   N   H
GACCACTACCAG        CAGAACACCCCC        ATCGGCGACGGC        CCCGTGCTGCTG        CCCGACAACCAC

Y   L   S   Y       Q   S   A   L       S   K   D   P       N   E   K   R       D   H   M   V
TACCTGAGCTAC        CAGTCCGCCCTG        AGCAAAGACCCC        AACGAGAAGCGC        GATCACATGGTC
```

FIGURE 29A-2

```
L   L   E   F   V   T   A   A   G   I   T   L   G   M   D   E   L   Y   K
CTGCTGGAGTTC GTGACCGCCGCC GGGATCACTCTC GGCATGGACGAG CTGTACAAG
```

EGFP: SEQ ID NO:45 (Nucleic acid); SEQ ID NO:46 (Amino acid)

```
M   V   S   K   G   E   E   L   F   T   G   V   V   P   I   L   V   E   L   D
ATGGTGAGCAAG GGCGAGGAGCTG TTCACCGGGGTG GTGCCCATCCTG GTCGAGCTGGAC

G   D   V   N   G   H   K   F   S   V   S   G   E   G   E   G   D   A   T   Y
GGCGACGTAAAC GGCCACAAGTTC AGCGTGTCCGGC GAGGGCGAGGGC GATGCCACCTAC

G   K   L   T   L   K   F   I   C   T   T   G   K   L   P   V   P   W   P   T
GGCAAGCTGACC CTGAAGTTCATC TGCACCACCGGC AAGCTGCCCGTG CCCTGGCCCACC

L   V   T   T   L   T   Y   G   V   Q   C   F   S   R   Y   P   D   H   M   K
CTCGTGACCACC CTGACCTACGGC GTGCAGTGCTTC AGCCGCTACCCC GACCACATGAAG

Q   H   D   F   F   K   S   A   M   P   E   G   Y   V   Q   E   R   T   I   F
CAGCACGACTTC TTCAAGTCCGCC ATGCCCGAAGGC TACGTCCAGGAG CGCACCATCTTC

F   K   D   D   G   N   Y   K   T   R   A   E   V   K   F   E   G   D   T   L
TTCAAGGACGAC GGCAACTACAAG ACCCGCGCCGAG GTGAAGTTCGAG GGCGACACCCTG

V   N   R   I   E   L   K   G   I   D   F   K   E   D   G   N   I   L   G   H
GTGAACCGCATC GAGCTGAAGGGC ATCGACTTCAAG GAGGACGGCAAC ATCCTGGGGCAC

K   L   E   Y   N   Y   N   S   H   N   V   Y   I   M   A   D   K   Q   K   N
AAGCTGGAGTAC AACTACAACAGC CACAACGTCTAT ATCATGGCCGAC AAGCAGAAGAAC

G   I   K   V   N   F   K   I   R   H   N   I   E   D   G   S   V   Q   L   A
GGCATCAAGGTG AACTTCAAGATC CGCCACAACATC GAGGACGGCAGC GTGCAGCTCGCC

D   H   Y   Q   Q   N   T   P   I   G   D   G   P   V   L   L   P   D   N   H
GACCACTACCAG CAGAACACCCCC ATCGGCGACGGC CCCGTGCTGCTG CCCGACAACCAC

Y   L   S   T   Q   S   A   L   S   K   D   P   N   E   K   R   D   H   M   V
TACCTGAGCACC CAGTCCGCCCTG AGCAAAGACCCC AACGAGAAGCGC GATCACATGGTC

L   L   E   F   V   T   A   A   G   I   T   L   G   M   D   E   L   Y   K
CTGCTGGAGTTC GTGACCGCCGCC GGGATCACTCTC GGCATGGACGAG CTGTACAAG
```

EBFP: SEQ ID NO:47 (Nucleic acid); SEQ ID NO:48 (Amino acid)

```
M   V   S   K   G   E   E   L   F   T   G   V   V   P   I   L   V   E   L   D
ATGGTGAGCAAG GGCGAGGAGCTG TTCACCGGGGTG GTGCCCATCCTG GTCGAGCTGGAC

G   D   V   N   G   H   K   F   S   V   S   G   E   G   E   G   D   A   T   Y
GGCGACGTAAAC GGCCACAAGTTC AGCGTGTCCGGC GAGGGCGAGGGC GATGCCACCTAC

G   K   L   T   L   K   F   I   C   T   T   G   K   L   P   V   P   W   P   T
GGCAAGCTGACC CTGAAGTTCATC TGCACCACCGGC AAGCTGCCCGTG CCCTGGCCCACC
```

FIGURE 29A-3

```
L    V    T    T         L    T    H    G         V    Q    C    F         S    R    Y    P         D    H    M    K
CTCGTGACCACC   CTGACCCACGGC   GTGCAGTGCTTC   AGCCGCTACCCC   GACCACATGAAG

Q    H    D    F         F    K    S    A         M    P    E    G         Y    V    Q    E         R    T    I    F
CAGCACGACTTC   TTCAAGTCCGCC   ATGCCCGAAGGC   TACGTCCAGGAG   CGCACCATCTTC

F    K    D    D         G    N    Y    K         T    R    A    E         V    K    F    E         G    D    T    L
TTCAAGGACGAC   GGCAACTACAAG   ACCCGCGCCGAG   GTGAAGTTCGAG   GGCGACACCCTG

V    N    R    I         E    L    K    G         I    D    F    K         E    D    G    N         I    L    G    H
GTGAACCGCATC   GAGCTGAAGGGC   ATCGACTTCAAG   GAGGACGGCAAC   ATCCTGGGGCAC

K    L    E    Y         N    F    N    S         H    N    V    Y         I    M    A    D         K    Q    K    N
AAGCTGGAGTAC   AACTTCAACAGC   CACAACGTCTAT   ATCATGGCCGAC   AAGCAGAAGAAC

G    I    K    V         N    F    K    I         R    H    N    I         E    D    G    S         V    Q    L    A
GGCATCAAGGTG   AACTTCAAGATC   CGCCACAACATC   GAGGACGGCAGC   GTGCAGCTCGCC

D    H    Y    Q         Q    N    T    P         I    G    D    G         P    V    L    L         P    D    N    H
GACCACTACCAG   CAGAACACCCCC   ATCGGCGACGGC   CCCGTGCTGCTG   CCCGACAACCAC

Y    L    S    T         Q    S    A    L         S    K    D    P         N    E    K    R         D    H    M    V
TACCTGAGCACC   CAGTCCGCCCTG   AGCAAAGACCCC   AACGAGAAGCGC   GATCACATGGTC

L    L    E    F         V    T    A    A         G    I    T    L         G    M    D    E         L    Y    K
CTGCTGGAGTTC   GTGACCGCCGCC   GGGATCACTCTC   GGCATGGACGAG   CTGTACAAG
```

ECFP: SEQ ID NO:49 (Nucleic acid); SEQ ID NO:50 (Amino acid)

```
M    V    S    K         G    E    E    L         F    T    G    V         V    P    I    L         V    E    L    D
ATGGTGAGCAAG   GGCGAGGAGCTG   TTCACCGGGGTG   GTGCCCATCCTG   GTCGAGCTGGAC

G    D    V    N         G    H    K    F         S    V    S    G         E    G    E    G         D    A    T    Y
GGCGACGTAAAC   GGCCACAAGTTC   AGCGTGTCCGGC   GAGGGCGAGGGC   GATGCCACCTAC

G    K    L    T         L    K    F    I         C    T    T    G         K    L    P    V         P    W    P    T
GGCAAGCTGACC   CTGAAGTTCATC   TGCACCACCGGC   AAGCTGCCCGTG   CCCTGGCCCACC

L    V    T    T         L    T    W    G         V    Q    C    F         S    R    Y    P         D    H    M    K
CTCGTGACCACC   CTGACCTGGGGC   GTGCAGTGCTTC   AGCCGCTACCCC   GACCACATGAAG

Q    H    D    F         F    K    S    A         M    P    E    G         Y    V    Q    E         R    T    I    F
CAGCACGACTTC   TTCAAGTCCGCC   ATGCCCGAAGGC   TACGTCCAGGAG   CGCACCATCTTC

F    K    D    D         G    N    Y    K         T    R    A    E         V    K    F    E         G    D    T    L
TTCAAGGACGAC   GGCAACTACAAG   ACCCGCGCCGAG   GTGAAGTTCGAG   GGCGACACCCTG

V    N    R    I         E    L    K    G         I    D    F    K         E    D    G    N         I    L    G    H
GTGAACCGCATC   GAGCTGAAGGGC   ATCGACTTCAAG   GAGGACGGCAAC   ATCCTGGGGCAC

K    L    E    Y         N    Y    I    S         H    N    V    Y         I    T    A    D         K    Q    K    N
AAGCTGGAGTAC   AACTACATCAGC   CACAACGTCTAT   ATCACCGCCGAC   AAGCAGAAGAAC

```
              GGCATCAAGGCC AACTTCAAGATC CGCCACAACATC GAGGACGGCAGC GTGCAGCTCGCC

D   H   Y   Q     Q   N   T   P     I   G   D   G     P   V   L   L     P   D   N   H
              GACCACTACCAG CAGAACACCCCC ATCGGCGACGGC CCCGTGCTGCTG CCCGACAACCAC

Y   L   S   T     Q   S   A   L     S   K   D   P     N   E   K   R     D   H   M   V
              TACCTGAGCACC CAGTCCGCCCTG AGCAAAGACCCC AACGAGAAGCGC GATCACATGGTC

L   L   E   F     V   T   A   A     G   I   T   L     G   M   D   E     L   Y   K
              CTGCTGGAGTTC GTGACCGCCGCC GGGATCACTCTC GGCATGGACGAG CTGTACAAG
```

Fred25: SEQ ID NO:51 (Nucleic acid); SEQ ID NO:52 (Amino acid)

```
  M   A   S   K     G   E   E   L     F   T   G   V     V   P   I   L     V   E   L   D
              ATGGCTAGCAAA GGAGAAGAACTC TTCACTGGAGTT GTCCCAATTCTT GTTGAATTAGAT

G   D   V   N     G   H   K   F     S   V   S   G     E   G   E   G     D   A   T   Y
              GGTGATGTTAAC GGCCACAAGTTC TCTGTCAGTGGA GAGGGTGAAGGT GATGCAACATAC

G   K   L   T     L   K   F   I     C   T   T   G     K   L   P   V     P   W   P   T
              GGAAAACTTACC CTGAAGTTCATC TGCACTACTGGC AAACTGCCTGTT CCATGGCCAACA

L   V   T   T     L   C   Y   G     V   Q   C   F     S   R   Y   P     D   H   M   K
              CTAGTCACTACT CTGTGCTATGGT GTTCAATGCTTT TCAAGATACCCG GATCATATGAAA

R   H   D   F     F   K   S   A     M   P   E   G     Y   V   Q   E     R   T   I   F
              CGGCATGACTTT TTCAAGAGTGCC ATGCCCGAAGGT TATGTACAGGAA AGGACCATCTTC

F   K   D   D     G   N   Y   K     T   R   A   E     V   K   F   E     G   D   T   L
              TTCAAAGATGAC GGCAACTACAAG ACACGTGCTGAA GTCAAGTTTGAA GGTGATACCCTT

V   N   R   I     E   L   K   G     I   D   F   K     E   D   G   N     I   L   G   H
              GTTAATAGAATC GAGTTAAAAGGT ATTGACTTCAAG GAAGATGGCAAC ATTCTGGGACAC

K   L   E   Y     N   Y   N   S     H   N   V   Y     I   M   A   D     K   Q   K   N
              AAATTGGAATAC AACTATAACTCA CACAATGTATAC ATCATGGCAGAC AAACAAAAGAAT

G   I   K   V     N   F   K   T     R   H   N   I     E   D   G   S     V   Q   L   A
              GGAATCAAAGTG AACTTCAAGACC CGCCACAACATT GAAGATGGAAGC GTTCAACTAGCA

D   H   Y   Q     Q   N   T   P     I   G   D   G     P   V   L   L     P   D   N   H
              GACCATTATCAA CAAAATACTCCA ATTGGCGATGGC CCTGTCCTTTTA CCAGACAACCAT

Y   L   S   T     Q   S   A   L     S   K   D   P     N   E   K   R     D   H   M   V
              TACCTGTCCACA CAATCTGCCCTT TCGAAAGATCCC AACGAAAAGAGA GACCACATGGTC

L   L   E   F     V   T   A   A     G   I   T   H     G   M   D   E     L   Y   N   *
              CTTCTTGAGTTT GTAACAGCTGCT GGGATTACACAT GGCATGGATGAA CTGTACAACTAG
```

FIGURE 29B-1

2. PROTEASE RECOGNITION SITES

| Substrate Recognitions Sequences | Source | Recognition Site | SEQ ID NO | Reference |
|---|---|---|---|---|
| Caspase-1,4,5 | peptide library | 5'(TGG,TTA)GAACATGACAA Seq:(W,L)EHD/ | 53 54 | Thornberry et al., 1997, J. Biol. Chem. 272:17907 |
| proCaspase-1 | peptide library | 5'TGGTTTAAAGAC AA Seq: WFKD/ | 55 56 | Thornberry et al., 1997, J. Biol. Chem. 272:17907 |
| Caspase-2 | peptide library | 5'GACGAACACGAC AA Seq: DEHD/ | 57 58 | Thornberry et al., 1997, J. Biol. Chem. 272:17907 |
| Caspase 3, 7 | PARP | 5'GACGAAGTTGAC AA Seq: DEVD/ | 59 60 | Beneke, et al., 1997. Biochem Mol Biol Int. 43:755-61; Thornberry et al., 1997, J. Biol. Chem. 272:17907 |
| ProCaspase 3 | Caspase-3 | 5'ATAGAAACAGAC AA Seq: IETD/ | 61 62 | Tewari, M., et al., 1995. Cell. 81:801-9. |
| ProCaspase-4,5 | peptide library | 5'TGGGTAAGAGAC AA Seq: WVRD/ | 63 64 | Thornberry, N.A. et al., 1997, J.Biol. Chem. 272, 17907-17911 |
| Caspase 6 | Lamin A, peptide library | 5'GTAGAAATAGAC AA Seq: VEID/ 5'GTAGAACACGAC AA Seq: VEHD/ | 65 66 67 68 | Nakajima and Sado. 1993. Biochim Biophys Acta. 1171:311-4; Thornberry et al., 1997, J. Biol. Chem. 272:17907 |
| proCaspase 6 | Caspase-6 | 5'ACAGAAGTAGAC AA Seq: TEVD/ | 69 70 | Fernandes-Alnemri, et al., 1994. J Biol Chem. 269:30761-4. |
| proCaspase-7 | peptide library | 5'ATACAAGCAGAC AA Seq: IQAD/ | 71 72 | Thornberry, N.A. et al., 1997, J.Biol. Chem. 272, 17907-17911 |
| Caspase 8 | peptide library | 5'GTAGAAACAGAC AA Seq: VETD/, | 73 74 | Muzio, M., et al., 1996. Cell. 85:817-27; Fernandes-Alnemri, et al., 1996. Proc Natl Acad Sci U S A. 93:7464-9;Thornberry et al., 1997, J. Biol. Chem. 272:17907 |
| proCaspase-8 | Caspase-8 | 5'TTAGAAACAGAC AA Seq: LETD/ | 75 76 | Muzio, M., et al., 1996. Cell. 85:817-27; Fernandes-Alnemri, et al., 1996. Proc Natl Acad Sci U S A. 93:7464-9;Thornberry et al., 1997, J. Biol. Chem. 272:17907 |
| Caspase 9 | peptide library | 5'TTAGAACACGAC AA Seq: LEHD/ | 77 78 | Thornberry, N.A. et al., 1997, J.Biol. Chem. 272, 17907-17911 |
| proCaspase 9 | Caspase-9 | 5'TTAGAACACGAC AA Seq: LEHD/ | 79 80 | Thornberry, N.A. et al., 1997, J.Biol. Chem. 272, 17907-17911 |
| HIV protease | | 5'AGCCAAAATTAC AA Seq: SQNY/ 5'CCAATAGTACAA AA Seq: PIVQ/ | 81 82 83 84 | Matayoshi, et al., 1990. Science. 247:954-8. |
| Adenovirus endopeptidase | | 5'AUGTTTGGAGGA AA Seq: MFGG/ 5'GCAAAAAAAGA AA Seq: AKKR/ | 85 86 87 88 | Weber and Tihanyi. 1994. Methods Enzymol. 244:595-604. |
| b-Secretase | Amyloid precursor protein | 5'GTAAAAAUG AA Seq: VKM/ 5'GACGCAGAATTC DAEF/ | 89 90 91 92 | Hardy et al., 1994, in Amyloid Protein Precursor in Development, Aging, and Alzheimer's Disease, ed. C.L. Masters et al., pp. 190-198. |
| Cathepsin D | | 5'AAACCAGCATTATTC AA Seq: KPALF 5'TTCAGATTA AA Seq: FRL/ | 93 94 95 96 | Dunn, et al., 1998. Adv Exp Med Biol. 436:133-8. |
| Matrix Metalloproteases | | 5'GGACCATTAGGACCA AA Seq: GPLGP | 97 98 | Bouvier et al., 1993; Garbett et al., 1999; Hill and Sakanari, 1997; Kojima et al., 1998; Tyagi et al., 1995; Wilhelm et al., 1993; Williams and Auld, 1986; Haugland, R., Handbook of fluorescent probes and research Chemicals 7th ed. |
| Granzyme B | peptide library | 5'ATAGAACCAGAC AA Seq: IEPD/ | 99 100 | Thornberry et al., 1997, J. Biol. Chem. 272:17907 |

FIGURE 29B-2

| Anthrax protease | MEK1 | 5'ATGCCCAAGAAGAAGCCGAC GCCCATCCAGCTGAACCC | 101 | Vitale et al., (1998) Biochem Biophys Res Commun 248 (3), 706-711 |
|---|---|---|---|---|
| | | AA Seq: MPKKKPTPIQLN | 102 | |
| Anthrax protease | MEK2 | 5'ATGCTGGCCCGGAGGAAGCCG GTGCTGCCGGCGCTCACCATCA ACCC | 103 | Vitale et al., (1998) Biochem Biophys Res Commun 248 (3), 706-711 |
| | | AA Seq: MLARRKPVLPALTIN | 104 | |
| tetanus/botulinum | cellubrevin | 5'GCCTCGCAGTTTGAAACA | 105 | McMahon et al., Nature 364:346-349; Martin et al., J. Cell Biol. In press |
| | | AA Seq: ASQFET | 106 | |
| tetanus/botulinum | synaptobrevin/ VAMP3 | 5'GCTTCTCAATTTGAAACG | 107 | Schiavo et al., (1992) Nature 359, 832-5 |
| | | AA Seq: ASQFET | 108 | |
| Botulinum neurotoxin A | SNAP-25 | 5'GCCAACCAACGTGCAACA | 109 | Zhao, et al. Gene 145 (2), 313-314 (1994) |
| | | AA Seq: ANQ/RAT | 110 | |
| Botulinum neurotoxin B | VAMP | 5'GCTTCTCAATTTGAAACG | 111 | |
| | | AA Seq: ASQ/FET | 112 | |
| Botulinum neurotoxin C | Syntaxin | 5'ACGAAAAAAGCTGTGAAA | 113 | Martin et al., J. Leukoc. Biol. 65 (3), 397-406 (1999) |
| | | AA Seq: TKK/AVK | 114 | |
| Botulinum neurotoxin D | VAMP | 5'GACCAGAAGCTCTCTGAG | 115 | |
| | | AA Seq: DQK/LSE | 116 | |
| Botulinum neurotoxin E | SNAP-25 | 5'ATCGACAGGATCATGGAG | 117 | |
| | | AA Seq: IDR/IME | 118 | |
| Botulinum neurotoxin F | VAMP | 5'AGAGACCAGAAGCTCTCT | 119 | |
| | | AA Seq: RDQ/KLS | 120 | |
| Botulinum neurotoxin G | VAMP | 5'ACGAGCGCAGCCAAGTTG | 121 | |
| | | AA Seq: TSA/AKL | 122 | |

FIGURE 29C-1

3. PRODUCT/REACTANT TARGET SEQUENCES

| Target | Target Source | Target domain (Product or Reactant) | SEQ ID NO | Reference |
|---|---|---|---|---|
| Cytoplasm/cytoskeleton | Annexin II | 5'ATGTCTACTGTCCACGAAATCCTGTGCAAG CTCAGCTTGGAGGGTGTTCATTCTACACCCCC AAGTGCC 3' | 123 | Eberhard, et al., 1997, Mol. Biol. Cell 8:293a. |
| | | (Amino acid seq: M S T V H E I L C K L S L E G V H S T P P S A) | 124 | |
| Inner surface of plasma membrane | farnesylation | 5'AUGGGATCTACATTAAGCGCAGAAGACAA AGCAGCAGTAGAAAGAAGCAAAAUGATAGA CAGAAACTTATTAAGAGAAGACGGAGAAAA AGCTGCTAGA3' | 125 | Ferruccio G, et al., J. Biol. Chem. 274, 5843-5850, 1999 |
| | | (AA seq: M G C T L S A E D K A A V E R S K M I D R N L R E D G E K A A R | 126 | |
| Nucleus | NFkB p50 | 5'AGAAGGAAACGACAAAAG | 127 | Henkel, T et al., Cell 68, 1121-1133, 1992 |
| | | (AA seq: R R K R Q K) | 128 | |
| Nucleolus | NOLP | 5'AGAAAACGTATACGTACTTACCTCAAGTCC TGCAGGCGGATGAAAAGAAGTGGTTTTGAGA TGTCTCGACCTATTCCTTCCCACCTTACT | 129 | Ueki, et al., 1998. Biochem Biophys Res Commun. 252:97-102. |
| | | (AA seq: R K R I R T Y L K S C R R M K R S G F E M S R P I P S H L T) | 130 | |
| Mitochondria | cytochrome c oxidase | 5'ATGTCCGTCCTGACGCCGCTGCTGCTGCGG GGCTTGACAGGCTCGGCCCGGCGGCTCCCAG TGCCGCGCGCCAAGATCCATTCGTTG | 131 | Rizzuto, et al., 1989. J Biol Chem. 264:10595-600. |
| | | (AA Seq: M S V L T P L L L R G L T G S A R R L P V P R A L I H S L) | 132 | |
| Nuclear Envelope | ODV-E66 & ODV-E25 | 5'AUGAGCATTGTTTTAATAATTGTTATTTGGA TTTTTTTAATATGTTTTTTATATTTAAGCAACA GCAAAGATCCCAGAGTACCAGTTGAATTAAU G | 133 | Hong, T, et al. PNAS, 94, 4050-4055, 1997 |
| | | (AA Seq: M S I V L I I V I V V I F L I C F L Y L S N S K D P R V P V E L M) | 134 | |
| Golgi | Calreticulin | 5'ATGAGGCTTCGGGAGCCGCTCCTGGCGGC AGCGCCGCGATGCCAGGCGCCTCCCTACAGC GGGCCTGCCGCCTGCTCGTGGCCGTCTGCGCT CTGCACCTTGGCGTCACCCTCGTTTACTACCT GGCTGGCCGCGACCTGAGCCGCCTGCCCCAA CTGGTCGGAGTCTCCACACCGCTGCAGGGCG GCTCGAACAGTGCCGCCGCCATCGGGCAGTC CTCCGGGGAGCTCCGGACCGGAGGGGCC | 135 | Fliegel, L., et al., J. Biol. Chem. 264, 21522-21528, 1989. |
| | | (AA Seq: M R L R E P L L S G S A A M P G A S L Q R A C R L L V A V C A L H L G V T L V Y Y L A G R D L S R L P Q L V G V S T P L Q G G S N S A A A I G Q S S G E L R T G G A) | 136 | |
| Endoplasmic reticulum | D-AKAP1 | 5'GAAACAATAAGACCTATAAGAAGATGTAGT ACATTTACATCTACAGACAGCAAAATGGCAA TTCAATTAAGATCTCCCTTTCCATTAGCATTA CCAGGAAUGTTAGCTTTATTAGGATGGTGGT GGTTTTTCAGTAGAAAAAAA | 137 | Huang, LJ. Et al., J. Cell. Biol. 145, 951-959, 1999 |
| | | (AA Seq: E T I R P I R I R R C S Y F T S T D S K M A I Q L R S P F P L A L P G M L A L L G W W W F F S R K K | 138 | |
| Nuclear Export | MEK1 | 5' GCCTTGCAGAAGAAGCTGGAGGAGCT AGAGCTTGATGAG | 139 | Fukuda, (1997) J. Biol. Chem 272, 51, 32642-32648 |
| | | (AA SEQ: A L Q K K L E E L E L D E | 140 | |

FIGURE 29C-2

| Size exclusion | PROJ domain of MAP4 | 5'GCCGACCTCAGTCTTGTGGATGCGTTGACA GAACCACCTCCAGAAATTGAGGGAGAAATAA AGCGAGACTTCATGGCTGCGCTGGAGGCAGA GCCCTATGATGACATCGTGGGAGAAACTGTG GAGAAAACTGAGTTTATTCCTCTCCTGGATGG TGATGAGAAAACCGGGAACTCAGAGTCCAAA AAGAAACCCTGCTTAGACACTAGCCAGGTTG AAGGTATCCCATCTTCTAAACCAACACTCCTA GCCAATGGTGATCATGGAATGGAGGGGAATA ACACTGCAGGGTCTCCAACTGACTTCCTTGAA GAGAGAGTGGACTATCCGGATTATCAGAGCA GCCAGAACTGGCCAGAAGATGCAAGCTTTTG TTTCCAGCCTCAGCAAGTGTTAGATACTGACC AGGCTGAGCCCTTTAACGAGCACCGTGATGA TGGTTTGGCAGATCTGCTCTTTGTCTCCAGTG GACCCACGAACGCTTCTGCATTTACAGAGCG AGACAATCCTTCAGAAGACAGTTACGGTATG CTTCCCTGTGACTCATTTGCTTCCACGGCTGT TGTATCTCAGGAGTGGTCTGTGGGAGCCCCA AACTCTCCATGTTCAGAGTCCTGTGTCTCCCC AGAGGTTACTATAGAAACCCTACAGCCAGCA ACAGAGCTCTCCAAGGCAGCAGAAGTGGAAT CAGTGAAAGAGCAGCTGCCAGCTAAAGCATT GGAAACGATGGCAGAGCAGACCACTGATGTG GTGCACTCTCCATCCACAGACACAACACCAG GCCCAGACACAGAGGCAGCACTGGCTAAAGA CATAGAAGAGATCACCAAGCCAGATGTGATA TTGGCAAATGTCACGCAGCCATCTACTGAAT CGGATATGTTCCTGGCCCAGGACATGGAACT ACTCACAGGAACAGAGGCAGCCCACGCTAAC AATATCATATTGCCTACAGAACCAGACGAAT CTTCAACCAAGGATGTAGCACCACCTATGGA AGAAGAAATTGTCCCAGGCAATGATA | 141 | West, (1991). J Biol Chem 266(32): 21886-96; Olson, K. R. (1995). J Cell Biol 130(3): 639-50. |
| | | (AA SEQ: A D L S L V D A L T E P P P E I E G E I K R D F M A A L E A E P Y D D I V G E T V E K T E F I P L L D G D E K T G N S E S K K K P C L D T S Q V E G I P S S K P T L L A N G D H G M E G N N T A G S P T D F L E E R V D Y P D Y Q S S Q N W P E D A S F C Q P Q Q V L D T D Q A E P F N E H R D D G L A D L L F V S S G P T N A S A F T E R D N P S E D S Y G M L P C D S F A S T A V V S Q E W S V G A P N S P C S E S C V S P E V T I E T L Q P A T E L S K A A E V E S V K E Q L P A K A L E T M A E Q T T D V V H S P S T D T T P G P D T E A A L A K D I E E I T K P D V I L A N V T Q P S T E S D M F L A Q D M E L L T G T E A A H A N N I I L P T E P D E S S T K D V A P P M E E E I V P G N D T T S P K E T E T T L P I K M D L A P P E D V L L T K E T E L A P A K G M V S L S E I E E A L A K N D V R S A E I P V A Q E T V V S E T E V V L A T E V V L P S D P I T T L T K D V T L P L E A E R P L V T D M T P S L E T E M T L G K E T A P P T E T N L G M A K D M S P L P E S E V T L G K D V V I L P E T K V A E F N N V T P L S E E E V T S V K D M S P S A E T E A P L A K N A D L H S G T E L I V D N S M A P A S D L A L P L E T K V A T V P I K D K G | 142 | |
| Vesicle membrane | Synaptobrevin | 5' ATGTGGGCAATCGGGATTACTGTTCT GGTTATCTTCATCATCATCATCGTG TGGGTTGTC | 143 | Schiavo et al., (1992) Nature 359, 832-5 |
| | | (AA SEQ: M W A I G I T V L V I F I I I I I V W V V) | 144 | |
| Vesicle membrane | Cellubrevin | 5' ATGTGGGCGATAGGGATCAGTGTCCT GGTGATCATTGTCATCATCATCATCGTG TGGTGTG | 145 | McMahon et al., Nature 364:346-349; Martin et al., J. Cell Biol. In press |
| | | (AA SEQ: M W A I G I S V L V I I V I I I I V W C) | 146 | |

FIGURE 29C-3

| Nuclear Export | MEK2 | 5' GACCTGCAGAAGAAGCTGGAGGAGCT GGAACTTGACGAG | 147 | Zheng and Guan, J. Biol. Chem. 268:11435-11439, 1993 |
|---|---|---|---|---|
| | | AA SEQ: D L Q K K L E E L E L D E | 148 | |
| Peroxisome | PX | 5' TCTAAACTG | 149 | Amery et al., Biochem. J. 336:367-371 (1998) |
| | | AA SEQ: S K L | 150 | |

Microtubules (MAP4) SEQ ID NO:151 (Nucleic acid); SEQ ID NO:152 (amino acid)

```
MAP4:
M    A    D    L    S    L    V    D    A    L    T    E    P    P    P    E    I    E    G    E
ATGGCCGACCTC AGTCTTGTGGAT GCGTTGACAGAA CCACCTCCAGAA ATTGAGGGAGAA
TACCGGCTGGAG TCAGAACACCTA CGCAACTGTCTT GGTGGAGGTCTT TAACTCCCTCTT

I    K    R    D    F    M    A    A    L    E    A    E    P    Y    D    D    I    V    G    E
ATAAAGCGAGAC TTCATGGCTGCG CTGGAGGCAGAG CCCTATGATGAC ATCGTGGGAGAA
TATTTCGCTCTG AAGTACCGACGC GACCTCCGTCTC GGGATACTACTG TAGCACCCTCTT

T    V    E    K    T    E    F    I    P    L    L    D    G    D    E    K    T    G    N    S
ACTGTGGAGAAA ACTGAGTTTATT CCTCTCCTGGAT GGTGATGAGAAA ACCGGGAACTCA
TGACACCTCTTT TGACTCAAATAA GGAGAGGACCTA CCACTACTCTTT TGGCCCTTGAGT

E    S    K    K    P    C    L    D    T    S    Q    V    E    G    I    P    S    S    K
GAGTCCAAAAAG AAACCCTGCTTA GACACTAGCCAG GTTGAAGGTATC CCATCTTCTAAA
CTCAGGTTTTTC TTTGGGACGAAT CTGTGATCGGTC CAACTTCCATAG GGTAGAAGATTT

P    T    L    L    A    N    G    D    H    G    M    E    G    N    N    T    A    G    S    P
CCAACACTCCTA GCCAATGGTGAT CATGGAATGGAG GGGAATAACACT GCAGGGTCTCCA
GGTTGTGAGGAT CGGTTACCACTA GTACCTTACCTC CCCTTATTGTGA CGTCCCAGAGGT

T    D    F    L    E    E    R    V    D    Y    P    D    Y    Q    S    S    Q    N    W    P
ACTGACTTCCTT GAAGAGAGAGTG GACTATCCGGAT TATCAGAGCAGC CAGAACTGGCCA
TGACTGAAGGAA CTTCTCTCTCAC CTGATAGGCCTA ATAGTCTCGTCG GTCTTGACCGGT

E    D    A    S    F    C    F    Q    P    Q    Q    V    L    D    T    D    Q    A    E    P
GAAGATGCAAGC TTTTGTTTCCAG CCTCAGCAAGTG TTAGATACTGAC CAGGCTGAGCCC
CTTCTACGTTCG AAAACAAAGGTC GGAGTCGTTCAC AATCTATGACTG GTCCGACTCGGG

F    N    E    H    R    D    D    G    L    A    D    L    F    V    S    G    P    T
TTTAACGAGCAC CGTGATGATGGT TTGGCAGATCTG CTCTTTGTCTCC AGTGGACCCACG
AAATTGCTCGTG GCACTACTACCA AACCGTCTAGAC GAGAAACAGAGG TCACCTGGGTGC

N    A    S    A    F    T    E    R    D    N    P    S    E    D    S    Y    G    M    L    P
AACGCTTCTGCA TTTACAGAGCGA GACAATCCTTCA GAAGACAGTTAC GGTATGCTTCCC
TTGCGAAGACGT AAATGTCTCGCT CTGTTAGGAAGT CTTCTGTCAATG CCATACGAAGGG

C    D    S    F    A    S    T    A    V    V    S    Q    E    W    S    V    G    A    P    N
TGTGACTCATTT GCTTCCACGGCT GTTGTATCTCAG GAGTGGTCTGTG GGAGCCCCAAAC
ACACTGAGTAAA CGAAGGTGCCGA CAACATAGAGTC CTCACCAGACAC CCTCGGGGTTTG

S    P    C    S    E    S    C    V    S    P    E    V    T    I    E    T    L    Q    P    A
TCTCCATGTTCA GAGTCCTGTGTC TCCCCAGAGGTT ACTATAGAAACC CTACAGCCAGCA
AGAGGTACAAGT CTCAGGACACAG AGGGGTCTCCAA TGATATCTTTGG GATGTCGGTCGT
```

FIGURE 29C-4

```
T   E   L   S       K   A   A   E       V   E   S   V       K   E   Q   L       P   A   K   A
ACAGAGCTCTCC    AAGGCAGCAGAA    GTGGAATCAGTG    AAAGAGCAGCTG    CCAGCTAAAGCA
TGTCTCGAGAGG    TTCCGTCGTCTT    CACCTTAGTCAC    TTTCTCGTCGAC    GGTCGATTTCGT

L   E   T   M       A   E   Q   T       T   D   V   V       H   S   P   S       T   D   T   T
TTGGAAACGATG    GCAGAGCAGACC    ACTGATGTGGTG    CACTCTCCATCC    ACAGACACAACA
AACCTTTGCTAC    CGTCTCGTCTGG    TGACTACACCAC    GTGAGAGGTAGG    TGTCTGTGTTGT

P   G   P   D       T   E   A   A       L   A   K   D       I   E   E   I       T   K   P   D
CCAGGCCCAGAC    ACAGAGGCAGCA    CTGGCTAAAGAC    ATAGAAGAGATC    ACCAAGCCAGAT
GGTCCGGGTCTG    TGTCTCCGTCGT    GACCGATTTCTG    TATCTTCTCTAG    TGGTTCGGTCTA

V   I   L   A       N   V   T   Q       P   S   T   E       S   D   M   F       L   A   Q   D
GTGATATTGGCA    AATGTCACGCAG    CCATCTACTGAA    TCGGATATGTTC    CTGGCCCAGGAC
CACTATAACCGT    TTACAGTGCGTC    GGTAGATGACTT    AGCCTATACAAG    GACCGGGTCCTG

M   E   L   L       T   G   T   E       A   A   H   A       N   N   I   I       L   P   T   E
ATGGAACTACTC    ACAGGAACAGAG    GCAGCCCACGCT    AACAATATCATA    TTGCCTACAGAA
TACCTTGATGAG    TGTCCTTGTCTC    CGTCGGGTGCGA    TTGTTATAGTAT    AACGGATGTCTT

P   D   E   S       S   T   K   D       V   A   P   P       M   E   E   E       I   V   P   G
CCAGACGAATCT    TCAACCAAGGAT    GTAGCACCACCT    ATGGAAGAAGAA    ATTGTCCCAGGC
GGTCTGCTTAGA    AGTTGGTTCCTA    CATCGTGGTGGA    TACCTTCTTCTT    TAACAGGGTCCG

N   D   T   T       S   P   K   E       T   E   T   T       L   P   I   K       M   D   L   A
AATGATACGACA    TCCCCCAAAGAA    ACAGAGACAACA    CTTCCAATAAAA    ATGGACTTGGCA
TTACTATGCTGT    AGGGGGTTTCTT    TGTCTCTGTTGT    GAAGGTTATTTT    TACCTGAACCGT

P   P   E   D       V   L   L   T       K   E   T   E       L   A   P   A       K   G   M   V
CCACCTGAGGAT    GTGTTACTTACC    AAAGAAACAGAA    CTAGCCCCAGCC    AAGGGCATGGTT
GGTGGACTCCTA    CACAATGAATGG    TTTCTTTGTCTT    GATCGGGGTCGG    TTCCCGTACCAA

S   L   S   E       I   E   E   A       L   A   K   N       D   V   R   S       A   E   I   P
TCACTCTCAGAA    ATAGAAGAGGCT    CTGGCAAAGAAT    GATGTTCGCTCT    GCAGAAATACCT
AGTGAGAGTCTT    TATCTTCTCCGA    GACCGTTTCTTA    CTACAAGCGAGA    CGTCTTTATGGA

V   A   Q   E       T   V   V   S       E   T   E   V       V   L   A   T       E   V   V   L
GTGGCTCAGGAG    ACAGTGGTCTCA    GAAACAGAGGTG    GTCCTGGCAACA    GAAGTGGTACTG
CACCGAGTCCTC    TGTCACCAGAGT    CTTTGTCTCCAC    CAGGACCGTTGT    CTTCACCATGAC

P   S   D   P       I   T   T   L       T   K   D   V       T   L   P   L       E   A   E   R
CCCTCAGATCCC    ATAACAACATTG    ACAAAGGATGTG    ACACTCCCCTTA    GAAGCAGAGAGA
GGGAGTCTAGGG    TATTGTTGTAAC    TGTTTCCTACAC    TGTGAGGGGAAT    CTTCGTCTCTCT

P   L   V   T       D   M   T   P       S   L   E   T       E   M   T   L       G   K   E   T
CCGTTGGTGACG    GACATGACTCCA    TCTCTGGAAACA    GAAATGACCCTA    GGCAAAGAGACA
GGCAACCACTGC    CTGTACTGAGGT    AGAGACCTTTGT    CTTTACTGGGAT    CCGTTTCTCTGT

A   P   P   T       E   T   N   L       G   M   A   K       D   M   S   P       L   P   E   S
GCTCCACCCACA    GAAACAAATTTG    GGCATGGCCAAA    GACATGTCTCCA    CTCCCAGAATCA
CGAGGTGGGTGT    CTTTGTTTAAAC    CCGTACCGGTTT    CTGTACAGAGGT    GAGGGTCTTAGT
```

FIGURE 29C-5

```
E   V   T   L   G   K   D   V   V   I   L   P   E   T   K   V   A   E   F   N
GAAGTGACTCTG GGCAAGGACGTG GTTATACTTCCA GAAACAAAGGTG GCTGAGTTTAAC
CTTCACTGAGAC CCGTTCCTGCAC CAATATGAAGGT CTTTGTTTCCAC CGACTCAAATTG

N   V   T   P   L   S   E   E   E   V   T   S   V   K   D   M   S   P   S   A
AATGTGACTCCA CTTTCAGAAGAA GAGGTAACCTCA GTCAAGGACATG TCTCCGTCTGCA
TTACACTGAGGT GAAAGTCTTCTT CTCCATTGGAGT CAGTTCCTGTAC AGAGGCAGACGT

E   T   E   A   P   L   A   K   N   A   D   L   H   S   G   T   E   L   I   V
GAAACAGAGGCT CCCCTGGCTAAG AATGCTGATCTG CACTCAGGAACA GAGCTGATTGTG
CTTTGTCTCCGA GGGGACCGATTC TTACGACTAGAC GTGAGTCCTTGT CTCGACTAACAC

D   N   S   M   A   P   A   S   D   L   A   L   P   L   E   T   K   V   A   T
GACAACAGCATG GCTCCAGCCTCC GATCTTGCACTG CCCTTGGAAACA AAAGTAGCAACA
CTGTTGTCGTAC CGAGGTCGGAGG CTAGAACGTGAC GGGAACCTTTGT TTTCATCGTTGT

V   P   I   K   D   K   G   T   V   Q   T   E   E   K   P   R   E   D   S   Q
GTTCCAATTAAA GACAAAGGAACT GTACAGACTGAA GAAAAACCACGT GAAGACTCCCAG
CAAGGTTAATTT CTGTTTCCTTGA CATGTCTGACTT CTTTTTGGTGCA CTTCTGAGGGTC

L   A   S   M   Q   H   K   G   Q   S   T   V   P   P   C   T   A   S   P   E
TTAGCATCTATG CAGCACAAGGGA CAGTCAACAGTA CCTCCTTGCACG GCTTCACCAGAA
AATCGTAGATAC GTCGTGTTCCCT GTCAGTTGTCAT GGAGGAACGTGC CGAAGTGGTCTT

P   V   K   A   A   E   Q   M   S   T   L   P   I   D   A   P   S   P   L   E
CCAGTCAAAGCT GCAGAACAAATG TCTACCTTACCA ATAGATGCACCT TCTCCATTAGAG
GGTCAGTTTCGA CGTCTTGTTTAC AGATGGAATGGT TATCTACGTGGA AGAGGTAATCTC

N   L   E   Q   K   E   T   P   G   S   Q   P   S   E   P   C   S   G   V   S
AACTTAGAGCAG AAGGAAACGCCT GGCAGCCAGCCT TCTGAGCCTTGC TCAGGAGTATCC
TTGAATCTCGTC TTCCTTTGCGGA CCGTCGGTCGGA AGACTCGGAACG AGTCCTCATAGG

R   Q   E   E   A   K   A   A   V   G   V   T   G   N   D   I   T   T   P   P
CGGCAAGAAGAA GCAAAGGCTGCT GTAGGTGTGACT GGAAATGACATC ACTACCCCGCCA
GCCGTTCTTCTT CGTTTCCGACGA CATCCACACTGA CCTTTACTGTAG TGATGGGGCGGT

N   K   E   P   P   P   S   P   E   K   K   A   K   P   L   A   T   T   Q   P
AACAAGGAGCCA CCACCAAGCCCA GAAAAGAAAGCA AAGCCTTTGGCC ACCACTCAACCT
TTGTTCCTCGGT GGTGGTTCGGGT CTTTTCTTTCGT TTCGGAAACCGG TGGTGAGTTGGA

A   K   T   S   T   S   K   A   K   T   Q   P   T   S   L   P   K   Q   P   A
GCAAAGACTTCA ACATCGAAAGCC AAAACACAGCCC ACTTCTCTCCCT AAGCAACCAGCT
CGTTTCTGAAGT TGTAGCTTTCGG TTTTGTGTCGGG TGAAGAGAGGGA TTCGTTGGTCGA

P   T   T   S   G   G   L   N   K   K   P   M   S   L   A   S   G   S   V   P
CCCACCACCTCT GGTGGGTTGAAT AAAAAACCCATG AGCCTCGCCTCA GGCTCAGTGCCA
GGGTGGTGGAGA CCACCCAACTTA TTTTTTGGGTAC TCGGAGCGGAGT CCGAGTCACGGT

A   A   P   H   K   R   P   A   A   A   T   A   T   A   R   P   S   T   L   P
GCTGCCCCACAC AAACGCCCTGCT GCTGCCACTGCT ACTGCCAGGCCT TCCACCCTACCT
CGACGGGGTGTG TTTGCGGGACGA CGACGGTGACGA TGACGGTCCGGA AGGTGGGATGGA
```

FIGURE 29C-6

```
A   R   D   V     K  P  K  P     I  T  E  A     K  V  A  E     K   R   S
GCCAGAGACGTG   AAGCCAAAGCCA   ATTACAGAAGCT   AAGGTTGCCGAA   AAGCGGACCTCT
CGGTCTCTGCAC   TTCGGTTTCGGT   TAATGTCTTCGA   TTCCAACGGCTT   TTCGCCTGGAGA

P   S   K   P     S  S  A  P     A  L  K  P     G  P  K  T     T   P   T   V
CCATCCAAGCCT   TCATCTGCCCCA   GCCCTCAAACCT   GGACCTAAAACC   ACCCCAACCGTT
GGTAGGTTCGGA   AGTAGACGGGGT   CGGGAGTTTGGA   CCTGGATTTTGG   TGGGGTTGGCAA

S   K   A   T     S  P  S  T     L  V  S  T     G  P  S  S     R   S   P   A
TCAAAAGCCACA   TCTCCCTCAACT   CTTGTTTCCACT   GGACCAAGTAGT   AGAAGTCCAGCT
AGTTTTCGGTGT   AGAGGGAGTTGA   GAACAAAGGTGA   CCTGGTTCATCA   TCTTCAGGTCGA

T   T   L       K  R  P  T     S  I  K  T     E  G  K  P     A   D   V   K
ACAACTCTGCCT   AAGAGGCCAACC   AGCATCAAGACT   GAGGGGAAACCT   GCTGATGTCAAA
TGTTGAGACGGA   TTCTCCGGTTGG   TCGTAGTTCTGA   CTCCCCTTTGGA   CGACTACAGTTT

R   M   T       K  S  A  S     A  D  L  S     R  S  K  T     T   S   A   S
AGGATGACTGCT   AAGTCTGCCTCA   GCTGACTTGAGT   CGCTCAAAGACC   ACCTCTGCCAGT
TCCTACTGACGA   TTCAGACGGAGT   CGACTGAACTCA   GCGAGTTTCTGG   TGGAGACGGTCA

S   V   K   R     N  T  T  P     T  G  A  A     P  P  A  G     M   T   S   T
TCTGTGAAGAGA   AACACCACTCCC   ACTGGGGCAGCA   CCCCCAGCAGGG   ATGACTTCCACT
AGACACTTCTCT   TTGTGGTGAGGG   TGACCCCGTCGT   GGGGGTCGTCCC   TACTGAAGGTGA

R   V   K   P     M  S  A  P     S  R  S  S     G  A  L  S     V   D   K   K
CGAGTCAAGCCC   ATGTCTGCACCT   AGCCGCTCTTCT   GGGGCTCTTTCT   GTGGACAAGAAG
GCTCAGTTCGGG   TACAGACGTGGA   TCGGCGAGAAGA   CCCCGAGAAAGA   CACCTGTTCTTC

P   T   S   T     K  P  S  S     S  A  P  R     V  S  R  L     A   T   T   V
CCCACTTCCACT   AAGCCTAGCTCC   TCTGCTCCCAGG   GTGAGCCGCCTG   GCCACAACTGTT
GGGTGAAGGTGA   TTCGGATCGAGG   AGACGAGGGTCC   CACTCGGCGGAC   CGGTGTTGACAA

S   A   P   D     L  K  S  V     R  S  K  V     G  S  T  E     N   I   K   H
TCTGCCCCTGAC   CTGAAGAGTGTT   CGCTCCAAGGTC   GGCTCTACAGAA   AACATCAAACAC
AGACGGGGACTG   GACTTCTCACAA   GCGAGGTTCCAG   CCGAGATGTCTT   TTGTAGTTTGTG

Q   P   G   G     G  R  A  K     V  E  K  K     T  E  A  A     T   T   A   G
CAGCCTGGAGGA   GGCCGGGCCAAA   GTAGAGAAAAAA   ACAGAGGCAGCT   ACCACAGCTGGG
GTCGGACCTCCT   CCGGCCCGGTTT   CATCTCTTTTTT   TGTCTCCGTCGA   TGGTGTCGACCC

K   P   E   P     N  A  V  T     K  A  A  G     S  I  A  S     A   Q   K   P
AAGCCTGAACCT   AATGCAGTCACT   AAAGCAGCCGGC   TCCATTGCGAGT   GCACAGAAACCG
TTCGGACTTGGA   TTACGTCAGTGA   TTTCGTCGGCCG   AGGTAACGCTCA   CGTGTCTTTGGC

P   A   G   K     V  Q  I  V     S  K  K  V     S  Y  S  H     I   Q   S   K
CCTGCTGGGAAA   GTCCAGATAGTA   TCCAAAAAGTG    AGCTACAGTCAT   ATTCAATCCAAG
GGACGACCCTTT   CAGGTCTATCAT   AGGTTTTTCAC    TCGATGTCAGTA   TAAGTTAGGTTC

C   V   S       K  D  N  I  K     H  V  P  G     C  G  N  V     Q   I   Q   N
TGTGTTTCCAAG   GACAATATTAAG   CATGTCCCTGGA   TGTGGCAATGTT   CAGATTCAGAAC
ACACAAAGGTTC   CTGTTATAATTC   GTACAGGGACCT   ACACCGTTACAA   GTCTAAGTCTTG
```

FIGURE 29-C7

```
K   K   V   D      I   S   K   V      S   S   K   C      G   S   K   A      N   I   K   H
AAGAAAGTGGAC       ATATCCAAGGTC       TCCTCCAAGTGT       GGGTCCAAAGCT       AATATCAAGCAC
TTCTTTCACCTG       TATAGGTTCCAG       AGGAGGTTCACA       CCCAGGTTTCGA       TTATAGTTCGTG

K   P   G          G   D   V   K      I   E   S   Q      K   L   N   F      K   E   K   A
AAGCCTGGTGGA       GGAGATGTCAAG       ATTGAAAGTCAG       AAGTTGAACTTC       AAGGAGAAGGCC
TTCGGACCACCT       CCTCTACAGTTC       TAACTTTCAGTC       TTCAACTTGAAG       TTCCTCTTCCGG

Q   A   K   V      G   S   L   D      N   V   G   H      F   P   A   G      G   A   V   K
CAAGCCAAAGTG       GGATCCCTTGAT       AACGTTGGCCAC       TTTCCTGCAGGA       GGTGCCGTGAAG
GTTCGGTTTCAC       CCTAGGGAACTA       TTGCAACCGGTG       AAAGGACGTCCT       CCACGGCACTTC

T   E   G          G   G   S   E   A      L   P   C   P      G   P   P   A      G   E   E   P
ACTGAGGGCGGT       GGCAGTGAGGCC       CTTCCGTGTCCA       GGCCCCCCCGCT       GGGGAGGAGCCA
TGACTCCCGCCA       CCGTCACTCCGG       GAAGGCACAGGT       CCGGGGGGGCGA       CCCCTCCTCGGT

V   I   P   E      A   A   P   D      R   G   A   P      T   S   A   S      G   L   S   G
GTCATCCCTGAG       GCTGCGCCTGAC       CGTGGCGCCCCT       ACTTCAGCCAGT       GGCCTCAGTGGC
CAGTAGGGACTC       CGACGCGGACTG       GCACCGCGGGGA       TGAAGTCGGTCA       CCGGAGTCACCG

H   T   T   L      S   G   G   G      D   Q   R   E      P   Q   T   L      D   S   Q   I
CACACCACCCTG       TCAGGGGGTGGT       GACCAAAGGGAG       CCCCAGACCTTG       GACAGCCAGATC
GTGTGGTGGGAC       AGTCCCCCACCA       CTGGTTTCCCTC       GGGGTCTGGAAC       CTGTCGGTCTAG

Q   E   T   S      I   *
CAGGAGACAAGC       ATCTAA
GTCCTCTGTTCG       TAGATT
```

Figure 30
A
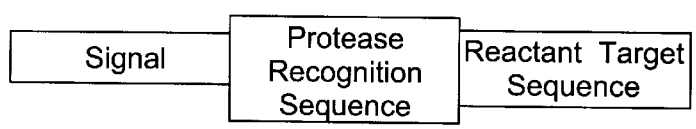
B
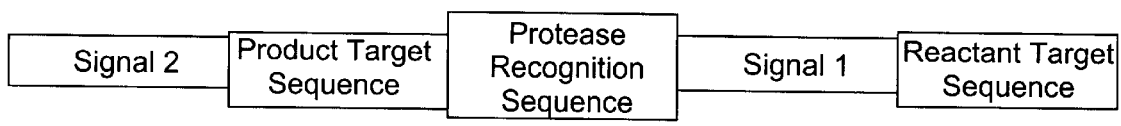
C
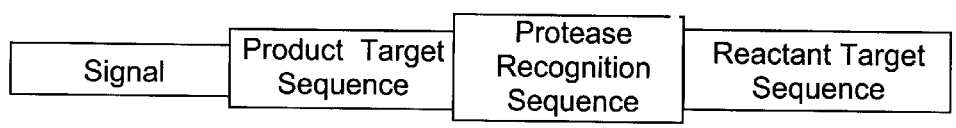

Figure 31
A
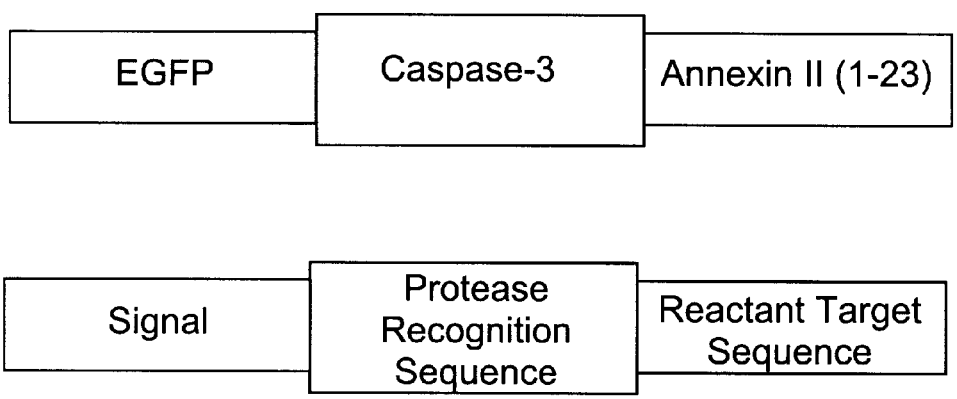
B
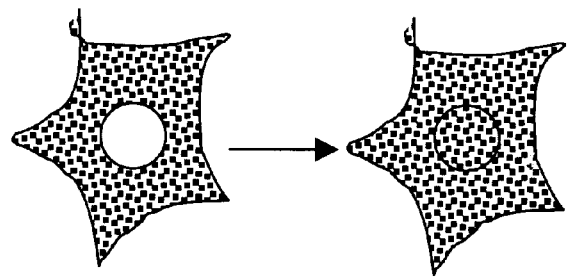

BHK cells transfected with DEVD-caspase biosensor. (A) Cells before stimulation of apoptosis. (B) Another field of cells after stimulation with 250 µg/ml cis-platin (4 h).

SYSTEM FOR CELL-BASED SCREENING

CROSS REFERENCE

This application claims priority to U.S. Provisional Applications for Patent Ser. No. 60/122,152 (Feb. 26, 1999), No. 60/123,399 (Mar. 8, 1999), No. 60/151,797 (Aug. 31, 1999), No. 60/168,408 (Dec. 1, 1999); and is a continuation in part of Ser. No. 09/430,656 (Oct. 29, 1999); Ser. No. 09/398,965 filed Sep. 17, 1999 which is a continuation in part of Ser. No. 09/352,171 filed Jul. 12, 1999, which is a continuation in part of 09/031,271 filed Feb. 27, 1998 which is a continuation in part of U.S. application Ser. No. 08/810,983, now U.S. Pat. No. 5,989,835, filed on Feb. 27, 1997, which claims benefit to U.S. Ser. No. 60/136,078 filed May 26, 1999 which claims benefit to U.S. Ser. No. 60/106,308 filed Oct. 30, 1998.

STATEMENT OF GOVERNMENT RIGHTS

This invention was made with Government support under Contract No. N00014-98-C-0326 awarded by the Office of Naval Research, and thus the Government may have certain rights in the invention.

FIELD OF THE INVENTION

This invention is in the field of fluorescence-based cell and molecular biochemical assays for drug discovery.

BACKGROUND OF THE INVENTION

Drug discovery, as currently practiced in the art, is a long, multiple step process involving identification of specific disease targets, development of an assay based on a specific target, validation of the assay, optimization and automation of the assay to produce a screen, high throughput screening of compound libraries using the assay to identify "hits", hit validation and hit compound optimization. The output of this process is a lead compound that goes into pre-clinical and, if validated, eventually into clinical trials. In this process, the screening phase is distinct from the assay development phases, and involves testing compound efficacy in living biological systems.

Historically, drug discovery is a slow and costly process, spanning numerous years and consuming hundreds of millions of dollars per drug created. Developments in the areas of genomics and high throughput screening have resulted in increased capacity and efficiency in the areas of target identification and volume of compounds screened. Significant advances in automated DNA sequencing, PCR application, positional cloning, hybridization arrays, and bioinformatics have greatly increased the number of genes (and gene fragments) encoding potential drug screening targets. However, the basic scheme for drug screening remians the same.

Validation of genomic targets as points for therapeutic intervention using the existing methods and protocols has become a bottleneck in the drug discovery process due to the slow, manual methods employed, such as in vivo functional models, functional analysis of recombinant proteins, and stable cell line expression of candidate genes. Primary DNA sequence data acquired through automated sequencing does not permit identification of gene function, but can provide information about common "motifs" and specific gene homology when compared to known sequence databases. Genomic methods such as subtraction hybridization and RADE (rapid amplification of differential expression) can be used to identify genes that are up or down regulated in a disease state model. However, identification and validation still proceed down the same pathway. Some proteomic methods use protein identification (global expression arrays, 2D electrophoresis, combinatorial libraries) in combination with reverse genetics to identify candidate genes of interest. Such putative "disease associated sequences" or DAS isolated as intact cDNA are a great advantage to these methods, but they are identified by the hundreds without providing any information regarding type, activity, and distribution of the encoded protein. Choosing a subset of DAS as drug screening targets is "random", and thus extremely inefficient, without functional data to provide a mechanistic link with disease. It is necessary, therefore, to provide new technologies to rapidly screen DAS to establish biological function, thereby improving target validation and candidate optimization in drug discovery.

There are three major avenues for improving early drug discovery productivity. First, there is a need for tools that provide increased information handling capability. Bioinformatics has blossomed with the rapid development of DNA sequencing systems and the evolution of the genomics database. Genomics is beginning to play a critical role in the identification of potential new targets. Proteomics has become indispensible in relating structure and function of protein targets in order to predict drug interactions. However, the next level of biological complexity is the cell. Therefore, there is a need to acquire, manage and search multi-dimensional information from cells. Secondly, there is a need for higher throughput tools. Automation is a key to improving productivity as has already been demonstrated in DNA sequencing and high throughput primary screening. The instant invention provides for automated systems that extract multiple parameter information from cells that meet the need for higher throughput tools. The instant invention also provides for miniaturizing the methods, thereby allowing increased throughput, while decreasing the volumes of reagents and test compounds required in each assay.

Radioactivity has been the dominant read-out in early drug discovery assays. However, the need for more information, higher throughput and miniaturization has caused a shift towards using fluorescence detection. Fluorescence-based reagents can yield more powerful, multiple parameter assays that are higher in throughput and information content and require lower volumes of reagents and test compounds. Fluorescence is also safer and less expensive than radioactivity-based methods.

Screening of cells treated with dyes and fluorescent reagents is well known in the art. There is a considerable body of literature related to genetic engineering of cells to produce fluorescent proteins, such as modified green fluorescent protein (GFP), as a reporter molecule. Some properties of wild-type GFP are disclosed by Morise et al. (*Biochemistry* 13 (1974), p. 2656–2662), and Ward et al. (*Photochem. Photobiol.* 31 (1980), p. 611–615). The GFP of the jellyfish *Aequorea Victoria* has an excitation maximum at 395 nm and an emission maximum at 510 mn, and does not require an exogenous factor for fluorescence activity. Uses for GFP disclosed in the literature are widespread and include the study of gene expression and protein localization (Chalfie et al., *Science* 263 (1994), p. 12501–12504)), as a tool for visualizing subcellular organelles (Rizzuto et al., *Curr. Biology* 5 (1995), p. 635–642)), visualization of protein transport along the secretory pathway (Kaether and Gerdes, *FEBS Letters* 369 (1995), p. 267–271)), expression in plant cells (Hu and Cheng, *FEBS Letters* 369 (1995), p. 331–334)) and Drosophila embryos (Davis et al., *Dev. Biology* 170 (1995), p. 726–729)), and as a reporter molecule fused to another protein of interest (U.S. Pat. No. 5,491,084). Similarly, WO96/23898 relates to methods of detecting biologically active substances affecting intracellular processes by utilizing a GFP construct having a protein kinase activation site. This patent, and all other patents referenced in this application are incorporated by reference in their entirety.

Numerous references are related to GFP proteins in biological systems. For example, WO 96/09598 describes a system for isolating cells of interest utilizing the expression of a GFP like protein. WO 96/27675 describes the expression of GFP in plants. WO 95/21191 describes modified GFP protein expressed in transformed organisms to detect mutagenesis. U.S. Pat. Nos. 5,401,629 and 5,436,128 describe assays and compositions for detecting and evaluating the intracellular transduction of an extracellular signal using recombinant cells that express cell surface receptors and contain reporter gene constructs that include transcriptional regulatory elements that are responsive to the activity of cell surface receptors.

Performing a screen on many thousands of compounds requires parallel handling and processing of many compounds and assay component reagents. Standard high throughput screens ("HTS") use mixtures of compounds and biological reagents along with some indicator compound loaded into arrays of wells in standard microtiter plates with 96 or 384 wells. The signal measured from each well, either fluorescence emission, optical density, or radioactivity, integrates the signal from all the material in the well giving an overall population average of all the molecules in the well.

Science Applications International Corporation (SAIC) 130 Fifth Avenue, Seattle, Wash. 98109) describes an imaging plate reader. This system uses a CCD camera to image the whole area of a 96 well plate. The image is analyzed to calculate the total fluorescence per well for all the material in the well.

Molecular Devices, Inc. (Sunnyvale, Calif.) describes a system (FLIPR) which uses low angle laser scanning illumination and a mask to selectively excite fluorescence within approximately 200 microns of the bottoms of the wells in standard 96 well plates in order to reduce background when imaging cell monolayers. This system uses a CCD camera to image the whole area of the plate bottom. Although this system measures signals originating from a cell monolayer at the bottom of the well, the signal measured is averaged over the area of the well and is therefore still considered a measurement of the average response of a population of cells. The image is analyzed to calculate the total fluorescence per well for cell-based assays. Fluid delivery devices have also been incorporated into cell based screening systems, such as the FLIPR system, in order to initiate a response, which is then observed as a whole well population average response using a macro-imaging system.

In contrast to high throughput screens, various high-content screens ("HCS") have been developed to address the need for more detailed information about the temporal-spatial dynamics of cell constituents and processes. High-content screens automate the extraction of multicolor fluorescence information derived from specific fluorescence-based reagents incorporated into cells (Giuliano and Taylor (1995), *Curr. Op. Cell Biol.* 7:4; Giuliano et al. (1995) *Ann. Rev. Biophys. Biomol. Struct.* 24:405). Cells are analyzed using an optical system that can measure spatial, as well as temporal dynamics. (Farkas et al. (1993) *Ann. Rev. Physiol* 55:785; Giuliano et al. (1990) In *Optical Microscopy for Biology*. B. Herman and K. Jacobson (eds.), pp. 543–557.

Wiley-Liss, New York; Hahn et al (1992) *Nature* 359:736; Waggoner et al. (1996) *Hum. Pathol.* 27:494). The concept is to treat each cell as a "well" that has spatial and temporal information on the activities of the labeled constituents.

The types of biochemical and molecular information now accessible through fluorescence-based reagents applied to cells include ion concentrations, membrane potential, specific translocations, enzyme activities, gene expression, as well as the presence, amounts and patterns of metabolites, proteins, lipids, carbohydrates, and nucleic acid sequences (DeBiasio et al., (1996) *Mol. Biol. Cell.* 7:1259;Giuliano et al., (1995) *Ann. Rev. Biophys. Biomol. Struct.* 24:405; Heim and Tsien, (1996) *Curr. Biol.* 6:178).

High-content screens can be performed on either fixed cells, using fluorescently labeled antibodies, biological ligands, and/or nucleic acid hybridization probes, or live cells using multicolor fluorescent indicators and "biosensors." The choice of fixed or live cell screens depends on the specific cell-based assay required.

Fixed cell assays are the simplest, since an array of initially living cells in a microtiter plate format can be treated with various compounds and doses being tested, then the cells can be fixed, labeled with specific reagents, and measured. No environmental control of the cells is required after fixation. Spatial information is acquired, but only at one time point. The availability of thousands of antibodies, ligands and nucleic acid hybridization probes that can be applied to cells makes this an attractive approach for many types of cell-based screens. The fixation and labeling steps can be automated, allowing efficient processing of assays.

Live cell assays are more sophisticated and powerful, since an array of living cells containing the desired reagents can be screened over time, as well as space. Environmental control of the cells (temperature, humidity, and carbon dioxide) is required during measurement, since the physiological health of the cells must be maintained for multiple fluorescence measurements over time. There is a growing list of fluorescent physiological indicators and "biosensors" that can report changes in biochemical and molecular activities within cells (Giuliano et al., (1995) *Ann. Rev. Biophys. Biomol. Struct.* 24:405; Hahn et al., (1993) In *Fluorescent and Luminescent Probes for Biological Activity*. W. T. Mason, (ed.), pp. 349–359, Academic Press, San Diego).

The availability and use of fluorescence-based reagents has helped to advance the development of both fixed and live cell high-content screens. Advances in instrumentation to automatically extract multicolor, high-content information has recently made it possible to develop HCS into an automated tool. An article by Taylor, et al. (*American Scientist* 80 (1992), p. 322–335) describes many of these methods and their applications. For example, Proffitt et. al. (*Cytometry* 24: 204–213 (1996)) describe a semi-automated fluorescence digital imaging system for quantifying relative cell numbers in situ in a variety of tissue culture plate formats, especially 96-well microtiter plates. The system consists of an epifluorescence inverted microscope with a motorized stage, video camera, image intensifier, and a microcomputer with a PC-Vision digitizer. Turbo Pascal software controls the stage and scans the plate taking multiple images per well. The software calculates total fluorescence per well, provides for daily calibration, and configures easily for a variety of tissue culture plate formats. Thresholding of digital images and reagents which fluoresce only when taken up by living cells are used to reduce background fluorescence without removing excess fluorescent reagent.

Scanning confocal microscope imaging (Go et al., (1997) *Analytical Biochemistry* 247:210–215; Goldman et al., (1995) *Experimental Cell Research* 221:311–319) and multiphoton microscope imaging (Denk et al., (1990) *Science* 248:73; Gratton et al., (1994) *Proc. of the Microscopical Society of America*, pp. 154–155) are also well established methods for acquiring high resolution images of microscopic samples. The principle advantage of these optical systems is the very shallow depth of focus, which allows features of limited axial extent to be resolved against the background. For example, it is possible to resolve internal cytoplasmic features of adherent cells from the features on the cell surface. Because scanning multiphoton imaging requires very short duration pulsed laser systems to achieve the high photon flux required, fluorescence lifetimes can also be measured in these systems (Lakowicz et al., (1992) *Anal. Biochem.* 202:316–33.0; Gerrittsen et al. (1997), *J. of Fluorescence* 7:11–15)), providing additional capability for different detection modes. Small, reliable and relatively inexpensive laser systems, such as laser diode pumped lasers, are now available to allow multiphoton confocal microscopy to be applied in a fairly routine fashion.

A combination of the biological heterogeneity of cells in populations (Bright, et al., (1989). *J. Cell. Physiol.* 141:410; Giuliano, (1996) *Cell Motil. Cytoskel* 35:237)) as well as the high spatial and temporal frequency of chemical and molecular information present within cells, makes it impossible to extract high-content information from populations of cells using existing whole microtiter plate readers. No existing high-content screening platform has been designed for multicolor, fluorescence-based screens using cells that are analyzed individually. Similarly, no method is currently available that combines automated fluid delivery to arrays of cells for the purpose of systematically screening compounds for the ability to induce a cellular response that is identified by HCS analysis, especially from cells grown in microtiter plates. Furthermore, no method exists in the art combining high throughput well-by-well measurements to identify "hits" in one assay followed by a second high content cell-by-cell measurement on the same plate of only those wells identified as hits.

The instant invention provides systems, methods, and screens that combine high throughput screening (HTS) and high content screening (HCS) that significantly improve target validation and candidate optimization by combining many cell screening formats with fluorescence-based molecular reagents and computer-based feature extraction, data analysis, and automation, resulting in increased quantity and speed of data collection, shortened cycle times, and, ultimately, faster evaluation of promising drug candidates. The instant invention also provides for miniaturizing the methods, thereby allowing increased throughput, while decreasing the volumes of reagents and test compounds required in each assay.

SUMMARY OF THE INVENTION

In one aspect, the present invention relates to a method for analyzing cells comprising providing cells containing fluorescent reporter molecules in an array of locations, treating the cells in the array of locations with one or more reagents, imaging numerous cells in each location with fluorescence optics, converting the optical information into digital data, utilizing the digital data to determine the distribution, environment or activity of the fluorescently labeled reporter molecules in the cells and the distribution of the cells, and interpreting that information in terms of a positive, negative or null effect of the compound being tested on the biological function.

In this embodiment, the method rapidly determines the distribution, environment, or activity of fluorescently labeled reporter molecules in cells for the purpose of screening large numbers of compounds for those that specifically affect particular biological functions. The array of locations may be a microtiter plate or a microchip which is a microplate having cells in an array of locations. In a preferred embodiment, the method includes computerized means for acquiring, processing, displaying and storing the data received. In a preferred embodiment, the method further comprises automated fluid delivery to the arrays of cells. In another preferred embodiment, the information obtained from high throughput measurements on the same plate are used to selectively perform high content screening on only a subset of the cell locations on the plate.

In another aspect of the present invention, a cell screening system is provided that comprises:

a high magnification fluorescence optical system having a microscope objective, an XY stage adapted for holding a plate containing an array of cells and having a means for moving the plate for proper alignment and focusing on the cell arrays;

a digital camera;

a light source having optical means for directing excitation light to cell arrays and a means for directing fluorescent light emitted from the cells to the digital camera; and a computer means for receiving and processing digital data from the digital camera wherein the computer means includes a digital frame grabber for receiving the images from the camera, a display for user interaction and display of assay results, digital storage media for data storage and archiving, and a means for control, acquisition, processing and display of results.

In a preferred embodiment, the cell screening system further comprises a computer screen operatively associated with the computer for displaying data. In another preferred embodiment, the computer means for receiving and processing digital data from the digital camera stores the data in a bioinformatics data base. In a further preferred embodiment, the cell screening system further comprises a reader that measures a signal from many or all the wells in parallel. In another preferred embodiment, the cell screening system further comprises a mechanical-optical means for changing the magnification of the system, to allow changing modes between high throughput and high content screening. In another preferred embodiment, the cell screening system further comprises a chamber and control system to maintain the temperature, $CO_2$ concentration and humidity surrounding the plate at levels required to keep cells alive. In a further preferred embodiment, the cell screening system utilizes a confocal scanning illumination and detection system.

In another aspect of the present invention, a machine readable storage medium comprising a program containing a set of instructions for causing a cell screening system to execute procedures for defining the distribution and activity of specific cellular constituents and processes is provided. In a preferred embodiment, the cell screening system comprises a high magnification fluorescence optical system with a stage adapted for holding cells and a means for moving the stage, a digital camera, a light source for receiving and processing the digital data from the digital camera, and a computer means for receiving and processing the digital data from the digital camera. Preferred embodiments of the machine readable storage medium comprise programs consisting of a set of instructions for causing a cell screening system to execute the procedures set forth in FIGS. 9, 11, 12, 13, 14 or 15. Another preferred embodiment comprises a program consisting of a set of instructions for causing a cell screening system to execute procedures for detecting the distribution and activity of specific cellular constituents and processes. In most preferred embodiments, the cellular processes include, but are not limited to, nuclear translocation of a protein, cellular hypertrophy, apoptosis, and protease-induced translocation of a protein.

In another preferred embodiment, a variety of automated cell screening methods are provided, including screens to identify compounds that affect transcription factor activity, protein kinase activity, cell morphology, microtubule structure, apoptosis, receptor internalization, and protease-induced translocation of a protein.

In another aspect, the present invention provides recombinant nucleic acids encoding a protease biosensor, comprising:
  a. a first nucleic acid sequence that encodes at least one detectable polypeptide signal;
  b. a second nucleic acid sequence that encodes at least one protease recognition site, wherein the second nucleic acid sequence is operatively linked to the first nucleic acid sequence that encodes the at least one detectable polypeptide signal; and
  c. a third nucleic acid sequence that encodes at least one reactant target sequence, wherein the third nucleic acid sequence is operatively linked to the second nucleic acid sequence that encodes the at least one protease recognition site.

The present invention also provides the recombinant expression vectors capable of expressing the recombinant nucleic acids encoding protease biosensors, as well as genetically modified host cells that are transfected with the expression vectors.

The invention further provides recombinant protease biosensors, comprising
  a. a first domain comprising at least one detectable polypeptide signal;
  b. a second domain comprising at least one protease recognition site; and
  c. a third domain comprising at least one reactant target sequence;
  wherein the first domain and the third domain are separated by the second domain.

In a further aspect, the present invention involves assays and reagents for characterizing a sample for the presence of a toxin. The method comprises the use of detector, classifier, and identifier classes of toxin biosensors to provide for various levels of toxin characterization.

BRIEF DESCRIPTION OF THE DRAWINGS

FIG. 2 shows a schematic of the microscope subassembly.

FIG. 9 is a flow chart of processing step for the cell-based scanning system.

FIG. 29 shows the nucleic acid and amino acid sequence for various types of protesae biosensor domains. A-1 through A-4 Signal sequences. B-1 through B-2 Protease recognition sites. C-1 through C-7 Product/Reactant target sequences FIG. 30 shows schematically shows some basic organization of domains in the protease biosensors of the invention.

FIG. 31 is a schematic diagram of a specific 3-domain protease biosensor.

DETAILED DESCRIPTION OF THE INVENTION

Figure 1:
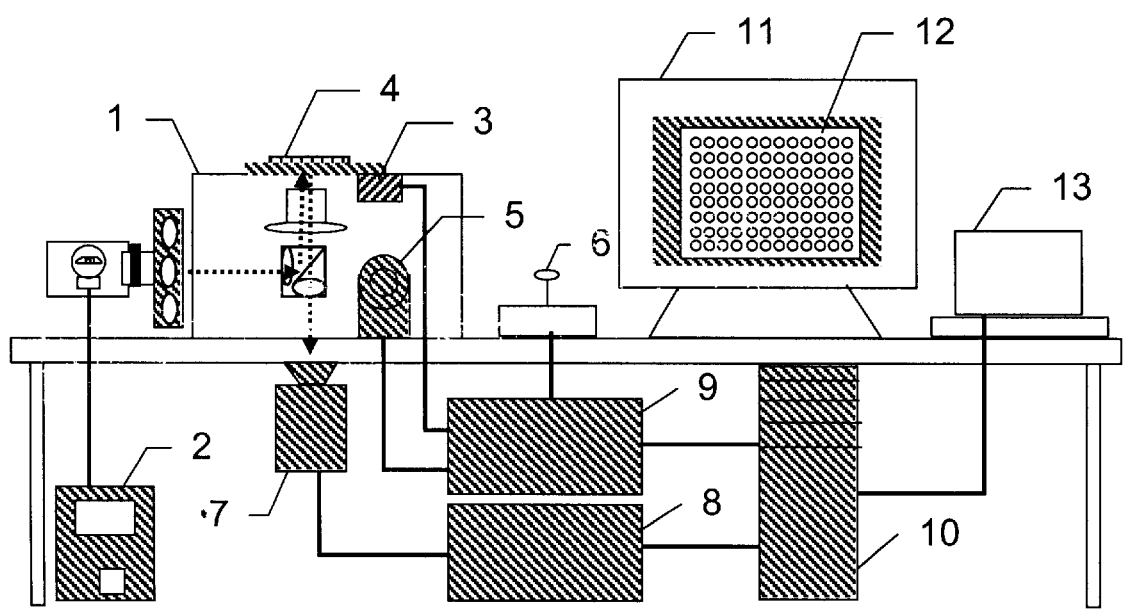
FIG. 1 shows a diagram of the components of the cell-based scanning system.

All cited patents, patent applications and other references are hereby incorporated by reference in their entirety.

As used herein, the following terms have the specified meaning:

Markers of cellular domains. Luminescent probes that have high affinity for specific cellular constituents including specific organelles or molecules. These probes can either be small luminescent molecules or fluorescently tagged macromolecules used as "labeling reagents", "environmental indicators", or "biosensors."

Labeling reagents. Labeling reagents include, but are not limited to, luminescently labeled macromolecules including fluorescent protein analogs and biosensors, luminescent macromolecular chimeras including those formed with the green fluorescent protein and mutants thereof, luminescently labeled primary or secondary antibodies that react with cellular antigens involved in a physiological response, luminescent stains, dyes, and other small molecules.

Markers of cellular translocations. Luminescently tagged macromolecules or organelles that move from one cell domain to another during some cellular process or physiological response. Translocation markers can either simply report location relative to the markers of cellular domains or they can also be "biosensors" that report some biochemical or molecular activity as well.

Biosensors. Macromolecules consisting of a biological functional domain and a luminescent probe or probes that report the environmental changes that occur either internally or on their surface. A class of luminescently labeled macromolecules designed to sense and report these changes have been termed "fluorescent-protein biosensors". The protein component of the biosensor provides a highly evolved molecular recognition moiety. A fluorescent molecule attached to the protein component in the proximity of an active site transduces environmental changes into fluorescence signals that are detected using a system with an appropriate temporal and spatial resolution such as the cell scanning system of the present invention. Because the modulation of native protein activity within the living cell is reversible, and because fluorescent-protein biosensors can be designed to sense reversible changes in protein activity, these biosensors are essentially reusable.

Disease associated sequences ("DAS"). This term refers to nucleic acid sequences identified by standard techniques, such as primary DNA sequence data, genomic methods such as subtraction hybridization and RADE, and proteomic methods in combination with reverse genetics, as being of drug candidate compounds. The term does not mean that the sequence is only associated with a disease state.

High content screening (HCS) can be used to measure the effects of drugs on complex molecular events such as signal transduction pathways, as well as cell functions including, but not limited to, apoptosis, cell division, cell adhesion, locomotion, exocytosis, and cell-cell communication. Multicolor fluorescence permits multiple targets and cell processes to be assayed in a single screen. Cross-correlation of cellular responses will yield a wealth of information required for target validation and lead optimization.

In one aspect of the present invention, a cell screening system is provided comprising a high magnification fluorescence optical system having a microscope objective, an XY stage adapted for holding a plate with an array of locations for holding cells and having a means for moving the plate to align the locations with the microscope objective and a means for moving the plate in the direction to effect focusing; a digital camera; a light source having optical means for directing excitation light to cells in the array of locations and a means for directing fluorescent light emitted from the cells to the digital camera; and a computer means for receiving and processing digital data from the digital camera wherein the computer means includes: a digital frame grabber for receiving the images from the camera, a display for user interaction and display of assay results, digital storage media for data storage and archiving, and means for control, acquisition, processing and display of results.

FIG. 1 is a schematic diagram of a preferred embodiment of the cell scanning system. An inverted fluorescence microscope is used 1, such as a Zeiss Axiovert inverted fluorescence microscope which uses standard objectives with magnification of 1–100× to the camera, and a white light source (e.g. 100W mercury-arc lamp or 75W xenon lamp) with power supply 2. There is an XY stage 3 to move the plate 4 in the XY direction over the microscope objective. A Z-axis focus drive 5 moves the objective in the Z direction for focusing. A joystick 6 provides for manual movement of the stage in the XYZ direction. A high resolution digital camera 7 acquires images from each well or location on the plate. There is a camera power supply 8, an automation controller 9 and a central processing unit 10. The PC 11 provides a display 12 and has associated software. The printer 13 provides for printing of a hard copy record.

FIG. 2 is a schematic of one embodiment of the microscope assembly 1 of the invention, showing in more detail the XY stage 3, Z-axis focus drive 5, joystick 6, light source 2, and automation controller 9. Cables to the computer 15 and microscope 16, respectively, are provided. In addition, FIG. 2 shows a 96 well microtiter plate 17 which is moved on the XY stage 3 in the XY direction. Light from the light source 2 passes through the PC controlled shutter 18 to a motorized filter wheel 19 with excitation filters 20. The light passes into filter cube 25 which has a dichroic mirror 26 and an emission filter 27. Excitation light reflects off the dichroic mirror to the wells in the microtiter plate 17 and fluorescent light 28 passes through the dichroic mirror 26 and the emission filter 27 and to the digital camera 7.

Figure 3:
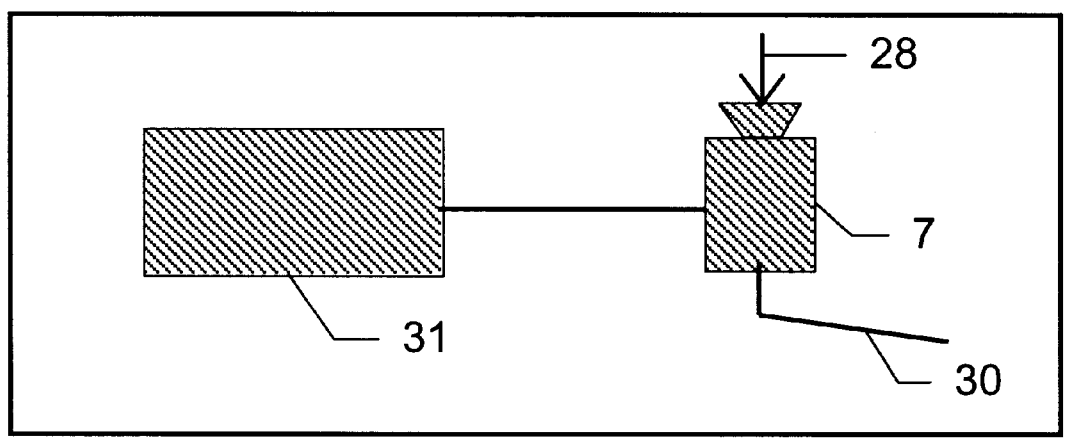
FIG. 3 shows the camera subassembly.

FIG. 3 shows a schematic drawing of a preferred camera assembly. The digital camera 7, which contains an automatic shutter for exposure control and a power supply 31, receives fluorescent light 28 from the microscope assembly. A digital cable 30 transports digital signals to the computer.

The standard optical configurations described above use microscope optics to directly produce an enlarged image of the specimen on the camera sensor in order to capture a high resolution image of the specimen. This optical system is commonly referred to as 'wide field' microscopy. Those skilled in the art of microscopy will recognize that a high resolution image of the specimen can be created by a variety of other optical systems, including, but not limited to, standard scanning confocal detection of a focused point or line of illumination scanned over the specimen (Go et al. 1997, supra), and multi-photon scanning confocal microscopy (Denk et al., 1990, supra), both of which can form images on a CCD detector or by synchronous digitization of the analog output of a photomultiplier tube.

In screening applications, it is often necessary to use a particular cell line, or primary cell culture, to take advantage of particular features of those cells. Those skilled in the art of cell culture will recognize that some cell lines are contact inhibited, meaning that they will stop growing when they become surrounded by other cells, while other cell lines will continue to grow under those conditions and the cells will literally pile up, forming many layers. An example of such a cell line is the HEK 293 (ATCC CRL-1573) line. An optical system that can acquire images of single cell layers in multilayer preparations is required for use with cell lines that tend to form layers. The large depth of field of wide field microscopes produces an image that is a projection through the many layers of cells, making analysis of subcellular spatial distributions extremely difficult in layer-forming cells. Alternatively, the very shallow depth of field that can be achieved on a confocal microscope, (about one micron), allows discrimination of a single cell layer at high resolution, simplifying the determination of the subcellular spatial distribution. Similarly, confocal imaging is preferable when detection modes such as fluorescence lifetime imaging are required.

The output of a standard confocal imaging attachment for a microscope is a digital image that can be converted to the same format as the images produced by the other cell screening system embodiments described above, and can therefore be processed in exactly the same way as those images. The overall control, acquisition and analysis in this embodiment is essentially the same. The optical configuration of the confocal microscope system, is essentially the same as that described above, except for the illuminator and detectors. Illumination and detection systems required for confocal microscopy have been designed as accessories to be attached to standard microscope optical systems such as that of the present invention (Zeiss, Germany). These alternative optical systems therefore can be easily integrated into the system as described above.

Figure 4:
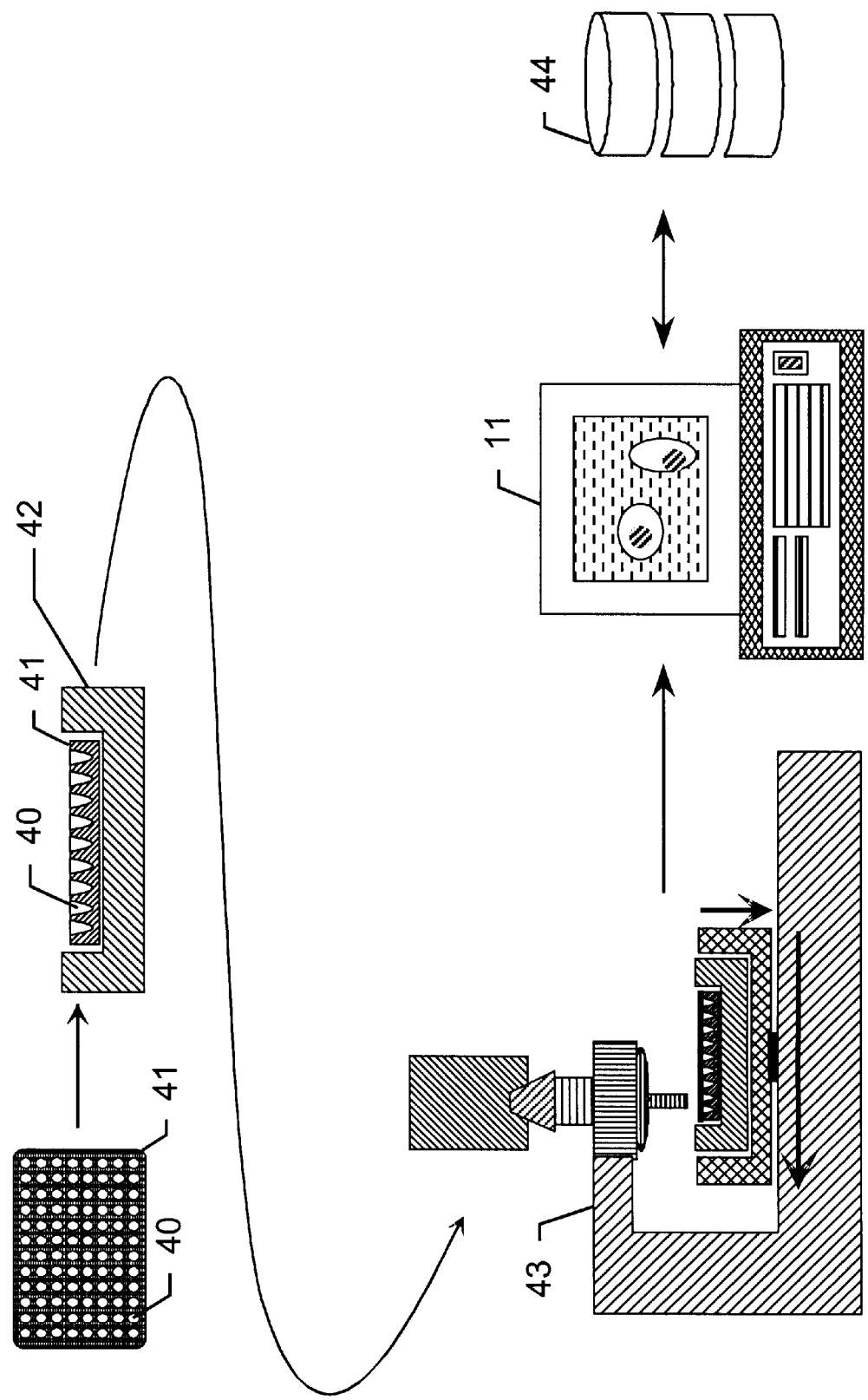
FIG. 4 illustrates cell scanning system process.

FIG. 4 illustrates an alternative embodiment of the invention in which cell arrays are in microwells 40 on a microplate 41 described ion co-pending U.S. application Ser. No. 08/865,341, incorporated by reference herein in its entirety. Typically the microplate is 20 mm by 30 mm as compared to a standard 96 well microtiter plate which is 86 mm by 129 mm. The higher density array of cells on a microplate allows the microplate to be imaged at a low resolution of a few microns per pixel for high throughput and particular locations on the microplate to be imaged at a higher resolution of less than 0.5 microns per pixel. These two resolution modes help to improve the overall throughput of the system.

Figure 5:
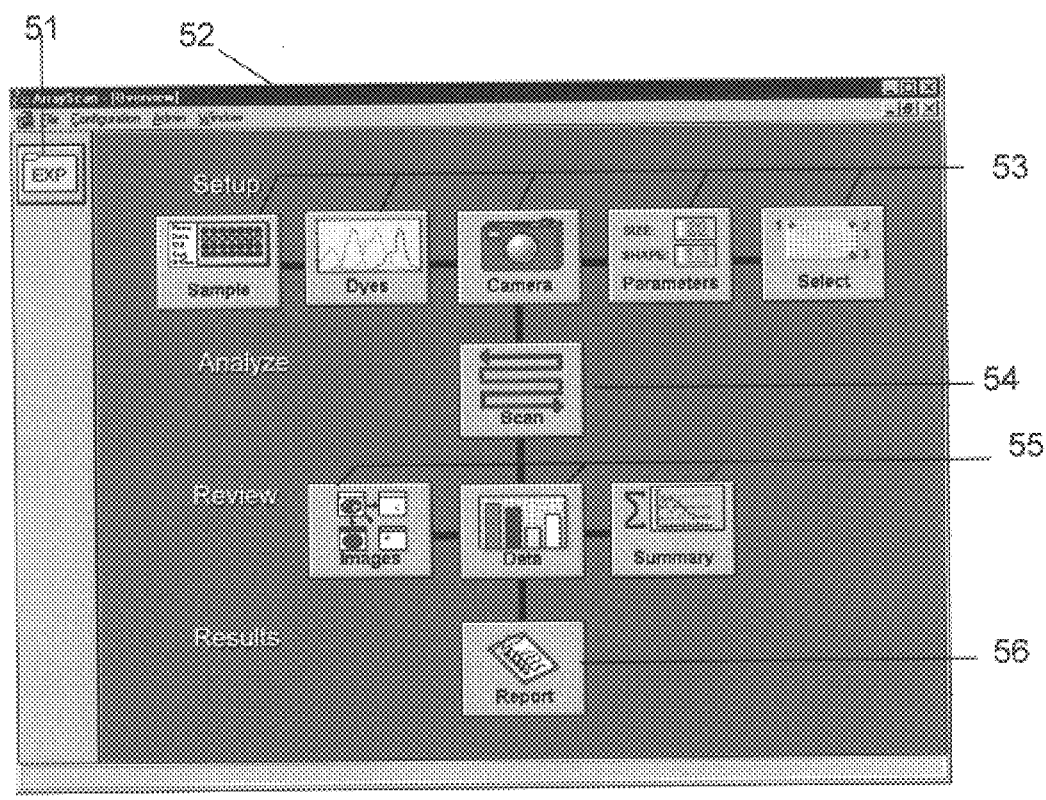
FIG. 5 illustrates a user interface showing major functions to guide the user.

The microplate chamber 42 serves as a microfluidic delivery system for the addition of compounds to cells. The microplate 41 in the microplate chamber 42 is placed in an XY microplate reader 43. Digital data is processed as described above. The small size of this microplate system increases throughput, minimizes reagent volume and allows control of the distribution and placement of cells for fast and precise cell-based analysis. Processed data can be displayed on a PC screen 11 and made part of a bioinformatics data base 44. This data base not only permits storage and retrieval of data obtained through the methods of this invention, but also permits acquisition and storage of external data relating to cells. FIG. 5 is a PC display which illustrates the operation of the software.

In an alternative embodiment, a high throughput system (HTS) is directly coupled with the HCS either on the same platform or on two separate platforms connected electronically (e.g. via a local area network). This embodiment of the invention, referred to as a dual mode optical system, has the advantage of increasing the throughput of a HCS by coupling it with a HTS and thereby requiring slower high resolution data acquisition and analysis only on the small subset of wells that show a response in the coupled HTS.

High throughput 'whole plate' reader systems are well known in the art and are commonly used as a component of an HTS system used to screen large numbers of compounds (Beggs (1997), *J. of Biomolec. Screening* 2:71–78; Macaffrey et al., (1996) *J. Biomolec. Screening* 1:187–190).

Figure 6:
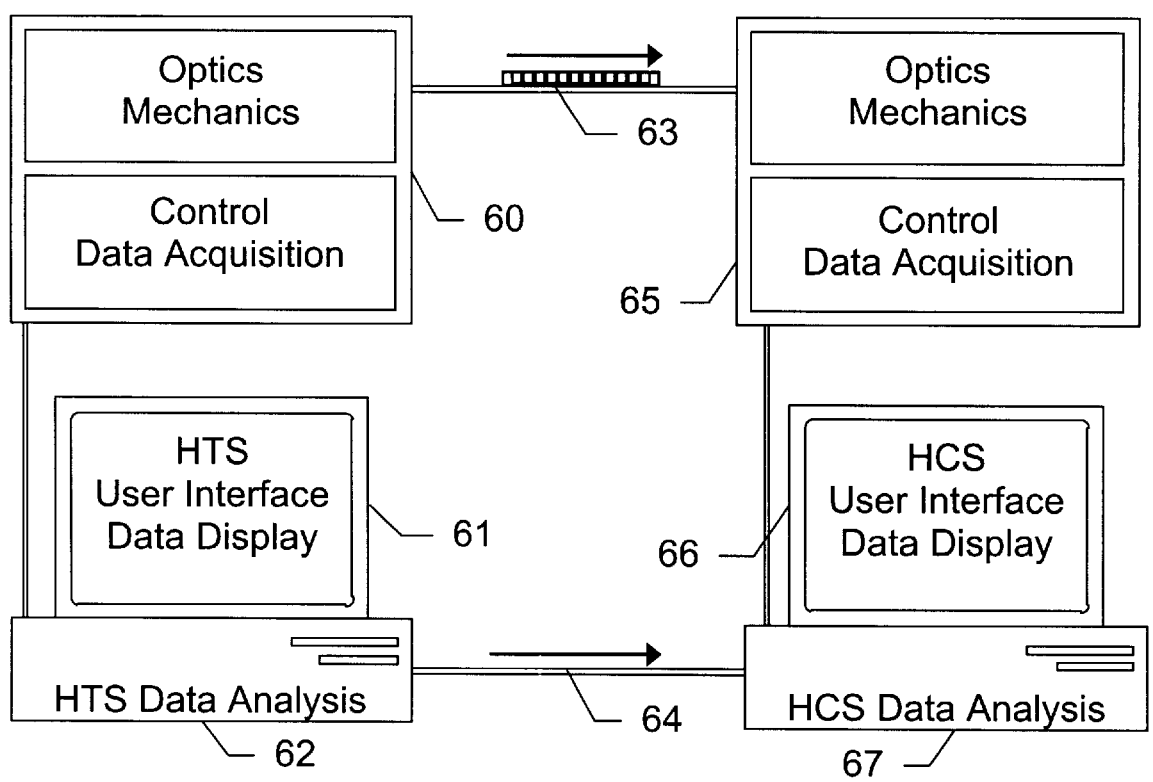
FIG. 6 is a block diagram of the two platform architecture of the Dual Mode System for Cell Based Screening in which one platform uses a telescope lens to read all wells of a microtiter plate and a second platform that uses a higher magnification lens to read individual cells in a well.

In one embodiment of dual mode cell based screening, a two platform architecture in which high throughput acquisition occurs on one platform and high content acquisition occurs on a second platform is provided (FIG. 6). Processing occurs on each platform independently, with results passed over a network interface, or a single controller is used to process the data from both platforms.

As illustrated in FIG. 6, an exemplified two platform dual mode optical system consists of two light optical instruments, a high throughput platform 60 and a high content platform 65, which read fluorescent signals emitted from cells cultured in microtiter plates or microwell arrays on a microplate, and communicate with each other via an electronic connection 64. The high throughput platform 60 analyzes all the wells in the whole plate either in parallel or rapid serial fashion. Those skilled in the art of screening will recognize that there are a many such commercially available high throughput reader systems that could be integrated into a dual mode cell based screening system (Topcount (Packard Instruments, Meriden, Conn.); Spectramax, Lumiskan (Molecular Devices, Sunnyvale, Calif.); Fluoroscan (Labsystems, Beverly, Mass.)). The high content platform 65, as described above, scans from well to well and acquires and analyzes high resolution image data collected from individual cells within a well.

The HTS software, residing on the system's computer 62, controls the high throughput instrument, and results are displayed on the monitor 61. The HCS software, residing on it's computer system 67, controls the high content instrument hardware 65, optional devices (e.g. plate loader, environmental chamber, fluid dispenser), analyzes digital image data from the plate, displays results on the monitor 66 and manages data measured in an integrated database. The two systems can also share a single computer, in which case all data would be collected, processed and displayed on that computer, without the need for a local area network to transfer the data. Microtiter plates are transferred from the high throughput system to the high content system 63 either manually or by a robotic plate transfer device, as is well known in the art (Beggs (1997), supra; Mcaffrey (1996), supra).

Figure 7:
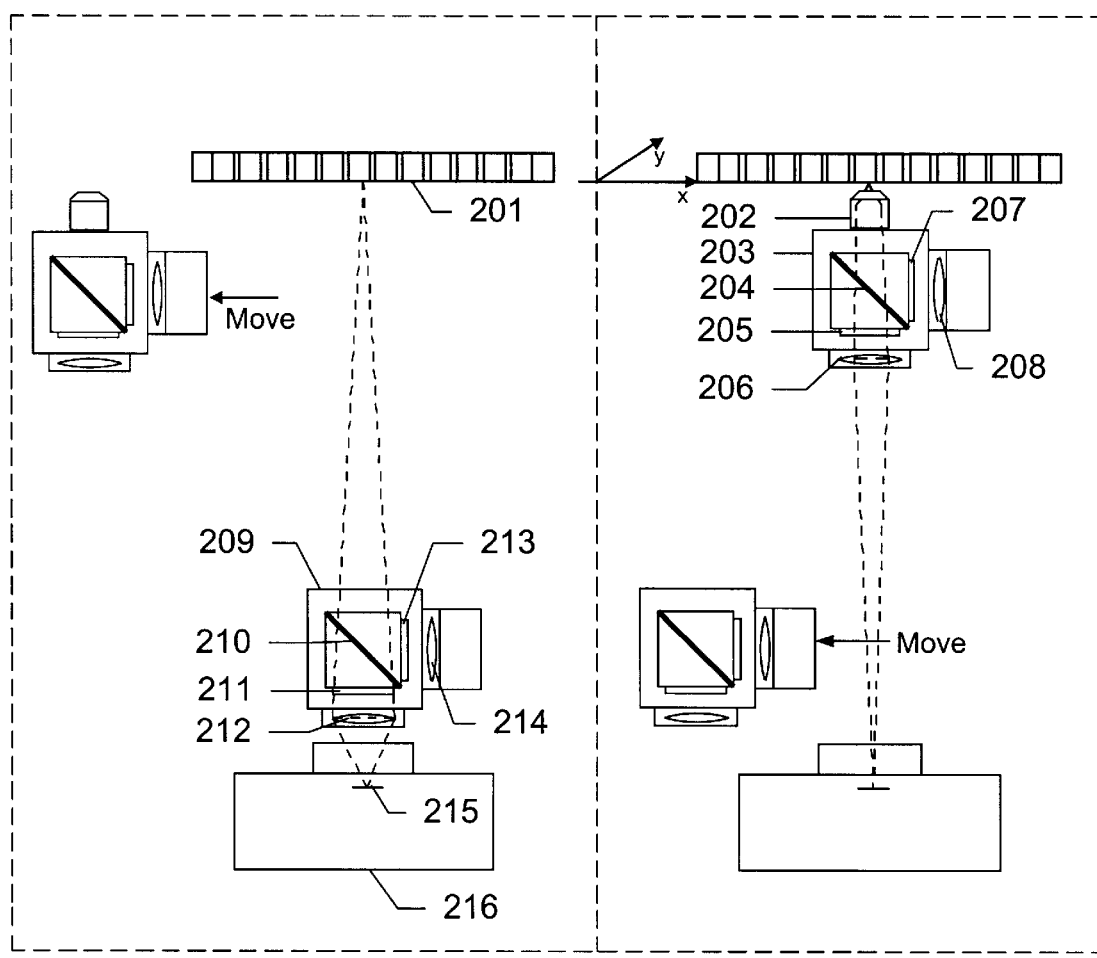
FIG. 7 is a detail of an optical system for a single platform architecture of the Dual Mode System for Cell Based Screening that uses a moveable 'telescope' lens to read all wells of a microtiter plate and a moveable higher magnification lens to read individual cells in a well.

In a preferred embodiment, the dual mode optical system utilizes a single platform system FIG. 7). It consists of two separate optical modules, an HCS module 203 and an HTS module 209 that can be independently or collectively moved so that only one at a time is used to collect data from the microtiter plate 201. The microtiter plate 201 is mounted in a motorized X,Y stage so it can be positioned for imaging in either HTS or HCS mode. After collecting and analyzing the HTS image data as described below, the HTS optical module 209 is moved out of the optical path and the HCS optical module 203 is moved into place.

The optical module for HTS 209 consists of a projection lens 214 excitation wavelength filter 213 and dichroic mirror 210 which are used to illuminate the whole bottom of the plate with a specific wavelength band from a conventional microscope lamp system (not illustrated). The fluorescence emission is collected through the dichroic mirror 210 and emission wavelength filter 211 by a lens 212 which forms an image on the camera 216 with sensor 215.

The optical module for HCS 203 consists of a projection lens 208 excitation wavelength filter 207 and dichroic mirror 204 which are used to illuminate the back aperture of the microscope objective 202, and thereby the field of that objective, from a standard microscope illumination system (not shown). The fluorescence emission is collected by the microscope objective 202, passes through the dichroic mirror 204 and emission wavelength filter 205 and is focused by a tube lens 206 which forms an image on the same camera 216 with sensor 215.

Figure 8:
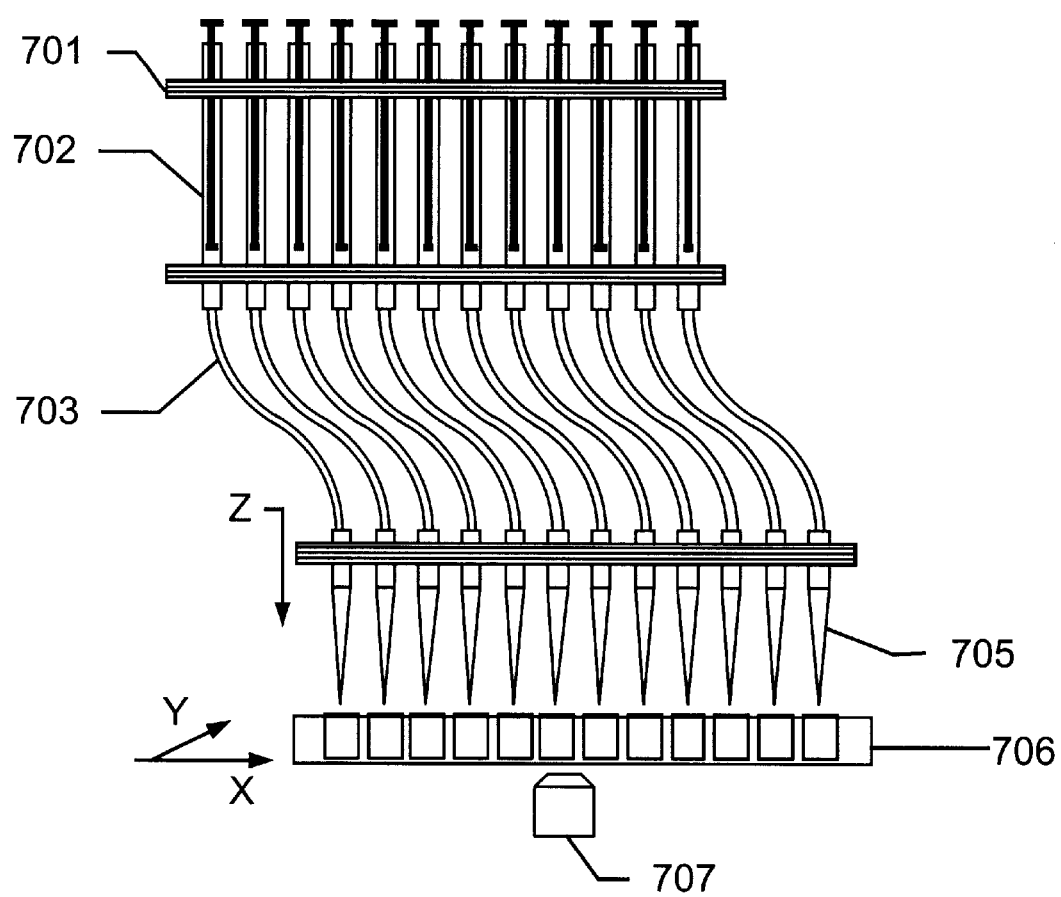
FIG. 8 is an illustration of the fluid delivery system for acquiring kinetic data on the Cell Based Screening System.

In an alternative embodiment of the present invention, the cell screening system further comprises a fluid delivery device for use with the live cell embodiment of the method of cell screening (see below). FIG. 8 exemplifies a fluid delivery device for use with the system of the invention. It consists of a bank of 12 syringe pumps 701 driven by a single motor drive. Each syringe 702 is sized according to the volume to be delivered to each well, typically between 1 and 100 $\mu$L. Each syringe is attached via flexible tubing 703 to a similar bank of connectors which accept standard pipette tips 705. The bank of pipette tips are attached to a drive system so they can be lowered and raised relative to the microtiter plate 706 to deliver fluid to each well. The plate is mounted on an X,Y stage, allowing movement relative to the optical system 707 for data collection purposes. This set-up allows one set of pipette tips, or even a single pipette tip, to deliver reagent to all the wells on the plate. The bank of syringe pumps can be used to deliver fluid to 12 wells simultaneously, or to fewer wells by removing some of the tips.

In another aspect, the present invention provides a method for analyzing cells comprising providing an array of locations which contain multiple cells wherein the cells contain one or more fluorescent reporter molecules; scanning multiple cells in each of the locations containing cells to obtain fluorescent signals from the fluorescent reporter molecule in the cells; converting the fluorescent signals into digital data; and utilizing the digital data to determine the distribution, environment or activity of the fluorescent reporter molecule within the cells.

Cell Arrays

Screening large numbers of compounds for activity with respect to a particular biological function requires preparing arrays of cells for parallel handling of cells and reagents. Standard 96 well microtiter plates which are 86 mm by 129 mm, with 6 mm diameter wells on a 9 mm pitch, are used for compatibility with current automated loading and robotic handling systems. The microplate is typically 20 mm by 30 mm, with cell locations that are 100–200 microns in dimension on a pitch of about 500 microns. Methods for making microplates are described in U.S. patent application Ser. No. 08/865,341, incorporated by reference herein in its entirety. Microplates may consist of coplanar layers of materials to which cells adhere, patterned with materials to which cells will not adhere, or etched 3-dimensional surfaces of similarly pattered materials. For the purpose of the following discussion, the terms 'well' and 'microwell' refer to a location in an array of any construction to which cells adhere and within which the cells are imaged. Microplates may also include fluid delivery channels in the spaces between the wells. The smaller format of a microplate increases the overall efficiency of the system by minimizing the quantities of the reagents, storage and handling during preparation and the overall movement required for the scanning operation. In addition, the whole area of the microplate can be imaged more efficiently, allowing a second mode of operation for the microplate reader as described later in this document.

Fluorescence Reporter Molecules

A major component of the new drug discovery paradigm is a continually growing family of fluorescent and luminescent reagents that are used to measure the temporal and spatial distribution, content, and activity of intracellular ions, metabolites, macromolecules, and organelles. Classes of these reagents include labeling reagents that measure the distribution and amount of molecules in living and fixed cells, environmental indicators to report signal transduction events in time and space, and fluorescent protein biosensors to measure target molecular activities within living cells. A multiparameter approach that combines several reagents in a single cell is a powerful new tool for drug discovery.

The method of the present invention is based on the high affinity of fluorescent or luminescent molecules for specific cellular components. The affinity for specific components is governed by physical forces such as ionic interactions, covalent bonding (which includes chimeric fusion with protein-based chromophores, fluorophores, and lumiphores), as well as hydrophobic interactions, electrical potential, and, in some cases, simple entrapment within a cellular component. The luminescent probes can be small molecules, labeled macromolecules, or genetically engineered proteins, including, but not limited to green fluorescent protein chimeras.

Those skilled in this art will recognize a wide variety of fluorescent reporter molecules that can be used in the present invention, including, but not limited to, fluorescently labeled biomolecules such as proteins, phospholipids and DNA hybridizing probes. Similarly, fluorescent reagents specifically synthesized with particular chemical properties of binding or association have been used as fluorescent reporter molecules (Barak et al., (1997), *J. Biol. Chem.* 272:27497–27500; Southwick et al., (1990), *Cytometry* 11:418–430; Tsien (1989) in *Methods in Cell Biology*, Vol. 29 Taylor and Wang (eds.), pp. 127–156). Fluorescently labeled antibodies are particularly useful reporter molecules due to their high degree of specificity for attaching to a single molecular target in a mixture of molecules as complex as a cell or tissue.

The luminescent probes can be synthesized within the living cell or can be transported into the cell via several non-mechanical modes including diffusion, facilitated or active transport, signal-sequence-mediated transport, and endocytotic or pinocytotic uptake. Mechanical bulk loading methods, which are well known in the art, can also be used to load luminescent probes into living cells (Barber et al. (1996), *Neuroscience Letters* 207:17–20; Bright et al. (1996), *Cytometry* 24:226–233; McNeil (1989) in *Methods in Cell Biology, Vol.* 29, Taylor and Wang (eds.), pp. 153–173). These methods include electroporation and other mechanical methods such as scrape-loading, bead-loading, impact-loading, syringe-loading, hypertonic and hypotonic loading. Additionally, cells can be genetically engineered to express reporter molecules, such as GFP, coupled to a protein of interest as previously described (Chalfie and Prasher U.S. Pat. No. 5,491,084; Cubitt et al. (1995), *Trends in Biochemical Science* 20:448–455).

Once in the cell, the luminescent probes accumulate at their target domain as a result of specific and high affinity interactions with the target domain or other modes of molecular targeting such as signal-sequence-mediated transport. Fluorescently labeled reporter molecules are useful for determining the location, amount and chemical environment of the reporter. For example, whether the reporter is in a lipophilic membrane environment or in a more aqueous environment can be determined (Giuliano et al. (1995), *Ann. Rev. of Biophysics and Biomolecular Structure* 24:405–434; Giuliano and Taylor (1995), *Methods in Neuroscience* 27:1–16). The pH environment of the reporter can be determined (Bright et al. (1989), *J. Cell Biology* 104:1019–1033; Giuliano et al. (1987), *Anal. Biochem.* 167:362–371; Thomas et al. (1979), *Biochemistry* 18:2210–2218). It can be determined whether a reporter having a chelating group is bound to an ion, such as Ca++, or not (Bright et al. (1989), In *Methods in Cell Biology*, Vol. 30, Taylor and Wang (eds.), pp. 157–192; Shimoura et al. (1988), *J. of Biochemistry* (Tokyo) 251:405–410; Tsien (1989) In *Methods in Cell Biology*, Vol. 30, Taylor and Wang (eds.), pp. 127–156).

Furthermore, certain cell types within an organism may contain components that can be specifically labeled that may not occur in other cell types. For example, epithelial cells often contain polarized membrane components. That is, these cells asymmetrically distribute macromolecules along their plasma membrane. Connective or supporting tissue cells often contain granules in which are trapped molecules specific to that cell type (e.g., heparin, histamine, serotonin, etc.). Most muscular tissue cells contain a sarcoplasmic reticulum, a specialized organelle whose function is to regulate the concentration of calcium ions within the cell cytoplasm. Many nervous tissue cells contain secretory granules and vesicles in which are trapped neurohormones or neurotransmitters. Therefore, fluorescent molecules can be designed to label not only specific components within specific cells, but also specific cells within a population of mixed cell types.

Those skilled in the art will recognize a wide variety of ways to measure fluorescence. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements (Giuliano et al. (1995), *Ann. Rev. of Biophysics and Biomol. Structure* 24:405–434; Giuliano et al. (1995), *Methods in Neuroscience* 27:1–16).

Scanning Cell Arrays

Referring to FIG. 9, a preferred embodiment is provided to analyze cells that comprises operator-directed parameters being selected based on the assay being conducted, data acquisition by the cell screening system on the distribution of fluorescent signals within a sample, and interactive data review and analysis. At the start of an automated scan the operator enters information 100 that describes the sample, specifies the filter settings and fluorescent channels to match the biological labels being used and the information sought, and then adjusts the camera settings to match the sample brightness. For flexibility to handle a range of samples, the software allows selection of various parameter settings used to identify nuclei and cytoplasm, and selection of different fluorescent reagents, identification of cells of interest based on morphology or brightness, and cell numbers to be analyzed per well. These parameters are stored in the system's for easy retrieval for each automated run. The system's interactive cell identification mode simplifies the selection of morphological parameter limits such as the range of size, shape, and intensity of cells to be analyzed. The user specifies which wells of the plate the system will scan and how many fields or how many cells to analyze in each well. Depending on the setup mode selected by the user at step 101, the system either automatically pre-focuses the region of the plate to be scanned using an autofocus procedure to fit "focus" of the plate 102 or the user interactively pre-focuses 103 the scanning region by selecting three "tag" points which define the rectangular area to be scanned. A least-squares fit "focal plane model" is then calculated from these tag points to estimate the focus of each well during an automated scan. The focus of each well is estimated by interpolating from the focal plane model during a scan.

During an automated scan, the software dynamically displays the scan status, including the number of cells analyzed, the current well being analyzed, images of each independent wavelength as they are acquired, and the result of the screen for each well as it is determined. The plate 4 (FIG. 1) is scanned in a serpentine style as the software automatically moves the motorized microscope XY stage 3 from well to well and field to field within each well of a 96-well plate. Those skilled in the programming art will recognize how to adapt software for scanning of other microplate formats such as 24, 48, and 384 well plates. The scan pattern of the entire plate as well as the scan pattern of fields within each well are programmed. The system adjusts sample focus with an autofocus procedure 104 (FIG. 9) through the Z axis focus drive 5, controls filter selection via a motorized filter wheel 19 and acquires and analyzes images of up to four different colors ("channels" or "wavelengths").

The autofocus procedure is called at a user selected frequency, typically for the first field in each well and then once every 4 to 5 fields within each well. The autofocus procedure calculates the starting Z-axis point by interpolating from the pre-calculated plane focal model. Starting a programmable distance above or below this set point, the procedure moves the mechanical Z-axis through a number of different positions, acquires an image at each position, and finds the maximum of a calculated focus score that estimates the contrast of each image. The Z position of the image with the maximum focus score determines the best focus for a particular field. Those skilled in the art will recognize this as a variant of automatic focusing methods as described in Harms et al. in *Cytometry* 5(1984), 236–243, Groen et al. in Cytometry 6 (1985), 81–91, and Firestone et al. in *Cytometry* 12 (1991), 195–206.

For image acquisition, the camera's exposure time is separately adjusted for each dye to ensure a high-quality image from each channel. Software procedures can be called, at the user's option, to correct for registration shifts between wavelengths by accounting for linear (X and Y) shifts between wavelengths before making any further measurements. The electronic shutter 18 is controlled so that sample photo-bleaching is kept to a minimum. Background shading and uneven illumination can be corrected by the software using methods known in the art (Bright et al. (1987), *J. Cell Biol.* 104:1019–1033).

In one channel, images are acquired of a primary marker 105 (FIG. 9) (typically cell nuclei counterstained with DAPI or PI fluorescent dyes) which are segmented ("identified") using an adaptive thresholding procedure. The adaptive thresholding procedure 106 is used to dynamically select the threshold of an image for separating cells from the background. The staining of cells with fluorescent dyes can vary to an unknown degree across cells in a microtiter plate sample as well as within images of a field of cells within each well of a microtiter plate. This variation can occur as a result of sample preparation and/or the dynamic nature of cells. A global threshold is calculated for the complete image to separate the cells from background and account for field to field variation. These global adaptive techniques are variants of those described in the art. (Kittler et al. in *Computer Vision, Graphics, and Image Processing* 30 (1985), 125–147, Ridler et al. in *IEEE Trans. Systems, Man, and Cybernetics* (1978), 630–632.)

An alternative adaptive thresholding method utilizes local region thresholding in contrast to global image thresholding. Image analysis of local regions leads to better overall segmentation since staining of cell nuclei (as well as other labeled components) can vary across an image. Using this global/local procedure, a reduced resolution image (reduced in size by a factor of 2 to 4) is first globally segmented (using adaptive thresholding) to find regions of interest in the image. These regions then serve as guides to more fully analyze the same regions at full resolution. A more localized threshold is then calculated (again using adaptive thresholding) for each region of interest.

The output of the segmentation procedure is a binary image wherein the objects are white and the background is black. This binary image, also called a mask in the art, is used to determine if the field contains objects 107. The mask is labeled with a blob labeling method whereby each object (or blob) has a unique number assigned to it. Morphological features, such as area and shape, of the blobs are used to differentiate blobs likely to be cells from those that are considered artifacts. The user pre-sets the morphological selection criteria by either typing in known cell morphological features or by using the interactive training utility. If objects of interest are found in the field, images are acquired for all other active channels 108, otherwise the stage is advanced to the next field 109 in the current well. Each object of interest is located in the image for further analysis 110. The software determines if the object meets the criteria for a valid cell nucleus 111 by measuring its morphological features (size and shape). For each valid cell, the XYZ stage location is recorded, a small image of the cell is stored, and features are measured 112.

Figure 10:
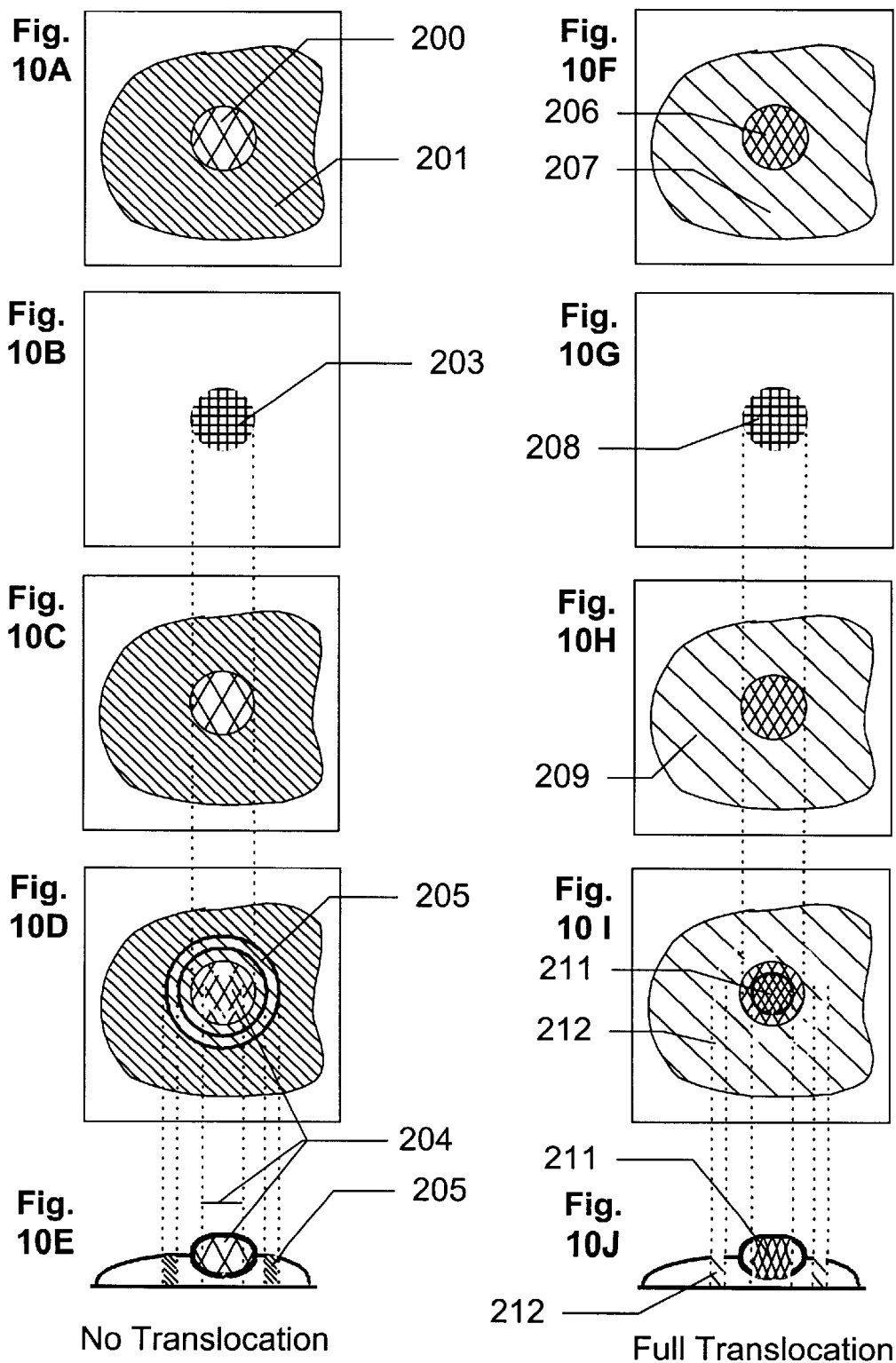
FIGS. 10A–J illustrates the strategy of the Nuclear Translocation Assay.

The cell scanning method of the present invention can be used to perform many different assays on cellular samples by applying a number of analytical methods simultaneously to measure features at multiple wavelengths. An example of one such assay provides for the following measurements:

1. The total fluorescent intensity within the cell nucleus for colors 1–4
2. The area of the cell nucleus for color 1 (the primary marker)
3. The shape of the cell nucleus for color 1 is described by three shape features:
   a) perimeter squared area
   b) box area ratio
   c) height width ratio
4. The average fluorescent intensity within the cell nucleus for colors 1–4 (i.e. #1 divided by #2)
5. The total fluorescent intensity of a ring outside the nucleus (see FIG. 10) that represents fluorescence of the cell's cytoplasm (cytoplasmic mask) for colors 2–4
6. The area of the cytoplasmic mask
7. The average fluorescent intensity of the cytoplasmic mask for colors 2–4 (i.e. #5 divided by #6)
8. The ratio of the average fluorescent intensity of the cytoplasmic mask to average fluorescent intensity within the cell nucleus for colors 2–4 (i.e. #7 divided by #4)
9. The difference of the average fluorescent intensity of the cytoplasmic mask and the average fluorescent intensity within the cell nucleus for colors 2–4 (i.e. #7 minus #4)
10. The number of fluorescent domains (also call spots, dots, or grains) within the cell nucleus for colors 2–4

Features 1 through 4 are general features of the different cell screening assays of the invention. These steps are commonly used in a variety of image analysis applications and are well known in art (Russ (1992) *The Image Processing Handbook*, CRC Press Inc.; Gonzales et al. (1987), *Digital Image Processing*. Addison-Wesley Publishing Co. pp. 391–448). Features 5–9 have been developed specifically to provide measurements of a cell's fluorescent molecules within the local cytoplasmic region of the cell and the translocation (i.e. movement) of fluorescent molecules from the cytoplasm to the nucleus. These features (steps 5–9) are used for analyzing cells in microplates for the inhibition of nuclear translocation. For example, inhibition of nuclear translocation of transcription factors provides a novel approach to screening intact cells (detailed examples of other types of screens will be provided below). A specific method measures the amount of probe in the nuclear region (feature 4) versus the local cytoplasmic region (feature 7) of each cell. Quantification of the difference between these two sub-cellular compartments provides a measure of cytoplasm-nuclear translocation (feature 9).

Feature 10 describes a screen used for counting of DNA or RNA probes within the nuclear region in colors 2–4. For example, probes are commercially available for identifying chromosome-specific DNA sequences (Life Technologies, Gaithersburg, Md.; Genosys, Woodlands, Tex.; Biotechnologies, Inc., Richmond, Calif.; Bio 101, Inc., Vista, Calif.) Cells are three-dimensional in nature and when examined at a high magnification under a microscope one probe may be in-focus while another may be completely out-of-focus. The cell screening method of the present invention provides for detecting three-dimensional probes in nuclei by acquiring images from multiple focal planes. The software moves the Z-axis motor drive 5 (FIG. 1) in small steps where the step distance is user selected to account for a wide range of different nuclear diameters. At each of the focal steps, an image is acquired. The maximum gray-level intensity from each pixel in each image is found and stored in a resulting maximum projection image. The maximum projection image is then used to count the probes. The above method works well in counting probes that are not stacked directly above or below another one. To account for probes stacked on top of each other in the Z-direction, users can select an option to analyze probes in each of the focal planes acquired. In this mode, the scanning system performs the maximum plane projection method as discussed above, detects probe regions of interest in this image, then further analyzes these regions in all the focal plane images.

After measuring cell features 112 (FIG. 9), the system checks if there are any unprocessed objects in the current field 113. If there are any unprocessed objects, it locates the next object 110 and determines whether it meets the criteria for a valid cell nucleus 111, and measures its features. Once all the objects in the current field are processed, the system determines whether analysis of the current plate is complete 114; if not, it determines the need to find more cells in the current well 115. If the need exists, the system advances the XYZ stage to the next field within the current well 109 or advances the stage to the next well 116 of the plate.

After a plate scan is complete, images and data can be reviewed with the system's image review, data review, and summary review facilities. All images, data, and settings from a scan are archived in the system's database for later review or for interfacing with a network information management system. Data can also be exported to other third-party statistical packages to tabulate results and generate other reports. Users can review the images alone of every cell analyzed by the system with an interactive image review procedure 117. The user can review data on a cell-by-cell basis using a combination of interactive graphs, a data spreadsheet of measured features, and images of all the fluorescence channels of a cell of interest with the interactive cell-by-cell data review procedure 118. Graphical plotting capabilities are provided in which data can be analyzed via interactive graphs such as histograms and scatter plots. Users can review summary data that are accumulated and summarized for all cells within each well of a plate with an interactive well-by-well data review procedure 119. Hard copies of graphs and images can be printed on a wide range of standard printers.

As a final phase of a complete scan, reports can be generated on one or more statistics of the measured features. Users can generate a graphical report of data summarized on a well-by-well basis for the scanned region of the plate using an interactive report generation procedure 120. This report includes a summary of the statistics by well in tabular and graphical format and identification information on the sample. The report window allows the operator to enter comments about the scan for later retrieval. Multiple reports can be generated on many statistics and be printed with the touch of one button. Reports can be previewed for placement and data before being printed.

The above-recited embodiment of the method operates in a single high resolution mode referred to as the high content screening (HCS) mode. The HCS mode provides sufficient spatial resolution within a well (on the order of 1 $\mu$m) to define the distribution of material within the well, as well as within individual cells in the well. The high degree of information content accessible in that mode, comes at the expense of speed and complexity of the required signal processing.

In an alternative embodiment, a high throughput system (HTS) is directly coupled with the HCS either on the same platform or on two separate platforms connected electronically (e.g. via a local area network). This embodiment of the invention, referred to as a dual mode optical system, has the advantage of increasing the throughput of an HCS by coupling it with an HTS and thereby requiring slower high resolution data acquisition and analysis only on the small subset of wells that show a response in the coupled HTS.

Figure 11:
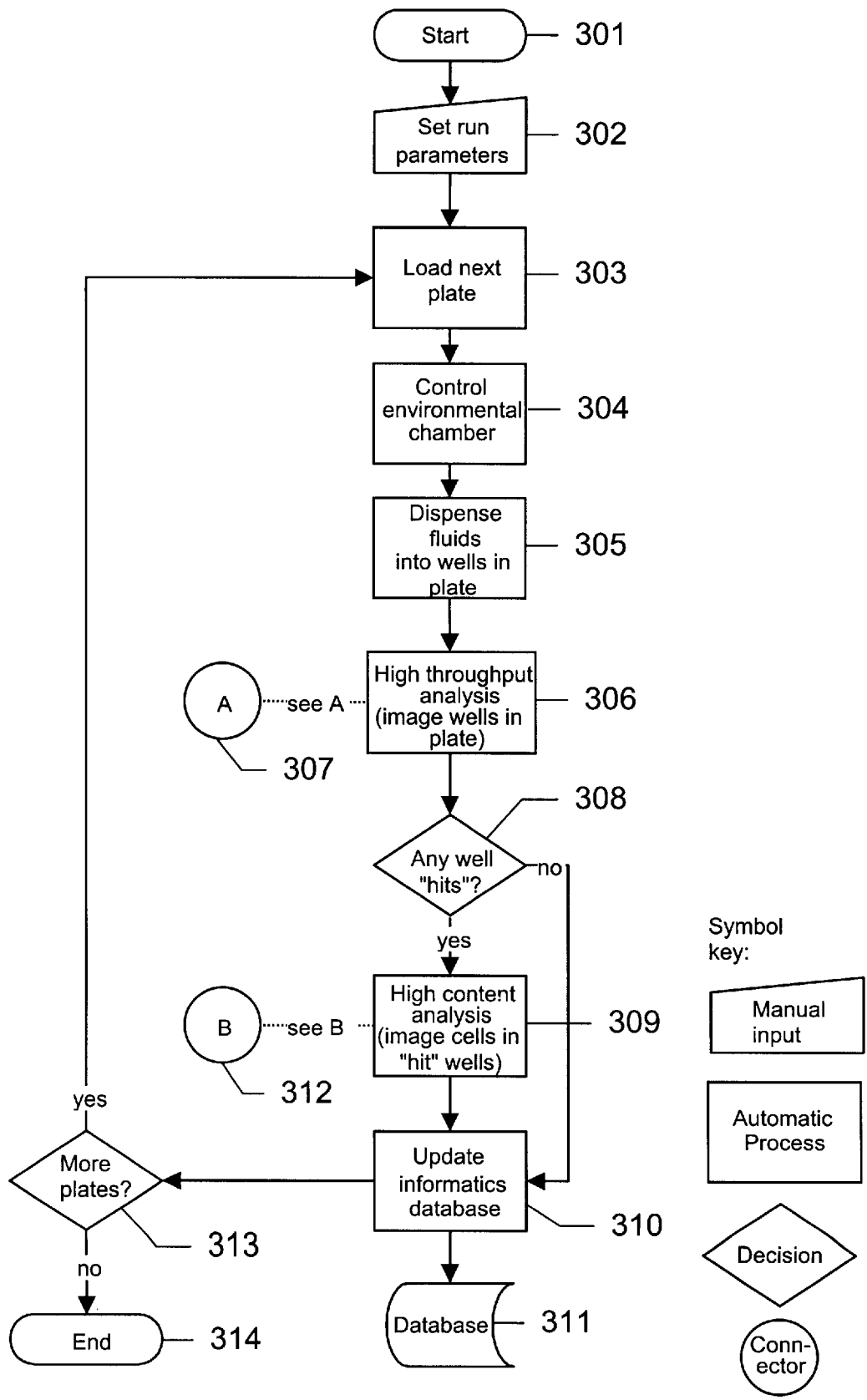
FIG. 11 is a flow chart defining the processing steps in the Dual Mode System for Cell Based Screening combining high throughput and high content screening of microtiter plates.

High throughput 'whole plate' reader systems are well known in the art and are commonly used as a component of an HTS system used to screen large numbers of compounds (Beggs et al. (1997), supra; McCaffrey et al. (1996), supra ). The HTS of the present invention is carried out on the microtiter plate or microwell array by reading many or all wells in the plate simultaneously with sufficient resolution to make determinations on a well-by-well basis. That is, calculations are made by averaging the total signal output of many or all the cells or the bulk of the material in each well. Wells that exhibit some defined response in the HTS (the 'hits') are flagged by the system. Then on the same microtiter plate or microwell array, each well identified as a hit is measured via HCS as described above. Thus, the dual mode process involves:

1. Rapidly measuring numerous wells of a microtiter plate or microwell array,
2. Interpreting the data to determine the overall activity of fluorescently labeled reporter molecules in the cells on a well-by-well basis to identify "hits" (wells that exhibit a defined response),
3. Imaging numerous cells in each "hit" well, and
4. Interpreting the digital image data to determine the distribution, environment or activity of the fluorescently labeled reporter molecules in the individual cells (i.e. intracellular measurements) and the distribution of the cells to test for specific biological functions In a preferred embodiment of dual mode processing (FIG. 11), at the start of a run 301 the operator enters information 302 that describes the plate and its contents, specifies the filter settings and fluorescent channels to match the biological labels being used, the information sought and the camera settings to match the sample brightness. These parameters are stored in the system's database for easy retrieval for each automated run. The microtiter plate or microwell array is loaded into the cell screening system 303 either manually or automatically by controlling a robotic loading device. An optional environmental chamber 304 is controlled by the system to maintain the temperature, humidity and $CO_2$ levels in the air surrounding live cells in the microtiter plate or microwell array. An optional fluid delivery device 305 (see FIG. 8) is controlled by the system to dispense fluids into the wells during the scan.

Figure 12:
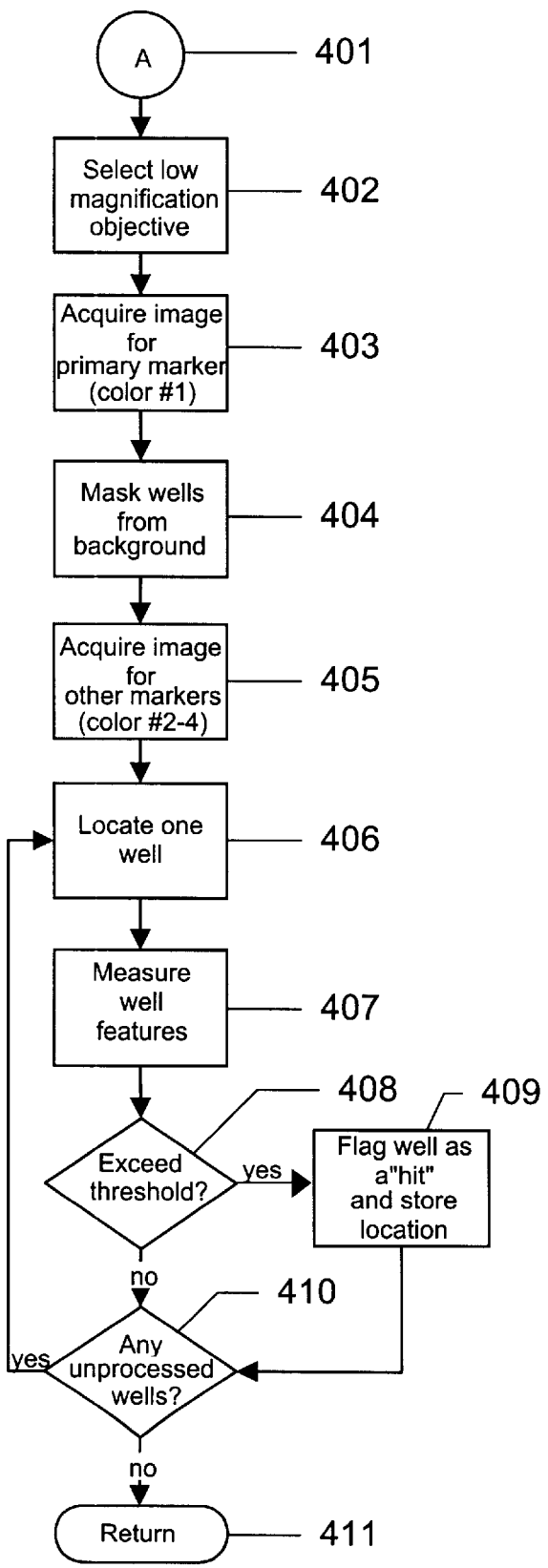
FIG. 12 is a flow chart defining the processing steps in the High Throughput mode of the System for Cell Based Screening.
Figure 13:
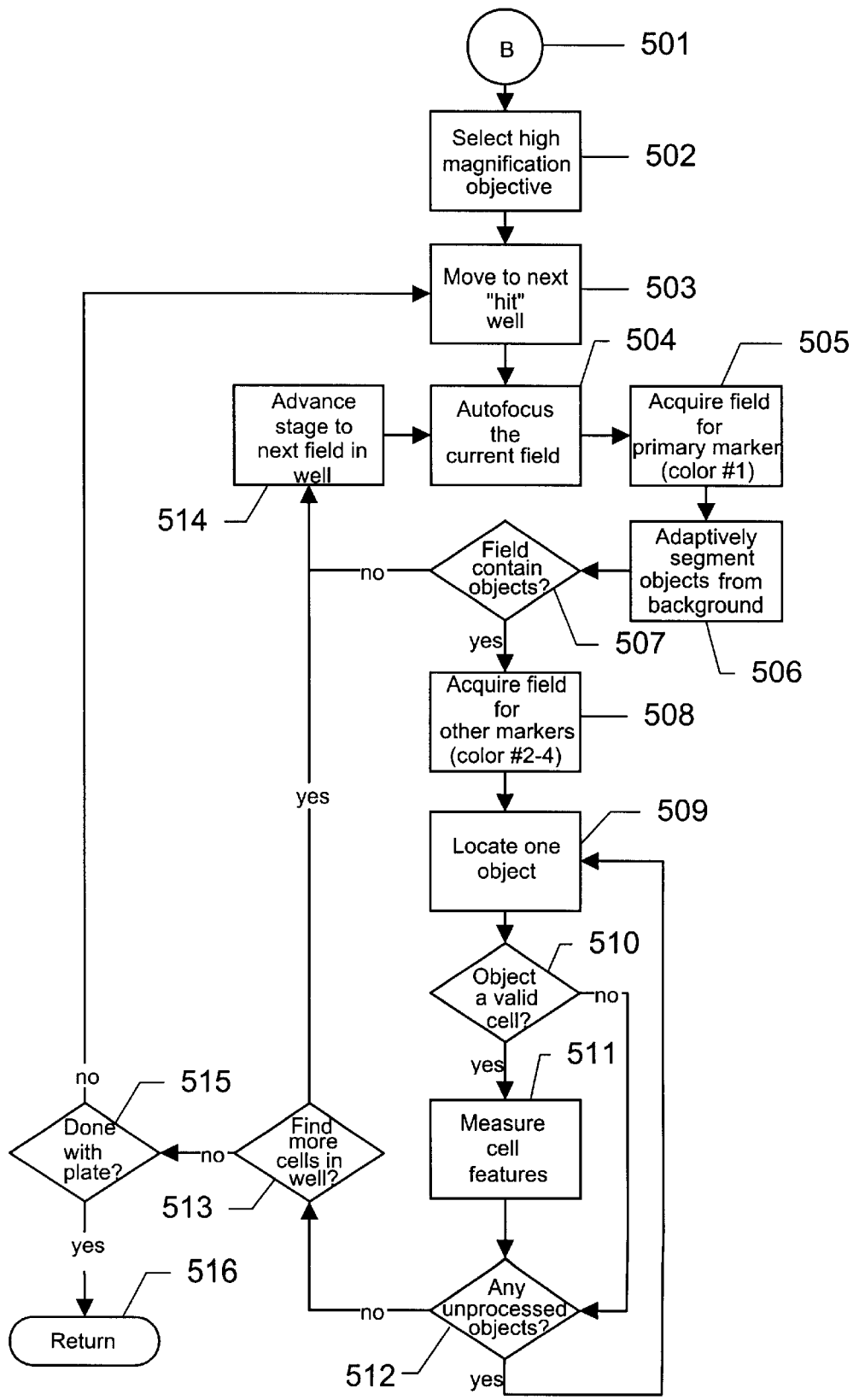
FIG. 13 is a flow chart defining the processing steps in the High Content mode of the System for Cell Based Screening.

High throughput processing 306 is first performed on the microtiter plate or microwell array by acquiring and analyzing the signal from each of the wells in the plate. The processing performed in high throughput mode 307 is illustrated in FIG. 12 and described below. Wells that exhibit some selected intensity response in this high throughput mode ("hits") are identified by the system. The system performs a conditional operation 308 that tests for hits. If hits are found, those specific hit wells are further analyzed in high content (micro level) mode 309. The processing performed in high content mode 312 is illustrated in FIG. 13. The system then updates 310 the informatics database 311 with results of the measurements on the plate. If there are more plates to be analyzed 313 the system loads the next plate 303; otherwise the analysis of the plates terminates 314.

The following discussion describes the high throughput mode illustrated in FIG. 12. The preferred embodiment of the system, the single platform dual mode screening system, will be described. Those skilled in the art will recognize that operationally the dual platform system simply involves moving the plate between two optical systems rather than moving the optics. Once the system has been set up and the plate loaded, the system begins the HTS acquisition and analysis 401. The HTS optical module is selected by controlling a motorized optical positioning device 402 on the dual mode system. In one fluorescence channel, data from a primary marker on the plate is acquired 403 and wells are isolated from the plate background using a masking procedure 404. Images are also acquired in other fluorescence channels being used 405. The region in each image corresponding to each well 406 is measured 407. A feature calculated from the measurements for a particular well is compared with a predefined threshold or intensity response 408, and based on the result the well is either flagged as a "hit" 409 or not. The locations of the wells flagged as hits are recorded for subsequent high content mode processing. If there are wells remaining to be processed 410 the program loops back 406 until all the wells have been processed 411 and the system exits high throughput mode.

Following HTS analysis, the system starts the high content mode processing 501 defined in FIG. 13. The system selects the HCS optical module 502 by controlling the motorized positioning system. For each "hit" well identified in high throughput mode, the XY stage location of the well is retrieved from memory or disk and the stage is then moved to the selected stage location 503. The autofocus procedure 504 is called for the first field in each hit well and then once every 5 to 8 fields within each well. In one channel, images are acquired of the primary marker 505 (typically cell nuclei counterstained with DAPI, Hoechst or PI fluorescent dye). The images are then segmented (separated into regions of nuclei and non-nuclei) using an adaptive thresholding procedure 506. The output of the segmentation procedure is a binary mask wherein the objects are white and the background is black. This binary image, also called a mask in the art, is used to determine if the field contains objects 507. The mask is labeled with a blob labeling method whereby each object (or blob) has a unique number assigned to it. If objects are found in the field, images are acquired for all other active channels 508, otherwise the stage is advanced to the next field 514 in the current well. Each object is located in the image for further analysis 509. Morphological features, such as area and shape of the objects, are used to select objects likely to be cell nuclei 510, and discard (do no further processing on) those that are considered artifacts. For each valid cell nucleus, the XYZ stage location is recorded, a small image of the cell is stored, and assay specific features are measured 511. The system then performs multiple tests on the cells by applying several analytical methods to measure features at each of several wavelengths. After measuring the cell features, the systems checks if there are any unprocessed objects in the current field 512. If there are any unprocessed objects, it locates the next object 509 and determines whether it meets the criteria for a valid cell nucleus 510, and measures its features. After processing all the objects in the current field, the system determines whether it needs to find more cells or fields in the current well 513. If it needs to find more cells or fields in the current well it advances the XYZ stage to the next field within the current well 515. Otherwise, the system checks whether it has any remaining hit wells to measure 515. If so, it advances to the next hit well 503 and proceeds through another cycle of acquisition and analysis, otherwise the HCS mode is finished 516.

In an alternative embodiment of the present invention, a method of kinetic live cell screening is provided. The previously described embodiments of the invention are used to characterize the spatial distribution of cellular components at a specific point in time, the time of chemical fixation. As such, these embodiments have limited utility for implementing kinetic based screens, due to the sequential nature of the image acquisition, and the amount of time required to read all the wells on a plate. For example, since a plate can require 30–60 minutes to read through all the wells, only very slow kinetic processes can be measured by simply preparing a plate of live cells and then reading through all the wells more than once. Faster kinetic processes can be measured by taking multiple readings of each well before proceeding to the next well, but the elapsed time between the first and last well would be too long, and fast kinetic processes would likely be complete before reaching the last well.

The kinetic live cell extension of the invention enables the design and use of screens in which a biological process is characterized by its kinetics instead of, or in addition to, its spatial characteristics. In many cases, a response in live cells can be measured by adding a reagent to a specific well and making multiple measurements on that well with the appropriate timing. This dynamic live cell embodiment of the invention therefore includes apparatus for fluid delivery to individual wells of the system in order to deliver reagents to each well at a specific time in advance of reading the well. This embodiment thereby allows kinetic measurements to be made with temporal resolution of seconds to minutes on each well of the plate. To improve the overall efficiency of the dynamic live cell system, the acquisition control program is modified to allow repetitive data collection from sub-regions of the plate, allowing the system to read other wells between the time points required for an individual well.

FIG. 8 describes an example of a fluid delivery device for use with the live cell embodiment of the invention and is described above. This set-up allows one set of pipette tips 705, or even a single pipette tip, to deliver reagent to all the wells on the plate. The bank of syringe pumps 701 can be used to deliver fluid to 12 wells simultaneously, or to fewer wells by removing some of the tips 705. The temporal resolution of the system can therefore be adjusted, without sacrificing data collection efficiency, by changing the number of tips and the scan pattern as follows. Typically, the data collection and analysis from a single well takes about 5 seconds. Moving from well to well and focusing in a well requires about 5 seconds, so the overall cycle time for a well is about 10 seconds. Therefore, if a single pipette tip is used to deliver fluid to a single well, and data is collected repetitively from that well, measurements can be made with about 5 seconds temporal resolution. If 6 pipette tips are used to deliver fluids to 6 wells simultaneously, and the system repetitively scans all 6 wells, each scan will require 60 seconds, thereby establishing the temporal resolution. For slower processes which only require data collection every 8 minutes, fluids can be delivered to one half of the plate, by moving the plate during the fluid delivery phase, and then repetitively scanning that half of the plate. Therefore, by adjusting the size of the sub-region being scanned on the plate, the temporal resolution can be adjusted without having to insert wait times between acquisitions. Because the system is continuously scanning and acquiring data, the overall time to collect a kinetic data set from the plate is then simply the time to perform a single scan of the plate, multiplied by the number of time points required. Typically, 1 time point before addition of compounds and 2 or 3 time points following addition should be sufficient for screening purposes.

Figure 14:
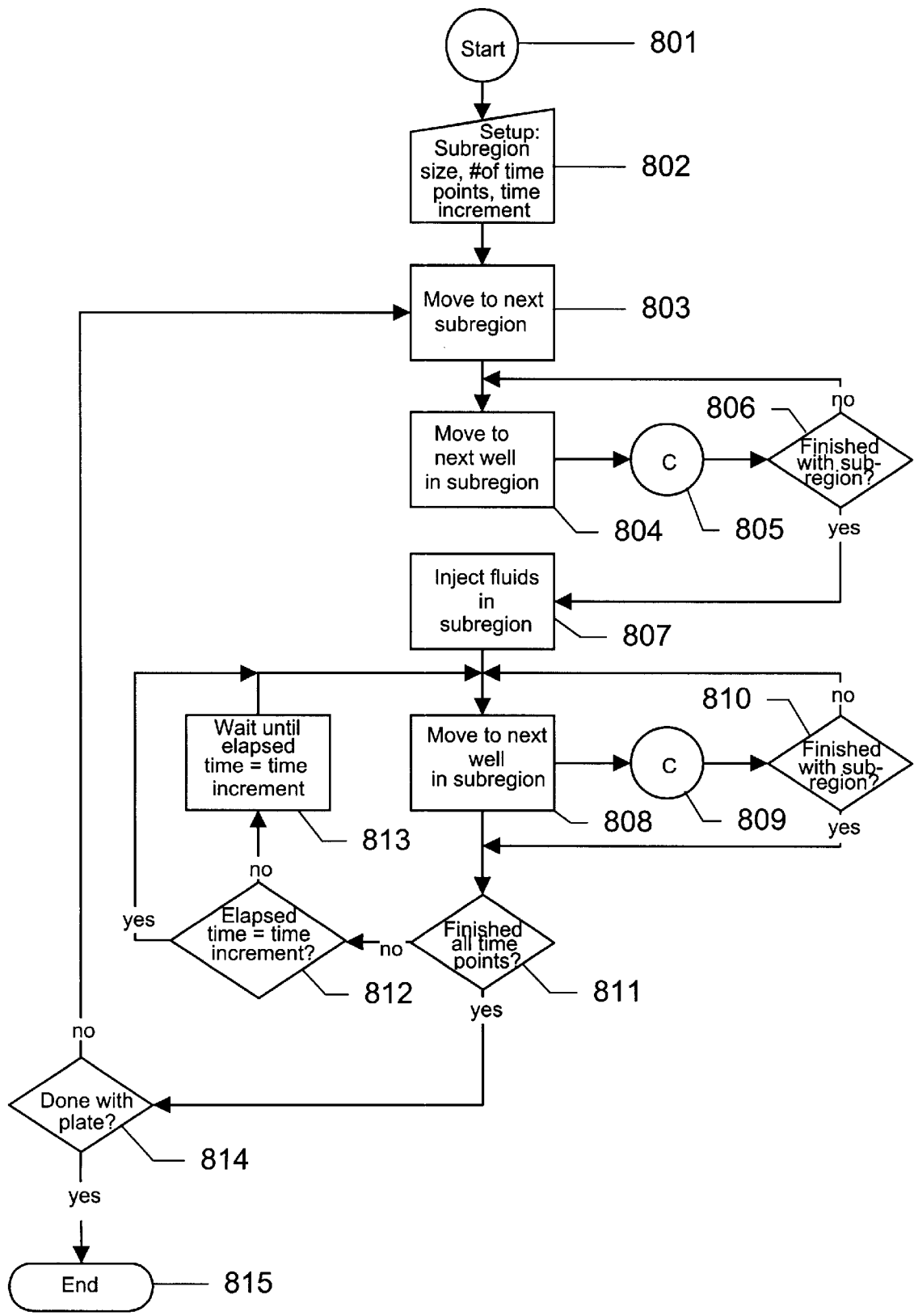
FIG. 14 is a flow chart defining the processing steps required for acquiring kinetic data in the High Content mode of the System for Cell Based Screening.
Figure 15:
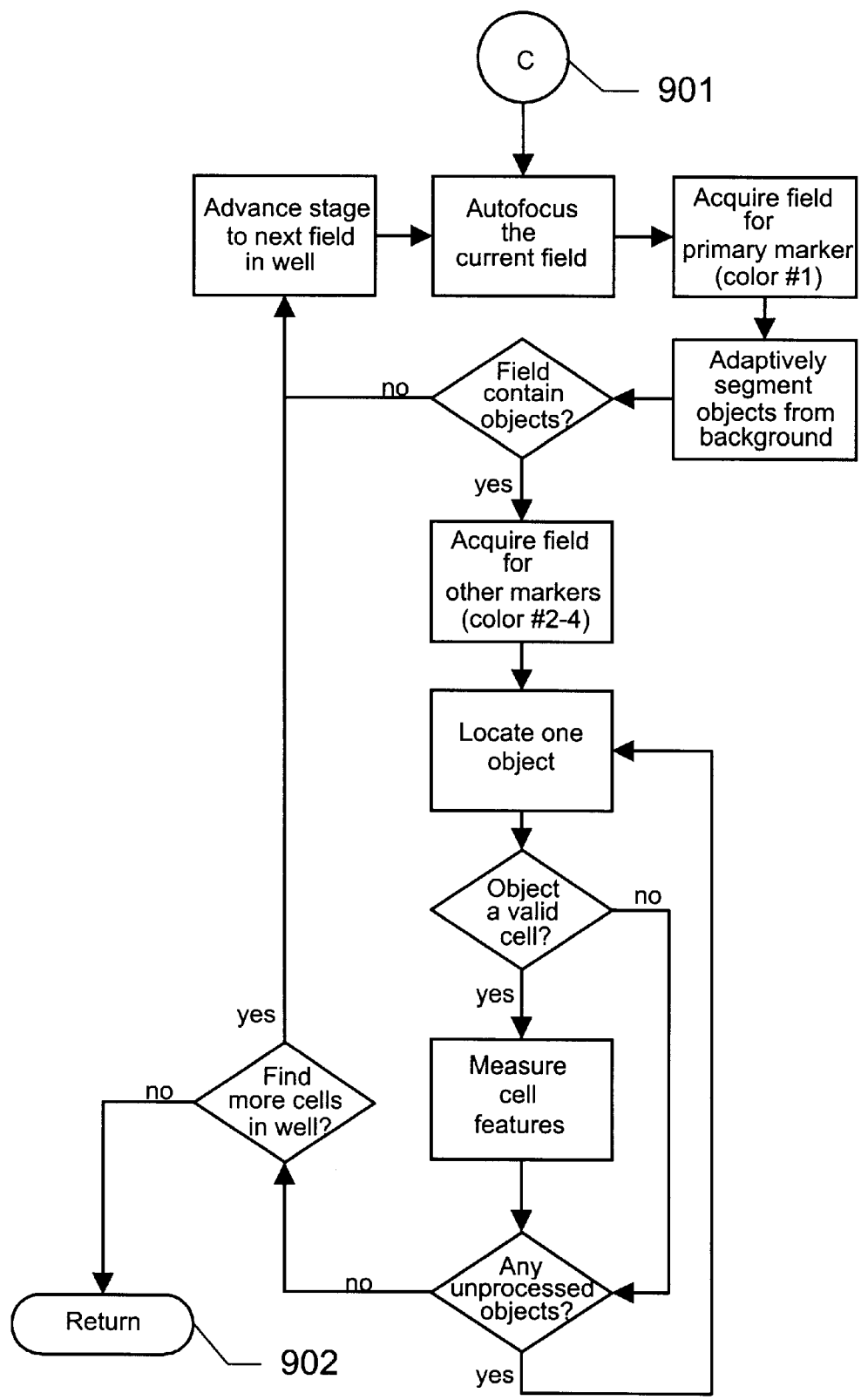
FIG. 15 is a flow chart defining the processing steps performed within a well during the acquisition of kinetic data.

FIG. 14 shows the acquisition sequence used for kinetic analysis. The start of processing 801 is configuration of the system, much of which is identical to the standard HCS configuration. In addition, the operator must enter information specific to the kinetic analysis being performed 802, such as the sub-region size, the number of time points required, and the required time increment. A sub-region is a group of wells that will be scanned repetitively in order to accumulate kinetic data. The size of the sub-region is adjusted so that the system can scan a whole sub-region once during a single time increment, thus minimizing wait times. The optimum sub-region size is calculated from the setup parameters, and adjusted if necessary by the operator. The system then moves the plate to the first sub-region 803, and to the first well in that sub-region 804 to acquire the prestimulation (time=0) time points. The acquisition sequence performed in each well is exactly the same as that required for the specific HCS being run in kinetic mode. FIG. 15 details a flow chart for that processing. All of the steps between the start 901 and the return 902 are identical to those described as steps 504–514 in FIG. 13.

After processing each well in a sub-region, the system checks to see if all the wells in the sub-region have been processed 806 (FIG. 14), and cycles through all the wells until the whole region has been processed. The system then moves the plate into position for fluid addition, and controls fluidic system delivery of fluids to the entire sub-region 807. This may require multiple additions for sub-regions which span several rows on the plate, with the system moving the plate on the X,Y stage between additions. Once the fluids have been added, the system moves to the first well in the sub-region 808 to begin acquisition of time points. The data is acquired from each well 809 and as before the system cycles through all the wells in the sub-region 810. After each pass through the sub-region, the system checks whether all the time points have been collected 811 and if not, pauses 813 if necessary 812 to stay synchronized with the requested time increment. Otherwise, the system checks for additional sub-regions on the plate 814 and either moves to the next sub-region 803 or finishes 815. Thus, the kinetic analysis mode comprises operator identification of sub-regions of the microtiter plate or microwells to be screened, based on the kinetic response to be investigated, with data acquisitions within a sub-region prior to data acquisition in subsequent sub-regions.

Specific Screens

In another aspect of the present invention, cell screening methods and machine readable storage medium comprising a program containing a set of instructions for causing a cell screening system to execute procedures for defining the distribution and activity of specific cellular constituents and processes is provided. In a preferred embodiment, the cell screening system comprises a high magnification fluorescence optical system with a stage adapted for holding cells and a means for moving the stage, a digital camera, a light source for receiving and processing the digital data from the digital camera, and a computer means for receiving and processing the digital data from the digital camera. This aspect of the invention comprises programs that instruct the cell screening system to define the distribution and activity of specific cellular constituents and processes, using the luminescent probes, the optical imaging system, and the pattern recognition software of the invention. Preferred embodiments of the machine readable storage medium comprise programs consisting of a set of instructions for causing a cell screening system to execute the procedures set forth in FIGS. 9, 11, 12, 13, 14 or 15. Another preferred embodiment comprises a program consisting of a set of instructions for causing a cell screening system to execute procedures for detecting the distribution and activity of specific cellular constituents and processes. In most preferred embodiments, the cellular processes include, but are not limited to, nuclear translocation of a protein, cellular morphology, apoptosis, receptor internalization, and protease-induced translocation of a protein.

In a preferred embodiment, the cell screening methods are used to identify compounds that modify the various cellular processes. The cells can be contacted with a test compound, and the effect of the test compound on a particular cellular process can be analyzed. Alternatively, the cells can be contacted with a test compound and a known agent that modifies the particular cellular process, to determine whether the test compound can inhibit or enhance the effect of the known agent. Thus, the methods can be used to identify test compounds that increase or decrease a particular cellular response, as well as to identify test compounds that affects the ability of other agents to increase or decrease a particular cellular response.

In another preferred embodiment, the locations containing cells are analyzed using the above methods at low resolution in a high throughput mode, and only a subset of the locations containing cells are analyzed in a high content mode to obtain luminescent signals from the luminescently labeled reporter molecules in subcellular compartments of the cells being analyzed.

The following examples are intended for purposes of illustration only and should not be construed to limit the scope of the invention, as defined in the claims appended hereto.

The various chemical compounds, reagents, dyes, and antibodies that are referred to in the following Examples are commercially available from such sources as Sigma Chemical (St. Louis, Mo.), Molecular Probes (Eugene, Oreg.), Aldrich Chemical Company (Milwaukee, Wis.), Accurate Chemical Company (Westbury, N.Y.), Jackson Immunolabs, and Clontech (Palo Alto, Calif.).

EXAMPLE 1

Cytoplasm to Nucleus Translocation Screening a. Transcription Factors

Regulation of transcription of some genes involves activation of a transcription factor in the cytoplasm, resulting in that factor being transported into the nucleus where it can initiate transcription of a particular gene or genes. This change in transcription factor distribution is the basis of a screen for the cell-based screening system to detect compounds that inhibit or induce transcription of a particular gene or group of genes. A general description of the screen is given followed by a specific example.

The distribution of the transcription factor is determined by labeling the nuclei with a DNA specific fluorophore like Hoechst 33423 and the transcription factor with a specific fluorescent antibody. After autofocusing on the Hoechst labeled nuclei, an image of the nuclei is acquired in the cell-based screening system and used to create a mask by one of several optional thresholding methods, as described supra. The morphological descriptors of the regions defined by the mask are compared with the user defined parameters and valid nuclear masks are identified and used with the following method to extract transcription factor distributions. Each valid nuclear mask is eroded to define a slightly smaller nuclear region. The original nuclear mask is then dilated in two steps to define a ring shaped region around the nucleus, which represents a cytoplasmic region. The average antibody fluorescence in each of these two regions is determined, and the difference between these averages is defined as the NucCyt Difference. Two examples of determining nuclear translocation are discussed below and illustrated in FIGS. 10A–J. FIG. 10A illustrates an unstimulated cell with its nucleus 200 labeled with a blue fluorophore and a transcription factor in the cytoplasm 201 labeled with a green fluorophore. FIG. 10B illustrates the nuclear mask 202 derived by the cell-based screening system. FIG. 10C illustrates the cytoplasm 203 of the unstimulated cell imaged at a green wavelength. FIG. 10D illustrates the nuclear mask 202 is eroded (reduced) once to define a nuclear sampling region 204 with minimal cytoplasmic distribution. The nucleus boundary 202 is dilated (expanded) several times to form a ring that is 2–3 pixels wide that is used to define the cytoplasmic sampling region 205 for the same cell. FIG. 10E further illustrates a side view which shows the nuclear sampling region 204 and the cytoplasmic sampling region 205. Using these two sampling regions, data on nuclear translocation can be automatically analyzed by the cell-based screening system on a cell by cell basis. FIGS. 10F–J illustrates the strategy for determining nuclear translocation in a stimulated cell. FIG. 10F illustrates a stimulated cell with its nucleus 206 labeled with a blue fluorophore and a transcription factor in the cytoplasm 207 labeled with a green fluorophore. The nuclear mask 208 in FIG. 10G is derived by the cell based screening system. FIG. 10H illustrates the cytoplasm 209 of a stimulated cell imaged at a green wavelength. FIG. 10I illustrates the nuclear sampling region 211 and cytoplasmic sampling region 212 of the stimulated cell. FIG. 10J further illustrates a side view which shows the nuclear sampling region 211 and the cytoplasmic sampling region 212.

Figure 16:
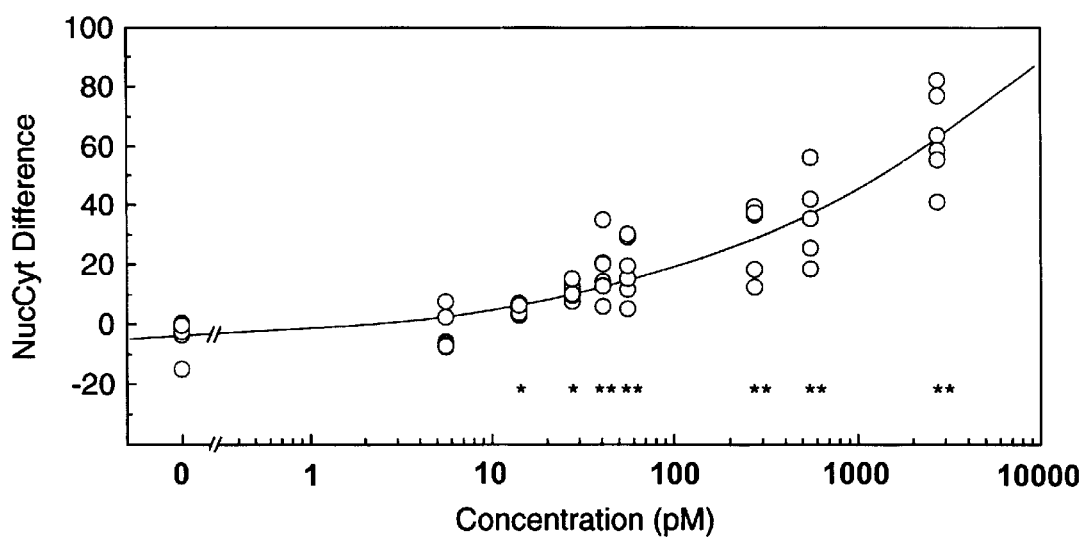
FIG. 16 is an example of data from a known inhibitor of translocation.
Figure 17:
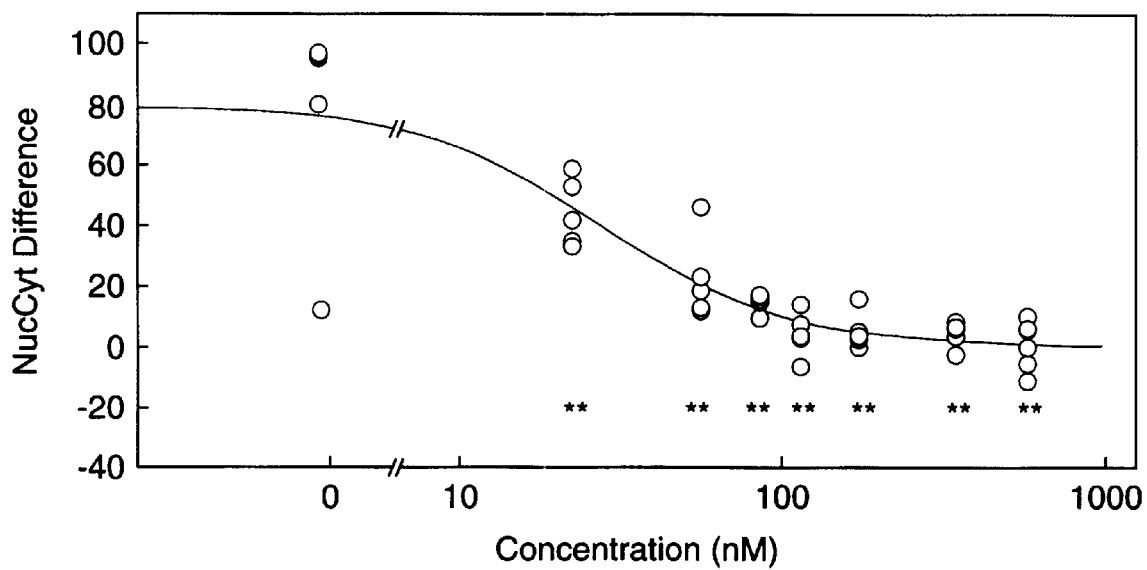
FIG. 17 is an example of data from a known stimulator of translocation.

A specific application of this method has been used to validate this method as a screen. A human cell line was plated in 96 well microtiter plates. Some rows of wells were titrated with IL-1, a known inducer of the NF-KB transcription factor. The cells were then fixed and stained by standard methods with a fluorescein labeled antibody to the transcription factor, and Hoechst 33423. The cell-based screening system was used to acquire and analyze images from this plate and the NucCyt Difference was found to be strongly correlated with the amount of agonist added to the wells as illustrated in FIG. 16. In a second experiment, an antagonist to the receptor for IL-1, IL-1RA was titrated in the presence of IL-1α, progressively inhibiting the translocation induced by IL-1α. The NucCyt Difference was found to strongly correlate with this inhibition of translocation, as illustrated in FIG. 17.

Additional experiments have shown that the NucCyt Difference, as well as the NucCyt ratio, gives consistent results over a wide range of cell densities and reagent concentrations, and can therefore be routinely used to screen compound libraries for specific nuclear translocation activity. Furthermore, the same method can be used with antibodies to other transcription factors, or GFP-transcription factor chimeras, or fluorescently labeled transcription factors introduced into living or fixed cells, to screen for effects on the regulation of transcription factor activity.

Figure 18:
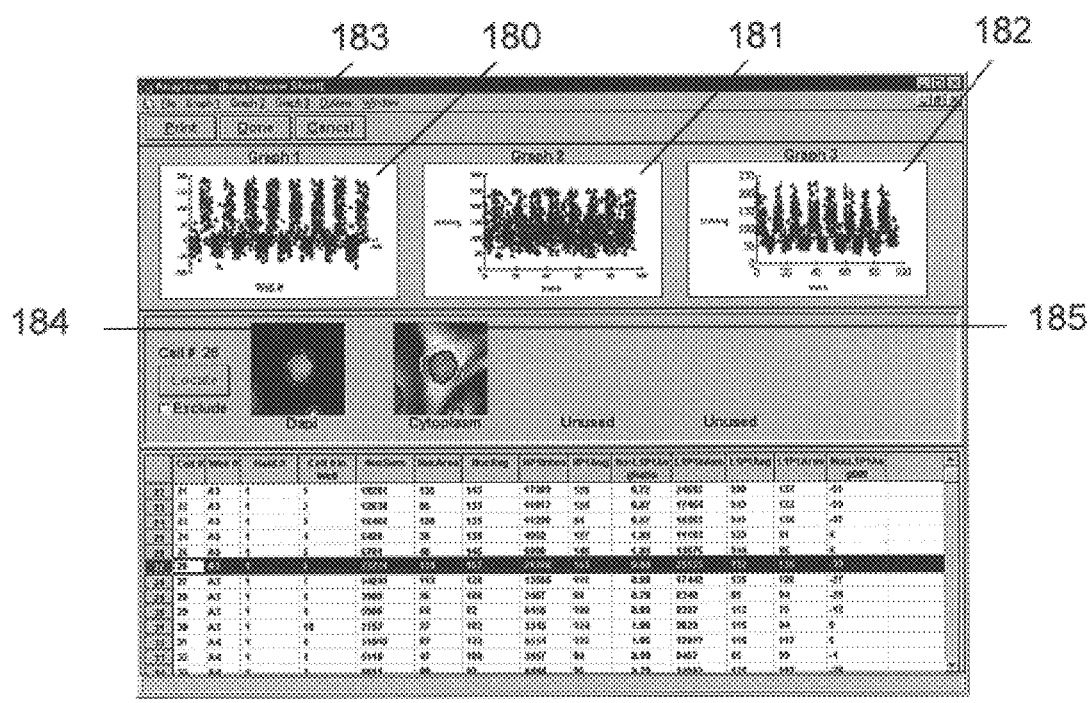
FIG. 18 illustrates data presentation on a graphical display.

FIG. 18 is a representative display on a PC screen of data which was obtained in accordance with Example 1. Graph 1 180 plots the difference between the average antibody fluorescence in the nuclear sampling region and cytoplasmic sampling region, NucCyt Difference verses Well #. Graph 2 181 plots the average fluorescence of the antibody in the nuclear sampling region, NP1 average, versus the Well #. Graph 3 182 plots the average antibody fluorescence in the cytoplasmic sampling region, L1P1 average, versus Well #. The software permits displaying data from each cell. For example, FIG. 18 shows a screen display 183, the nuclear image 184, and the fluorescent antibody image 185 for cell #26.

NucCyt Difference referred to in graph 1 180 of FIG. 18 is the difference between the average cytoplasmic probe (fluorescent reporter molecule) intensity and the average nuclear probe (fluorescent reporter molecule) intensity. NP1 average referred to in graph 2 181 of FIG. 18 is the average of cytoplasmic probe (fluorescent reporter molecule) intensity within the nuclear sampling region. L1P1 average referred to in graph 3 182 of FIG. 18 is the average probe (fluorescent reporter molecule) intensity within the cytoplasmic sampling region.

It will be understood by one of skill in the art that this aspect of the invention can be performed using other transcription factors that translocate from the cytoplasm to the nucleus upon activation. In another specific example, activation of the c-fos transcription factor was assessed by defining its spatial position within cells. Activated c-fos is found only within the nucleus, while inactivated c-fos resides within the cytoplasm.

3T3 cells were plated at 5000–10000 cells per well in a Polyfiltronics 96-well plate. The cells were allowed to attach and grow overnight. The cells were rinsed twice with 100 μl serum-free medium, incubated for 24–30 hours in serum-free MEM culture medium, and then stimulated with platelet derived growth factor (PDGF-BB) (Sigma Chemical Co., St. Louis, Mo.) diluted directly into serum free medium at concentrations ranging from 1–50 ng/ml for an average time of 20 minutes.

Following stimulation, cells were fixed for 20 minutes in 3.7% formaldehyde solution in 1X Hanks buffered saline solution (HBSS). After fixation, the cells were washed with HBSS to remove residual fixative, permeabilized for 90 seconds with 0.5% Triton X-100 solution in HBSS, and washed twice with HBSS to remove residual detergent. The cells were then blocked for 15 minutes with a 0.1% solution of BSA in HBSS, and further washed with HBSS prior to addition of diluted primary antibody solution.

c-Fos rabbit polyclonal antibody (Calbiochem, PC05) was diluted 1:50 in HBSS, and 50 μl of the dilution was applied to each well. Cells were incubated in the presence of primary antibody for one hour at room temperature, and then incubated for one hour at room temperature in a light tight container with goat anti-rabbit secondary antibody conjugated to ALEXA™ 488 (Molecular Probes), diluted 1:500 from a 100 μg/ml stock in HBSS. Hoechst DNA dye (Molecular Probes) was then added at a 1:1000 dilution of the manufacturer's stock solution (10 mg/ml). The cells were then washed with HBSS, and the plate was sealed prior to analysis with the cell screening system of the invention. The data from these experiments demonstrated that the methods of the invention could be used to measure transcriptional activation of c-fos by defining its spatial position within cells.

One of skill in the art will recognize that while the following method is applied to detection of c-fos activation, it can be applied to the analysis of any transcription factor that translocates from the cytoplasm to the nucleus upon activation. Examples of such transcription factors include, but are not limited to fos and jun homologs, NF-KB (nuclear factor kappa from B cells), NFAT (nuclear factor of activated T-lymphocytes), and STATs (signal transducer and activator of transcription) factors (For example, see Strehlow, I., and Schindler, C. 1998. *J. Biol. Chem.* 273:28049–28056; Chow, et al. 1997 *Science.* 278:1638–1641; Ding et al. 1998 J. Biol. Chem. 273:28897–28905; Baldwin, 1996. *Annu Rev Immunol.* 14:649–83; Kuo, C. T., and J. M. Leiden. 1999. *Annu Rev Immunol.* 17:149–87; Rao, et al. 1997. Annu Rev Immunol. 15:707–47; Masuda,et al. 1998. *Cell Signal.* 10:599–611; Hoey, T., and U. Schindler. 1998. *Curr Opin Genet Dev.* 8:582–7; Liu, et al. 1998. *Curr Opin Immunol.* 10:271–8.) Thus, in this aspect of the invention, indicator cells are treated with test compounds and the distribution of luminescently labeled transcription factor is measured in space and time using a cell screening system, such as the one disclosed above. The luminescently labeled transcription factor may be expressed by or added to the cells either before, together with, or after contacting the cells with a test compound. For example, the transcription factor may be expressed as a luminescently labeled protein chimera by transfected indicator cells. Alternatively, the luminescently labeled transcription factor may be expressed, isolated, and bulk-loaded into the indicator cells as described above, or the transcription factor may be luminescently labeled after isolation. As a further alternative, the transcription factor is expressed by the indicator cell, which is subsequently contacted with a luminescent label, such as an antibody, that detects the transcription factor.

In a further aspect, kits are provided for analyzing transcription factor activation, comprising an antibody that specifically recognizes a transcription factor of interest, and instructions for using the antibody for carrying out the methods described above. In a preferred embodiment, the transcription factor-specific antibody, or a secondary antibody that detects the transcription factor antibody, is luminescently labeled. In further preferred embodiments, the kit contains cells that express the transcription factor of interest, and/or the kit contains a compound that is known to modify activation of the transcription factor of interest, including but not limited to platelet derived growth factor (PDGF) and serum, which both modify fos activation; and interleukin 1(IL-1) and tumor necrosis factor (TNF), which both modify NF-KB activation.

In another embodiment, the kit comprises a recombinant expression vector comprising a nucleic acid encoding a transcription factor of interest that translocates from the cytoplasm to the nucleus upon activation, and instructions for using the expression vector to identify compounds that modify transcription factor activation in a cell of interest. Alternatively, the kits contain a purified, luminescently labeled transcription factor. In a preferred embodiment, the transcription factor is expressed as a fusion protein with a luminescent protein, including but not limited to green fluorescent protein, luceriferase, or mutants or fragments thereof. In various preferred embodiments, the kit further contains cells that are transfected with the expression vector, an antibody or fragment that specifically bind to the transcription factor of interest, and/or a compound that is known to modify activation of the transcription factor of interest (as above).

b. Protein Kinases

The cytoplasm to nucleus screening methods can also be used to analyze the activation of any protein kinase that is present in an inactive state in the cytoplasm and is transported to the nucleus upon activation, or that phosphorylates a substrate that translocates from the cytoplasm to the nucleus upon phosphorylation. Examples of appropriate protein kinases include, but are not limited to extracellular signal-regulated protein kinases (ERKs), c-Jun aminoterminal kinases (JNKs), Fos regulating protein kinases (FRKs), p38 mitogen activated protein kinase (p38MAPK), protein kinase A (PKA), and mitogen activated protein kinase kinases (MAPKKs). (For example, see Hall, et al. 1999. *J Biol Chem.* 274:376–83; Han, et al. 1995. *Biochim. Biophys. Acta.* 1265:224–227; Jaaro et al. 1997. *Proc. Natl. Acad. Sci. U.S.A.* 94:3742–3747; Taylor, et al. 1994. *J. Biol. Chem.* 269:308–318; Zhao, Q., and F. S. Lee. 1999. *J Biol Chem.* 274:8355–8; Paolilloet al. 1999. *J Biol Chem.* 274:6546–52; Coso et al. 1995. Cell 81:1137–1146; Tibbles, L. A., and J. R. Woodgett. 1999. *Cell Mol Life Sci.* 55:1230–54; Schaeffer, H. J., and M. J. Weber. 1999. *Mol Cell Biol.* 19:2435–44.)

Alternatively, protein kinase activity is assayed by monitoring translocation of a luminescently labeled protein kinase substrate from the cytoplasm to the nucleus after being phosphorylated by the protein kinase of interest. In this embodiment, the substrate is non-phosphorylated and cytoplasmic prior to phosphorylation, and is translocated to the nucleus upon phosphorylation by the protein kinase. There is no requirement that the protein kinase itself translocates from the cytoplasm to the nucleus in this embodiment. Examples of such substrates (and the corresponding protein kinase) include, but are not limited to c-jun (JNK substrate); fos (FRK substrate), and p38 (p38 MAPK substrate).

Thus, in these embodiments, indicator cells are treated with test compounds and the distribution of luminescently labeled protein kinase or protein kinase substrate is measured in space and time using a cell screening system, such as the one disclosed above. The luminescently labeled protein kinase or protein kinase substrate may be expressed by or added to the cells either before, together with, or after contacting the cells with a test compound. For example, the protein kinase or protein kinase substrate may be expressed as a luminescently labeled protein chimera by transfected indicator cells. Alternatively, the luminescently labeled protein kinase or protein kinase substrate may be expressed, isolated, and bulk-loaded into the indicator cells as described above, or the protein kinase or protein kinase substrate may be luminescently labeled after isolation. As a further alternative, the protein kinase or protein kinase substrate is expressed by the indicator cell, which is subsequently contacted with a luminescent label, such as a labeled antibody, that detects the protein kinase or protein kinase substrate.

In a further embodiment, protein kinase, activity is assayed by monitoring the phosphorylation state (ie: phosphorylated or not phosphorylated) of a protein kinase substrate. In this embodiment, there is no requirement that either the protein kinase or the protein kinase substrate translocate from the cytoplasm to the nucleus upon activation. In a preferred embodiment, phosphorylation state is monitored by contacting the cells with an antibody that binds only to the phosphorylated form of the protein kinase substrate of interest (For example, as disclosed in U.S. Pat. No. 5,599,681).

In another preferred embodiment, a biosensor of phosphorylation is used. For example, a luminescently labeled protein or fragment thereof can be fused to a protein that has been engineered to contain (a) a phosphorylation site that is recognized by a protein kinase of interest; and (b) a nuclear localization signal that is unmasked by the phosphorylation. Such a biosensor will thus be translocated to the nucleus upon phosphorylation, and its translocation can be used as a measure of protein kinase activation.

In another aspect, kits are provided for analyzing protein kinase activation, comprising a primary antibody that specifically binds to a protein kinase, a protein kinase substrate, or a phosphorylated form of the protein kinase substrate of interest and instructions for using the primary antibody to identify compounds that modify protein kinase activation in a cell of interest. In a preferred embodiment, the primary antibody, or a secondary antibody that detects the primary antibody, is luminescently labeled. In other preferred embodiments, the kit further comprises cells that express the protein kinase of interest, and/or a compound that is known to modify activation of the protein kinase of interest, including but not limited to dibutyryl cAMP (modifies PKA), forskolin (PKA), and anisomycin (p38MAPK).

Alternatively, the kits comprise an expression vector encoding a protein kinase or a protein kinase substrate of interest that translocates from the cytoplasm to the nucleus upon activation and instructions for using the expression vector to identify compounds that modify protein kinase activation in a cell of interest. Alternatively, the kits contain a purified, luminescently labeled protein kinase or protein kinase substrate. In a preferred embodiment, the protein kinase or protein kinase substrate of interest is expressed as a fusion protein with a luminescent protein. In further preferred embodiments, the kit further comprises cells that are transfected with the expression vector, an antibody or fragment thereof that specifically binds to the protein kinase or protein kinase substrate of interest, and/or a compound that is known to modify activation of the protein kinase of interest. (as above)

In another aspect, the present invention comprises a machine readable storage medium comprising a program containing a set of instructions for causing a cell screening system to execute the methods disclosed for analyzing transcription factor or protein kinase activation, wherein the cell screening system comprises an optical system with a stage adapted for holding a plate containing cells, a digital camera, a means for directing fluorescence or luminescence emitted from the cells to the digital camera, and a computer means for receiving and processing the digital data from the digital camera.

EXAMPLE 2

Automated Screen for Compounds that Modify Cellular Morphology

Changes in cell size are associated with a number of cellular conditions, such as hypertrophy, cell attachment and spreading, differentiation, growth and division, necrotic and programmed cell death, cell motility, morphogenesis, tube formation, and colony formation.

For example, cellular hypertrophy has been associated with a cascade of alterations in gene expression and can be characterized in cell culture by an alteration in cell size, that is clearly visible in adherent cells growing on a coverslip.

Cell size can also be measured to determine the attachment and spreading of adherent cells. Cell spreading is the result of selective binding of cell surface receptors to substrate ligands and subsequent activation of signaling pathways to the cytoskeleton. Cell attachment and spreading to substrate molecules is an important step for the metastasis of cancer cells, leukocyte activation during the inflammatory response, keratinocyte movement during wound healing, and endothelial cell movement during angiogenesis. Compounds that affect these surface receptors, signaling pathways, or the cytoskeleton will affect cell spreading and can be screened by measuring cell size.

Total cellular area can be monitored by labeling the entire cell body or the cell cytoplasm using cytoskeletal markers, cytosolic volume markers, or cell surface markers, in conjunction with a DNA label. Examples of such labels (many available from Molecular Probes (Eugene, Oreg.) and Sigma Chemical Co. (St. Louis, Mo.)) include the following:

| CELL SIZE AND AREA MARKERS |
|---|
| Cytoskeletal Markers |
| ALEXA ™ 488 phalloidin (Molecular Probes, Oregon) |
| Tubulin-green fluorescent protein chimeras |
| Cytokeratin-green fluorescent protein chimeras |
| Antibodies to cytoskeletal proteins |
| Cytosolic Volume Markers |
| Green fluorescent proteins |
| Chloromethylfluorescein diacetate (CMFDA) |
| Calcein green |
| BCECF/AM ester |
| Rhodamine dextran |
| Cell Surface Markers for Lipid, Protein, or Oligosaccharide |
| Dihexadecyl tetramethylindocarbocyanine perchlorate (DiIC16) lipid dyes |
| Triethylammonium propyl dibutylamino styryl pyridinium (FM 4–64, FM 1–43) lipid dyes |
| MITOTRACKER ™ Green FM |
| Lectins to oligosaccharides such as fluorescein concanavalin A or wheat germ agglutinin |
| SYPRO ™ Red non-specific protein markers |
| Antibodies to various surface proteins such as epidermal growth factor |
| Biotin labeling of surface proteins followed by fluorescent strepavidin labeleing |

Protocols for cell staining with these various agents are well known to those skilled in the art. Cells are stained live or after fixation and the cell area can be measured. For example, live cells stained with DiIC16 have homogeneously labeled plasma membranes, and the projected cross-sectional area of the cell is uniformly discriminated from background by fluorescence intensity of the dye. Live cells stained with cytosolic stains such as CMFDA produce a fluorescence intensity that is proportional to cell thickness. Although cell labeling is dimmer in thin regions of the cell, total cell area can be discriminated from background. Fixed cells can be stained with cytoskeletal markers such as ALEXA™ 488 phalloidin that label polymerized actin. Phalloidin does not homogeneously stain the cytoplasm, but still permits discrimination of the total cell area from background.

Cellular Hypertrophy

A screen to analyze cellular hypertrophy is implemented using the following strategy. Primary rat myocytes can be cultured in 96 well plates, treated with various compounds and then fixed and labeled with a fluorescent marker for the cell membrane or cytoplasm, or cytoskeleton, such as an antibody to a cell surface marker or a fluorescent marker for the cytoskeleton like rhodamine-phalloidin, in combination with a DNA label like Hoechst.

After focusing on the Hoechst labeled nuclei, two images are acquired, one of the Hoechst labeled nuclei and one of the fluorescent cytoplasm image. The nuclei are identified by thresholding to create a mask and then comparing the morphological descriptors of the mask with a set of user defined descriptor values. Each non-nucleus image (or "cytoplasmic image") is then processed separately. The original cytoplasm image can be thresholded, creating a cytoplasmic mask image. Local regions containing cells are defined around the nuclei. The limits of the cells in those regions are then defined by a local dynamic threshold operation on the same region in the fluorescent antibody image. A sequence of erosions and dilations is used to separate slightly touching cells and a second set of morphological descriptors is used to identify single cells. The area of the individual cells is tabulated in order to define the distribution of cell sizes for comparison with size data from normal and hypertrophic cells.

Responses from entire 96-well plates (measured as average cytoplasmic area/cell) were analyzed by the above methods, and the results demonstrated that the assay will perform the same on a well-to-well, plate-to-plate, and day-to-day basis (below a 15% cov for maximum signal). The data showed very good correlation for each day, and that there was no variability due to well position in the plate.

The following totals can be computed for the field. The aggregate whole nucleus area is the number of nonzero pixels in the nuclear mask. The average whole nucleus area is the aggregate whole nucleus area divided by the total number of nuclei. For each cytoplasm image several values can be computed. These are the total cytoplasmic area, which is the count of nonzero pixels in the cytoplasmic mask. The aggregate cytoplasm intensity is the sum of the intensities of all pixels in the cytoplasmic mask. The cytoplasmic area per nucleus is the total cytoplasmic area divided by the total nucleus count. The cytoplasmic intensity per nucleus is the aggregate cytoplasm -intensity divided by the total nucleus count. The average cytoplasm intensity is the aggregate cytoplasm intensity divided by the cytoplasm area. The cytoplasm nucleus ratio is the total cytoplasm area divided by the total nucleus area.

Additionally, one or more fluorescent antibodies to other cellular proteins, such as the major muscle proteins actin or myosin, can be included. Images of these additional labeled proteins can be acquired and stored with the above images, for later review, to identify anomalies in the distribution and morphology of these proteins in hypertrophic cells. This example of a multi-parametric screen allows for simultaneous analysis of cellular hypertrophy and changes in actin or myosin distribution.

One of skill in the art will recognize that while the example analyzes myocyte hypertrophy, the methods can be applied to analyzing hypertrophy, or general morphological changes in any cell type.

Cell Morphology Assays for Prostate Carcinoma

Cell spreading is a measure of the response of cell surface receptors to substrate attachment ligands. Spreading is proportional to the ligand concentration or to the concentration of compounds that reduce receptor-ligand function. One example of selective cell-substrate attachment is prostate carcinoma cell adhesion to the extracellular matrix protein collagen. Prostate carcinoma cells metastasize to bone via selective adhesion to collagen.

Compounds that interfere with metastasis of prostate carcinoma cells were screened as follows. PC3 human prostate carcinoma cells were cultured in media with appropriate stimulants and are passaged to collagen coated 96 well plates. Ligand concentration can be varied or inhibitors of cell spreading can be added to the wells. Examples of compounds that can affect spreading are receptor antagonists such as integrin- or proteoglycan-blocking antibodies, signaling inhibitors including phosphatidyl inositol-3 kinase inhibitors, and cytoskeletal inhibitors such as cytochalasin D. After two hours, cells were fixed and stained with ALEXA™ 488 phalloidin (Molecular Probes) and Hoechst 33342 as per the protocol for cellular hypertrophy. The size of cells under these various conditions, as measured by cytoplasmic staining, can be distinguished above background levels. The number of cells per field is determined by measuring the number of nuclei stained with the Hoechst DNA dye. The area per cell is found by dividing the cytoplasmic area (phalloidin image) by the cell number (Hoechst image). The size of cells is proportional to the ligand-receptor function. Since the area is determined by ligand concentration and by the resultant function of the cell, drug efficacy, as well as drug potency, can be determined by this cell-based assay. Other measurements can be made as discussed above for cellular hypertrophy.

The methods for analyzing cellular morphology can be used in a combined high throughput-high content screen. In one example, the high throughput mode scans the whole well for an increase in fluorescent phalloidin intensity. A threshold is set above which both nuclei (Hoechst) and cells (phalloidin) are measured in a high content mode. In another example, an environmental biosensor (examples include, but are not limited to, those biosensors that are sensitive to calcium and pH changes) is added to the cells, and the cells are contacted with a compound. The cells are scanned in a high throughput mode, and those wells that exceed a predetermined threshold for luminescence of the biosensor are scanned in a high content mode.

In a further aspect, kits are provided for analyzing cellular morphology, comprising a luminescent compound that can be used to specifically label the cell cytoplasm, membrane, or cytoskeleton (such as those described above), and instructions for using the luminescent compound to identify test stimuli that induce or inhibit changes in cellular morphology according to the above methods. In a preferred embodiment, the kit further comprises a luminescent marker for cell nuclei. In a further preferred embodiment, the kit comprises at least one compound that is known to modify cellular morphology, including, but not limited to integrin- or proteoglycan-blocking antibodies, signaling inhibitors including phosphatidyl inositol-3 kinase inhibitors, and cytoskeletal inhibitors such as cytochalasin D.

In another aspect, the present invention comprises a machine readable storage medium comprising a program containing a set of instructions for causing a cell screening system to execute the disclosed methods for analyzing cellular morphology, wherein the cell screening system comprises an optical system with a stage adapted for holding a plate containing cells, a digital camera, a means for directing fluorescence or luminescence emitted from the cells to the digital camera, and a computer means for receiving and processing the digital data from the digital camera.

EXAMPLE 3

Dual Mode High Throughput and High-Content Screen

The following example is a screen for activation of a G-protein coupled receptor (GPCR) as detected by the translocation of the GPCR from the plasma membrane to a proximal nuclear location. This example illustrates how a high throughput screen can be coupled with a high-content screen in the dual mode System for Cell Based Screening.

G-protein coupled receptors are a large class of 7 transmembrane domain cell surface receptors. Ligands for these receptors stimulate a cascade of secondary signals in the cell, which may include, but are not limited to, $Ca^{++}$ transients, cyclic AMP production, inositol triphosphate ($IP_3$) production and phosphorylation. Each of these signals are rapid, occuring in a matter of seconds to minutes, but are also generic. For example, many different GPCRs produce a secondary $Ca^{++}$ signal when activated. Stimulation of a GPCR also results in the transport of that GPCR from the cell surface membrane to an internal, proximal nuclear compartment. This internalization is a much more receptor-specific indicator of activation of a particular receptor than are the secondary signals described above.

Figure 19:
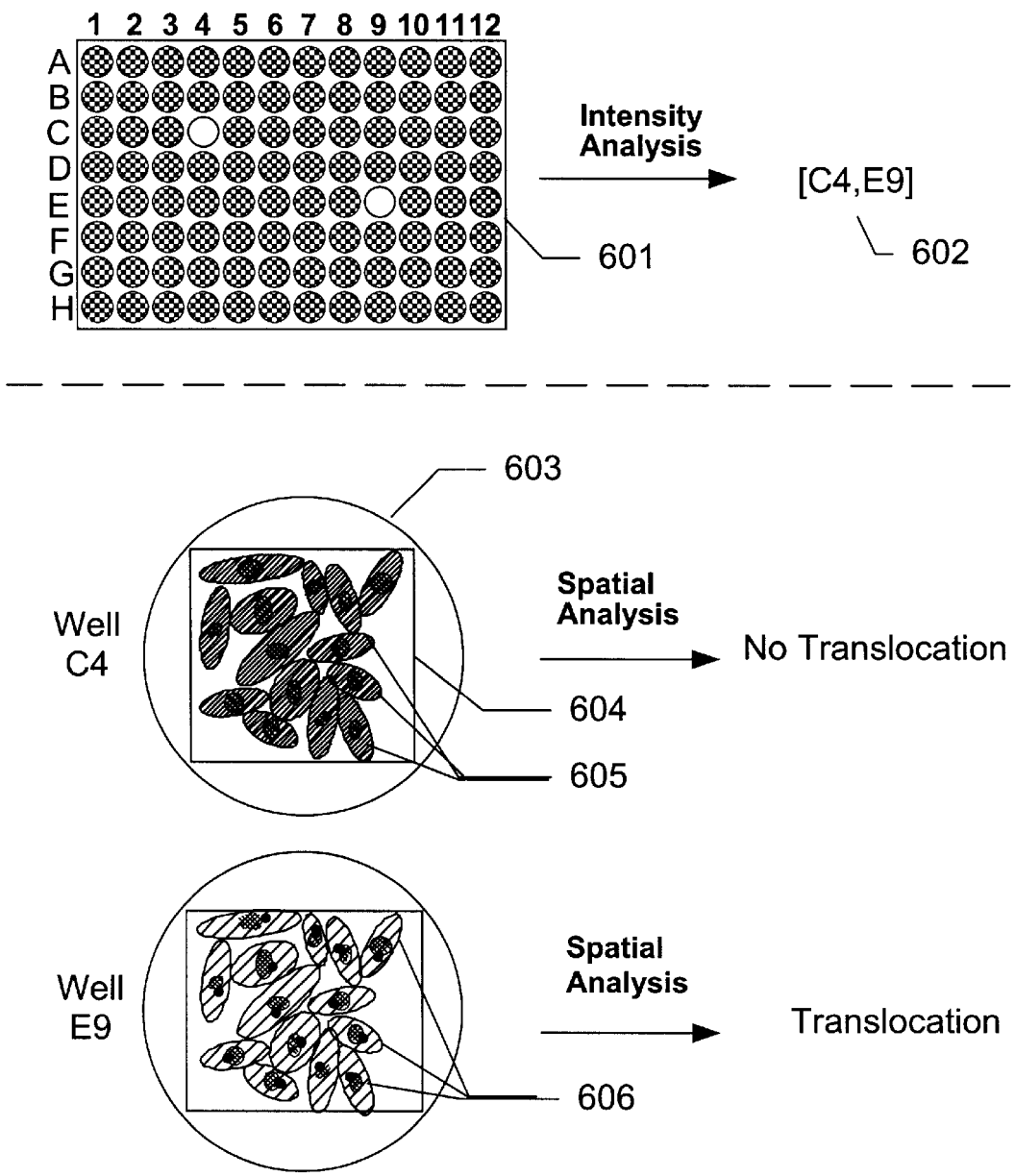
FIG. 19 is an illustration of the data from the High Throughput mode of the System for Cell Based Screening, an example of the data passed to the High Content mode, the data acquired in the high content mode, and the results of the analysis of that data.

FIG. 19 illustrates a dual mode screen for activation of a GPCR. Cells carrying a stable chimera of the GPCR with a blue fluorescent protein (BFP) would be loaded with the acetoxymethylester form of Fluo-3, a cell permeable calcium indicator (green fluorescence) that is trapped in living cells by the hydrolysis of the esters. They would then be deposited into the wells of a microtiter plate 601. The wells would then be treated with an array of test compounds using a fluid delivery system, and a short sequence of Fluo-3 images of the whole microtiter plate would be acquired and analyzed for wells exhibiting a calcium response (i.e., high throughput mode). The images would appear like the illustration of the microtiter plate 601 in FIG. 19. A small number of wells, such as wells C4 and E9 in the illustration, would fluoresce more brightly due to the $Ca^{++}$ released upon stimulation of the receptors. The locations of wells containing compounds that induced a response 602 would then be transferred to the HCS program and the optics switched for detailed cell by cell analysis of the blue fluorescence for evidence of GPCR translocation to the perinuclear region. The bottom of FIG. 19 illustrates the two possible outcomes of the analysis of the high resolution cell data. The camera images a sub-region 604 of the well area 603, producing images of the fluorescent cells 605. In well C4, the uniform distribution of the fluorescence in the cells indicates that the receptor has not internalized, implying that the $Ca^{++}$ response seen was the result of the stimulation of some other signalling system in the cell. The cells in well E9 606 on the other hand, clearly indicate a concentration of the receptor in the perinuclear region clearly indicating the full activation of the receptor. Because only a few hit wells have to be analyzed with high resolution, the overall throughput of the dual mode system can be quite high, comparable to the high throughput system alone.

EXAMPLE 4

Kinetic High Content Screen

The following is an example of a screen to measure the kinetics of internalization of a receptor. As described above, the stimulation of a GPCR, results in the internalization of the receptor, with a time course of about 15 min. Simply detecting the endpoint as internalized or not, may not be sufficient for defining the potency of a compound as a GPCR agonist or antagonist. However, 3 time points at 5 min intervals would provide information not only about potency during the time course of measurement, but would also allow extrapolation of the data to much longer time periods. To perform this assay, the sub-region would be defined as two rows, the sampling interval as 5 minutes and the total number of time points 3. The system would then start by scanning two rows, and then adding reagent to the two rows, establishing the time=0 reference. After reagent addition, the system would again scan the two row sub-region acquiring the first time point data. Since this process would take about 250 seconds, including scanning back to the beginning of the sub-region, the system would wait 50 seconds to begin acquisition of the second time point. Two more cycles would produce the three time points and the system would move on to the second 2 row sub-region. The final two 2-row sub-regions would be scanned to finish all the wells on the plate, resulting in four time points for each well over the whole plate. Although the time points for the wells would be offset slightly relative to time=0, the spacing of the time points would be very close to the required 5 minutes, and the actual acquisition times and results recorded with much greater precision than in a fixed-cell screen.

EXAMPLE 5

High-content Screen of Human Glucocorticoid Receptor Translocation

One class of HCS involves the drug-induced dynamic redistribution of intracellular constituents. The human glucocorticoid receptor (hGR), a single "sensor" in the complex environmental response machinery of the cell, binds steroid molecules that have diffused into the cell. The ligand-receptor complex translocates to the nucleus where transcriptional activation occurs (Htun et al., *Proc. Natl. Acad. Sci.* 93:4845, 1996).

In general, hormone receptors are excellent drug targets because their activity lies at the apex of key intracellular signaling pathways. Therefore, a high-content screen of hGR translocation has distinct advantage over in vitro ligand-receptor binding assays. The availability of up to two more channels of fluorescence in the cell screening system of the present invention permits the screen to contain two additional parameters in parallel, such as other receptors, other distinct targets or other cellular processes.

Plasmid Construct

A eukaryotic expression plasmid containing a coding sequence for a green fluorescent protein—human glucocorticoid receptor (GFP-hGR) chimera was prepared using GFP mutants (Palm et al., *Nat. Struct. Biol.* 4:361 (1997). The construct was used to transfect a human cervical carcinoma cell line (HeLa).

Cell Preparation and Transfection

HeLa cells (ATCC CCL-2) were trypsinized and plated using DMEM containing 5% charcoal/dextran-treated fetal bovine serum (FBS) (HyClone) and 1% penicillin-streptomycin (C-DMEM) 12–24 hours prior to transfection and incubated at 37° C. and 5% $CO_2$. Transfections were performed by calcium phosphate co-precipitation (Graham and Van der Eb, *Virology* 52:456, 1973; Sambrook et al., (1989). *Molecular Cloning: A Laboratory Manual*, Second ed. Cold Spring Harbor Laboratory Press, Cold Spring Harbor, 1989) or with Lipofectamine (Life Technologies, Gaithersburg, Md.). For the calcium phosphate transfections, the medium was replaced, prior to transfection, with DMEM containing 5% charcoal/dextran-treated FBS. Cells were incubated with the calcium phosphate-DNA precipitate for 4–5 hours at 37° C. and 5% $CO_2$, washed 3–4 times with DMEM to remove the precipitate, followed by the addition of C-DMEM.

Lipofectamine transfections were performed in serum-free DMEM without antibiotics according to the manufacturer's instructions (Life Technologies, Gaithersburg, Md.). Following a 2–3 hour incubation with the DNA-liposome complexes, the medium was removed and replaced with C-DMEM. All transfected cells in 96-well microtiter plates were incubated at 33° C. and 5% $CO_2$ for 24–48 hours prior to drug treatment. Experiments were performed with the receptor expressed transiently in HeLa cells.

Dexamethasone Induction of GFP-hGR Translocation

To obtain receptor-ligand translocation kinetic data, nuclei of transfected cells were first labeled with 5 μg/ml Hoechst 33342 (Molecular Probes) in C-DMEM for 20 minutes at 33° C and 5% $CO_2$. Cells were washed once in Hank's Balanced Salt Solution (HBSS) followed by the addition of 100 nM dexamethasone in HBSS with 1% charcoal/dextran-treated FBS. To obtain fixed time point dexamethasone titration data, transfected HeLa cells were first washed with DMEM and then incubated at 33° C. and 5% $CO_2$ for 1 h in the presence of 0–1000 nM dexamethasone in DMEM containing 1% charcoal/dextran-treated FBS. Cells were analyzed live or they were rinsed with HBSS, fixed for 15 min with 3.7% formaldehyde in HBSS, stained with Hoechst 33342, and washed before analysis. The intracellular GFP-hGR fluorescence signal was not diminished by this fixation procedure.

Image Acquisition and Analysis

Kinetic data were collected by acquiring fluorescence image pairs (GFP-hGR and Hoechst 33342-labeled nuclei) from fields of living cells at 1 min intervals for 30 min after the addition of dexamethasone. Likewise, image pairs were obtained from each well of the fixed time point screening plates 1 h after the addition of dexamethasone. In both cases, the image pairs obtained at each time point were used to define nuclear and cytoplasmic regions in each cell. Translocation of GFP-hGR was calculated by dividing the integrated fluorescence intensity of GFP-hGR in the nucleus by the integrated fluorescence intensity of the chimera in the cytoplasm or as a nuclear-cytoplasmic difference of GFP fluorescence. In the fixed time point screen this translocation ratio was calculated from data obtained from at least 200 cells at each concentration of dexamethasone tested. Drug-induced translocation of GFP-hGR from the cytoplasm to the nucleus was therefore correlated with an increase in the translocation ratio.

Results

Figures 20, 20A, 20B:
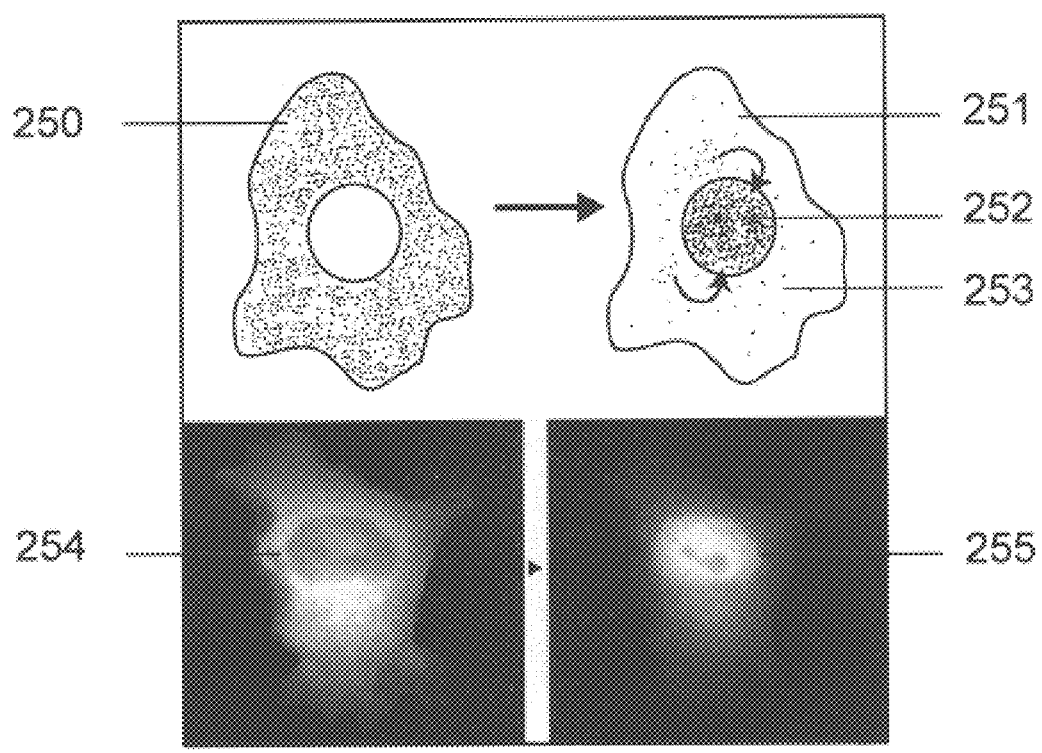
FIG. 20 shows the measurement of a drug-induced cytoplasm to nuclear translocation.

FIG. 20 schematically displays the drug-induced cytoplasm 253 to nucleus 252 translocation of the human glucocorticoid receptor. The upper pair of schematic diagrams depicts the localization of GFP-hGR within the cell before 250 (A) and after 251 (B) stimulation with dexamethasone. Under these experimental conditions, the drug induces a large portion of the cytoplasmic GFP-hGR to translocate into the nucleus. This redistribution is quantified by determining the integrated intensities ratio of the cytoplasmic and nuclear fluorescence in treated 255 and untreated 254 cells. The lower pair of fluorescence micrographs show the dynamic redistribution of GFP-hGR in a single cell, before 254 and after 255 treatment. The HCS is performed on wells containing hundreds to thousands of transfected cells and the translocation is quantified for each cell in the field exhibiting GFP fluorescence. Although the use of a stably transfected cell line would yield the most consistently labeled cells, the heterogeneous levels of GFP-hGR expression induced by transient transfection did not interfere with analysis by the cell screening system of the present invention.

Figure 21:
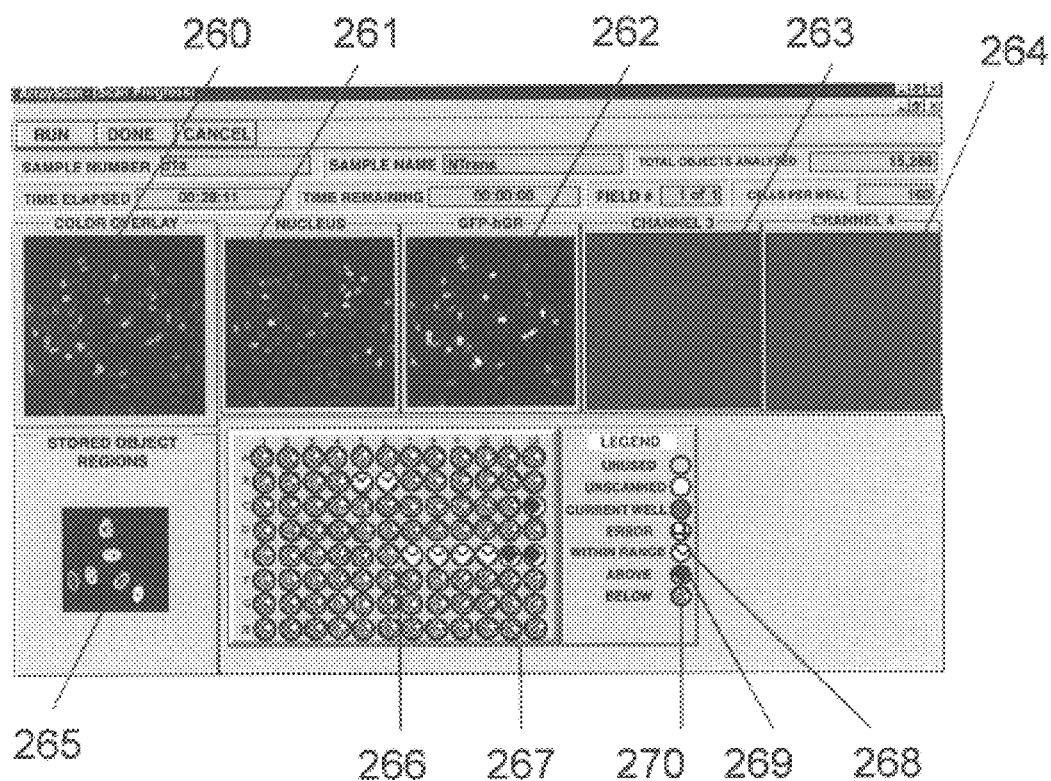
FIG. 21 illustrates a graphical user interface of the measurement shown in FIG. 20.

To execute the screen, the cell screening system scans each well of the plate, images a population of cells in each, and analyzes cells individually. Here, two channels of fluorescence are used to define the cytoplasmic and nuclear distribution of the GFP-hGR within each cell. Depicted in FIG. 21 is the graphical user interface of the cell screening system near the end of a GFP-hGR screen. The user interface depicts the parallel data collection and analysis capability of the system. The windows labeled "Nucleus" 261 and "GFP-hGR" 262 show the pair of fluorescence images being obtained and analyzed in a single field. The window labeled "Color Overlay" 260 is formed by pseudocoloring the above images and merging them so the user can immediately identify cellular changes. Within the "Stored Object Regions" window 265, an image containing each analyzed cell and its neighbors is presented as it is archived. Furthermore, as the HCS data are being collected, they are analyzed, in this case for GFP-hGR translocation, and translated into an immediate "hit" response. The 96 well plate depicted in the lower window of the screen 267 shows which wells have met a set of user-defined screening criteria. For example, a white-colored well 269 indicates that the drug-induced translocation has exceeded a predetermined threshold value of 50%. On the other hand, a black-colored well 270 indicates that the drug being tested induced less than 10% translocation. Gray-colored wells 268 indicate "hits" where the translocation value fell between 10% and 50%. Row "E" on the 96 well plate being analyzed 266 shows a titration with a drug known to activate GFP-hGR translocation, dexamethasone. This example screen used only two fluorescence channels. Two additional channels (Channels 3 263 and 4 264) are available for parallel analysis of other specific targets, cell processes, or cytotoxicity to create multiple parameter screens.

Figure 22:
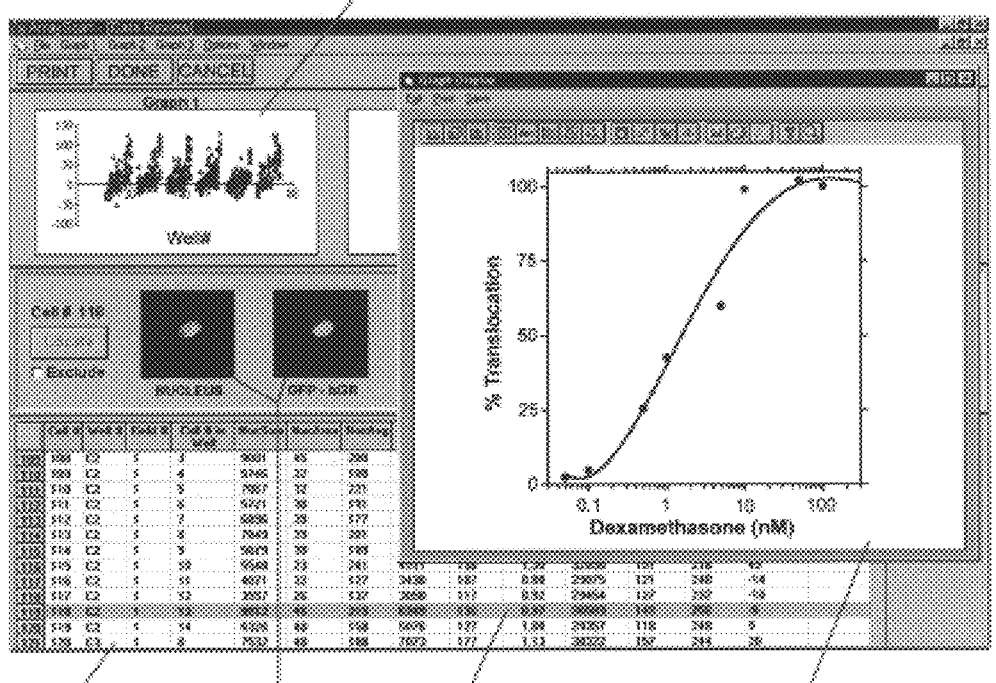
FIG. 22 illustrates a graphical user interface, with data presentation, of the measurement shown in FIG. 20.

There is a link between the image database and the information database that is a powerful tool during the validation process of new screens. At the completion of a screen, the user has total access to image and calculated data (FIG. 22). The comprehensive data analysis package of the cell screening system allows the user to examine HCS data at multiple levels. Images 276 and detailed data in a spread sheet 279 for individual cells can be viewed separately, or summary data can be plotted. For example, the calculated results of a single parameter for each cell in a 96 well plate are shown in the panel labeled Graph 1 275. By selecting a single point in the graph, the user can display the entire data set for a particular cell that is recalled from an existing database. Shown here are the image pair 276 and detailed fluorescence and morphometric data from a single cell (Cell #118, gray line 277). The large graphical insert 278 shows the results of dexamethasone concentration on the translocation of GFP-hGR. Each point is the average of data from at least 200 cells. The calculated $EC_{50}$ for dexamethasone in this assay is 2 nM.

Figure 23:
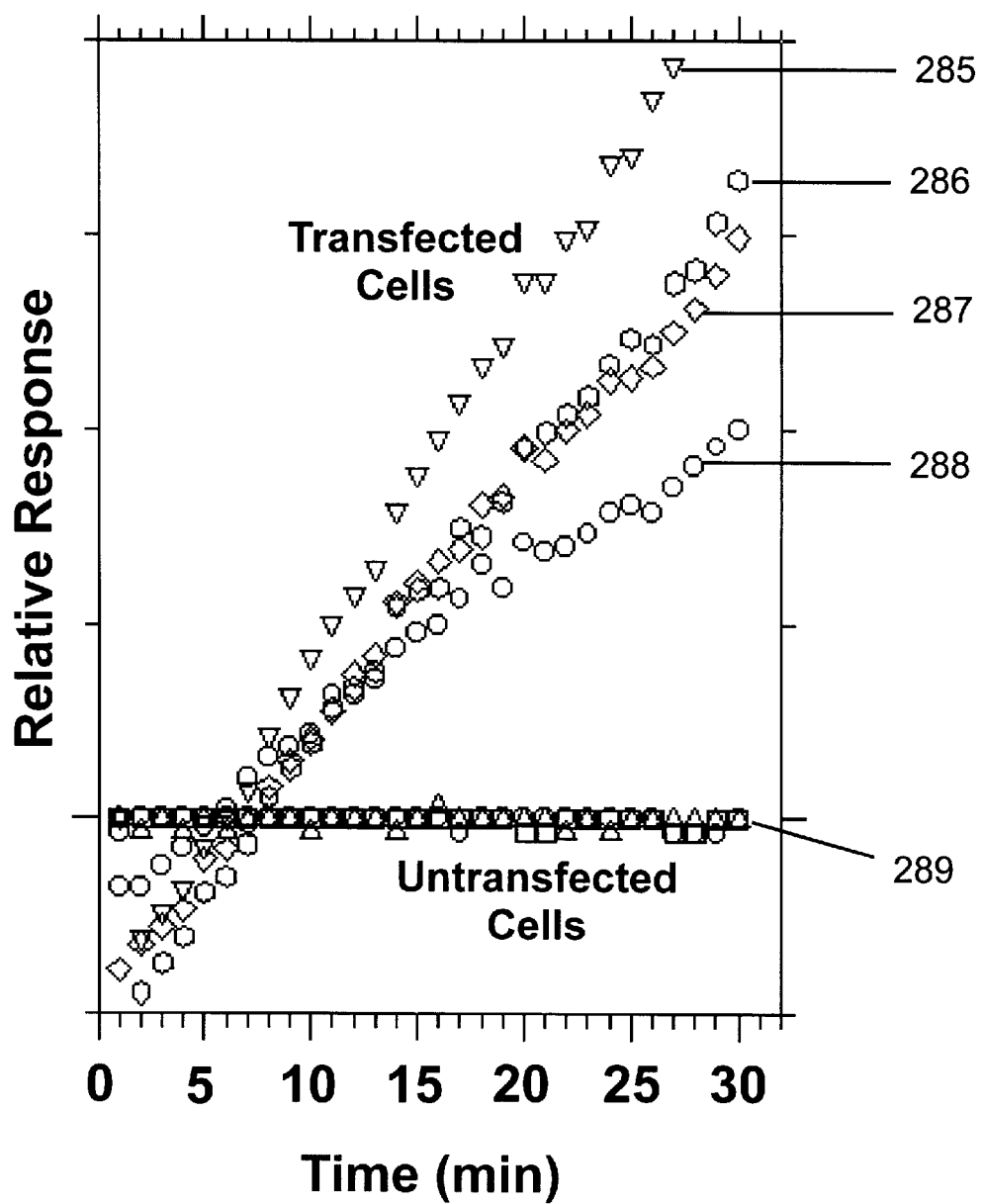
FIG. 23 is a graph representing the kinetic data obtained from the measurements depicted in FIG. 20.

A powerful aspect of HCS with the cell screening system is the capability of kinetic measurements using multicolor fluorescence and morphometric parameters in living cells. Temporal and spatial measurements can be made on single cells within a population of cells in a field. FIG. 23 shows kinetic data for the dexamethasone-induced translocation of GFP-hGR in several cells within a single field. Human HeLa cells transfected with GFP-hGR were treated with 100 nM dexamethasone and the translocation of GFP-hGR was measured over time in a population of single cells. The graph shows the response of transfected cells 285, 286, 287, and 288 and non-transfected cells 289. These data also illustrate the ability to analyze cells with different expression levels.

EXAMPLE 6

High-content Screen of Drug-induced Apoptosis

Apoptosis is a complex cellular program that involves myriad molecular events and pathways. To understand the mechanisms of drug action on this process, it is essential to measure as many of these events within cells as possible with temporal and spatial resolution. Therefore, an apoptosis screen that requires little cell sample preparation yet provides an automated readout of several apoptosis-related parameters would be ideal. A cell-based assay designed for the cell screening system has been used to simultaneously quantify several of the morphological, organellar, and macromolecular hallmarks of paclitaxel-induced apoptosis.

Cell Preparation

The cells chosen for this study were mouse connective tissue fibroblasts (L-929; ATCC CCL-1) and a highly invasive glioblastoma cell line (SNB-19; ATCC CRL-2219) (Welch et al., *In Vitro Cell. Dev. Biol.* 31:610, 1995). The day before treatment with an apoptosis inducing drug, 3500 cells were placed into each well of a 96-well plate and incubated overnight at 37° C. in a humidified 5% $CO_2$ atmosphere. The following day, the culture medium was removed from each well and replaced with fresh medium containing various concentrations of paclitaxel (0–50 $\mu$M) from a 20 mM stock made in DMSO. The maximal concentration of DMSO used in these experiments was 0.25%. The cells were then incubated for 26 h as above. At the end of the paclitaxel treatment period, each well received fresh medium containing 750 nM MITOTRACKER™ Red (Molecular Probes; Eugene, Oreg.) and 3 $\mu$g/ml Hoechst 33342 DNA-binding dye (Molecular Probes) and was incubated as above for 20 min. Each well on the plate was then washed with HBSS and fixed with 3.7% formaldehyde in HBSS for 15 min at room temperature. The formaldehyde was washed out with HBSS and the cells were permeabilized for 90 s with 0.5% (v/v) Triton X-100, washed with HBSS, incubated with 2 U ml$^{-1}$ BODIPY™ FL phallacidin (Molecular Probes) for 30 min, and washed with HBSS. The wells on the plate were then filled with 200 $\mu$l HBSS, sealed, and the plate stored at 4° C. if necessary. The fluorescence signals from plates stored this way were stable for at least two weeks after preparation. As in the nuclear translocation assay, fluorescence reagents can be designed to convert this assay into a live cell high-content screen.

Image Acquisition and Analysis on the ArrayScan System

The fluorescence intensity of intracellular MITOTRACKER™ Red, Hoechst 33342, and BODIPY™ FL phallacidin was measured with the cell screening system as described supra. Morphometric data from each pair of images obtained from each well was also obtained to detect each object in the image field (e.g., cells and nuclei), and to calculate its size, shape, and integrated intensity.

Calculations and Output

A total of 50–250 cells were measured per image field. For each field of cells, the following calculations were performed: (1) The average nuclear area ($\mu$m$^2$) was calculated by dividing the total nuclear area in a field by the number of nuclei detected. (2) The average nuclear perimeter ($\mu$m) was calculated by dividing the sum of the perimeters of all nuclei in a field by the number of nuclei detected in that field. Highly convoluted apoptotic nuclei had the largest nuclear perimeter values. (3) The average nuclear brightness was calculated by dividing the integrated intensity of the entire field of nuclei by the number of nuclei in that field. An increase in nuclear brightness was correlated with increased DNA content. (4) The average cellular brightness was calculated by dividing the integrated intensity of an entire field of cells stained with MITOTRACKER™ dye by the number of nuclei in that field. Because the amount of MITOTRACKER™ dye that accumulates within the mitochondria is proportional to the mitochondrial potential, an increase in the average cell brightness is consistent with an increase in mitochondrial potential. (5) The average cellular brightness was also calculated by dividing the integrated intensity of an entire field of cells stained with BODIPY™ FL phallacidin dye by the number of nuclei in that field. Because the phallotoxins bind with high affinity to the polymerized form of actin, the amount of BODIPY™ FL phallacidin dye that accumulates within the cell is proportional to actin polymerization state. An increase in the average cell brightness is consistent with an increase in actin polymerization.

Results

Figure 24:
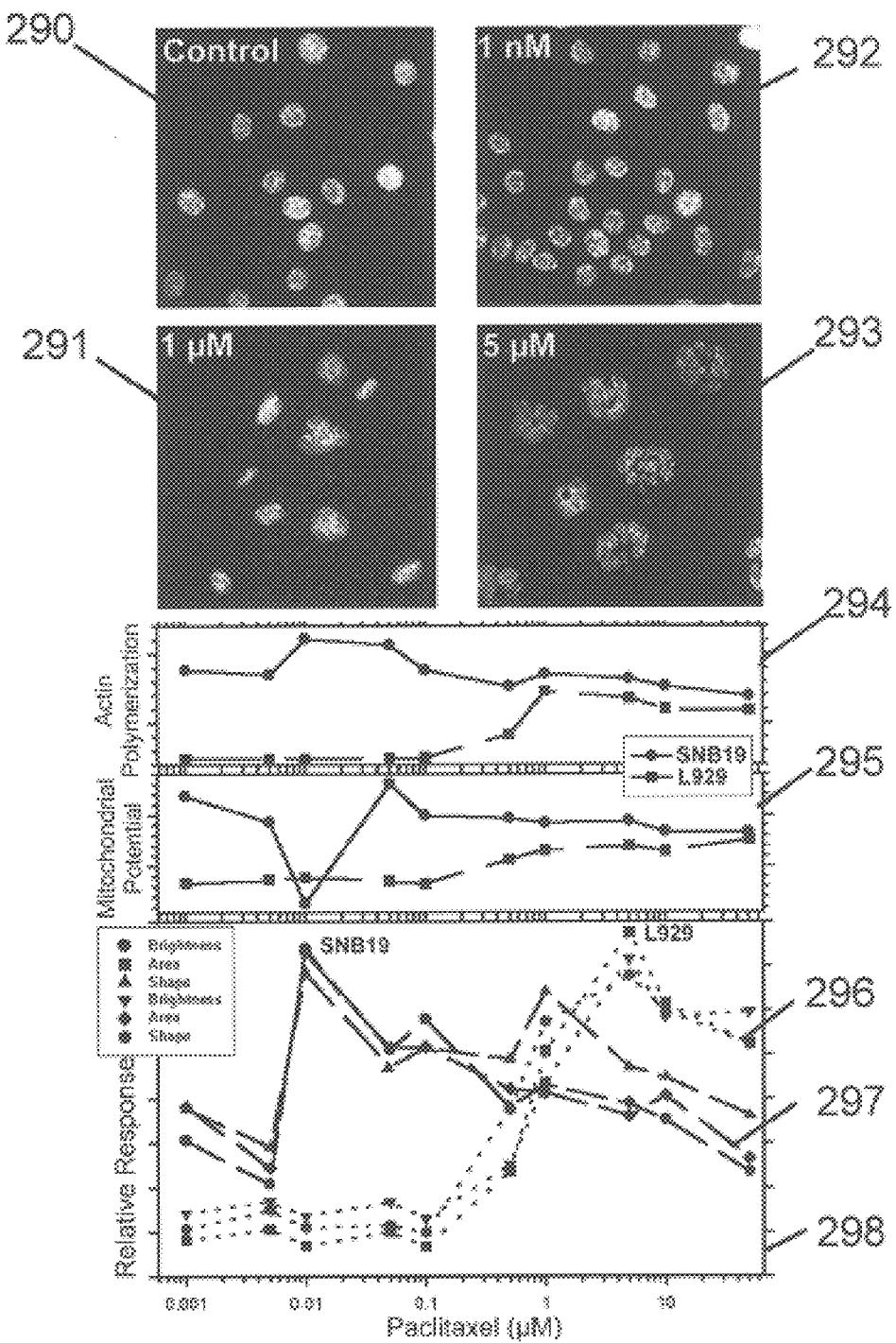
FIG. 24 details a high-content screen of drug-induced apoptosis.

FIG. 24 (top panels) shows the changes paclitaxel induced in the nuclear morphology of L-929 cells. Increasing amounts of paclitaxel caused nuclei to enlarge and fragment 293, a hallmark of apoptosis. Quantitative analysis of these and other images obtained by the cell screening system is presented in the same figure. Each parameter measured showed that the L-929 cells 296 were less sensitive to low concentrations of paclitaxel than were SNB-1 9 cells 297. At higher concentrations though, the L-929 cells showed a response for each parameter measured. The multiparameter approach of this assay is useful in dissecting the mechanisms of drug action. For example, the area, brightness, and fragmentation of the nucleus 298 and actin polymerization values 294 reached a maximum value when SNB-19 cells were treated with 10 nM paclitaxel (FIG. 24; top and bottom graphs). However, mitochondrial potential 295 was minimal at the same concentration of paclitaxel (FIG. 24; middle graph). The fact that all the parameters measured approached control levels at increasing paclitaxel concentrations (>10 nM) suggests that SNB-19 cells have low affinity drug metabolic or clearance pathways that are compensatory at sufficiently high levels of the drug. Contrasting the drug sensitivity of SNB-19 cells 297, L-929 showed a different response to paclitaxel 296. These fibroblastic cells showed a maximal response in many parameters at 5 $\mu$M paclitaxel, a 500-fold higher dose than SNB-19 cells. Furthermore, the L-929 cells did not show a sharp decrease in mitochondrial potential 295 at any of the paclitaxel concentrations tested. This result is consistent with the presence of unique apoptosis pathways between a normal and cancer cell line. Therefore, these results indicate that a relatively simple fluorescence labeling protocol can be coupled with the cell screening system of the present invention to produce a high-content screen of key events involved in programmed cell death.

Background

A key to the mechanism of apoptosis was the discovery that, irrespective of the lethal stimulus, death results in identical apoptotic morphology that includes cell and organelle dismantling and repackaging, DNA cleavage to nucleosome sized fragments, and engulfment of the fragmented cell to avoid an inflammatory response. Apoptosis is therefore distinct from necrosis, which is mediated more by acute trauma to a cell, resulting in spillage of potentially toxic and antigenic cellular components into the intercellular milieu, leading to an inflammatory response.

The criteria for determining whether a cell is undergoing apoptosis (Wyllie et al. 1980. *Int Rev Cytol.* 68:251–306; Thompson, 1995. *Science.* 267:1456–62; Majno and Joris. 1995. *Am J Pathol.* 146:3–15; Allen et al. 1998. *Cell Mol Life Sci.* 54:427–45) include distinct morphological changes in the appearance of the cell, as well as alterations in biochemical and molecular markers. For example, apoptotic cells often undergo cytoplasmic membrane blebbing, their chromosomes rapidly condense and aggregate around the nuclear periphery, the nucleus fragments, and small apoptotic bodies are formed. In many, but not all, apoptotic cells, chromatin becomes a target for specific nucleases that cleave the DNA.

Apoptosis is commonly accompanied by a characteristic change in nuclear morphology (chromatin condensation or fragmentation) and a step-wise fragmentation of DNA culminating in the formation of mono- and/or oligomeric fragments of 200 base pairs. Specific changes in organellar function, such as mitochondrial membrane potential, occur. In addition, specific cysteine proteases (caspases) are activated, which catalyzes a highly selective pattern of protein degradation by proteolytic cleavage after specific aspartic acid residues. In addition, the external surface exposure of phosphatidylserine residues (normally on the inner membrane leaflet) allows for the recognition and elimination of apoptotic cells, before the membrane breaks up and cytosol or organelles spill into the intercellular space and elicit inflammatory reactions. Moreover, cells undergoing apoptosis tend to shrink, while also having a reduced intracellular potassium level.

The general patterns of apoptotic signals are very similar among different cell types and apoptotic inducers. However, the details of the pathways actually vary significantly depending on cell type and inducer. The dependence and independence of various signal transduction pathways involved in apoptosis are currently topics of intense research. We show here that the pathway also varies depending upon the dose of the inducer in specific cell types.

Nuclear Morphology

Cells undergoing apoptosis generally exhibit two types of nuclear change, fragmentation or condensation ((Majno and Joris, 1995), (Earnshaw, 1995)). The response in a given cell type appears to vary depending on the apoptotic inducer. During nuclear fragmentation, a circular or oval nucleus becomes increasingly lobular. Eventually, the nucleus fragments dramatically into multiple sub-nuclei. Sometimes the density of the chromatin within the lobular nucleus may show spatial variations in distribution (heterochromatization), approximating the margination seen in nuclear condensation.

Nuclear condensation has been reported in some cell types, such as MCF-7 (Saunders et al. 1997. *Int J Cancer.* 70:214–20). Condensation appears to arise as a consequence of the loss of structural integrity of the euchromatin, nuclear matrix and nuclear lamina (Hendzel et al. 1998. *J Biol Chem.* 273:24470–8). During nuclear condensation, the chromatin concentrates near the margin of the nucleus, leading to the overall shrinkage of the nucleus. Thus, the use of nuclear morphology as a measure of apoptosis must take both condensation and fragmentation into account.

Material and Methods

Cells were plated into 96-well plates at densities of $3 \times 10^3$ to $1 \times 10^4$ cells/well. The following day apoptotic inducers were added at indicated concentrations and cells were incubated for indicated time periods (usually 16–30 hours). The next day medium was removed and cells were stained with 5 µg/ml Hoechst (Molecular Probes, Inc.) in fresh medium and incubated for 30 minutes at 37° C. Cells were washed in Hank's Balanced Salt Solution (HBSS) and fixed with 3.7% formaldehyde in HBSS at room temperature. Cells were washed 2× with HBSS at room temperature and the plate was sealed.

Quantitation of changes in nuclear morphology upon induction of apoptosis was accomplished by (1) measuring the effective size of the nuclear region; and (2) measuring the degree of convolution of the perimeter. The size parameter provides the more sensitive measure of nuclear condensation, whereas the perimeter measure provides a more sensitive measure of nuclear fragmentation.

Results & Discussion

Figure 25:
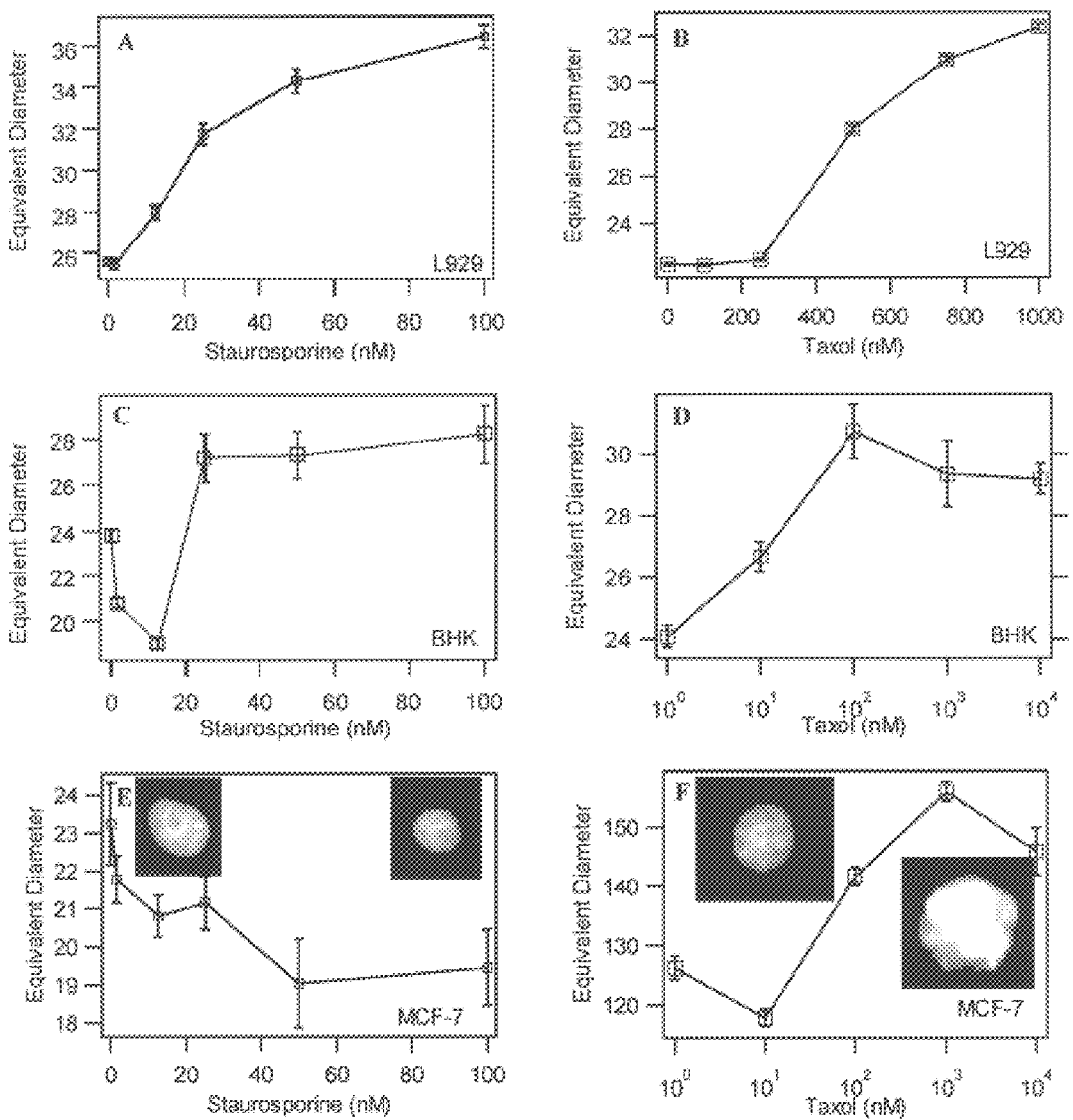
FIG. 25. Graphs depicting changes in morphology upon induction of apoptosis. Staurosporine (A) and paclitaxel (B) induce classic nuclear fragmentation in L929 cells. BHK cells exhibit concentration dependent changes in response to staurosporine (C), but a more classical response to paclitaxel (D). MCF-7 cells exhibit either nuclear condensation (E) or fragmentation (F) in response to staurosporine and paclitaxel, respectively. In all cases, cells were exposed to the compounds for 30 hours.

L929 cells responded to both staurosporine (30 hours) and paclitaxel (30 hours) with a dose-dependent change in nuclear morphology (FIGS. 25A and 25B). BHK cells illustrated a slightly more complicated, yet clearly visible response. Staurosporine appeared to stimulate nuclear condensation at lower doses and nuclear fragmentation at higher doses (FIGS. 25C and 25D). In contrast, paclitaxel induced a consistent increase in nuclear fragmentation with increasing concentrations. The response of MCF-7 cells varied dramatically depending upon the apoptotic inducer. Staurosporine appeared to elicit nuclear condensation whereas paclitaxel induced nuclear fragmentation (FIGS. 25E and 25F).

Figure 26:
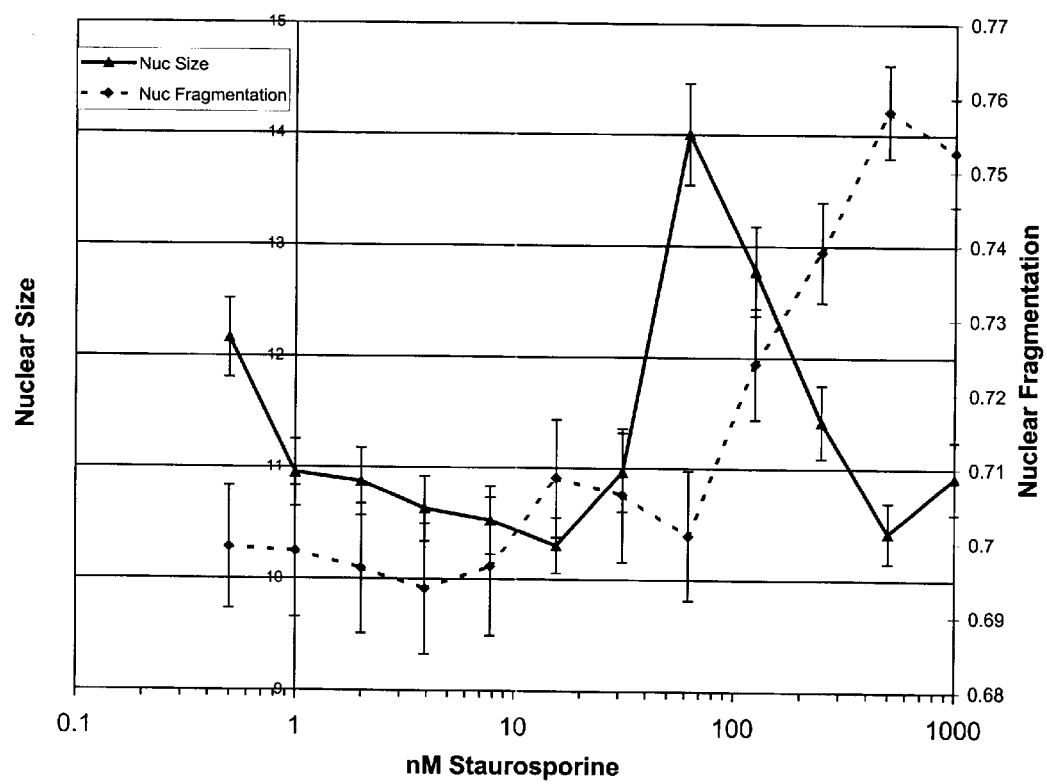
FIG. 26 illustrates the dose response of cells to staurosporine in terms of both nuclear size and nuclear perimeter convolution.

FIG. 26 illustrates the dose response of cells in terms of both nuclear size and nuclear perimeter convolution. There appears to be a swelling of the nuclei that precedes the fragmentation.

Result of Evaluation

Differential responses by cell lines and by apoptotic inducers were observed in a dose dependent manner, indicating that this assay will be useful for detecting changes in the nucleus characteristic of apoptosis.

Actin Reorganization

We assessed changes in the actin cytoskeleton as a potential parameter related to apoptotic changes. This was based on preliminary observations of an early increase in f-actin content detected with fluorescent phalloidin labeling, an f-actin specific stain (our unpublished data; Levee et al. 1996. *Am J Physiol.* 271:C1981–92; Maekawa et al. 1996. *Clin Exp Immunol.* 105:389–96). Changes in the actin cytoskeleton during apoptosis have not been observed in all cell types. (Endresen et al. 1995. *Cytometry.* 20:162–71, van Engeland et al. 1997. *Exp Cell Res.* 235:421–30).

Material and Methods

Cells were plated in 96-well plates at densities of $3 \times 10^3$ to $1 \times 10^4$ cells/well. The following day apoptotic inducers were added at indicated concentrations. Cells were incubated for the indicated time periods (usually 16–30 hours). The next day the medium was removed and cells were stained with 5 µg/ml Hoechst (Molecular Probes, Inc.) in fresh medium and incubated for 30 minutes at 30° C. Cells were washed in HBSS and fixed with 3.7% formaldehyde in HBSS at room temperature. Plates were washed with HBSS and permeabilized with 0.5% v/v Triton X-100 in HBSS at room temperature. Plates were washed in HBSS and stained with 100 µl of 1 U/ml of Alexa 488 Phalloidin stock (100 µl/well, Molecular Probes, Inc.). Cells were washed 2× with HBSS at RT and the plate was sealed.

Quantitation of f-actin content was accomplished by measuring the intensity of phalloidin staining around the nucleus. This was determined to be a reasonable approximation of a full cytoplasmic average of the intensity. The mask used to approximate this cytoplasmic measure was derived from the nuclear mask defined by the Hoechst stain. Derivation was accomplished by combinations of erosions and dilations.

Results and Discussion

Figure 27:
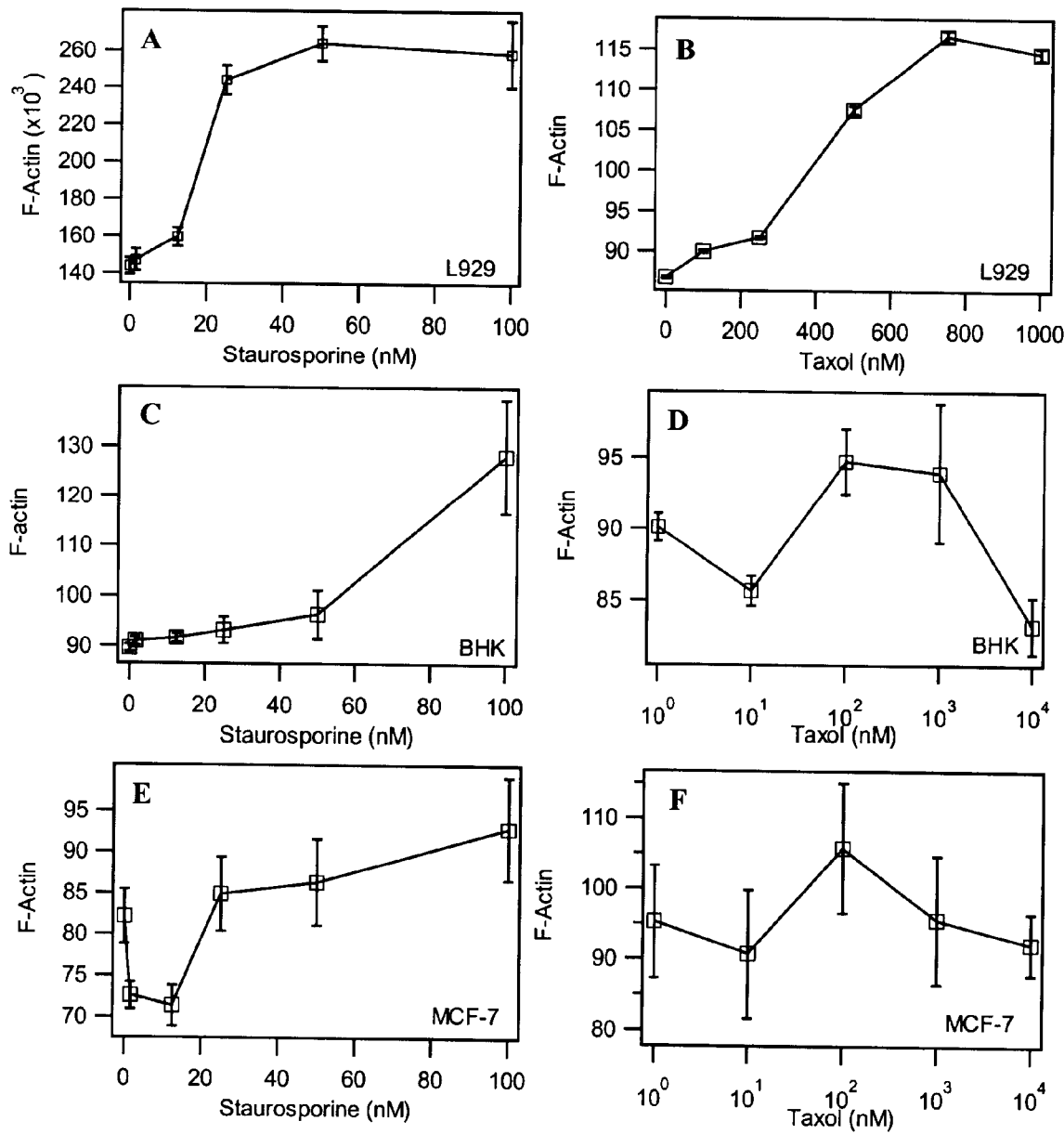
FIG. 27. Graphs depicting induction of apoptosis by staurosporine and paclitaxel leading to changes in peri-nuclear f-actin content. (A, B) Both apoptotic stimulators induce dose-dependent increases in f-actin content in L929 cells. (C) In BHK cells, staurosporine induces a dose-dependent increase in f-actin, whereas paclitaxel (D) produces results that are more variable. (E) MCF-7 cells exhibit either a decrease or increase depending on the concentration of staurosporine. (F) Paclitaxel induced changes in f-actin content were highly variable and not significant. Cells were exposed to the compounds for 30 hours.

Changes in f-actin content varied based on cell type and apoptotic inducer (FIG. 27). Staurosporine (30 hours) induced increases in f-actin in L929 (FIG. 27A) and BHK (FIG. 27B) cells. MCF-7 cells exhibited a concentration-dependent response. At low concentrations (FIG. 27E) there appeared to be a decrease in f-actin content. At higher concentrations, f-actin content increased. Paclitaxel (30 hours) treatment led to a wide variety of responses. L929 cells responded with graded increases in f-actin (FIG. 27B) whereas both BHK and MCF-7 responses were highly variable (FIGS. 27D & 27F, respectively).

Result of Evaluation

Both increases and decreases in signal intensity were measured for several cell lines and found to exhibit a concentration dependent response. For certain cell line/apoptotic inducer pairs this could be a statistically significant apoptotic indicator.

Changes in Mitochondrial Mass/Potential

Introduction

Changes in mitochondria play a central role in apoptosis (Henkart and Grinstein. 1996. *J Exp Med.* 183:1293–5). Mitochondria release apoptogenic factors through the outer membrane and dissipate the electrochemical gradient of the inner membrane. This is thought to occur via formation of the mitochondria permeability transition (MPT), although it is apparently not true in all cases. An obvious manifestation of the formation of the MPT is collapse of the mitochondrial membrane potential. Inhibition of MPT by pharmacological intervention or mitochondrial expression of the anti-apoptotic protein Bcl-2 prevents cell death, suggesting the formation of the MPT may be a rate-limiting event of the death process (For review see: Kroemer et al. 1998. *Annu Rev Physiol.* 60:619–42). It has also been observed that mitochondria can proliferate during stimulation of apoptosis (Mancini et al. 1997. *J Cell Biol.* 138:449–69; Camilleri-Broet et al. 1998. *Exp Cell Res.* 239:277–92).

One approach for measuring apoptosis-induced changes in mitochondria is to measure the mitochondrial membrane potential. Of the methods available, the simplest measure is the redistribution of a cationic dye that distributes within intracellular organelles based on the membrane potential. Such an approach traditionally requires live cells for the measurements. The recent introduction of the MITOTRACKER™ dyes (Poot et al. 1997. *Cytometry.* 27:358–64; available from Molecular Probes, Inc., Oregon) provides a means of measuring mitochondrial membrane potential after fixation.

Given the observations of a possible increase in mitochondrial mass during apoptosis, the amount of dye labeling the mitochondria is related to both membrane potential and the number of mitochondria. If the number of mitochondria remains constant then the amount of dye is directly related to the membrane potential. If the number of mitochondria is not constant, then the signal will likely be dominated by the increase in mass (Reipert et al. 1995. *Exp Cell Res.* 221:281–8).

Probes are available that allow a clear separation between changes in mass and potential in HCS assays. Mitochondrial mass is measured directly by labeling with MITOTRACKER™ Green FM (Poot and Pierce, 1999, *Cytometry.* 35:311–7; available from Molecular Probes, Inc., Oregon). The labeling is independent of mitochondrial membrane potential but proportional to mitochondrial mass. This also provides a means of normalizing other mitochondrial measures in each cell with respect to mitochondrial mass.

Material and Methods

Cells were plated into 96-well plates at densities of $3 \times 10^3$ to $1 \times 10^4$ cells/well. The following day apoptotic inducers were added at the indicated concentrations and cells were incubated for the indicated time periods (usually 16–30 hours). Cells were stained with 5 μg/ml Hoechst (Molecular Probes, Inc.) and 750 nM MITOTRACKER™ Red (CMXRos, Molecular Probes, Inc.) in fresh medium and incubated for 30 minutes at 37° C. Cells were washed in HBSS and fixed with 3.7% formaldehyde in HBSS at room temperature. Plates were washed with HBSS and permeabilized with 0.5% v/v Triton X-100 in HBSS at room temperature. Cells were washed 2x with HBSS at room temperature and the plate was sealed. For dual labeling of mitochondria, cells were treated with 200 nM MITOTRACKER™ Green and 200 nM MITOTRACKER™ Red for 0.5 hours before fixation.

Results & Discussion

Figure 28:
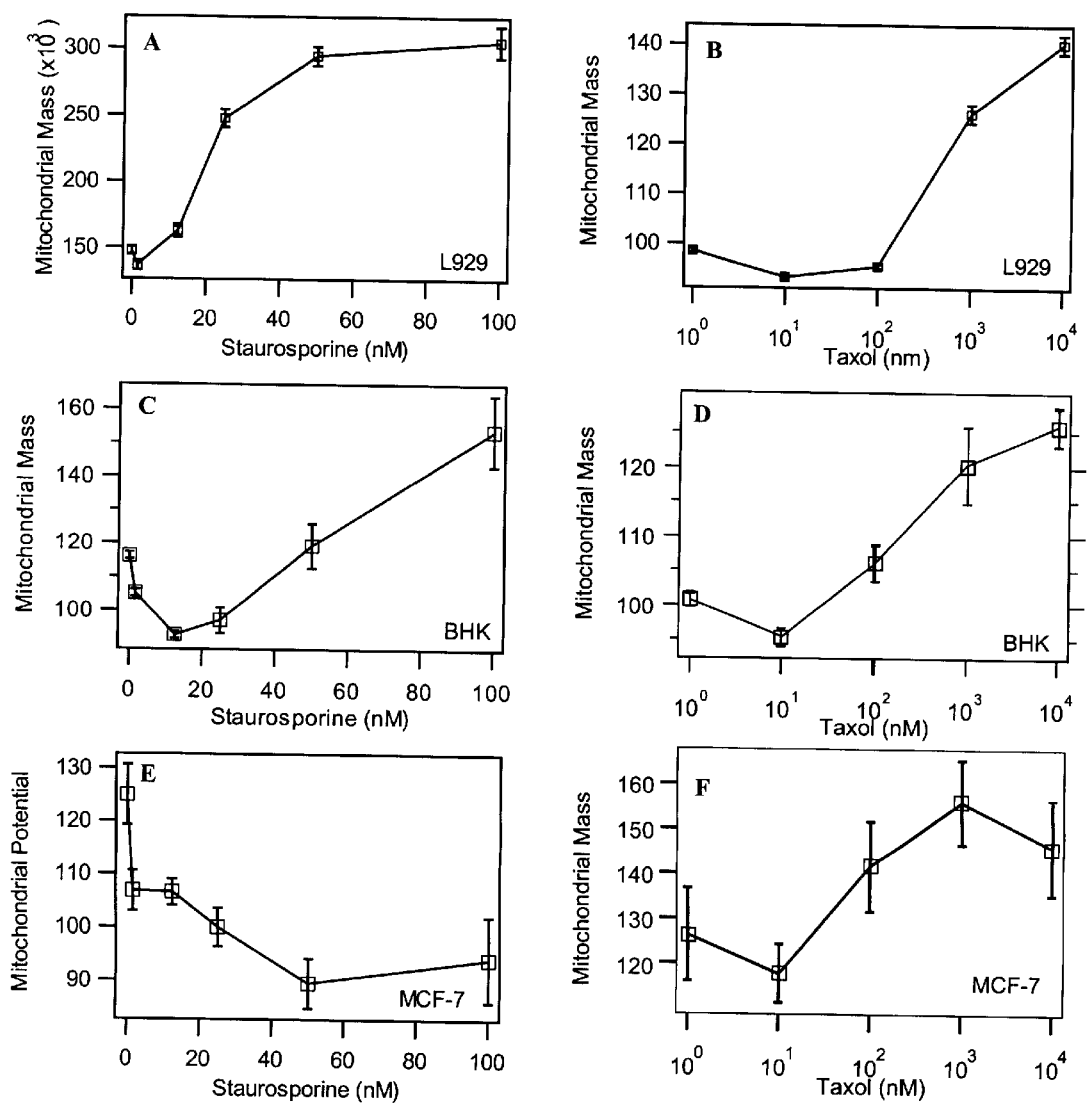
FIG. 28. Graphs depicting mitochondrial changes in response to induction of apoptosis. L929 (A,B) and BHK (C,D) cells responded to both staurosporine (A,C) and paclitaxel (B,D) with increases in mitochondrial mass. MCF-7 cells exhibit either a decrease in membrane potential (E, staurosporine) or an increase in mitochondrial mass (F, paclitaxel) depending on the stimulus. Cells were exposed to the compounds for 30 hours. 28G is a graph showing the simultaneous measurement of staurosporine effects on mitochondrial mass and mitochondrial potential in BHK cells.

Induction of apoptosis by staurosporine and paclitaxel led to varying mitochondrial changes depending upon the stimulus. L929 cells exhibited a clear increase in mitochondrial mass with increasing staurosporine concentrations (FIG. 28). BHK cells exhibited either a decrease in membrane potential at lower concentrations of staurosporine, or an increase in mass at higher concentrations of staurosporine (FIG. 28C). MCF-7 cells responded by a consistent decrease in mitochondrial membrane potential in response to increasing concentrations of staurosporine (FIG. 28E). Increasing concentrations of paclitaxel caused consistent increases in mitochondrial mass (FIGS. 28B, 28D, and 28F).

Figure 28G:
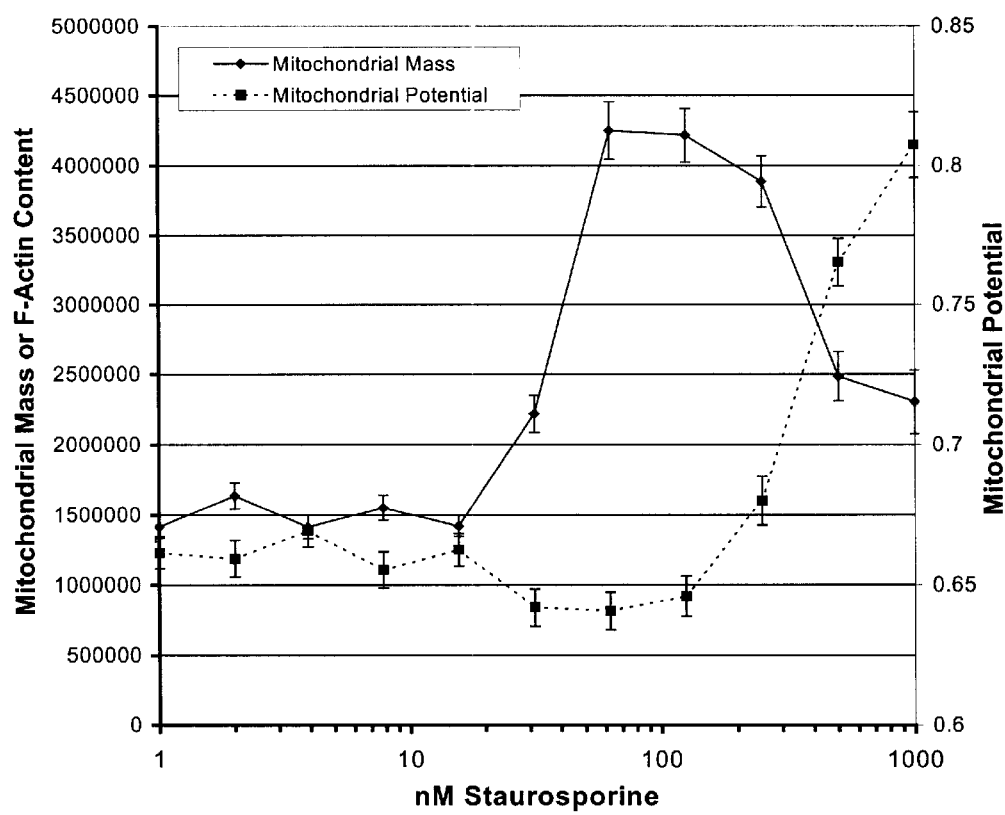

The mitochondrial membrane potential is measured by labeling mitochondria with both MITOTRACKER™ Green FM and MITOTRACKER™ Red (Molecular Probes, Inc). MITOTRACKER™ Red labeling is proportional to both mass and membrane potential. MITOTRACKER™ Green FM labeling is proportional to mass. The ratio of MITOTRACKER™ Red signal to the MITOTRACKER™ Green FM signal provides a measure of mitochondrial membrane potential (Poot and Pierce, 1999). This ratio normalizes the mitochondrial mass with respect to the MITOTRACKER™ Red signal. (See FIG. 28G) Combining the ability to normalize to mitochondrial mass with a measure of the membrane potential allows independent assessment of both parameters.

Result of Evaluation

Both decreases in potential and increases in mass were observed depending on the cell line and inducer tested. Dose dependent correlation demonstrates that this is a promising apoptotic indicator.

It is possible to combine multiple measures of apoptosis by exploiting the spectral domain of fluorescence spectroscopy. In fact, all of the nuclear morphology/f-actin content/mitochondrial mass/mitochondrial potential data shown earlier were collected as multiparameter assays, but were presented individually for clarity.

EXAMPLE 7

Protease Induced Translocation of a Signaling Enzyme Containing a Disease-associated Sequence from Cytoplasm to Nucleus.

Plasmid Construct

A eukaryotic expression plasmid containing a coding sequence for a green fluorescent protein—caspase (Cohen (1997), *Biochemical J.* 326:1–16; Liang et al. (1997), *J. of Molec. Biol.* 274:291–302) chimera is prepared using GFP mutants. The construct is used to transfect eukaryotic cells.

Cell Preparation and Transfection

Cells are trypsinized and plated 24 h prior to transfection and incubated at 37° C. and 5% $CO_2$. Transfections are performed by methods including, but not limited to calcium phosphate coprecipitation or lipofection. Cells are incubated with the calcium phosphate-DNA precipitate for 4–5 hours at 37° C. and 5% $CO_2$, washed 3–4 times with DMEM to remove the precipitate, followed by the addition of C-DMEM. Lipofectamine transfections are performed in serum-free DMEM without antibiotics according to the manufacturer's instructions. Following a 2–3 hour incubation with the DNA-liposome complexes, the medium is removed and replaced with C-DMEM.

Apopototic Induction of Caspase-GFP Translocation

To obtain Caspase-GFP translocation kinetic data, nuclei of transfected cells are first labeled with 5 µg/ml Hoechst 33342 (Molecular Probes) in C-DMEM for 20 minutes at 37° C. and 5% $CO_2$. Cells are washed once in Hank's Balanced Salt Solution (HBSS) followed by the addition of compounds that induce apoptosis. These compounds include, but are not limited to paclitaxel, staurosporine, ceramide, and tumor necrosis factor. To obtain fixed time point titration data, transfected cells are first washed with DMEM and then incubated at 37° C. and 5% $CO_2$ for 1 h in the presence of 0–1000 nM compound in DMEM. Cells are analyzed live or they are rinsed with HBSS, fixed for 15 min with 3.7% formaldehyde in HBSS, stained with Hoechst 33342, and washed before analysis.

Image Acquisition and Analysis

Kinetic data are collected by acquiring fluorescence image pairs (Caspase-GFP and Hoechst 33342-labeled nuclei) from fields of living cells at 1 min intervals for 30 min after the addition of compound. Likewise, image pairs are obtained from each well of the fixed time point screening plates 1 h after the addition of compound. In both cases, the image pairs obtained at each time point, are used to define nuclear and cytoplasmic regions in each cell. Translocation of Caspase-GFP is calculated by dividing the integrated fluorescence intensity of Caspase-GFP in the nucleus by the integrated fluorescence intensity of the chimera in the cytoplasm or as a nuclear-cytoplasmic difference of GFP fluorescence. In the fixed time point screen this translocation ratio is calculated from data obtained from at least 200 cells at each concentration of compound tested. Drug-induced translocation of Caspase-GFP from the cytoplasm to the nucleus is therefore correlated with an increase in the translocation ratio. Molecular interaction libraries including, but not limited to those comprising putative activators or inhibitors of apoptosis-activated enzymes are use to screen the indicator cell lines and identify a specific ligand for the DAS, and a pathway activated by compound activity.

EXAMPLE 8

Identification of Novel Steroid Receptors from DAS

Two sources of material and/or information are required to make use of this embodiment, which allows assessment of the function of an uncharacterized gene. First, disease associated sequence bank(s) containing cDNA sequences suitable for transfection into mammalian cells can be used. Because every RADE or differential expression experiment generates up to several hundred sequences, it is possible to generate an ample supply of DAS. Second, information from primary sequence database searches can be used to place DAS into broad categories, including, but not limited to, those that contain signal sequences, seven trans-membrane motifs, conserved protease active site domains, or other identifiable motifs. Based on the information acquired from these sources, method types and indicator cell lines to be transfected are selected. A large number of motifs are already well characterized and encoded in the linear sequences contained within the large number genes in existing genomic databases.

In one embodiment, the following steps are taken:

1) Information from the DAS identification experiment (including database searches) is used as the basis for selecting the relevant biological processes. (for example, look at the DAS from a tumor line for cell cycle modulation, apoptosis, metastatic proteases, etc.)

2) Sorting of DNA sequences or DAS by identifiable motifs (ie. signal sequences, 7-transmembrane domains, conserved protease active site domains, etc.) This initial grouping will determine fluorescent tagging strategies, host cell lines, indicator cell lines, and banks of bioactive molecules to be screened, as described supra.

3) Using well established molecular biology methods, ligate DAS into an expression vector designed for this purpose. Generalized expression vectors contain promoters, enhancers, and terminators for which to deliver target sequences to the cell for transient expression. Such vectors may also contain antibody tagging sequences, direct association sequences, chromophore fusion sequences like GFP, etc. to facilitate detection when expressed by the host.

4) Transiently transfect cells with DAS containing vectors using standard transfection protocols including: calcium phosphate co-precipitation, liposome mediated, DEAE dextran mediated, polycationic mediated, viral mediated, or electroporation, and plate into microtiter plates or microwell arrays. Alternatively, transfection can be done directly in the microtiter plate itself.

5) Carry out the cell screening methods as described supra.

In this embodiment, DAS shown to possess a motif(s) suggestive of transcriptional activation potential (for example, DNA binding domain, amino terminal modulating domain, hinge region, or carboxy terminal ligand binding domain) are utilized to identify novel steroid receptors.

Defining the fluorescent tags for this experiment involves identification of the nucleus through staining, and tagging the DAS by creating a GFP chimera via insertion of DAS into an expression vector, proximally fused to the gene encoding GFP. Alternatively, a single chain antibody fragment with high affinity to some portion of the expressed DAS could be constructed using technology available in the art (Cambridge Antibody Technologies) and linked to a fluorophore (FITC) to tag the putative transcriptional activator/receptor in the cells. This alternative would provide an external tag requiring no DNA transfection and therefore would be useful if distribution data were to be gathered from the original primary cultures used to generate the DAS.

Plasmid Construct

A eukaryotic expression plasmid containing a coding sequence for a green fluorescent protein—DAS chimera is prepared using GFP mutants. The construct is used to transfect HeLa cells. The plasmid, when transfected into the host cell, produces a GFP fused to the DAS protein product, designated GFP-DASpp.

Cell Preparation and Transfection

HeLa cells are trypsinized and plated using DMEM containing 5% charcoal/dextran-treated fetal bovine serum (FBS) (Hyclone) and 1% penicillin-streptomycin (C-DMEM) 12–24 hours prior to transfection and incubated at 37° C. and 5% $CO_2$. Transfections are performed by calcium phosphate coprecipitation or with Lipofectamine (Life Technologies). For the calcium phosphate transfections, the medium is replaced, prior to transfection, with DMEM containing 5% charcoal/dextran-treated FBS. Cells are incubated with the calcium phosphate-DNA precipitate for 4–5 hours at 37° C. and 5% $CO_2$, and washed 3–4 times with DMEM to remove the precipitate, followed by the addition of C-DMEM. Lipofectamine transfections are performed in serum-free DMEM without antibiotics according to the manufacturer's instructions. Following a 2–3 hour incubation with the DNA-liposome complexes, the medium is removed and replaced with C-DMEM. All transfected cells in 96-well microtiter plates are incubated at 33° C. and 5% $CO_2$ for 24–48 hours prior to drug treatment. Experiments are performed with the receptor expressed transiently in HeLa cells.

Localization of Expressed GFP-DASpp Inside Cells

To obtain cellular distribution data, nuclei of transfected cells are first labeled with 5 μg/ml Hoechst 33342 (Molecular Probes) in C-DMEM for 20 minutes at 33° C. and 5% $CO_2$. Cells are washed once in Hank's Balanced Salt Solution (HBSS). The cells are analyzed live or they are rinsed with HBSS, fixed for 15 min with 3.7% formaldehyde in HBSS, stained with Hoechst 33342, and washed before analysis.

In a preferred embodiment, image acquisition and analysis are performed using the cell screening system of the present invention. The intracellular GFP-DASpp fluorescence signal is collected by acquiring fluorescence image pairs (GFP-DASpp and Hoechst 33342-labeled nuclei) from field cells. The image pairs obtained at each time point are used to define nuclear and cytoplasmic regions in each cell. Data demonstrating dispersed signal in the cytoplasm would be consistent with known steroid receptors that are DNA transcriptional activators.

Screening for Induction of GFP-DASpp Translocation

Using the above construct, confirmed for appropriate expression of the GFP-DASpp, as an indicator cell line, a screen of various ligands is performed using a series of steroid type ligands including, but not limited to: estrogen, progesterone, retinoids, growth factors, androgens, and many other steroid and steroid based molecules. Image acquisition and analysis are performed using the cell screening system of the invention. The intracellular GFP-DASpp fluorescence signal is collected by acquiring fluorescence image pairs (GFP-DASpp and Hoechst 33342-labeled nuclei) from fields cells. The image pairs obtained at each time point are used to define nuclear and cytoplasmic regions in each cell. Translocation of GFP-DASpp is calculated by dividing the integrated fluorescence intensity of GFP-DASpp in the nucleus by the integrated fluorescence intensity of the chimera in the cytoplasm or as a nuclear-cytoplasmic difference of GFP fluorescence. A translocation from the cytoplasm into the nucleus indicates a ligand binding activation of the DASpp thus identifying the potential receptor class and action. Combining this data with other data obtained in a similar fashion using known inhibitors and modifiers of steroid receptors, would either validate the DASpp as a target, or more data would be generated from various sources.

EXAMPLE 9

Additional Screens Translocation Between the Plasma Membrane and the Cytoplasm

Profilactin Complex Dissociation and Binding of Profilin to the Plasma Membrane

In one embodiment, a fluorescent protein biosensor of profilin membrane binding is prepared by labeling purified profilin (Federov et al.(1994), *J. Molec. Biol.* 241:480–482; Lanbrechts et al. (1995), *Eur. J. Biochem.* 230:281–286) with a probe possessing a fluorescence lifetime in the range of 2–300 ns. The labeled profilin is introduced into living indicator cells using bulk loading methodology and the indicator cells are treated with test compounds. Fluorescence anisotropy imaging microscopy (Gough and Taylor (1993), *J. Cell Biol.* 121:1095–1107) is used to measure test-compound dependent movement of the fluorescent derivative of profilin between the cytoplasm and membrane for a period of time after treatment ranging from 0.1 s to 10 h.

Rho-RhoGDI Complex Translocation to the Membrane

In another embodiment, indicator cells are treated with test compounds and then fixed, washed, and permeabilized. The indicator cell plasma membrane, cytoplasm, and nucleus are all labeled with distinctly colored markers followed by immunolocalization of Rho protein (Self et al. (1995), *Methods in Enzymology* 256:3–10; Tanaka et al. (1995), *Methods in Enzymology* 256:41–49) with antibodies labeled with a fourth color. Each of the four labels is imaged separately using the cell screening system, and the images used to calculate the amount of inhibition or activation of translocation effected by the test compound. To do this calculation, the images of the probes used to mark the plasma membrane and cytoplasm are used to mask the image of the immunological probe marking the location of intracellular Rho protein. The integrated brightness per unit area under each mask is used to form a translocation quotient by dividing the plasma membrane integrated brightness/area by the cytoplasmic integrated brightness/area. By comparing the translocation quotient values from control and experimental wells, the percent translocation is calculated for each potential lead compound.

β-Arrestin Translocation to the Plasma Membrane Upon G-protein Receptor Activation In another embodiment of a cytoplasm to membrane translocation high-content screen, the translocation of β-arrestin protein from the cytoplasm to the plasma membrane is measured in response to cell treatment. To measure the translocation, living indicator cells containing luminescent domain markers are treated with test compounds and the movement of the β-arrestin marker is measured in time and space using the cell screening system of the present invention. In a preferred embodiment, the indicator cells contain luminescent markers consisting of a green fluorescent protein β-arrestin (GFP-β-arrestin) protein chimera (Barak et al. (1997), *J. Biol. Chem.* 272:27497–27500; Daaka et al. (1998), *J. Biol. Chem.* 273:685–688) that is expressed by the indicator cells through the use of transient or stable cell transfection and other reporters used to mark cytoplasmic and membrane domains. When the indicator cells are in the resting state, the domain marker molecules partition predominately in the plasma membrane or in the cytoplasm. In the high-content screen, these markers are used to delineate the cell cytoplasm and plasma membrane in distinct channels of fluorescence. When the indicator cells are treated with a test compound, the dynamic redistribution of the GFP-β-arrestin is recorded as a series of images over a time scale ranging from 0.1 s to 10 h. In a preferred embodiment, the time scale is 1 h. Each image is analyzed by a method that quantifies the movement of the GFP-β-arrestin protein chimera between the plasma membrane and the cytoplasm. To do this calculation, the images of the probes used to mark the plasma membrane and cytoplasm are used to mask the image of the GFP-β-arrestin probe marking the location of intracellular GFP-β-arrestin protein. The integrated brightness per unit area under each mask is used to form a translocation quotient by dividing the plasma membrane integrated brightness/area by the cytoplasmic integrated brightness/area. By comparing the translocation quotient values from control and experimental wells, the percent translocation is calculated for each potential lead compound. The output of the high-content screen relates quantitative data describing the magnitude of the translocation within a large number of individual cells that have been treated with test compounds of interest.

Translocation Between the Endoplasmic Reticulum and the Golgi

In one embodiment of an endoplasmic reticulum to Golgi translocation high-content screen, the translocation of a VSVG protein from the ts045 mutant strain of vesicular stomatitis virus (Ellenberg et al. (1997), *J. Cell Biol.* 138:1193–1206; Presley et al. (1997) *Nature* 389:81–85) from the endoplasmic reticulum to the Golgi domain is measured in response to cell treatment. To measure the translocation, indicator cells containing luminescent reporters are treated with test compounds and the movement of the reporters is measured in space and time using the cell screening system of the present invention. The indicator cells contain luminescent reporters consisting of a GFP-VSVG protein chimera that is expressed by the indicator cell through the use of transient or stable cell transfection and other domain markers used to measure the localization of the endoplasmic reticulum and Golgi domains. When the indicator cells are in their resting state at 40° C., the GFP-VSVG protein chimera molecules are partitioned predominately in the endoplasmic reticulum. In this high-content screen, domain markers of distinct colors used to delineate the endoplasmic reticulum and the Golgi domains in distinct channels of fluorescence. When the indicator cells are treated with a test compound and the temperature is simultaneously lowered to 32° C., the dynamic redistribution of the GFP-VSVG protein chimera is recorded as a series of images over a time scale ranging from 0.1 s to 10 h. Each image is analyzed by a method that quantifies the movement of the GFP-VSVG protein chimera between the endoplasmic reticulum and the Golgi domains. To do this calculation, the images of the probes used to mark the endoplasmic reticulum and the Golgi domains are used to mask the image of the GFP-VSVG probe marking the location of intracellular GFP-VSVG protein. The integrated brightness per unit area under each mask is used to form a translocation quotient by dividing the endoplasmic reticulum integrated brightness/area by the Golgi integrated brightness/area. By comparing the translocation quotient values from control and experimental wells, the percent translocation is calculated for each potential lead compound. The output of the high-content screen relates quantitative data describing the magnitude of the translocation within a large number of individual cells that have been treated with test compounds of interest at final concentrations ranging from $10^{-12}$ to $10^{-3}$ M for a period ranging from 1 min to 10 h.

Induction and Inhibition of Organellar Function

Intracellular Microtubule Stability

In another aspect of the invention, an automated method for identifying compounds that modify microtubule structure is provided. In this embodiment, indicator cells are treated with test compounds and the distribution of luminescent microtubule-labeling molecules is measured in space and time using a cell screening system, such as the one disclosed above. The luminescent microtubule-labeling molecules may be expressed by or added to the cells either before, together with, or after contacting the cells with a test compound.

In one embodiment of this aspect of the invention, living cells express a luminescently labeled protein biosensor of microtubule dynamics, comprising a protein that labels microtubules fused to a luminescent protein. Appropriate microtubule-labeling proteins for this aspect of the invention include, but are not limited to α and β tubulin isoforms, and MAP4. Preferred embodiments of the luminescent protein include, but are not limited to green fluorescent protein (GFP) and GFP mutants. In a preferred embodiment, the method involves transfecting cells with a microtubule labeling luminescent protein, wherein the microtubule labeling protein can be, but is not limited to, α-tubulin, β-tubulin, or microtubule-associated protein 4 (MAP4). The approach outlined here enables those skilled in the art to make live cell measurements to determine the effect of lead compounds on tubulin activity and microtubule stability in vivo.

In a most preferred embodiment, MAP4 is fused to a modified version of the *Aequorea victoria* green fluorescent protein (GFP). A DNA construct has been made which consists of a fusion between the EGFP coding sequence (available from Clontech) and the coding sequence for mouse MAP4. (Olson et al., (1995), J. Cell Biol. 130(3): 639–650). MAP4 is a ubiquitous microtubule-associated protein that is known to interact with microtubules in interphase as well as mitotic cells (Olmsted and Murofushi, (1993), MAP4. In "Guidebook to the Cytoskeleton and Motor Proteins." Oxford University Press. T. Kreis and R. Vale, eds.) Its localization, then, can serve as an indicator of the localization, organization, and integrity of microtubules in living (or fixed) cells at all stages of the cell cycle for cell-based HCS assays. While MAP2 and tau (microtubule associated proteins expressed specifically in neuronal cells) have been used to form GFP chimeras (Kaech et al., (1996) Neuron. 17: 1189–1199; Hall et al., (1997), Proc. Nat. Acad. Sci. 94: 4733–4738) their restricted cell type distribution and the tendency of these proteins to bundle microtubules when overexpressed make these proteins less desirable as molecular reagents for analysis in live cells originating from varied tissues and organs. Moderate overexpression of GFP-MAP4 does not disrupt microtubule function or integrity (Olson et al., 1995). Similar constructs can be made using β-tubulin or α-tubulin via standard techniques in the art. These chimeras will provide a means to observe and analyze microtubule activity in living cells during all stages of the cell cycle.

In another embodiment, the luminescently labeled protein biosensor of microtubule dynamics is expressed, isolated, and added to the cells to be analyzed via bulk loading techniques, such as microinjection, scrape loading, and impact-mediated loading. In this embodiment, there is not an issue of overexpression within the cell, and thus α and β tubulin isoforms, MAP4, MAP2 and/or tau can all be used.

In a further embodiment, the protein biosensor is expressed by the cell, and the cell is subsequently contacted with a luminescent label, such as a labeled antibody, that detects the protein biosensor, endogenous levels of a protein antigen, or both. In this embodiment, a luminescent label that detects α and β tubulin isoforms, MAP4, MAP2 and/or tau, can be used.

A variety of GFP mutants are available, all of which would be effective in this invention, including, but not limited to, GFP mutants which are commercially available (Clontech, California).

The MAP4 construct has been introduced into several mammalian cell lines (BHK-21, Swiss 3T3, HeLa, HEK 293, LLCPK) and the organization and localization of tubulin has been visualized in live cells by virtue of the GFP fluorescence as an indicator of MAP4 localization. The construct can be expressed transiently or stable cell lines can be prepared by standard methods. Stable HeLa cell lines expressing the EGFP-MAP4 chimera have been obtained, indicating that expression of the chimera is not toxic and does not interfere with mitosis.

Possible selectable markers for establishment and maintenance of stable cell lines include, but are not limited to the neomycin resistance gene, hygromycin resistance gene, zeocin resistance gene, puromycin resistance gene, bleomycin resistance gene, and blastacidin resistance gene.

The utility of this method for the monitoring of microtubule assembly, disassembly, and rearrangement has been demonstrated by treatment of transiently and stably transfected cells with microtubule drugs such as paclitaxel, nocodazole, vincristine, or vinblastine.

The present method provides high-content and combined high throughput-high content cell-based screens for anti-microtubule drugs, particularly as one parameter in a multi-parametric cancer target screen. The EGFP-MAP4 construct used herein can also be used as one of the components of a high-content screen that measures multiple signaling pathways or physiological events. In a preferred embodiment, a combined high throughput and high content screen is employed, wherein multiple cells in each of the locations containing cells are analyzed in a high throughput mode, and only a subset of the locations containing cells are analyzed in a high content mode. The high throughput screen can be any screen that would be useful to identify those locations containing cells that should be further analyzed, including, but not limited to, identifying locations with increased luminescence intensity, those exhibiting expression of a reporter gene, those undergoing calcium changes, and those undergoing pH changes.

In addition to drug screening applications, the present invention may be applied to clinical diagnostics, the detection of chemical and biological warfare weapons, and the basic research market since fundamental cell processes, such as cell division and motility, are highly dependent upon microtubule dynamics.

Image Acquisition and Analysis

Image data can be obtained from either fixed or living indicator cells. To extract morphometric data from each of the images obtained the following method of analysis is used:

1. Threshold each nucleus and cytoplasmic image to produce a mask that has value=0 for each pixel outside a nucleus or cell boundary.
2. Overlay the mask on the original image, detect each object in the field (i.e., nucleus or cell), and calculate its size, shape, and integrated intensity.
3. Overlay the whole cell mask obtained above on the corresponding luminescent microtubule image and apply one or more of the following set of classifiers to determine the microtubule morphology and the effect of drugs on microtubule morphology.

Microtubule morphology is defined using a set of classifiers to quantify aspects of microtubule shape, size, aggregation state, and polymerization state. These classifiers can be based on approaches that include co-occurrence matrices, texture measurements, spectral methods, structural methods, wavelet transforms, statistical methods, or combinations thereof.

Examples of such classifiers are as follows:

1. A classifier to quantify microtubule length and width using edge detection methods such as that discussed in Kolega et al. ((1993). *BioImaging* 1:136–150), which discloses a non-automated method to determine edge strength in individual cells), to calculate the total edge strength within each cell. To normalize for cell size, the total edge strength can be divided by the cell area to give a "microtubule morphology" value. Large microtubule morphology values are associated with strong edge strength values and are therefore maximal in cells containing distinct microtubule structures. Likewise, small microtubule morphology values are associated with weak edge strength and are minimal in cells with depolymerized microtubules. The physiological range of microtubule morphology values is set by treating cells with either the microtubule stabilizing drug paclitaxel (10 $\mu$M) or the microtubule depolymerizing drug nocodazole (10 $\mu$g/ml).
2. A classifier to quantify microtubule aggregation into punctate spots or foci using methodology from the receptor internalization methods discussed supra.
3. A classifier to quantify microtubule depolymerization using a measure of image texture.
4. A classifier to quantify apparent interconnectivity, or branching (or both), of the microtubules.
5. Measurement of the kinetics of microtubule reorganization using the above classifiers on a time series of images of cells treated with test compounds.

In a further aspect, kits are provided for analyzing microtubule stability, comprising an expression vector comprising a nucleic acid that encodes a microtubule labeling protein and instructions for using the expression vector for carrying out the methods described above. In a preferred embodiment, the expression vector further comprises a nucleic acid that encodes a luminescent protein, wherein the microtubule binding protein and the luminescent protein thereof are expressed as a fusion protein. Alternatively, the kit may contain an antibody that specifically binds to the microtubule-labeling protein. In a further embodiment, the kit includes cells that express the microtubule labeling protein. In a preferred embodiment, the, cells are transfected with the expression vector. In another preferred embodiment, the kits further contain a compound that is known to disrupt microtubule structure, including but not limited to curacin, nocodazole, vincristine, or vinblastine. In another preferred embodiment, the kits further comprise a compound that is known to stabilize microtubule structure, including but not limited to taxol (paclitaxel), and discodermolide.

In another aspect, the present invention comprises a machine readable storage medium comprising a program containing a set of instructions for causing a cell screening system to execute the disclosed methods for analyzing microtubule stability, wherein the cell screening system comprises an optical system with a stage adapted for holding a plate containing cells, a digital camera, a means for directing fluorescence or luminescence emitted from the cells to the digital camera, and a computer means for receiving and processing the digital data from the digital camera.

High-content Screens Involving the Functional Localization of Macromolecules

Within this class of high-content screen, the functional localization of macromolecules in response to external stimuli is measured within living cells.

Glycolytic Enzyme Activity Regulation

In a preferred embodiment of a cellular enzyme activity high-content screen, the activity of key glycolytic regulatory enzymes are measured in treated cells. To measure enzyme activity, indicator cells containing luminescent labeling reagents are treated with test compounds and the activity of the reporters is measured in space and time using cell screening system of the present invention.

In one embodiment, the reporter of intracellular enzyme activity is fructose-6-phosphate, 2-kinase/fructose-2,6-bisphosphatase (PFK-2), a regulatory enzyme whose phosphorylation state indicates intracellular carbohydrate anabolism or catabolism (Deprez et al. (1997) *J. Biol. Chem.* 272:17269–17275; Kealer et al. (1996) *FEBS Letters* 395:225–227; Lee et al. (1996), *Biochemistry* 35:6010–6019). The indicator cells contain luminescent reporters consisting of a fluorescent protein biosensor of PFK-2 phosphorylation. The fluorescent protein biosensor is constructed by introducing an environmentally sensitive fluorescent dye near to the known phosphorylation site of the enzyme (Deprez et al. (1997), supra; Giuliano et al. (1995), supra). The dye can be of the ketocyanine class (Kessler and Wolfbeis (1991), *Spectrochimica Acta* 47A:187–192) or any class that contains a protein reactive moiety and a fluorochrome whose excitation or emission spectrum is sensitive to solution polarity. The fluorescent protein biosensor is introduced into the indicator cells using bulk loading methodology.

Living indicator cells are treated with test compounds, at final concentrations ranging from $10^{-12}$ M to $10^{-3}$ M for times ranging from 0.1 s to 10 h. In a preferred embodiment, ratio image data are obtained from living treated indicator cells by collecting a spectral pair of fluorescence images at each time point. To extract morphometric data from each time point, a ratio is made between each pair of images by numerically dividing the two spectral images at each time point, pixel by pixel. Each pixel value is then used to calculate the fractional phosphorylation of PFK-2. At small fractional values of phosphorylation, PFK-2 stimulates carbohydrate catabolism. At high fractional values of phosphorylation, PFK-2 stimulates carbohydrate anabolism.

Protein Kinase A Activity and Localization of Subunits

In another embodiment of a high-content screen, both the domain localization and activity of protein kinase A (PKA) within indicator cells are measured in response to treatment with test compounds.

The indicator cells contain luminescent reporters including a fluorescent protein biosensor of PKA activation. The fluorescent protein biosensor is constructed by introducing an environmentally sensitive fluorescent dye into the catalytic subunit of PKA near the site known to interact with the regulatory subunit of PKA (Harootunian et al. (1993), *Mol. Biol. of the Cell* 30 4:993–1002; Johnson et al. (1996), *Cell* 85:149–158; Giuliano et al. (1995), supra). The dye can be of the ketocyanine class (Kessler, and Wolfbeis (1991), *Spectrochimica Acta* 47A:187–192) or any class that contains a protein reactive moiety and a fluorochrome whose excitation or emission spectrum is sensitive to solution polarity. The fluorescent protein biosensor of PKA activation is introduced into the indicator cells using bulk loading methodology.

In one embodiment, living indicator cells are treated with test compounds, at final concentrations ranging from $10^{-12}$ M to $10^{-3}$ M for times ranging from 0.1 s to 10 h. In a preferred embodiment, ratio image data are obtained from living treated indicator cells. To extract biosensor data from each time point, a ratio is made between each pair of images, and each pixel value is then used to calculate the fractional activation of PKA (e.g., separation of the catalytic and regulatory subunits after cAMP binding). At high fractional values of activity, PFK-2 stimulates biochemical cascades within the living cell.

To measure the translocation of the catalytic subunit of PKA, indicator cells containing luminescent reporters are treated with test compounds and the movement of the reporters is measured in space and time using the cell screening system. The indicator cells contain luminescent reporters consisting of domain markers used to measure the localization of the cytoplasmic and nuclear domains. When the indicator cells are treated with a test compounds, the dynamic redistribution of a PKA fluorescent protein biosensor is recorded intracellularly as a series of images over a time scale ranging from 0.1 s to 10 h. Each image is analyzed by a method that quantifies the movement of the PKA between the cytoplasmic and nuclear domains. To do this calculation, the images of the probes used to mark the cytoplasmic and nuclear domains are used to mask the image of the PKA fluorescent protein biosensor. The integrated brightness per unit area under each mask is used to form a translocation quotient by dividing the cytoplasmic integrated brightness/area by the nuclear integrated brightness/area. By comparing the translocation quotient values from control and experimental wells, the percent translocation is calculated for each potential lead compound. The output of the high-content screen relates quantitative data describing the magnitude of the translocation within a large number of individual cells that have been treated with test compound in the concentration range of $10^{-12}$ M to $10^{-3}$ M.

High-content Screens Involving the Induction or Inhibition of Gene Expression RNA-based Fluorescent Biosensors Cytoskeletal Protein Transcription and Message Localization Regulation of the general classes of cell physiological responses including cell-substrate adhesion, cell-cell adhesion, signal transduction, cell-cycle events, intermediary and signaling molecule metabolism, cell locomotion, cell-cell communication, and cell death can involve the alteration of gene expression. High-content screens can also be designed to measure this class of physiological response.

In one embodiment, the reporter of intracellular gene expression is an oligonucleotide that can hybridize with the target mRNA and alter its fluorescence signal. In a preferred embodiment, the oligonucleotide is a molecular beacon (Tyagi and Kramer (1996) *Nat. Biotechnol.* 14:303–308), a luminescence-based reagent whose fluorescence signal is dependent on intermolecular and intramolecular interactions. The fluorescent biosensor is constructed by introducing a fluorescence energy transfer pair of fluorescent dyes such that there is one at each end (5' and 3') of the reagent. The dyes can be of any class that contains a protein reactive moiety and fluorochromes whose excitation and emission spectra overlap sufficiently to provide fluorescence energy transfer between the dyes in the resting state, including, but not limited to, fluorescein and rhodamine (Molecular Probes, Inc.). In a preferred embodiment, a portion of the message coding for β-actin (Kislauskis et al. (1994), *J. Cell Biol.* 127:441–451; McCann et al. (1997), *Proc. Natl. Acad. Sci.* 94:5679–5684; Sutoh (1982), *Biochemistry* 21:3654–3661) is inserted into the loop region of a hairpin-shaped oligonucleotide with the ends tethered together due to intramolecular hybridization. At each end of the biosensor a fluorescence donor (fluorescein) and a fluorescence acceptor (rhodamine) are covalently bound. In the tethered state, the fluorescence energy transfer is maximal and therefore indicative of an unhybridized molecule. When hybridized with the mRNA coding for β-actin, the tether is broken and energy transfer is lost. The complete fluorescent biosensor is introduced into the indicator cells using bulk loading methodology.

In one embodiment, living indicator cells are treated with test compounds, at final concentrations ranging from $10^{-12}$ M to $10^{-3}$ M for times ranging from 0.1 s to 10 h. In a preferred embodiment, ratio image data are obtained from living treated indicator cells. To extract morphometric data from each time point, a ratio is made between each pair of images, and each pixel value is then used to calculate the fractional hybridization of the labeled nucleotide. At small fractional values of hybridization little expression of β-actin is indicated. At high fractional values of hybridization, maximal expression of β-actin is indicated. Furthermore, the distribution of hybridized molecules within the cytoplasm of the indicator cells is also a measure of the physiological response of the indicator cells.

Cell Surface Binding of a Ligand

Labeled Insulin Binding to its Cell Surface Receptor in Living Cells

Cells whose plasma membrane domain has been labeled with a labeling reagent of a particular color are incubated with a solution containing insulin molecules (Lee et al. (1997), *Biochemistry* 36:2701–2708; Martinez-Zaguilan et al. (1996), *Am. J. Physiol.* 270:C1438–C1446) that are labeled with a luminescent probe of a different color for an appropriate time under the appropriate conditions. After incubation, unbound insulin molecules, are washed away, the cells fixed and the distribution and concentration of the insulin on the plasma membrane is measured. To do this, the cell membrane image is used as a mask for the insulin image. The integrated intensity from the masked insulin image is compared to a set of images containing known amounts of labeled insulin. The amount of insulin bound to the cell is determined from the standards and used in conjunction with the total concentration of insulin incubated with the cell to calculate a dissociation constant or insulin to its cell surface receptor.

Labeling of Cellular Compartments

Whole Cell Labeling

Whole cell labeling is accomplished by labeling cellular components such that dynamics of cell shape and motility of the cell can be measured over time by analyzing fluorescence images of cells.

In one embodiment, small reactive fluorescent molecules are introduced into living cells. These membrane-permeant molecules both diffuse through and react with protein components in the plasma membrane. Dye molecules react with intracellular molecules to both increase the fluorescence signal emitted from each molecule and to entrap the fluorescent dye within living cells. These molecules include reactive chloromethyl derivatives of aminocoumarins, hydroxycoumarins, eosin diacetate, fluorescein diacetate, some BODIPY™ dye derivatives, and tetramethylrhodamine. The reactivity of these dyes toward macromolecules includes free primary amino groups and free sulffiydryl groups.

In another embodiment, the cell surface is labeled by allowing the cell to interact with fluorescently labeled antibodies or lectins (Sigma Chemical Company, St. Louis, Mo.) that react specifically with molecules on the cell surface. Cell surface protein chimeras expressed by the cell of interest that contain a green fluorescent protein, or mutant thereof, component can also be used to fluorescently label the entire cell surface. Once the entire cell is labeled, images of the entire cell or cell array can become a parameter in high content screens, involving the measurement of cell shape, motility, size, and growth and division.

Plasma Membrane Labeling

In one embodiment, labeling the whole plasma membrane employs some of the same methodology described above for labeling the entire cells. Luminescent molecules that label the entire cell surface act to delineate the plasma membrane.

In a second embodiment subdomains of the plasma membrane, the extracellular surface, the lipid bilayer, and the intracellular surface can be labeled separately and used as components of high content screens. In the first embodiment, the extracellular surface is labeled using a brief treatment with a reactive fluorescent molecule such as the succinimidyl ester or iodoacetamde derivatives of fluorescent dyes such as the fluoresceins, rhodamines, cyanines, and BODIPYS™.

In a third embodiment, the extracellular surface is labeled using fluorescently labeled macromolecules with a high affinity for cell surface molecules. These include fluorescently labeled lectins such as the fluorescein, rhodamine, and cyanine derivatives of lectins derived from jack bean (Con A), red kidney bean (erytlroagglutinin PAC-E), or wheat germ.

In a fourth embodiment, fluorescently labeled antibodies with a high affinity for cell surface components are used to label the extracellular region of the plasma membrane. Extracellular regions of cell surface receptors and ion channels are examples of proteins that can be labeled with antibodies.

In a fifth embodiment, the lipid bilayer of the plasma membrane is labeled with fluorescent molecules. These molecules include fluorescent dyes attached to long chain hydrophobic molecules that interact strongly with the hydrophobic region in the center of the plasma membrane lipid bilayer. Examples of these dyes include the PKH series of dyes (U.S. Pat. Nos. 4,783,401, 4,762701, and 4,859,584; available commercially from Sigma Chemical Company, St. Loius, Mo.), fluorescent phospholipids such as nitrobenzoxadiazole glycerophosphoethanolamine and fluorescein-derivatized dihexadecanoylglycerophosphoethanolamine, fluorescent fatty acids such as 5-butyl-4,4-difluoro-4-bora-3a,4a-diaza-s-indacene-3-nonanoic acid and 1-pyrenedecanoic acid (Molecular Probes, Inc.), fluorescent sterols including cholesteryl 4,4-difluoro-5,7-dimethyl-4-bora-3a,4a-diaza-s-indacene-3-dodecanoate and cholesteryl 1-pyrenehexanoate, and fluorescently labeled proteins that interact specifically with lipid bilayer components such as the fluorescein derivative of annexin V (Caltag Antibody Co, Burlingame, Calif.).

In another embodiment, the intracellular component of the plasma membrane is labeled with fluorescent molecules. Examples of these molecules are the intracellular components of the trimeric G-protein receptor, adenylyl cyclase, and ionic transport proteins. These molecules can be labeled as a result of tight binding to a fluorescently labeled specific antibody or by the incorporation of a fluorescent protein chimera that is comprised of a membrane-associated protein and the green fluorescent protein, and mutants thereof.

Endosome Fluorescence Labeling

In one embodiment, ligands that are transported into cells by receptor-mediated endocytosis are used to trace the dynamics of endosomal organelles. Examples of labeled ligands include BODIPY™ FL-labeled low density lipoprotein complexes, tetramethylrhodamine transferrin analogs, and fluorescently labeled epidermal growth factor (Molecular Probes, Inc.)

In a second embodiment, fluorescently labeled primary or secondary antibodies (Sigma Chemical Co. St. Louis, Mo.; Molecular Probes, Inc. Eugene, Oreg.; Caltag Antibody Co.) that specifically label endosomal ligands are used to mark the endosomal compartment in cells.

In a third embodiment, endosomes are fluorescently labeled in cells expressing protein chimeras formed by fusing a green fluorescent protein, or mutants thereof, with a receptor whose internalization labels endosomes. Chimeras of the EGF, transferrin, and low density lipoprotein receptors are examples of these molecules.

Lysosome Labeling

In one embodiment, membrane permeant lysosome-specific luminescent reagents are used to label the lysosomal compartment of living and fixed cells. These reagents include the luminescent molecules neutral red, N-(3-((2,4-dinitrophenyl)amino)propyl)-N-(3-aminopropyl) methylamine, and the LysoTracker probes which report intralysosomal pH as well as the dynamic distribution of lysosomes (Molecular Probes, Inc.)

In a second embodiment, antibodies against lysosomal antigens (Sigma Chemical Co.; Molecular Probes, Inc.; Caltag Antibody Co.) are used to label lysosomal components that are localized in specific lysosomal domains. Examples of these components are the degradative enzymes involved in cholesterol ester hydrolysis, membrane protein proteases, and nucleases as well as the ATP-driven lysosomal proton pump.

In a third embodiment, protein chimeras consisting of a lysosomal protein genetically fused to an intrinsically luminescent protein such as the green fluorescent protein, or mutants thereof, are used to label the lysosomal domain. Examples of these components are the degradative enzymes involved in cholesterol ester hydrolysis, membrane protein proteases, and nucleases as well as the ATP-driven lysosomal proton pump.

Cytoplasmic Fluorescence Labeling

In one embodiment, cell permeant fluorescent dyes (Molecular Probes, Inc.) with a reactive group are reacted with living cells. Reactive dyes including monobromobimane, 5-chloromethylfluorescein diacetate, carboxy fluorescein diacetate succinimidyl ester, and chloromethyl tetramethylrhodamine are examples of cell permeant fluorescent dyes that are used for long term labeling of the cytoplasm of cells.

In a second embodiment, polar tracer molecules such as Lucifer yellow and cascade blue-based fluorescent dyes (Molecular Probes, Inc.) are introduced into cells using bulk loading methods and are also used for cytoplasmic labeling.

In a third embodiment, antibodies against cytoplasmic components (Sigma Chemical Co.; Molecular Probes, Inc.; Caltag Antibody Co.) are used to fluorescently label the cytoplasm. Examples of cytoplasmic antigens are many of the enzymes involved in intermediary metabolism. Enolase, phosphofructokinase, and acetyl-CoA dehydrogenase are examples of uniformly distributed cytoplasmic antigens.

In a fourth embodiment, protein chimeras consisting of a cytoplasmic protein genetically fused to an intrinsically luminescent protein such as the green fluorescent protein, or mutants thereof, are used to label the cytoplasm. Fluorescent chimeras of uniformly distributed proteins are used to label the entire cytoplasmic domain. Examples of these proteins are many of the proteins involved in intermediary metabolism and include enolase, lactate dehydrogenase, and hexokinase.

In a fifth embodiment, antibodies against cytoplasmic antigens (Sigma Chemical Co.; Molecular Probes, Inc.; Caltag Antibody Co.) are used to label cytoplasmic components that are localized in specific cytoplasmic sub-domains. Examples of these components are the cytoskeletal proteins actin, tubulin, and cytokeratin. A population of these proteins within cells is assembled into discrete structures, which in this case, are fibrous. Fluorescence labeling of these proteins with antibody-based reagents therefore labels a specific sub-domain of the cytoplasm.

In a sixth embodiment, non-antibody-based fluorescently labeled molecules that interact strongly with cytoplasmic proteins are used to label specific cytoplasmic components. One example is a fluorescent analog of the enzyme DNAse I (Molecular Probes, Inc.) Fluorescent analogs of this enzyme bind tightly and specifically to cytoplasmic actin, thus labeling a sub-domain of the cytoplasm. In another example, fluorescent analogs of the mushroom toxin phalloidin or the drug paclitaxel (Molecular Probes, Inc.) are used to label components of the actin- and microtubule-cytoskeletons, respectively.

In a seventh embodiment, protein chimeras consisting of a cytoplasmic protein genetically fused to an intrinsically luminescent protein such as the green fluorescent protein, or mutants thereof, are used to label specific domains of the cytoplasm. Fluorescent chimeras of highly localized proteins are used to label cytoplasmic sub-domains. Examples of these proteins are many of the proteins involved in regulating the cytoskeleton. They include the structural proteins actin, tubulin, and cytokeratin as well as the regulatory proteins microtubule associated protein 4 and α-actinin.

Nuclear Labeling

In one embodiment, membrane permeant nucleic-acid-specific luminescent reagents (Molecular Probes, Inc.) are used to label the nucleus of living and fixed cells. These reagents include cyanine-based dyes (e.g., TOTO®, YOYO®, and BOBO™), phenanthidines and acridines (e.g., ethidium bromide, propidium iodide, and acridine orange), indoles and imidazoles (e.g., Hoechst 33258, Hoechst 33342, and 4',6-diamidino-2-phenylindole), and other similar reagents (e.g., 7-aminoactinomycin D, hydroxystilbamidine, and the psoralens).

In a second embodiment, antibodies against nuclear antigens (Sigma Chemical Co.; Molecular Probes, Inc.; Caltag Antibody Co.) are used to label nuclear components that are localized in specific nuclear domains. Examples of these components are the macromolecules involved in maintaining DNA structure and function. DNA, RNA, histones, DNA polymerase, RNA polymerase, lamins, and nuclear variants of cytoplasmic proteins such as actin are examples of nuclear antigens.

In a third embodiment, protein chimeras consisting of a nuclear protein genetically fused to an intrinsically luminescent protein such as the green fluorescent protein, or mutants thereof, are used to label the nuclear domain. Examples of these proteins are many of the proteins involved in maintaining DNA structure and function. Histones, DNA polymerase, RNA polymerase, lamins, and nuclear variants of cytoplasmic proteins such as actin are examples of nuclear proteins.

Mitochondrial Labeling

In one embodiment, membrane permeant mitochondrial-specific luminescent reagents (Molecular Probes, Inc.) are used to label the mitochondria of living and fixed cells. These reagents include rhodamine 123, tetramethyl rosamine, JC-1, and the MITOTRACKER™ reactive dyes.

In a second embodiment, antibodies against mitochondrial antigens (Sigma Chemical Co.; Molecular Probes, Inc.; Caltag Antibody Co.) are used to label mitochondrial components that are localized in specific mitochondrial domains. Examples of these components are the macromolecules involved in maintaining mitochondrial DNA structure and function. DNA, RNA, histones, DNA polymerase, RNA polymerase, and mitochondrial variants of cytoplasmic macromolecules such as mitochondrial tRNA and rRNA are examples mitochondrial antigens. Other examples of mitochondrial antigens are the components of the oxidative phosphorylation system found in the mitochondria (e.g., cytochrome c, cytochrome c oxidase, and succinate dehydrogenase).

In a third embodiment, protein chimeras consisting of a mitochondrial protein genetically fused to an intrinsically luminescent protein such as the green fluorescent protein, or mutants thereof, are used to label the mitochondrial domain. Examples of these components are the macromolecules involved in maintaining mitochondrial DNA structure and function. Examples include histones, DNA polymerase, RNA polymerase, and the components of the oxidative phosphorylation system found in the mitochondria (e.g., cytochrome c, cytochrome c oxidase, and succinate dehydrogenase).

Endoplasmic Reticulum Labeling

In one embodiment, membrane permeant endoplasmic reticulum-specific luminescent reagents (Molecular Probes, Inc.) are used to label the endoplasmic reticulum of living and fixed cells. These reagents include short chain carbocyanine dyes (e.g., $DiOC_6$ and $DiOC_3$), long chain carbocyanine dyes (e.g., $DiIC_{16}$ and $DiIC_{18}$), and luminescently labeled lectins such as concanavalin A.

In a second embodiment, antibodies against endoplasmic reticulum antigens (Sigma Chemical Co.; Molecular Probes, Inc.; Caltag Antibody Co.) are used to label endoplasmic reticulum components that are localized in specific endoplasmic reticulum domains. Examples of these components are the macromolecules involved in the fatty acid elongation systems, glucose-6-phosphatase, and HMG CoA-reductase.

In a third embodiment, protein chimeras consisting of a endoplasmic reticulum protein genetically fried to an intrinsically luminescent protein such as the green fluorescent protein, or mutants thereof, are used to label the endoplasmic reticulum domain. Examples of these components are the macromolecules involved in the fatty acid elongation systems, glucose-6-phosphatase, and HMG CoA-reductase.

Golgi Labeling

In one embodiment, membrane permeant Golgi-specific luminescent reagents (Molecular Probes, Inc.) are used to label the Golgi of living and fixed cells. These reagents include luminescently labeled macromolecules such as wheat germ agglutinin and Brefeldin A as well as luminescently labeled ceramide.

In a second embodiment, antibodies against Golgi antigens (Sigma Chemical Co.; Molecular Probes, Inc.; Caltag Antibody Co.) are used to label Golgi components that are localized in specific Golgi domains. Examples of these components are N-acetylglucosamine phosphotransferase, Golgi-specific phosphodiesterase, and mannose-6-phosphate receptor protein.

In a third embodiment, protein chimeras consisting of a Golgi protein genetically fused to an intrinsically luminescent protein such as the green fluorescent protein, or mutants thereof, are used to label the Golgi domain. Examples of these components are N-acetylglucosamine phosphotransferase, Golgi-specific phosphodiesterase, and mannose-6-phosphate receptor protein.

While many of the examples presented involve the measurement of single cellular processes, this is again is intended for purposes of illustration only. Multiple parameter high-content screens can be produced by combining several single parameter screens into a multiparameter high-content screen or by adding cellular parameters to any existing high-content screen. Furthermore, while each example is described as being based on either live or fixed cells, each high-content screen can be designed to be used with both live and fixed cells.

Those skilled in the art will recognize a wide variety of distinct screens that can be developed based on the disclosure provided herein. There is a large and growing list of known biochemical and molecular processes in cells that involve translocations or reorganizations of specific components within cells. The signaling pathway from the cell surface to target sites within the cell involves the translocation of plasma membrane-associated proteins to the cytoplasm. For example, it is known that one of the src family of protein tyrosine kinases, pp60c-src (Walker et al (1993), *J. Biol. Chem.* 268:19552–19558) translocates from the plasma membrane to the cytoplasm upon stimulation of fibroblasts with platelet-derived growth factor (PDGF). Additionally, the targets for screening can themselves be converted into fluorescence-based reagents that report molecular changes including ligand-binding and post-translocational modifications.

EXAMPLE 10

Protease Biosensors (1) Background

As used herein, the following terms are defined as follows:

Reactant—the parent biosensor that interacts with the proteolytic enzyme.

Product—the signal-containing proteolytic fragment(s) generated by the interaction of the reactant with the enzyme.

Reactant Target Sequence—an amino acid sequence that imparts a restriction on the cellular distribution of the reactant to a particular subcellular domain of the cell.

Product Target Sequence—an amino acid sequence that imparts a restriction on the cellular distribution of the signal-containing product(s) of the targeted enzymatic reaction to a particular subcellular domain of the cell. If the product is initially localized within a membrane bound compartment, then the Product Target Sequence must incorporate the ability to export the product out of the membrane-bound compartment. A bi-functional sequence can be used, which first moves the product out of the membrane-bound compartment, and then targets the product to the final compartment. In general, the same amino acid sequences can act as either or both reactant target sequences and product target sequences. Exceptions to this include amino acid sequences which target the nuclear envelope, Golgi apparatus, endoplasmic reticulum, and which are involved in farnesylation, which are more suitable as reactant target sequences.

Protease Recognition Site—an amino acid sequence that imparts specificity by mimicking the substrate, providing a specific binding and cleavage site for a protease. Although typically a short sequence of amino acids representing the minimal cleavage site for a protease (e.g. DEVD for caspase-3, Villa, P., S. H. Kaufmann, and W. C. Earnshaw. 1997. Caspases and caspase inhibitors. *Trends Biochem Sci.* 22:388–93), greater specificity may be established by using a longer sequence from an established substrate.

Compartment—any cellular sub-structure or macromolecular component of the cell, whether it is made of protein, lipid, carbohydrate, or nucleic acid. It could be a macromolecular assembly or an organelle (a membrane delimited cellular component). Compartments include, but are not limited to, cytoplasm, nucleus, nucleolus, inner and outer surface of nuclear envelope, cytoskeleton; peroxisome, endosome, lysosome, inner leaflet of plasma membrane, outer leaflet of plasma membrane, outer leaflet of mitochondrial membrane, inner leaflet of mitochondrial membrane, Golgi, endoplasmic reticulum, or extracellular space.

Signal—an amino acid sequence that can be detected. This includes, but is not limited to inherently fluorescent proteins (e.g. Green Fluorescent Protein), cofactor-requiring fluorescent or luminescent proteins (e.g. phycobiliproteins or luciferases), and epitopes recognizable by specific antibodies or other specific natural or unnatural binding probes, including but not limited to dyes, enzyme cofactors and engineered binding molecules, which are fluorescently or luminescently labeled. Also included are site-specifically labeled proteins that contain a luminescent dye. Methodology for site-specific labeling of proteins includes, but is not limited to, engineered dye-reactive amino acids (Post, et al., *J. Biol. Chem.* 269:12880–12887 (1994)), enzyme-based incorporation of luminescent substrates into proteins (Buckler, et al., *Analyt. Biochem.* 209:20–31 (1993); Takashi, Biochemistry. 21:938–943 (1988)), and the incorporation of unnatural labeled amino acids into proteins (Noren, et al., *Science.* 244:182–188 (1989)).

Detection—a means for recording the presence, position, or amount of the signal. The approach may be direct, if the signal is inherently fluorescent, or indirect, if, for example, the signal is an epitope that must be subsequently detected with a labeled antibody. Modes of detection include, but are not limited to, the spatial position of fluorescence, luminescence, or phosphorescence: (1) intensity; (2) polarization; (3) lifetime; (4) wavelength; (5) energy transfer; and (6) recovery after photobleaching.

The basic principle of the protease biosensors of the present invention is to spatially separate the reactants from the products generated during a proteolytic reaction. The separation of products from reactants occurs upon proteolytic cleavage of the protease recognition site within the biosensor, allowing the products to bind to, diffuse into, or be imported into compartments of the cell different from those of the reactant. This spatial separation provides a means of quantitating a proteolytic process directly in living or fixed cells. Some designs of the biosensor provide a means of restricting the reactant (uncleaved biosensor) to a particular compartment by a protein sequence ("reactant target sequence") that binds to or imports the biosensor into a compartment of the cell. These compartments include, but are not limited to any cellular substructure, macromolecular cellular component, membrane-limited organelles, or the extracellular space. Given that the characteristics of the proteolytic reaction are related to product concentration divided by the reactant concentration, the spatial separation of products and reactants provides a means of uniquely quantitating products and reactants in single cells, allowing a more direct measure of proteolytic activity.

The molecular-based biosensors may be introduced into cells via transfection and the expressed chimeric proteins analyzed in transient cell populations or stable cell lines. They may also be pre-formed, for example by production in a prokaryotic or eukaryotic expression system, and the purified protein introduced into the cell via a number of physical mechanisms including, but not limited to, microinjection, scrape loading, electroporation, signal-sequence mediated loading, etc.

Measurement modes may include, but are not limited to, the ratio or difference in fluorescence, luminescence, or phosphorescence: (a) intensity; (b) polarization; or (c) lifetime between reactant and product. These latter modes require appropriate spectroscopic differences between products and reactants. For example, cleaving a reactant containing a limited-mobile signal into a very small translocating component and a relatively large non-translocating component may be detected by polarization. Alternatively, significantly different emission lifetimes between reactants and products allow detection in imaging and non-imaging modes.

One example of a family of enzymes for which this biosensor can be constructed to report activity is the caspases. Caspases are a class of proteins that catalyze proteolytic cleavage of a wide variety of targets during apoptosis. Following initiation of apoptosis, the Class II "downstream" caspases are activated and are the point of no return in the pathway leading to cell death, resulting in cleavage of downstream target proteins. In specific examples, the biosensors described here were engineered to use nuclear translocation of cleaved GFP as a measurable indicator of caspase activation. Additionally, the use of specific recognition sequences that incorporate surrounding amino acids involved in secondary structure formation in naturally occurring proteins may increase the specificity and sensitivity of this class of biosensor.

Another example of a protease class for which this biosensor can be constructed to report activity is zinc metalloproteases. Two specific examples of this class are the biological toxins derived from Clostridial species (*C. botulinum* and *C. tetani*) and *Bacillus anthracis*. (Herreros et al. In The Comprehensive Sourcebook of Bacterial Protein Toxins. J. E. Alouf and J. H. Freer, Eds. $2^{nd}$ edition, San Diego, Academic Press, 1999; pp 202–228.) These bacteria express and secrete zinc metalloproteases that enter eukaryotic cells and specifically cleave distinct target proteins. For example, the anthrax protease from *Bacillus anthracis* is delivered into the cytoplasm of target cells via an accessory pore-forming protein, where its proteolytic activity inactivates the MAP-kinase signaling cascade through cleavage of mitogen activated protein kinase kinases 1 or 2 (MEK1 or MEK2). (Leppla, S. A. In The Comprehensive Sourcebook of Bacterial Protein Toxins. J. E. Alouf and J. H. Freer, Eds. $2^{nd}$ edition, San Diego, Academic Press, 1999; pp243–263.) The toxin biosensors described here take advantage of the natural subcellular localization of these and other target proteins to achieve reactant targeting. Upon cleavage, the signal (with or without a product target sequence) is separated from the reactant to create a high-content biosensor.

One of skill in the art will recognize that the protein biosensors of this aspect of the invention can be adapted to report the activity of any member of the caspase family of proteases, as well as any other protease, by a substitution of the appropriate protease recognition site in any of the constructs (see FIG. 29B). These biosensors can be used in high-content screens to detect in vivo activation of enzymatic activity and to identify specific activity based on cleavage of a known recognition motif. This screen can be used for both live cell and fixed end-point assays, and can be combined with additional measurements to provide a multi-parameter assay.

Thus, in another aspect the present invention provides recombinant nucleic acids encoding a protease biosensor, comprising:

a. a first nucleic acid sequence that encodes at least one detectable polypeptide signal;

b. a second nucleic acid sequence that encodes at least one protease recognition site, wherein the second nucleic acid sequence is operatively linked to the first nucleic acid sequence that encodes the at least one detectable polypeptide signal; and c. a third nucleic acid sequence that encodes at least one reactant target sequence, wherein the third nucleic acid sequence is operatively linked to the second nucleic acid sequence that encodes the at least one protease recognition site.

In this aspect, the first and third nucleic acid sequences are separated by the second nucleic acid sequence, which encodes the protease recognition site.

In a further embodiment, the recombinant nucleic acid encoding a protease biosensor comprises a fourth nucleic acid sequence that encodes at least one product target sequence, wherein the fourth nucleic acid sequence is operatively linked to the first nucleic acid sequence that encodes the at least one detectable polypeptide signal.

In a further embodiment, the recombinant nucleic acid encoding a protease biosensor comprises a fifth nucleic acid sequence that encodes at least one detectable polypeptide signal, wherein the fifth nucleic acid sequence is operatively linked to the third nucleic acid sequence that encodes the reactant target sequence.

In a preferred embodiment, the detectable polypeptide signal is selected from the group consisting of fluorescent proteins, luminescent proteins, and sequence epitopes. In a most preferred embodiment, the first nucleic acid encoding a polypeptide sequence comprises a sequence selected from the group consisting of SEQ ID NOS: 35, 37, 39, 41, 43, 45, 47, 49, and 51.

In another preferred embodiment, the second nucleic acid encoding a protease recognition site comprises a sequence selected from the group consisting of SEQ ID NOS: 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, and 121. In another preferred embodiment, the third nucleic acid encoding a reactant target sequence comprises a sequence selected from the group consisting of SEQ ID NOS: 123, 125, 127, 129, 131, 133, 135, 137, 139, 141, 143, 145, 147, 149, and 151.

In a most preferred embodiment, the recombinant nucleic acid encoding a protease biosensor comprises a sequence substantially similar to sequences selected from the group consisting of SEQ ID NOS:1, 3, 5,7,9, 11, 13, 15, 17, 19, 21, 23, 25, 27, 29, 31, and 33.

In another aspect, the present invention provides a recombinant expression vector comprising nucleic acid control sequences operatively linked to the above-described recombinant nucleic acids. In a still further aspect, the present invention provides genetically engineered host cells that have been transfected with the recombinant expression vectors of the invention.

In another aspect, the present invention provides recombinant protease biosensors comprising a. a first domain comprising at least one detectable polypeptide signal;

b. a second domain comprising at least one protease recognition site; and c. a third domain comprising at least one reactant target sequence;

wherein the first domain and the third domain are separated by the second domain.

Inherent in this embodiment is the concept that the reactant target sequence restricts the cellular distribution of the reactant, with redistribution of the product occurring after activation (ie: protease cleavage). This redistribution does not require a complete sequestration of products and reactants, as the product distribution can partially overlap the reactant distribution in the absence of a product targeting signal (see below).

In a preferred embodiment, the recombinant protease biosensor further comprises a fourth domain comprising at least one product target sequence, wherein the fourth domain and the first domain are operatively linked and are separated from the third domain by the second domain. In another embodiment, the recombinant protease biosensor further comprises a fifth domain comprising at least one detectable polypeptide signal, wherein the fifth domain and the third domain are operatively linked and are separated from the first domain by the second domain.

In a preferred embodiment, the detectable polypeptide signal domain (first or fifth domain) is selected from the group consisting of fluorescent proteins, luminescent proteins, and sequence epitopes. In a most preferred embodiment, the detectable polypeptide signal domain comprises a sequence selected from the group consisting of SEQ ID NOS:36, 38, 40, 42, 44, 46, 48, 50, and 52.

In another preferred embodiment, the second domain comprising a protease recognition site comprises a sequence selected from the group consisting of SEQ ID NOS:54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, and 122. In another preferred embodiment, the reactant and/or target sequence domains comprise a sequence selected from the group consisting of SEQ ID NOS:124, 126, 128, 130, 132, 134, 136, 138, 140, 142, 144, 146, 148, 150, and 152.

In a most preferred embodiment, the recombinant protease biosensor comprises a sequence substantially similar to sequences selected from the group consisting of SEQ ID NO:2, 4, 6, 8, 10, 12, 14, 16, 18, 20, 22, 24, 26, 28, 30, 32, and 34.

In a still further embodiment, the present invention provides methods and kits for automated analysis of cells, comprising using cells that possess the protease biosensors of the invention to identify compounds that affect protease activity. The method can be combined with the other methods of the invention in a variety of possible multi-parametric assays.

In these various embodiments, the basic protease biosensor is composed of multiple domains, including at least a first detectable polypeptide signal domain, at least one reactant target domain, and at least one protease recognition domain, wherein the detectable signal domain and the reactant target domain are separated by the protease recognition domain. Thus, the exact order of the domains in the molecule is not generally critical, so long as the protease recognition domain separates the reactant target and first detectable signal domain. For each domain, one or more one of the specified recognition sequences is present.

In some cases, the order of the domains in the biosensor may be critical for appropriate targeting of product(s) and/or reactant to the appropriate cellular compartment(s). For example, the targeting of products or reactants to the peroxisome requires that the peroxisomal targeting domain comprise the last three amino acids of the protein. Determination of those biosensor in which the relative placement of targeting domains within the biosensor is critical can be determined by one of skill in the art through routine experimentation.

Some examples of the basic organization of domains within the protease biosensor are shown in FIG. 30. One of skill in the art will recognize that any one of a wide variety of protease recognition sites, product target sequences, polypeptide signals, and/or product target sequences can be used in various combinations in the protein biosensor of the present invention, by substituting the appropriate coding sequences into the multi-domain construct. Non-limiting examples of such alternative sequences are shown in FIGS. 29A–29C. Similarly, one of skill in the art will recognize that modifications, substitutions, and deletions can be made to the coding sequences and the amino acid sequence of each individual domain within the biosensor, while retaining the function of the domain. Such various combinations of domains and modifications, substitutions and deletions to individual domains are within the scope of the invention.

As used herein, the term "coding sequence" or a sequence which "encodes" a particular polypeptide sequence, refers to a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the coding sequence.

As used herein, the term DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control sequences need always be present in a recombinant vector so long as the DNA sequence of interest is capable of being transcribed and translated appropriately.

As used herein, the term "operatively linked" refers to an arrangement of elements wherein the components so described are configured so as to perform their usual function. Thus, control sequences operatively linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operatively linked" to the coding sequence.

Furthermore, a nucleic acid coding sequence is operatively linked to another nucleic acid coding sequences when the coding region for both nucleic acid molecules are capable of expression in the same reading frame. The nucleic acid sequences need not be contiguous, so long as they are capable of expression in the same reading flame. Thus, for example, intervening coding regions can be present between the specified nucleic acid coding sequences, and the specified nucleic acid coding regions can still be considered "operatively linked".

The intervening coding sequences between the various domains of the biosensors can be of any length so long as the function of each domain is retained. Generally, this requires that the two-dimensional and three-dimensional structure of the intervening protein sequence does not preclude the binding or interaction requirements of the domains of the biosensor, such as product or reactant targeting, binding of the protease of interest to the biosensor, fluorescence or luminescence of the detectable polypeptide signal, or binding of fluorescently labeled epitope-specific antibodies. One case where the distance between domains of the protease biosensor is important is where the goal is to create a fluorescence resonance energy transfer pair. In this case, the FRET signal will only exist if the distance between the donor and acceptor is sufficiently small as to allow energy transfer (Tsien, Heim and Cubbit, WO 97/28261). The average distance between the donor and acceptor moieties should be between 1 nm and 10 nm with a preference of between 1 nm and 6 nm. This is the physical distance between donor and acceptor. The intervening sequence length can vary considerably since the three dimensional structure of the peptide will determine the physical distance between donor and acceptor.

"Recombinant expression vector" includes vectors that operatively link a nucleic acid coding region or gene to any promoter capable of effecting expression of the gene product. The promoter sequence used to drive expression of the protease biosensor may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In a preferred embodiment, the expression vector comprises a plasmid. However, the invention is intended to include any other suitable expression vectors, such as viral vectors.

The phrase "substantially similar" is used herein in reference to the nucleotide sequence of DNA, or the amino acid sequence of protein, having one or more conservative or non-conservative variations from the protease biosensor sequences disclosed herein, including but not limited to deletions, additions, or substitutions wherein the resulting nucleic acid and/or amino acid sequence is functionally equivalent to the sequences disclosed and claimed herein. Functionally equivalent sequences will function in substantially the same manner to produce substantially the same protease biosensor as the nucleic acid and amino acid compositions disclosed and claimed herein. For example, functionally equivalent DNAs encode protease biosensors that are the same as those disclosed herein or that have one or more conservative amino acid variations, such as substitutions of non-polar residues for other non-polar residues or charged residues for similarly charged residues, or addition to/deletion from regions of the protease biosensor not critical for functionality. These changes include those recognized by those of skill in the art as substitutions, deletions, and/or additions that do not substantially alter the tertiary structure of the protein.

As used herein, substantially similar sequences of nucleotides or amino acids share at least about 70%–75% identity, more preferably 80–85% identity, and most preferably 90–95% identity. It is recognized, however, that proteins (and DNA or mRNA encoding such proteins) containing less than the above-described level of homology (due to the degeneracy of the genetic code) or that are modified by conservative amino acid substitutions (or substitution of degenerate codons) are contemplated to be within the scope of the present invention.

The term "heterologous" as it relates to nucleic acid sequences such as coding sequences and control sequences, denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), *Gene Transfer and Expression Protocols*, pp. 109–128, ed. E. J. Murray, The Humana Press Inc., Clifton, N.J.), and the Ambion 1998 Catalog (Ambion, Austin, Tex.).

The biosensors of the present invention are constructed and used to transfect host cells using standard techniques in the molecular biological arts. Any number of such techniques, all of which are within the scope of this invention, can be used to generate protease biosensor-encoding DNA constructs and genetically transfected host cells expressing the biosensors. The non-limiting examples that follow demonstrate one such technique for constructing the biosensors of the invention.

EXAMPLE OF PROTEASE BIOSENSOR CONSTRUCTION AND USE

In the following examples, caspase-specific biosensors with specific product target sequences have been constructed using sets of 4 primers (2 sense and 2 antisense). These primers have overlap regions at their termini, and are used for PCR via a primer walking technique. (Sambrook, J., Fritsch, E. F. and Maniatis, T. (1989) Molecular Cloning: A Laboratory Manual. Cold Spring Harbor Laboratory Press, Cold Spring Harbor, N.Y.) The two sense primers were chosen to start from the 5' polylinker (BspI) of the GFP-containing vector (Clontech, California) to the middle of the designed biosensor sequence. The two antisense primers start from a 3' GFP vector site (Bam HI), and overlap with the sense primers by 12 nucleotides in the middle.

PCR conditions were as follows: 94° C. for 30 seconds for denaturation, 55° C. for 30 seconds for annealing, and 72° C. for 30 seconds for extension for 15 cycles. The primers have restriction endonuclease sites at both ends, facilitating subsequent cloning of the resulting PCR product.

The resulting PCR product was gel purified, cleaved at BspE1 and BamH1 restriction sites present in the primers, and the resulting fragment was gel purified. Similarly, the GFP vector (Clontech, San Francisco, Calif.) was digested at BspE1 and BamH1 sites in the polylinker. Ligation of the GFP vector and the PCR product was performed using standard techniques at 16° C. overnight. *E. coli* cells were transfected with the ligation mixtures using standard techniques. Transformed cells were selected on LB-agar with an appropriate antibiotic.

Cells and Transfections

For DNA transfection, BHK cells and MCF-7 cells were cultured to 50–70% confluence in 6 well plates containing 3 ml of minimal Eagle's medium (MEM) with 10% fetal calf serum, 1 mM L-glutamine, 50 $\mu$g/ml streptomycin, 50 $\mu$g/ml penicillin, 0.1 mM non-essential amino acids, 1 mM sodium pyruvate and 10 $\mu$g/ml of bovine insulin (for MCF-7 cell only) at 37 ° C. in a 5% $CO_2$ incubator for about 36 hours. The cells were washed with serum free MEM media and incubated for 5 hours with 1 ml of transfection mixture containing 1 $\mu$g of the appropriate plasmid and 4 $\mu$g of lipofectimine (BRL) in the serum free MEM media. Subsequently, the transfection medium was removed and replaced with 3 ml of normal culture media. The transfected cells were maintained in growth medium for at least 16 hours before performing selection of the stable cells based on standard molecular biology methods (Ausubel. et al 1995).

Apoptosis Assay

For apoptosis assays, the cells (BHK, MCF-7) stably transfected with the appropriate protease biosensor expression vector were plated on tissue culture treated 96-well plates at 50–60% confluence and cultured overnight at 37° C., 5% $CO_2$. Varying concentrations of cis-platin, staurosporine, or paclitaxel in normal culture media were freshly prepared from stock and added to cell culture dishes to replace the old culture media. The cells were then observed with the cell screening system of the present invention at the indicated time points either as live cell experiments or as fixed end-point experiments.

1. Construction of 3-domain Protease Biosensors a. Caspase-3 Biosensor with an Annexin II Reactant Targeting Domain (pljkGFP)

The design of this biosensor is outlined in FIG. 31, and its sequence is shown in SEQ ID NO:1 and 2.
Primers for Caspase 3, Product target sequence=none (CP3GFP -CYTO):
1) TCA TCA TCC GGA GCT GGA GCC GGA GCT GGC CGA TCG GCT GTT AAA TCT GAA GGA AAG AGA AAG TGT GAC GAA GTT GAT GGA ATT GAT GAA GTA GCA (SEQ ID NO:153)
2) GAA GAA GGA TCC GGC ACT TGG GGG TGT AGA ATG AAC ACC CTC CAA GCT GAG CTT GAAG GAT TTC GTG GAC AGT AGA AT AGT ACT TGC TAC TTC ATC (SEQ ID NO:154)
3) TCA TCA TCC GGA GCT GGA (SEQ ID NO:155)
4) GAA GAA GGA TCC GGC ACT (SEQ ID NO:156)

Figure 32:
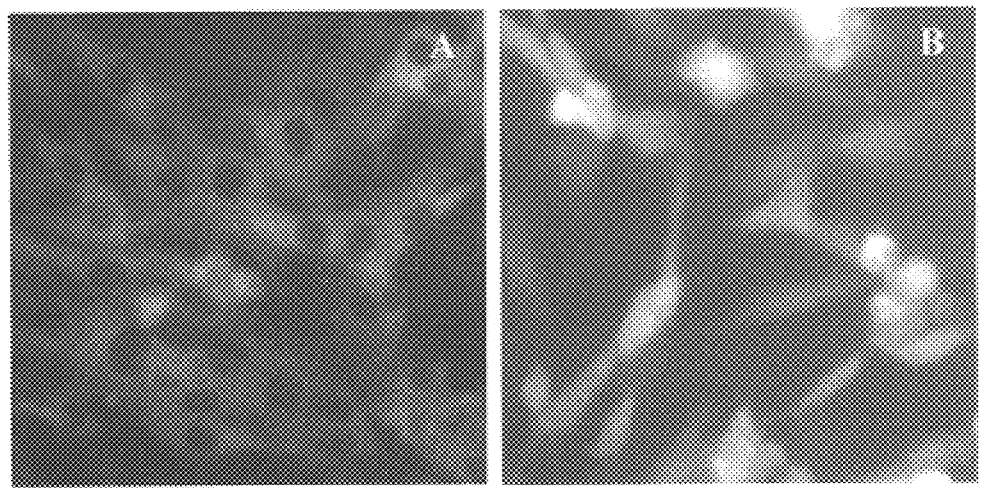
FIG. 32 is a photograph showing the effect of stimulation of apoptosis by cis-platin on BHK cells transfected with an expression vector that expresses the caspase biosensor shown in FIG. 32.

This biosensor is restricted to the cytoplasm by the reactant target sequence. The reactant target sequence is the annexin II cytoskeletal binding domain (MSTVHEILCKLSLEGVHSTPPSA) (SEQ ID NO:124) (FIG. 29C) (Eberhard et al. 1997. *Mol. Biol. Cell* 8:293a). The enzyme recognition site corresponds to two copies of the amino acid sequence DEVD (SEQ ID NO:60) (FIG. 29B), which serves as the recognition site of caspase-3. Other examples with different numbers of protease recognition sites and/or additional amino acids from a naturally occurring protease recognition site are shown below. The signal domain is EGFP (SEQ ID NO:46) (FIG. 29A) (Clontech, California). The parent biosensor (the reactant) is restricted to the cytoplasm by binding of the annexin II domain to the cytoskeleton, and is therefore excluded from the nucleus. Upon cleavage of the protease recognition site by caspase 3, the signal domain (EGFP) is released from the reactant targeting domain (annexin II), and is distributed throughout the whole volume of the cell, because it lacks any specific targeting sequence and is small enough to enter the nucleus passively. (FIG. 32)

The biosensor response is measured by quantitating the effective cytoplasm-to-nuclear translocation of the signal (see above). Measurement of the response is by one of several modes, including integrated or average nuclear region intensity, the ratio or difference of the integrated or average cytoplasm intensity to integrated or average nuclear intensity. The nucleus is defined using a DNA-specific dye, such as Hoechst 33342.

This biosensor provides a measure of the proteolytic activity around the annexin II cytoskeleton binding sites within the cell. Given the dispersed nature of the cytoskeleton and the effectively diffuse state of cytosolic enzymes, this provides an effective measure of the cytoplasm in general.

Results & Discussion

FIG. 32 illustrates images before and after stimulation of apoptosis by cis-platin in BHK cells, transfected with the caspase 3 biosensor. The images clearly illustrate accumulation of fluorescence in the nucleus. Generation of the spatial change in fluorescence is non-reversible and thus the timing of the assay is flexible. Controls for this biosensor include using a version in which the caspase-3-specific site has been omitted. In addition, disruption of the cytoskeleton with subsequent cell rounding did not produce the change in fluorescence distribution. Our experiments demonstrate the correlation of nuclear condensation with activation of caspase activity. We have also tested this biosensor in MCF-7 cells. A recent report measured a peak response in caspase-3 activity 6 h after stimulation of MCF-7 cells with etoposide accompanied by cleavage of PARP (Benjamin et al. 1998.*Mol Pharmacol.* 53:446–50). However, another recent report found that MCF-7 cells do not possess caspase-3 activity and, in fact, the caspase-3 gene is functionally deleted (Janicke et al. 1998. *J Biol Chem.* 273:9357–60). Caspase-3 activity was not detected with the caspase biosensor in MCF:7 cells after a 15 h treatment with 100 μM etoposide.

Janicke et al., (1998) also indicated that many of the conventional substrates of caspase-3 were cleaved in MCF-7 cells upon treatment with staurosporine. Our experiments demonstrate that caspase activity can be measured using the biosensor in MCF-7 cells when treated with staurosporine. The maximum magnitude of the activation by staurosporine was approximately one-half that demonstrated with cis-platin in BHK cells. This also implies that the current biosensor, although designed to be caspase-3-specific, is indeed specific for a class of caspases rather than uniquely specific for caspase-3. The most likely candidate is caspase-7 (Janicke et al., 1998). These experiments also demonstrated that the biosensor can be used in multiparameter experiments, with the correlation of decreases in mitochondrial membrane potential, nuclear condensation, and caspase activation.

We have specifically tested the effects of paclitaxel on caspase activation using the biosensor. Caspase activity in BHK and MCF-7 cells was stimulated by paclitaxel. It also appears that caspase activation occurred after nuclear morphology changes. One caveat is that, based on the above discussions, the caspase activity reported by the biosensor in this assay is likely to be due to the combination of caspase-3 and, at least, caspase-7 activity.

Consistent with the above results using staurosporine stimulation on MCF-7 cells, paclitaxel also stimulated the activation of caspase activity. The magnitude was similar to that of staurosporine. This experiment used a much narrower range of paclitaxel than previous experiments where nuclear condensation appears to dominate the response.

b. Caspase Biosensor with the Microtubule Associated Protein 4 (MAP4) Projection Domain (CP8GFPNLS-SIZEPROJ)

Another approach for restricting the reactant to the cytoplasm is to make the biosensor too large to penetrate the nuclear pores Cleavage of such a biosensor liberates a product capable of diffusing into the nucleus.

The additional size required for this biosensor is provided by using the projection domain of MAP4 (SEQ ID NO:142) (FIG. 29C) (CP8GFPNLS-SIZEPROJ). The projection domain of MAP4 does not interact with microtubules on its own, and, when expressed, is diffusely distributed throughout the cytoplasm, but is excluded from the nucleus due to its size (~120 kD). Thus, this biosensor is distinct from the one using the full length MAP4 sequence. (see below) One of skill in the art will recognize that many other such domains could be substituted for the MAP4 projection domain, including but not limited to multiple copies of any GFP or one or more copies of any other protein that lacks an active NLS and exceeds the maximum size for diffusion into the nucleus (approximately 60 kD; Alberts, B., Bray, D., Raff, M., Roberts, K., Watson, J. D. (Eds.) *Molecular Biology of the Cell,* third edition, New York: Garland publishing, 1994. pp 561–563). The complete sequence of the resulting biosensor is shown in SEQ ID NO: 3–4. A similar biosensor with a different protease recognition domain is shown in SEQ ID NO:5–6.

c. Caspase Biosensor with a Nuclear Export Signal

Another approach for restricting the reactant to the cytoplasm is to actively restrict the reactant from the nucleus by using a nuclear export signal. Cleavage of such a biosensor liberates a product capable of diffusing into the nucleus.

The *Bacillus anthracis* bacterium expresses a zinc metalloprotease protein complex called anthrax protease. Human mitogen activated protein kinase kinase 1 (MEK 1) (Seger et al., J. Biol. Chem. 267:25628–25631, 1992) possesses an anthrax protease recognition site (amino acids 1–13) (SEQ ID NO:102) (FIG. 29B) that is cleaved after amino acid 8, as well as a nuclear export signal at amino acids 32–44 (SEQ ID NO:.140) (FIG. 29C). Human MEK 2 (Zheng and Guan, J. Biol. Chem. 268:11435–11439, 1993) possesses an anthrax protease recognition site comprising amino acid residues 1–16 (SEQ ID NO:104) (FIG. 29B) and a nuclear export signal at amino acids 36–48. (SEQ ID NO:148) (FIG. 29C).

The anthrax protease biosensor comprises Fret25 (SEQ ID NO:48) (FIG. 29A) as the signal, the anthrax protease recognition site, and the nuclear export signal from MEK 1 or MEK2. (SEQ ID NOS: 7–8 (MEK1); 9–10 (MEK2)) The intact biosensor will be retained in the cytoplasm by virtue of this nuclear export signal (eg., the reactant target site). Upon cleavage of the fusion protein by anthrax protease, the NES will be separated from the GFP allowing the GFP to diffuse into the nucleus.

2. Construction of 4- and 5-domain Biosensors

For all of the examples presented above for 3-domain protease biosensors, a product targeting sequence, including but not limited to those in FIG. 29C, such as a nuclear localization sequence (NLS), can be operatively linked to the signal sequence, and thus cause the signal sequence to segregate from the reactant target domain after proteolytic cleavage. Addition of a second detectable signal domain, including but not limited to those in FIG. 29A, operatively linked with the reactant target domain is also useful in allowing measurement of the reaction by multiple means. Specific examples of such biosensors are presented below.

a. 4 Domain Biosensors
1. Caspase Biosensors with Nuclear Localization Sequences (pcas3nlsGFP; CP3GFPNLS-CYTO)

Figure 33:
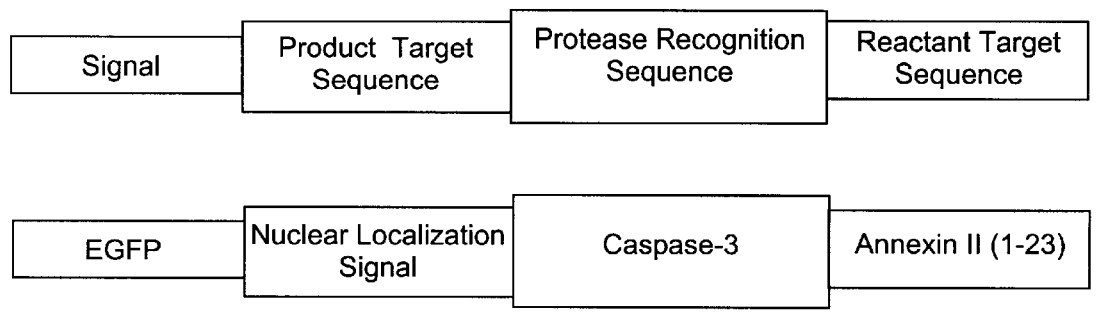
FIG. 33 is a schematic diagram of a specific 4-domain protease biosensor.

The design of the biosensor is outlined in FIG. 33, and its sequence is shown in SEQ ID NO:11–12. PCR and cloning procedures were performed as described above, except that the following oligonucleotides were used:

Primers for Caspase 3, Product target sequence=NLS (CP3GFPNLS-CYTO):
1) TCA TCA TCC GGA AGA AGG AAA CGA CAA AAG CGA TCG GCT GTT AAA TCT GAA GGA AAG AGA AAG TGT GAC GAA GTT GAT GGA ATT GAT GAA GTA GCA (SEQ ID NO:157),
2) GAA GAA GGA TCC GGC ACT TGG GGG TGT AGA ATG AAC ACC CTC CAA GCT GAG CTT GA AG GAT TTC GTG GAC AGT AGA CAT AGT ACT TGC TAC TTC ATC (SEQ ID NO:154)
3) TCA TCA TCC GGA AGA AGG (SEQ ID NO:158)
25 4) GAA GAA GGA TCC GGC ACT (SEQ ID NO:156)

This biosensor is similar to that shown in SEQ ID NO:2 except upon recognition and cleavage of the protease recognition site, the product is released and the signal accumulates specifically in the nucleus due to the presence of a nuclear localization sequence, RRKRQK (SEQ ID NO:128) (FIG. 29C)(Briggs et al., J. Biol. Chem. 273:22745, 1998) attached to the signal. A specific benefit of this construct is that the products are clearly separated from the reactants. The reactants remain in the cytoplasm, while the product of the enzymatic reaction is restricted to the nuclear compartment. The response is measured by quantitating the effective cytoplasm-to-nuclear translocation of the signal, as described above.

With the presence of both product and reactant targeting sequences in the parent biosensor, the reactant target sequence should be dominant prior to activation (e.g., protease cleavage) of the biosensor. One way to accomplish this is by masking the product targeting sequence in the parent biosensor until after protease cleavage. In one such example, the product target sequence is functional only when relatively near the end of a polypeptide chain (ie: after protease cleavage). Alternatively, the biosensor may be designed so that its tertiary structure masks the function of the target sequence until after protease cleavage. Both of these approaches include comparing targeting sequences with different relative strengths for targeting. Using the example of the nuclear localization sequence (NLS) and annexin II sequences, different strengths of NLS have been tried with clone selection based on cytoplasmic restriction of the parent biosensor. Upon activation, the product targeting sequence will naturally dominate the localization of its associated detectable sequence domain because it is then separated from the reactant targeting sequence.

An added benefit of using this biosensor is that the product is targeted, and thus concentrated, into a smaller region of the cell. Thus, smaller amounts of product are detectable due to the increased concentration of the product. This concentration effect is relatively insensitive to the cellular concentration of the reactant. The signal-to-noise ratio (SNR) of such a measurement is improved over the more dispersed distribution of biosensor #1.

Similar biosensors that incorporate either the caspase 6 (SEQ ID NO:66) (FIG. 29B) or the caspase 8 protease recognition sequence (SEQ ID NO:74) (FIG. 29B) can be made using the methods described above, but using the following primer sets:
Primers for Caspase 6, Product target sequence=NLS (CP6GFPNLS-CYTO)
1) TCA TCA TCC GGA AGA AGG AAA CGA CAA AAG CGA TCG ACA AGA CTT GTT GAA ATT GAC AAC (SEQ ID NO:159)
2) GAA GAA GGA TCC GGC ACT TGG GGG TGT AGA ATG AAC ACC CTC CAA GCT GAG CTT GA AG GAT TTC GTG GAC AGT AGA AT AGT ACT GTT GTC AAT TTC (SEQ ID NO:160)
3) TCA TCA TCC GGA AGA AGG (SEQ ID NO:158)
4) GAA GAA GGA TCC GGC ACT (SEQ ID NO:156)
Primers for Caspase 8, Product target sequence=NLS (CP8GFPNLS-CYTO)
1) TCA TCA TCC GGA AGA AGG AAA CGA CAA AAG CGA TCG TAT CAA AAA GGA ATA CCA GTT GAA ACA GAC AGC GAA GAG CAA CCT TAT (SEQ ID NO:161)
2) GAA GAA GGA TCC GGC ACT TGG GGG TGT AGA ATG AAC ACC CTC CAA GCT GAG CTT GA AG GAT TTC GTG GAC AGT AGA AT AGT ACT ATA AGG TTG CTC (SEQ ID NO:162)
3) TCA TCA TCC GGA AGA AGG (SEQ ID NO:158)
4) GAA GAA GGA TCC GGC ACT (SEQ ID NO:156)

The sequence of the resulting biosensors is shown in SEQ ID NO:13–14 (Caspase 6) and SEQ ID NO: 15–16 (Caspase 8). Furthermore, multiple copies of the protease recognition sites can be inserted into the biosensor, yielding the biosensors shown in SEQ ID NO: 17–18 (Caspase 3) and SEQ ID NO:19–20 (Caspase 8).

2. Caspase 3 Biosensor with a Second Signal Domain

An alternative embodiment employs a second signal domain operatively linked to the reactant target domain. In this example, full length MAP4 serves as the reactant target sequence. Upon recognition and cleavage, one product of the reaction, containing the reactant target sequence, remains bound to microtubules in the cytoplasm with its own unique signal, while the other product, containing the product target sequence, diffuses into the nucleus. This biosensor provides a means to measure two activities at once: caspase 3 activity using a translocation of GFP into the nucleus and microtubule cytoskeleton integrity in response to signaling cascades initiated during apoptosis, monitored by the MAP4 reactant target sequence.

The basic premise for this biosensor is that the reactant is tethered to the microtubule cytoskeleton by virtue of the reactant target sequence comprising the full length microtubule associated protein MAP4 (SEQ ID NO:152) (FIG. 29C) In this case, a DEVD (SEQ ID NO:60) (FIG. 29B) recognition motif is located between the EYFP signal (SEQID NO:44) (FIG. 29A) operatively linked to the reactant target sequence, as well as the EBFP signal (SEQ ID NO:48) (FIG. 29A) operatively linked to the C-terminus of MAP4. The resulting biosensor is shown in SEQ ID NO:21–22.

This biosensor can also include a product targeting domain, such as an NLS, operatively linked to the signal domain.

With this biosensor, caspase-3 cleavage still releases the N-terminal GFP, which undergoes translocation to the nucleus (directed there by the NLS). Also, the MAP4 fragment, which is still intact following proteolysis by caspase-3, continues to report on the integrity of the microtubule cytoskeleton during the process of apoptosis via the second GFP molecule fused to the C-terminus of the biosensor. Therefore, this single chimeric protein allows simultaneous analysis of caspase-3 activity and the polymerization state of the microtubule cytoskeleton during apoptosis induced by a variety of agents. This biosensor is also useful for analysis of potential drug candidates that specifically target the microtubule cytoskeleton, since one can determine whether a particular drug induced apoptosis in addition to affecting microtubules.

This biosensor potentially combines a unique signal for the reactant, fluorescence resonance energy transfer (FRET) from signal 2 to signal 1, and a unique signal localization for the product, nuclear accumulation of signal 1. The amount of product generated will also be indicated by the magnitude of the loss in FRET, but this will be a smaller SNR than the combination of FRET detection of reactant and spatial localization of the product.

FRET can occur when the emission spectrum of a donor overlaps significantly the absorption spectrum of an acceptor molecule. (dos Remedios, C. G., and P. D. Moens. 1995. Fluorescence resonance energy transfer spectroscopy is a reliable "ruler" for measuring structural changes in proteins. Dispelling the problem of the unknown orientation factor. *J Struct Biol.* 115:175–85; Emmanouilidou, E., A. G. Teschemacher, A. E. Pouli, L. I. Nicholls, E. P. Seward, and G. A. Rutter. 1999. Imaging Ca(2+) concentration changes at the secretory vesicle surface with a recombinant targeted cameleon. *Curr Biol.* 9:915–918.) The average physical distance between the donor and acceptor molecules should be between 1 nm and 10 nm with a preference of between 1 nm and 6 nm. The intervening sequence length can vary considerably since the three dimensional structure of the peptide will determine the physical distance between donor and acceptor. This FRET signal can be measured as (1) the amount of quenching of the donor in the presence of the acceptor, (2) the amount of acceptor emission when exciting the donor, and/or (3) the ratio between the donor and acceptor emission. Alternatively, fluorescent lifetimes of donor and acceptor could be measured.

This case adds value to the above FRET biosensor by nature of the existence of the reactant targeting sequence. This sequence allows the placement of the biosensor into specific compartments of the cell for a more direct readout of activity in those compartments such as the inner surface of the plasma membrane.

The cytoplasmic second signal represents both original reactant plus one part of the product. The nuclear first signal represents another product of the reaction. Thus the enzymatic reaction has the added flexibility in that it can be represented as (1) nuclear intensity; (2) the nucleus/ cytoplasm ratio; (3) the nucleus /cytoplasm FRET ratio; (4) cytoplasmic /cytoplasmic FRET ratio.

The present FRET biosensor design differs from previous FRET-based biosensors (see WO 97/28261; WO9837226) in that it signal measurement is based on spatial position rather than intensity. The products of the reaction are segregated from the reactants. It is this change in spatial position that is measured. The FRET-based biosensor is based on the separation, but not to another compartment, of a donor and acceptor pair. The intensity change is due to the physical separation of the donor and acceptor upon proteolytic cleavage. The disadvantages of FRET-based biosensors are (1) the SNR is rather low and difficult to measure, (2) the signal is not fixable. It must be recorded using living cells. Chemical fixation, for example with formaldehyde, cannot preserve both the parent and resultant signal; (3) the range of wavelengths are limiting and cover a larger range of the spectrum due to the presence of two fluorophores or a fluorophore and chromophore; (4) the construction has greater limitations in that the donor and acceptor must be precisely arranged to ensure that the distance falls within 1–10 nm.

Benefits of the positional biosensor includes: (1) ability to concentrate the signal in order to achieve a higher SNR. (2) ability to be used with either living or fixed cells; (3) only a single fluorescent signal is needed; (4) the arrangement of the domains of the biosensor is more flexible. The only limiting factor in the application of the positional biosensor is the need to define the spatial position of the signal which requires an imaging method with sufficient spatial resolution to resolve the difference between the reactant compartment and the product compartment.

One of skill in the art will recognize that this approach can be adapted to report any desired combination of activities by simply making the appropriate substitutions for the protease recognition sequence and the reactant target sequence, including but not limited to those sequences shown in FIGS. 29A–C.

3. Caspase 8 Biosensor with a Nucleolar Localization Domain (CP8GFPNUC-CYTO)

Figure 34:
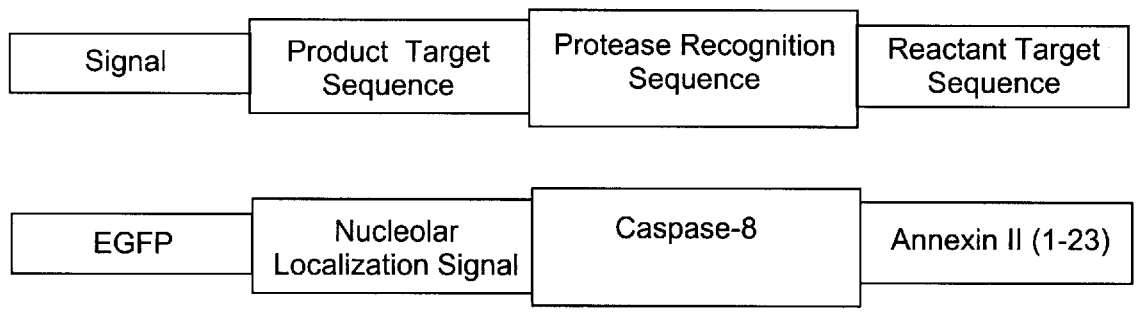
FIG. 34 is a schematic diagram of a specific 4-domain protease biosensor, containing a nucleolar localization signal.

This approach (diagrammed in FIG. 34) utilizes a biosensor for the detection of caspase-8 activity. In this biosensor, a nucleolar localization signal (RKRIRTYLKSCRRMKRSGFEMSRPIPSHLT) (SEQ ID NO:130) (FIG. 29C) (Ueki et al., Biochem. Biophys. Res. Comm. 252:97–100, 1998) was used as the product target sequence, and made by PCR using the primers described below. The PCR product was digested with BspE1 and Pvu1 and gel purified. The vector and the PCR product were ligated as described above.

Primers for Caspase 8, Nucleolar Localization Signal (CP8GFPNUC-CYTO):
1) TCA TCA TCC GGA AGA AAA CGT ATA CGT ACT TAC CTC AAG TCC TGC AGG CGG ATG AAA AGA (SEQ ID NO:163)
2) GAA GAA CGA TCG AGT AAG GTG GGA AGG AAT AGG TCG AGA CAT CTC AAA ACC ACT TCT TTT CAT (SEQ ID NO;164)
3) TCA TCA TCC GGA AGA AAA (SEQ ID NO:165)
4) GAA GAA CGA TCG AGT AAG (SEQ ID NO:166)

The sequence of the resulting biosensor is shown in SEQ ID NO: 23–24. This biosensor includes the protease recognition site for caspase-8 (SEQ ID NO:74) (FIG. 29B). A similar biosensor utilizes the protease recognition site for caspase-3. (SEQ ID NO:25–26).

These biosensors could be used with other biosensors that possess the same product signal color that are targeted to separate compartments, such as CP3GFPNLS-CYTO. The products of each biosensor reaction can be uniquely measured due to separation of the products based on the product targeting sequences. Both products from CP8GFPNUC-CYTO and CP3GFPNLS-CYTO are separable due to the different spatial positions, nucleus vs. nucleolus, even though the colors of the products are exactly the same. Assessing the non-nucleolar, nuclear region in order to avoid the spatial overlap of the two signals would perform the measurement of CP3GFPNLS in the presence of CP8GFPNUC. The loss of the nucleolar region from the nuclear signal is insignificant and does not significantly affect the SNR. The principle of assessing multiple parameters using the same product color significantly expands the number of parameters that can be assessed simultaneously in living cells. This concept can be extended to other nonoverlapping product target compartments.

Measurement of translocation to the nucleolar compartment is performed by (1) defining a mask corresponding to the nucleolus based on a nucleolus-specific marker, including but not limited to an antibody to nucleolin (Lischwe et al., 1981. *Exp. Cell Res.* 136:101–109); (2) defining a mask for the reactant target compartment, and (3) determining the relative distribution of the signal between these two compartments. This relative distribution could be represented by the difference in the two intensities or, preferably, the ratio of the intensities between compartments.

The combination of multiple positional biosensors can be complicated if the reactant compartments are overlapping. Although each signal could be measured by simply determining the amount of signal in each product target compartment, higher SNR will be possible if each reactant is uniquely identified and quantitated. This higher SNR can be maximized by adding a second signal domain of contrasting fluorescent property. This second signal may be produced by a signal domain operatively linked to the product targeting sequence, or by FRET (see above), or by a reactant targeting sequence uniquely identifying it within the reactant compartment based on color, spatial position, or fluorescent property including but not limited to polarization or lifetime. Alternatively, for large compartments, such as the cytoplasm, it is possible to place different, same colored biosensors in different parts of the same compartment.

4. Protease Biosensors with Multiple Copies of a Second Signal Domain Serving as a Reactant Target Domain In another example, (CP8YFPNLS-SIZECFPn) increasing the size of the reactant is accomplished by using multiple inserts of a second signal sequence, for example, ECFP (SEQ ID NO:50) (FIG. 29A) (Tsien, R. Y. 1998. Annu Rev Biochem. 67:509–44). Thus, the multiple copies of the second signal sequence serve as the reactant target domain by excluding the ability of the biosensor to diffuse into the nucleus. This type of biosensor provides the added benefit of additional signal being available per biosensor molecule. Aggregation of multiple fluorescent probes also can result in unique signals being manifested, such as FRET, self quenching, eximer formation, etc. This could provide a unique signal to the reactants.

5. Tetanus/Botulinum Biosensor with Trans-membrane Targeting Domain

In an alternative embodiment, a trans-membrane targeting sequence is used to tether the reactant to cytoplasmic vesicles, and an alternative protease recognition site is used. The tetanus/botulinum biosensor (SEQ ID NOS:27–28 (cellubrevin); 29–30 (synaptobrevin) consists of an NLS (SEQ ID NO:128) (FIG. 29C), Fret25 signal domain (SEQ ID NO:52) (FIG. 29A), a tetanus or botulinum zinc metalloprotease recognition site from cellubrevin (SEQ ID NO:106) (FIG. 29B) (McMahon et al., Nature 364:346–349, 1993; Martin et al., J. Cell Biol., in press) or synaptobrevin (SEQ ID NO:108) (FIG. 29B) (GenBank Accession #U64520), and a trans-membrane sequence from cellubrevin (SEQ ID NO:146) (FIG. 29C) or synaptobrevin (SEQ ID NO:144) (FIG. 29C) at the 3'-end which tethers the biosensor to cellular vesicles. The N-terminus of each protein is oriented towards the cytoplasm. In the intact biosensor, GFP is tethered to the vesicles. Upon cleavage by the tetanus or botulinum zinc metalloprotease, GFP will no longer be associated with the vesicle and is free to diffuse throughout the cytoplasm and the nucleus.

b. 5-domain Biosensors

Figure 35:
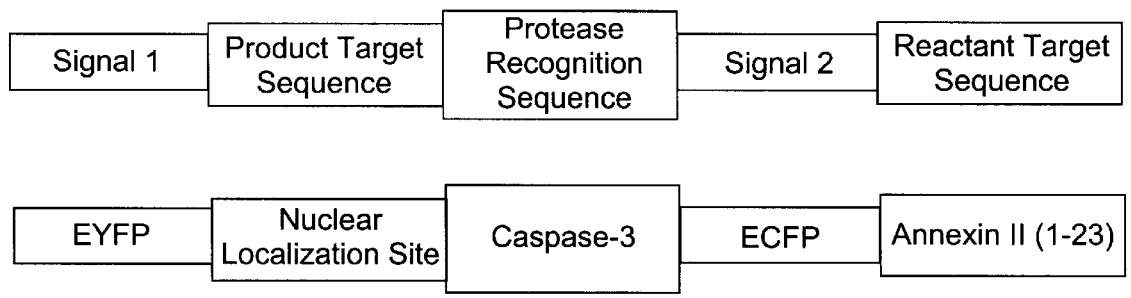
FIG. 35 is a schematic diagram of a specific 5-domain protease biosensor.

1. Caspase 3 Biosensor with a Nuclear Localization Domain and a Second Signal Domain Operatively Linked to an Annexin II Domain The design of this biosensor is outlined in FIG. 35, and the sequence is shown in SEQ ID NO:33–34. This biosensor differs from SEQ ID NO 11–12 by including a second detectable signal, ECFP (SEQ ID NO:50) (FIG. 29A) (signal 2) operatively linked to the reactant target sequence.

2. Caspase 3 Biosensor with a Nuclear Localization Sequence and a Second Signal Domain Operatively Linked to a MAP4 Projection Domain (CP3YFPNLS-CFPCYTO)

In this biosensor (SEQ ID NO:31–32), an NLS product targeting domain (SEQ ID NO:128) (FIG. 29C) is present upstream of an EYFP signal domain (SEQ ID NO:44) (FIG. 29A). A DEVD protease recognition domain (SEQ ID NO:60) (FIG. 29B) is between after the EYFP signal domain and before the MAP4 projection domain (SEQ ID NO:142) (FIG. 29C).

EXAMPLE 11

Fluorescent Biosensor Toxin Characterization

As used herein, "toxin" refers to any organism, macromolecule, or organic or inorganic molecule or ion that alters normal physiological processes found within a cell, or any organism, macromolecule, or organic or inorganic molecule or ion that alters the physiological response to modulators of known physiological processes. Thus, a toxin can mimic a normal cell stimulus, or can alter a response to a normal cell stimulus.

Living, cells are the targets of toxic agents that can comprise organisms, macromolecules, or organic or inorganic molecules. A cell-based approach to toxin detection, classification, and identification would exploit the sensitive and specific molecular detection and amplification system developed by cells to sense minute changes in their external milieu. By combining the evolved sensing capability of cells with the luminescent reporter molecules and assays described herein, intracellular molecular and chemical events caused by toxic agents can be converted into detectable spatial and temporal luminescent signals.

When a toxin interacts with a cell, whether it is at the cell surface or within a specific intracellular compartment, the toxin invariably undermines one or more components of the molecular pathways active within the cell. Because the cell is comprised of complex networks of interconnected molecular pathways, the effects of a toxin will likely be transmitted throughout many cellular pathways. Therefore, our strategy is to use molecular markers within key pathways likely to be affected by toxins, including but not limited to cell stress pathways, metabolic pathways, signaling pathways, and growth and division pathways.

We have developed and characterized three classes of cell based luminescent reporter molecules to serve as reporters of toxic threat agents. These 3 classes are as follows:

(1) Detectors: general cell stress detection of a toxin;

(2) Classifiers: perturbation of key molecular pathway(s) for detection and classification of a toxin; and (3) Identifiers: activity mediated detection and identification of a toxin or a group of toxins.

Thus, in another aspect of the present invention, living cells are used as biosensors to interrogate the environment for the presence of toxic agents. In one embodiment of this aspect, an automated method for cell based toxin characterization is disclosed that comprises providing an array of locations containing cells to be treated with a test substance, wherein the cells possess at least a first luminescent reporter molecule comprising a detector and a second luminescent reporter molecule selected from the group consisting of a classifier or an identifier; contacting the cells with the test substance either before or after possession of the first and second luminescent reporter molecules by the cells; imaging or scanning multiple cells in each of the locations containing multiple cells to obtain luminescent signals from the detector; converting the luminescent signals from the detector into digital data to automatically measure changes in the localization, distribution, or activity of the detector on or in the cell, which indicates the presence of a toxin in the test substance; selectively imaging or scanning the locations containing cells that were contacted with test sample indicated to have a toxin in it to obtain luminescent signals from the second reporter molecule; converting the luminescent signals from the second luminescent reporter molecule into digital data to automatically measure changes in the localization, distribution, or activity of the classifier or identifier on or in the cell, wherein a change in the localization, distribution, structure or activity of the classifier identifies a cell pathway that is perturbed by the toxin present in the test substance, or wherein a change in the localization, distribution, structure or activity of the identifier identifies the specific toxin that is present in the test substance. In a preferred embodiment, the cells possess at least a detector, a classifier, and an identifier. In a further preferred embodiment, the digital data derived from the classifier is used to determine which identifier(s) to employ for identifying the specific toxin or group of toxins.

As used herein, the phrase "the cells possess one or more luminescent reporter molecules" means that the luminescent reporter molecule may be expressed as a luminescent reporter molecule by the cells, added to the cells as a luminescent reporter molecule, or luminescently labeled by contacting the cell with a luminescently labeled molecule that binds to the reporter molecule, such as a dye or antibody, that binds to the reporter molecule. The luminescent reporter molecule can be expressed or added to the cell either before or after treatment with the test substance.

The luminescent reporters comprising detectors, classifiers, and identifiers may also be distributed separately into single or multiple cell types. For example, one cell type may contain a toxin detector, which, when activated by toxic activity, implies to the user that the same toxin sample should be screened with reporters of the classifier or identifier type in yet another population of cells identical to or different from the cells containing the toxin detector.

The detector, classifier, and identifier can comprise the same reporter molecule, or they can comprise different reporters.

Screening for changes in the localization, distribution, structure or activity of the detectors, classifiers, and/or identifiers can be carried out in either a high throughput or a high content mode. In general, a high-content assay can be converted to a high-throughput assay if the spatial information rendered by the high-content assay can be recoded in such a way as to no longer require optical spatial resolution on the cellular or subcellular levels. For example, a high-content assay for microtubule reorganization can be carried out by optically resolving luminescently labeled cellular microtubules and measuring their morphology (e.g., bundled vs. non-bundled or normal). A high-throughput version of a microtubule reorganization assay would involve only a measurement of total microtubule polymer mass after cellular extraction with a detergent. That is, destabilized microtubules, being more easily extracted, would result in a lower total microtubule mass luminescence signal than unperturbed or drug-stabilized luminescently labeled microtubules in another treated cell population. The luminescent signal emanating from a domain containing one or more cells will therefore be proportional to the total microtubule mass remaining in the cells after toxin treatment and detergent extraction.

The methods for detecting, classifying, and identifying toxins can utilize the same screening methods described throughout the instant application, including but not limited to detecting changes in cytoplasm to nucleus translocation, nucleus or nucleolus to cytoplasm translocation, receptor internalization, mitochondrial membrane potential, signal intensity, the spectral response of the reporter molecule, phosphorylation, intracellular free ion concentration, cell size, cell shape, cytoskeleton organization, metabolic processes, cell motility, cell substrate attachment, cell cycle events, and organellar structure and function.

In all of these embodiments, the methods can be operated in both toxin-mimetic and toxin-inhibitory modes.

Such techniques to assess the presence of toxins are useful for methods including, but not limited to, monitoring the presence of environmental toxins in test samples and for toxins utilized in chemical and biological weapons; and for detecting the presence and characteristics of toxins during environmental remediation, drug discovery, clinical applications, and during the normal development and manufacturing process by virtually any type of industry, including but not limited to agriculture, food processing, automobile, electronic, textile, medical device, and petroleum industries.

We have developed and characterized examples of luminescent cell-based reporters, distributed across the 3 sensor classes. The methods disclosed herein can be utilized in conjunction with computer databases, and data management, mining, retrieval, and display methods to extract meaningful patterns from the enormous data set generated by each individual reporter or a combinatorial of reporters in response to toxic agents. Such databases and bioinformatics methods include, but are not limited to, those disclosed in U.S. patent application Ser. No. 09/437,976, filed Nov. 10, 1999; No. 60/145,770 filed Jul. 27, 1999 and U.S. patent application Ser. No. to be assigned, filed Feb. 19, 2000. (98,068-C)

Any cell type can be used to carry out this aspect of the invention, including prokaryotes such as bacteria and archaebacteria, and eukaryotes, such as single celled fungi (for example, yeast), molds (for example, Dictyostelium), and protozoa (for example, Euglena). Higher eukaryotes, including, but not limited to, avian, amphibian, insect, and mammalian cells can also be used.

Examples of Biosensors

| | | | | Response to model toxins | |
|---|---|---|---|---|---|
| Number | Name | Class | Cell Types | Positive | Negative |
| 1 | Mitochondrial Potential [Donnan Equilibrium Dye] | D | LLCPK (pig epithelia) Rat primary hepatocytes | Valinomycin (10 nM–100 μM) FCCP (10 nM–100 μM) | Oligomycin (10 nM) |
| 2 | Heat Shock Protein (Hsp 27, Hsp 70) GFP-chimera | D | HeLa 3T3 | Cadmium (10 mM) | TNF-α (100 ng/ml) |

-continued

| Number | Name | Class | Cell Types | Response to model toxins Positive | Response to model toxins Negative |
|---|---|---|---|---|---|
| 3 | Tubulin-cytoskeleton [β-tubulin-GFP chimera] | C | BHK HeLa LLCPK | Paclitaxel (10 nM–20 μM) Curacin-A (5 nM–10 μM) Nocadazole (7 nM–12 μM) Colchicine (5 nM–10 μM) Vinblastine (5 nM–10 μM) | Staurosporine (1 nM–1 μM) |
| 4 | pp38 MAPK-stress signaling [antibody and GFP-chimera] | C | 3T3 LLCPK | Anisomycin (100 μM) Cadmium (10 μM) | TNF-α (100 ng/ml) |
| 5 | NF-κB-stress signaling [antibody and GFP-chimera] | C | HeLa 3T3 BHK SNB19 HepG2 LLCPK | TNF-α (100 ng/ml-0.38 pg/ml) IL-1 (4 ng/ml-.095 pg/ml) Nisin (2–1000 μg/ml) Streptolysin (10 μg/ml) Anisomycin (100 μM) | Anisomycin (10 nM–10 μM) Cadmium (1–10 μM) Penitrem A (10 μM) Valinomycin (1 μM) |
| 6 | IκB [complement to NF-κB] | C | In many cell types | | |
| 7 | Tetanus Toxin [Protease activity-based sensor] | I | In many cell types | | |
| 8 | Anthrax LF [Protease activity-based sensor] | I | In many cell types | | |

Sensor Class:
D = Detector of toxins;
C = Classifier of toxins;
I = Identifier of toxin or group of toxins
The model toxins can generally be purchased from Sigma Chemical Company (St. Louis, MO)

Examples of Detectors

This class of sensors provides a first line signal that indicates the presence of a toxic agent. This class of sensors provides detection of general cellular stress that requires resolution limited only to the domain over which the measurement is being made, and they are amenable to high content screens as well. Thus, either high throughput or high content screening modes may be used, including but not limited to translocation of heat shock factors from the cytoplasm to the nucleus, and changes in mitochondrial membrane potential, intracellular free ion concentration detection (for example, $Ca^{2+}$; $H^+$), general metabolic status, cell cycle timing events, and organellar structure and function.

1. Mitochondrial Potential

A key to maintenance of cellular homeostasis is a constant ATP energy charge. The cycling of ATP and its metabolites ADP, AMP, inorganic phosphate, and solution-phase protons is continuously adjusted to meet the catabolic and anabolic needs of the cell. Mitochondria are primarily responsible for maintaining a constant energy charge throughout the entire cell. To produce ATP from its constituents, mitochondria must maintain a constant membrane potential within the organelle itself. Therefore, measurement of this electrical potential with specific luminescent probes provides a sensitive and rapid readout of cellular stress.

We have utilized a positively charged cyanine dye, JC-1 (Molecular Probes, Eugene, Oreg.), which diffuses into the cell and readily partitions into the mitochondrial membrane, for measurement of mitochondrial potential. The photophysics of JC-1 are such that when the probe partitions into the mitochondrial membrane and it experiences an electrical potential>140 mV, the probe aggregates and its spectral response is shifted to the red. At membrane potential values<140 mV, JC-1 is primarily monomeric and its spectral response is shifted toward the blue. Therefore, the ratio of two emission wavelengths (645 nm and 530 nm) of JC-1 partitioned into mitochondria provides a sensitive and continuous measure of mitochondrial membrane potential.

We have been making live cell measurements in a high throughput mode as the basis of a generalized indicator of toxic stress. The goal of our initial experiments was to determine the ratio of J-aggregates of JC-1 dye to its monomeric form both before and after toxic stress.

Procedure

1. Cells were plated and cultured up to overnight.
2. Cells were stained with JC-1 (10 μg/ml) for 30 minutes at 37° C. in a $CO_2$ incubator.
3. Cells were then washed quickly with HBSS at 37° C. (2 times, 150 μl/well), the toxins were added if required, and the entire plate was scanned in a plate reader. The JC-1 monomer was measured optimally with a 485 nm excitation/530 nm emission wavelength filter set, and the aggregates were best measured with a 590 nm excitation/645 nm emission wavelength set.

Results

The mitochondrial potential within several types of living cells, and the effects of toxins on the potential were measured using the fluorescence ratio Em 645 (590)/Em 530 (485) (excitation wavelengths in parentheses). For example, we measured the effect of 10 μM valinomycin on the mitochondrial potential within LLCPK cells (pig epithelia). Within seconds of treatment, the toxin induced a more rapid and higher magnitude decrease (an approximately 50% reduction) in mitochondrial potential than that found in untreated cells. Hepatocytes were also determined to be sensitive to valinomycin, and the changes in mitochondrial potential were nearly complete within seconds to minutes after addition of various concentrations of the toxin.

These results are consistent with mitochondrial potential being a model intracellular detector of cell stress. Because these measurements require no spatial resolution within individual cells, mitochondrial potential measurements can be made rapidly on an entire cell array (e.g. high throughput). This means, for example, that complex arrays of many cell types can be probed simultaneously and continuously as a generalized toxic response. Such an indicator can provide a first line signal to indicate that a general toxic stress is present in a sample. Further assays can then be conducted to more specifically identify the toxin using cells classifier or identifier type reporter molecules.

2. Heat Shock Proteins

Most mammalian cells will respond to a variety of environmental stimuli with the induction of a family of proteins called stress proteins. Anoxia, amino acid analogues, sulfhydryl-reacting reagents, transition metal ions, decouplers of oxidative phosphorylation, viral infections, ethanol, antibiotics, ionophores, non-steroidal antiinflammatory drugs, thermal stress and metal chelators are all inducers of cell stress protein synthesis, function, or both. Upon induction, cell stress proteins play a role in folding and unfolding proteins, stabilizing proteins in abnormal configurations, and repairing DNA damage.

There is evidence that at least four heat shock proteins translocate from the cytoplasm to the nucleus upon stress activation of the cell. These proteins include the heat shock proteins HSP27 and HSP70, the heat shock cognate HSC70, and the heat shock transcription factor HSF1. Therefore, measurement of cytoplasm to nuclear translocation of these proteins (and other stress proteins that translocate from the cytoplasm to the nucleus upon a cell stress) will provide a rapid readout of cellular stress.

We have tested the response of an HSP27-GFP biosensor (SEQ ID 169–170) in two cell lines (BHK and HeLa) using a library of heavy metal chemical compounds as biological toxin stimulants to stress the cells. Briefly, cells expressing the HSP27-GFP biosensor are plated into 96-well microplates, and allowed to attach. The cells are then treated with a panel of cell stress-inducing compounds. Exclusively cytoplasmic localization of the fusion protein was found in unstimulated cells.

Other similar heat shock protein biosensors (HSP-70, HSC70, and HSF1 fused to GFP) can be used as detectors, and are shown in SEQ ID NO: 171–176.

Examples of Classifiers

This class of sensors detects the presence of, and further classifies toxins by identifying the cellular pathway(s) perturbed by the toxin. As such, this suite of sensors can detect and/or classify toxins into broad categories, including but not limited to "toxins affecting signal transduction," "toxins affecting the cytoskeleton," and "toxins affecting protein synthesis". Either high throughput or high content screening modes may be used. Classifiers can comprise compounds including but not limited to tubulin, microtubule-associated proteins, actin, actin-binding proteins including but not limited to vinculin, α-actinin, actin depolymerizing factor/cofilin, profilin, and myosin; NF-κB, IκB, GTP-binding proteins including but not limited to rac, rho, and cdc42, and stress-activated protein kinases including but not limited to p38 mitogen-activated protein kinase.

1. Tubulin-cytoskeleton

The cell cytoskeleton plays a major role in cellular functions and processes, such as endo- and exocytosis, vesicle transport, and mitosis. Cytoskeleton-affecting toxins, of proteinaceous and non-proteinaceous form, such as C2 toxin, and several classes of enterotoxins, act either directly on the cytoskeleton, or indirectly via regulatory components controlling the organization to of the cytoskeleton. Therefore, measurement of structural changes in the cytoskeleton can provide classification of the toxin into a class of cytoskeleton-affecting toxins. This assay can be conducted in a high content mode, as described previously, or in a high throughput mode. For high throughput as discussed previously.

Such measurements will be valuable for identification of toxins including, but not limited to anti-microtubule agents, agents that generally affect cell cycle progression and cell proliferation, intracellular signal transduction, and metabolic processes.

For microtubule disruption assays, LLCPK cells stably transfected with a tubulin-GFP biosensor plasmid were plated on 96 well cell culture dishes at 50–60% confluence and cultured overnight at 37° C., 5% $CO_2$. A series of concentrations (10–500 nM) of 5 compounds (paclitaxel, curacin A, nocodazole, vinblastine, and colchicine) in normal culture media were freshly prepared from stock, and were added to cell culture dishes to replace the old culture media. The cells were then observed with the cell screening system described above, at a 12 hour time point.

Our data indicate that the tubulin chimera localizes to and assembles into microtubules throughout the cell. The microtubule arrays in cells expressing the chimera respond as follows to a variety of anti-microtubule compounds:

| Drug | Response |
| --- | --- |
| Vinblastine | Destabilization |
| Nocodazole | Destabilization |
| Paclitaxel | Stabilization |
| Colchicine | Destabilization |
| Curacin A | Destabilization |

Similar data were obtained using cells expressing the tubulin biosensor that were patterned onto cell arrays (such as those described in U.S. patent application Ser. No. 08/865,341 filed May 29, 1997, incorporated by reference herein in its entirety) and dosed as above.

2. NF-κB

NF-κB is cytoplasmic at basal levels of stimulation, but upon insult translocates to the nucleus where it binds specific DNA response elements and activates transcription of a number of genes. Translocation occurs when IkB is degraded by the proteosome in response to specific phosphorylation and ubiquitination events. IkB normally retains NF-κB in the cytoplasm via direct interaction with the protein, and masking of the NLS sequence of NF-κB. Therefore, although not the initial or defining event of the whole signal cascade, NF-κB translocation to the nucleus can serve as an indicator of cell stress.

We have generated an NF-κB-GFP chimera for analysis in live cells. This was accomplished using standard polymerase chain reaction techniques using a characterized NF-κB p65 cDNA purchased from Invitrogen (Carlsbad, Calif.) fused to an EYFP PCR amplimer that was obtained from Clontech Laboratories (Palo Alto, Calif.). The resulting chimera is shown in SEQ ID NO:177–178. The two PCR products were ligated into an eukaryotic expression vector designed to produce the chimeric protein at high levels using the ubiquitous CMV promoter.

NF-κB Immunolocalization

For further studies, we characterized endogenous NF-κB activation by immunolocalization in toxin treated cells. The NF-κB antibodies used in this study were purchased from Santa Cruz Biotechnology, Inc. (Santa Cruz, Calif.), and secondary antibodies are from Molecular Probes (Eugene, Oreg.).

For the 3T3 and SNB19 cell types, we determined the effective concentrations that yield response levels of 50% of the maximum (EC50), expressed in units of mass per volume (ng/ml) and units of molarity. Based on molecular weights of 17 kD for both TNFα and IL-1α, the EC50 levels for these two compounds with 3T3 and SNB19 cell types are given in units of molarity in Table 1. Our results demonstrated reproducibility of the relative responses from zero to maximum dose, but from sample to sample there have been occasional shifts in the baseline intensities of the response at zero concentration.

For these experiments, either 10 or 100 TNFα-treated 3T3 or SNB19 cells/well were tested. On the basis of the standard deviations measured for these samples, and by taking t-values for the student's t-test, we have estimated the minimum detectable doses for each case of cell type, compound, number of cells per well, and for different choices of how many wells are sampled per condition. The latter factor determines the number of degrees of freedom that are provided in the sample of data. Increasing the number of wells from 4 to 16, and increasing the number of cells per well from 10 to 100, improves the minimum detectable doses considerably. For 3T3 cells, which show lower minimum detectable doses than the SNB19 cells, and for the case of 1% false negative and 1% false positive rates, we estimate that 100 cells per well and a sampling of 12 or 16 wells are sufficient to detect a dose approximately equal to the EC50 value of 0.15 ng/ml. If the false positive rate is relaxed to 20%, a concentration of approximately half that value can be detected (0.83 ng/ml). One hundred cells can conveniently be sampled over a cell culture surface area of less than 1 mm$^2$.

TABLE 1

EC50 levels for TNFα and IL-1α (based on molecular weights of 17 kD for both)

| Compound | Cell Type | EC50 ($10^{-12}$ moles/liter) |
|---|---|---|
| TNFα | 3T3 | 8.8 |
|  | SNB19 | 5.9 |
| IL-1α | 3T3 | 0.24 |
|  | SNB19 | 59 |

3. Phospho-p38 Mitogen Activated Protein Kinase (pp38MAPK)

MAPKs play a role in not only cell growth and division, but as mediators of cellular stress responses. One MAPK, p38, is activated by chemical stress inducers such as hyperosmolar sorbitol, hydrogen peroxide, arsenite, cadmium ions, anisomycin, sodium salicylate, and LPS. Activation of p38 is also accompanied by its translocation into the nucleus from the cytoplasm.

MAPK p38 lies in a pathway that is a cascade of kinases. Thus, p38 is a substrate of one or more kinases, and it acts to phosphorylate one or more substrates in time and space within the living cell.

The assay we present here measures, as one of its parameters, p38 activation using immunolocalization of the phosphorylated form of p38 in toxin-treated cells. The assay was developed to be flexible enough to include the simultaneous measurement of other parameters within the same individual cells. Because the signal transduction pathway mediated by the transcription factor NF-κB is also known to be involved in the cell stress response, we included the activation of NF-κB as a second parameter in the same assay.

Figure 36:
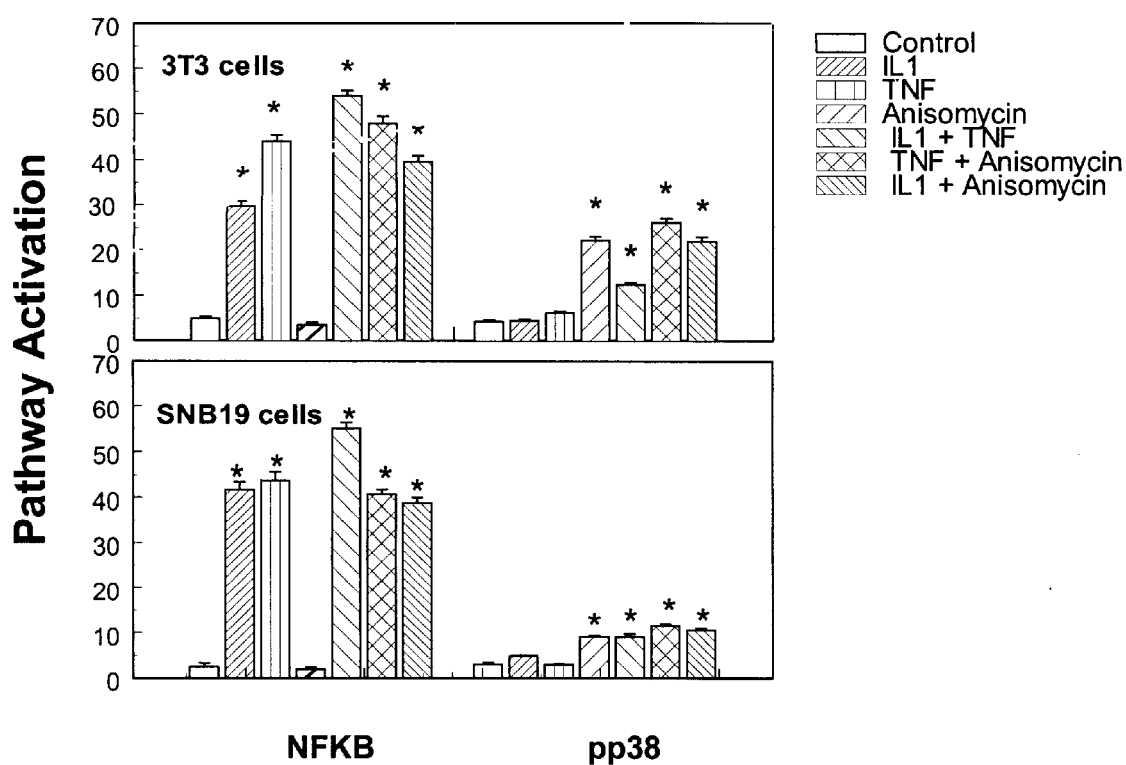
FIG. 36 shows the differential response in a dual labeling assay of the p38 MAPK and NF-κB pathways across three model toxins and two different cell types. Treatments marked with an asterisk are different from controls at a 99% confidence level (p<0.01).

Our experiments demonstrate an immunofluorescence approach can be used to measure p38 MAPK activation either alone or in combination with NF-κB activation in the same cells. Multiple cell types, model toxins, and antibodies were tested, and significant stimulation of both pathways was measured in a high-content mode. The phospho-p38 antibodies used in this study were purchased from Sigma Chemical Company (St. Louis, Mo.). We report that at least two cell stress signaling pathways can not only be measured simultaneously, but are differentially responsive to classes of model toxins. FIG. 36 shows the differential response of the p38 MAPK and NF-κB pathways across three model toxins and two different cell types. Note that when added alone, three of the model toxins (IL1α, TNFα and Anisomycin) can be differentiated by the two assays as activators of specific pathways.

IκB chimera

IκB degradation is the key event leading to nuclear translocation of NF-kB and activation of the NFkB-mediated stress response. We have chosen this sensor to complement the NF-kB sensor as a classifier in a high-throughput mode: the measurement of loss of signal due to degradation of the IκB-GFP fusion protein requires no spatial resolution within individual cells, and as such we envision IkB degradation measurements being made rapidly on an entire cell substrate.

This biosensor is based on fusion of the first 60 amino acids of IkB to the Fred25 variant of GFP. SEQ ID 179–180 This region of IkB contains all the regulatory sequences, including phosphorylation sites and ubiquitination sites, necessary to confer proteosome degradation upon the biosensor. Knowing this, stimulation of any pathway that would typically lead to NFkB translocation results in degradation of this biosensor. Monitoring the fluorescence intensity of cells expressing IkB-GFP identifies the degradation process.

Examples of Identifiers

In our toxin identification strategy, the first two levels of characterization ensure a rapid readout of toxin class without sacrificing the ability to detect many new mutant toxins or dissect several complex mixtures of known toxins. The third level of biosensors are identifiers, which can identify a specific toxin or group of toxins. In one embodiment, an identifier comprises a protease biosensor that responds to the activity of a specific toxin. Other identifiers are produced with reporters/biosensors specific to their activities. These include, but are not limited to post-translational modifications such as phosphorylation or ADP-ribosylation, translocation between cellular organelles or compartments, effects on specific organelles or cellular components (for example, membrane permeabilization, cytoskeleton rearrangement, etc.).

ADP-ribosylating toxins—These toxins include Pseudomonas toxin A, diptheria toxin, botulinum toxin, pertussis toxin, and cholera toxin. For example, C. botulinum C2 toxin induces the ADP-ribosylation of Arg177 in the cytoskeletal protein actin, thus altering its assembly properties. Besides the construction of a classifier assay to measure actin-cytoskeleton regulation, an identifier assay can be constructed to detect the specific actin ADP-ribosylation. Because the ADP-ribosylation induces a conformational change that no longer permits the modified actin to polymerize, this conformational change can be detected intracellularly in several possible ways using luminescent reagents. For example, actin can be luminescently labeled using a fluorescent reagent with an appropriate excited state lifetime that allows for the measurement of the rotational diffusion of the intracellular actin using steady state fluorescence anisotropy. That is, toxin-modified actin will no longer be able to assemble into rigid filaments and will therefore produce only luminescent signals with relatively low anisotropy, which can be readily measured with an imaging system. In another embodiment, actin can be labeled with a polarity-sensitive fluorescent reagent that reports changes in actin-conformation through spectral shifts of the attached reagent. That is, toxin-treatment will induce a conformational change in intracellular actin such that a ratio of two fluorescence wavelengths will provide a measure of actin ADP-ribosylation.

Cytotoxic phospholipases—Several gram-positive bacterial species produce cytotoxic phospholipases. For example, Clostridium perfringens produces a phospholipase C specific for the cleavage of phosphoinositides. These phosphoinositides (e.g., inositol 1,4,5-trisphosphate) induce the release of calcium ions from intracellular organelles. An assay that can be conducted as either high-content or high-throughput can be constructed to measure the release of calcium ions using fluorescent reagents that have altered spectral properties when complexed with the metal ion. Therefore, a direct consequence of the action of a phospholipase C based toxin can be measured as a change in cellular calcium ion concentration.

Exfoliative toxins—These toxins are produced by several Staphylococcal species and can consist of several serotypes. A specific identifier for these toxins can be constructed by measuring the morphological changes in their target organelle, the desmosome, which occur at the junctions between cells. The exfoliative toxins are known to change the morphology of the desmosomes into two smaller components called hemidesmosomes. In the high-content assay for exfoliative toxins, epithelial cells whose desmosomes are luminescently labeled are subjected to image analysis. An method that detects the morphological change between desmosomes and hemidesmosomes is used to quantify the activity of the toxins on the cells.

Most of these identifiers can be used in high throughput assays requiring no spatial resolution, as well as in high content assays.

Several biological threat agents act as specific proteases, and thus we have focused on the development of fluorescent protein biosensors that report the proteolytic cleavage of specific amino acid sequences found within the target proteins.

A number of such protease biosensors (including FRET biosensors) are disclosed above, such as the caspase biosensors, anthrax, tetanus, Botulinum, and the zinc metalloproteases. FRET is a powerful technique in that small changes in protein conformation, many of which are associated with toxin activity, can not only be measured with high precision in time and space within living cells, but can be measured in a high-throughput mode, as discussed above.

As described above, one of skill in the art will recognize that the protease biosensors of this aspect of the invention can be adapted to report the activity of any protease, by a substitution of the appropriate protease recognition site in any of the constructs (see FIG. 29B). As disclosed above, these biosensors can be used in high-content or high throughput screens to detect in vivo activation of enzymatic activity by toxins, and to identify specific activity based on cleavage of a known recognition motif. These biosensors can be used in both live cell and fixed end-point assays, and can be combined with additional measurements to provide a multi-parameter assay.

Anthrax LF

Anthrax is a well-known agent of biological warfare and is an excellent target for development of a biosensor in the identifier class. Lethal factor (LF) is one of the protein components that confer toxicity to anthrax, and recently two of its targets within cells were identified. LF is a metalloprotease that specifically cleaves Mek1 and Mek2 proteins, kinases that are part of the MAP-kinase signaling pathway. Construction of lethal factor protease biosensors are described above. (SEQ ID NO:7–8; 9–10) Green fluorescent protein (GFP) is fused in-frame at the amino terminus of either Mek1 or Mek2 (or both), resulting in a chimeric protein that is retained in the cytoplasm due to the presence of a nuclear export sequence (NES) present in both of the target molecules. Upon cleavage by active lethal factor, GFP is released from the chimera and is free to diffuse into the nucleus. Therefore, measuring the accumulation of GFP in the nucleus provides a direct measure of LF activity on its natural target, the living cell.

While a preferred form of the invention has been shown in the drawings and described, since variations in the preferred form will be apparent to those skilled in the art, the invention should not be construed as limited to the specific form shown and described, but instead is as set forth in the claims.

SEQUENCE LISTING

```
<160> NUMBER OF SEQ ID NOS:  180

<210> SEQ ID NO 1
<211> LENGTH: 1770
<212> TYPE: DNA
<213> ORGANISM: Artificial Sequence
<220> FEATURE:
<221> NAME/KEY: CDS
```

<222> LOCATION: (1)..(882)
<223> OTHER INFORMATION: Description of Artificial Sequence:
      GFP-DEVD-Annexin II construct

<400> SEQUENCE: 1

```
atg gtg agc aag ggc gag gag ctg ttc acc ggg gtg gtg ccc atc ctg      48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
     50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
 65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg     624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc     672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc     720
Val Thr Ala Ala Gly Ile Thr Leu Gly Met Asp Glu Leu Tyr Lys Ser
225                 230                 235                 240 gga ctc aga tct ggc gcc ggc gct gga gcc gga gct ggc gcc gga gcc     768
Gly Leu Arg Ser Gly Ala Gly Ala Gly Ala Gly Ala Gly Ala Gly Ala
                245                 250                 255 gac gag gtg gac ggc gcc ggc gcc gat gaa gta gat ggc gcc atg tct     816
Asp Glu Val Asp Gly Ala Gly Ala Asp Glu Val Asp Gly Ala Met Ser
            260                 265                 270 act gtc cac gaa atc ctg tgc aag ctc agc ttg gag ggt gat cat tct     864
Thr Val His Glu Ile Leu Cys Lys Leu Ser Leu Glu Gly Asp His Ser
        275                 280                 285 aca ccc cca agt gcc tat tgaatggtga gcaagggcga ggagctgttc            912
Thr Pro Pro Ser Ala Tyr
```

-continued

```
Thr Pro Pro Ser Ala Tyr
    290 accggggtgg tgcccatcct ggtcgagctg gacggcgacg taaacggcca caagttcagc      972 gtgtccggcg agggcgaggg cgatgccacc tacggcaagc tgaccctgaa gttcatctgc     1032 accaccggca agctgcccgt gccctggccc accctcgtga ccaccctgac ctacggcgtg     1092 cagtgcttca gccgctaccc cgaccacatg aagcagcacg acttcttcaa gtccgccatg     1152 cccgaaggct acgtccagga gcgcaccatc ttcttcaagg acgacggcaa ctacaagacc     1212 cgcgccgagg tgaagttcga gggcgacacc ctggtgaacc gcatcgagct gaagggcatc     1272 gacttcaagg aggacggcaa catcctgggg cacaagctgg agtacaacta caacagccac     1332 aacgtctata tcatggccga caagcagaag aacggcatca aggtgaactt caagatccgc     1392 cacaacatcg aggacggcag cgtgcagctc gccgaccact accagcagaa cacccccatc     1452 ggcgacggcc ccgtgctgct gcccgacaac cactacctga gcacccagtc cgccctgagc     1512 aaagacccca acgagaagcg cgatcacatg gtcctgctgg agttcgtgac cgccgccggg     1572 atcactctcg gcatggacga gctgtacaag tccggactca gatctggcgc cggcgctgga     1632 gccggagctg gcgccggagc cgacgaggtg gacggcgccg cgccgatga agtagatggc     1692 gccatgtcta ctgtccacga aatcctgtgc aagctcagct ggagggtga tcattctaca     1752 cccccaagtg cctattga                                                    1770
```

<210> SEQ ID NO 2
<211> LENGTH: 294
<212> TYPE: PRT
<213> ORGANISM: Artificial Sequence
<220> FEATURE:
<223> OTHER INFORMATION: Description of Artificial Sequence:
      GFP-DEVD-Annexin II construct

<400> SEQUENCE: 2

```
Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Gly Ala Gly Ala Gly Ala Gly Ala Gly Ala Gly Ala
                245                 250                 255

Asp Glu Val Asp Gly Ala Gly Ala Asp Glu Val Asp Gly Ala Met Ser
                260                 265                 270

Thr Val His Glu Ile Leu Cys Lys Leu Ser Leu Glu Gly Asp His Ser
        275                 280                 285

Thr Pro Pro Ser Ala Tyr
        290

<210> SEQ ID NO 3
<211> LENGTH: 2439
<212> TYPE: DNA
<213> ORGANISM: Artificial Sequence
<220> FEATURE:
<221> NAME/KEY: CDS
<222> LOCATION: (1)..(2436)
<223> OTHER INFORMATION: Description of Artificial Sequence:
      EYFP-DEVD-MAPKDM construct

<400> SEQUENCE: 3 atg gtg agc aag ggc gag gag ctg ttc acc ggg gtg gtg ccc atc ctg     48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc     96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc    144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc    192
Cys Thr Thr Gly Lys Leu Pro Val Pro Trp Pro Thr Leu Val Thr Thr
    50                  55                  60 ttc ggc tac ggc ctg cag tgc ttc gcc cgc tac ccc gac cac atg aag    240
Phe Gly Tyr Gly Leu Gln Cys Phe Ala Arg Tyr Pro Asp His Met Lys
65                  70                  75                  80 cag cac gac ttc ttc aag tcc gcc atg ccc gaa ggc tac gtc cag gag    288
Gln His Asp Phe Phe Lys Ser Ala Met Pro Glu Gly Tyr Val Gln Glu
                85                  90                  95 cgc acc atc ttc ttc aag gac gac ggc aac tac aag acc cgc gcc gag    336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc    384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac    432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac    480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc    528
Gly Ile Lys Val Asn Phe Lys Ile Arg His Asn Ile Glu Asp Gly Ser
                165                 170                 175
```

```
gtg cag ctc gcc gac cac tac cag cag aac acc ccc atc ggc gac ggc      576
Val Gln Leu Ala Asp His Tyr Gln Gln Asn Thr Pro Ile Gly Asp Gly
        180                 185                 190 ccc gtg ctg ctg ccc gac aac cac tac ctg agc tac cag tcc gcc ctg      624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
        210                 215                 220 gtg acc gcc gcc ggg atc act ctc ggc atg gac gag ctg tac aag aag      720
Val Thr Ala Ala Gly Ile Thr Leu Gly Met Asp Glu Leu Tyr Lys Lys
225                 230                 235                 240 gga gac gaa gtg gac gga gcc gac ctc agt ctt gtg gat gcg ttg aca      768
Gly Asp Glu Val Asp Gly Ala Asp Leu Ser Leu Val Asp Ala Leu Thr
                245                 250                 255 gaa cca cct cca gaa att gag gga gaa ata aag cga gac ttc atg gct      816
Glu Pro Pro Pro Glu Ile Glu Gly Glu Ile Lys Arg Asp Phe Met Ala
                260                 265                 270 gcg ctg gag gca gag ccc tat gat gac atc gtg gga gaa act gtg gag      864
Ala Leu Glu Ala Glu Pro Tyr Asp Asp Ile Val Gly Glu Thr Val Glu
        275                 280                 285 aaa act gag ttt att cct ctc ctg gat ggt gat gag aaa acc ggg aac      912
Lys Thr Glu Phe Ile Pro Leu Leu Asp Gly Asp Glu Lys Thr Gly Asn
        290                 295                 300 tca gag tcc aaa aag aaa ccc tgc tta gac act agc cag gtt gaa ggt      960
Ser Glu Ser Lys Lys Lys Pro Cys Leu Asp Thr Ser Gln Val Glu Gly
305                 310                 315                 320 atc cca tct tct aaa cca aca ctc cta gcc aat ggt gat cat gga atg     1008
Ile Pro Ser Ser Lys Pro Thr Leu Leu Ala Asn Gly Asp His Gly Met
                325                 330                 335 gag ggg aat aac act gca ggg tct cca act gac ttc ctt gaa gag aga     1056
Glu Gly Asn Asn Thr Ala Gly Ser Pro Thr Asp Phe Leu Glu Glu Arg
                340                 345                 350 gtg gac tat ccg gat tat cag agc agc cag aac tgg cca gaa gat gca     1104
Val Asp Tyr Pro Asp Tyr Gln Ser Ser Gln Asn Trp Pro Glu Asp Ala
        355                 360                 365 agc ttt tgt ttc cag cct cag caa gtg tta gat act gac cag gct gag     1152
Ser Phe Cys Phe Gln Pro Gln Gln Val Leu Asp Thr Asp Gln Ala Glu
        370                 375                 380 ccc ttt aac gag cac cgt gat gat ggt ttg gca gat ctg ctc ttt gtc     1200
Pro Phe Asn Glu His Arg Asp Asp Gly Leu Ala Asp Leu Leu Phe Val
385                 390                 395                 400 tcc agt gga ccc acg aac gct tct gca ttt aca gag cga gac aat cct     1248
Ser Ser Gly Pro Thr Asn Ala Ser Ala Phe Thr Glu Arg Asp Asn Pro
                405                 410                 415 tca gaa gac agt tac ggt atg ctt ccc tgt gac tca ttt gct tcc acg     1296
Ser Glu Asp Ser Tyr Gly Met Leu Pro Cys Asp Ser Phe Ala Ser Thr
                420                 425                 430 gct gtt gta tct cag gag tgg tct gtg gga gcc cca aac tct cca tgt     1344
Ala Val Val Ser Gln Glu Trp Ser Val Gly Ala Pro Asn Ser Pro Cys
        435                 440                 445 tca gag tcc tgt gtc tcc cca gag gtt act ata gaa acc cta cag cca     1392
Ser Glu Ser Cys Val Ser Pro Glu Val Thr Ile Glu Thr Leu Gln Pro
450                 455                 460 gca aca gag ctc tcc aag gca gca gaa gtg gaa tca gtg aaa gag cag     1440
Ala Thr Glu Leu Ser Lys Ala Ala Glu Val Glu Ser Val Lys Glu Gln
465                 470                 475                 480 ctg cca gct aaa gca ttg gaa acg atg gca gag cag acc act gat gtg     1488
Leu Pro Ala Lys Ala Leu Glu Thr Met Ala Glu Gln Thr Thr Asp Val
                485                 490                 495
```

-continued

```
gtg cac tct cca tcc aca gac aca aca cca ggc cca gac aca gag gca    1536
Val His Ser Pro Ser Thr Asp Thr Thr Pro Gly Pro Asp Thr Glu Ala
        500                 505                 510 gca ctg gct aaa gac ata gaa gag atc acc aag cca gat gtg ata ttg    1584
Ala Leu Ala Lys Asp Ile Glu Glu Ile Thr Lys Pro Asp Val Ile Leu
        515                 520                 525 gca aat gtc acg cag cca tct act gaa tcg gat atg ttc ctg gcc cag    1632
Ala Asn Val Thr Gln Pro Ser Thr Glu Ser Asp Met Phe Leu Ala Gln
    530                 535                 540 gac atg gaa cta ctc aca gga aca gag gca gcc cac gct aac aat atc    1680
Asp Met Glu Leu Leu Thr Gly Thr Glu Ala Ala His Ala Asn Asn Ile
545                 550                 555                 560 ata ttg cct aca gaa cca gac gaa tct tca acc aag gat gta gca cca    1728
Ile Leu Pro Thr Glu Pro Asp Glu Ser Ser Thr Lys Asp Val Ala Pro
                565                 570                 575 cct atg gaa gaa gaa att gtc cca ggc aat gat acg aca tcc ccc aaa    1776
Pro Met Glu Glu Glu Ile Val Pro Gly Asn Asp Thr Thr Ser Pro Lys
            580                 585                 590 gaa aca gag aca aca ctt cca ata aaa atg gac ttg gca cca cct gag    1824
Glu Thr Glu Thr Thr Leu Pro Ile Lys Met Asp Leu Ala Pro Pro Glu
        595                 600                 605 gat gtg tta ctt acc aaa gaa aca gaa cta gcc cca gcc aag ggc atg    1872
Asp Val Leu Leu Thr Lys Glu Thr Glu Leu Ala Pro Ala Lys Gly Met
    610                 615                 620 gtt tca ctc tca gaa ata gaa gag gct ctg gca aag aat gat gtt cgc    1920
Val Ser Leu Ser Glu Ile Glu Glu Ala Leu Ala Lys Asn Asp Val Arg
625                 630                 635                 640 tct gca gaa ata cct gtg gct cag gag aca gtg gtc tca gaa aca gag    1968
Ser Ala Glu Ile Pro Val Ala Gln Glu Thr Val Val Ser Glu Thr Glu
                645                 650                 655 gtg gtc ctg gca aca gaa gtg gta ctg ccc tca gat ccc ata aca aca    2016
Val Val Leu Ala Thr Glu Val Val Leu Pro Ser Asp Pro Ile Thr Thr
            660                 665                 670 ttg aca aag gat gtg aca ctc ccc tta gaa gca gag aga ccg ttg gtg    2064
Leu Thr Lys Asp Val Thr Leu Pro Leu Glu Ala Glu Arg Pro Leu Val
        675                 680                 685 acg gac atg act cca tct ctg gaa aca gaa atg acc cta ggc aaa gag    2112
Thr Asp Met Thr Pro Ser Leu Glu Thr Glu Met Thr Leu Gly Lys Glu
    690                 695                 700 aca gct cca ccc aca gaa aca aat ttg ggc atg gcc aaa gac atg tct    2160
Thr Ala Pro Pro Thr Glu Thr Asn Leu Gly Met Ala Lys Asp Met Ser
705                 710                 715                 720 cca ctc cca gaa tca gaa gtg act ctg ggc aag gac gtg gtt ata ctt    2208
Pro Leu Pro Glu Ser Glu Val Thr Leu Gly Lys Asp Val Val Ile Leu
                725                 730                 735 cca gaa aca aag gtg gct gag ttt aac aat gtg act cca ctt tca gaa    2256
Pro Glu Thr Lys Val Ala Glu Phe Asn Asn Val Thr Pro Leu Ser Glu
            740                 745                 750 gaa gag gta acc tca gtc aag gac atg tct ccg tct gca gaa aca gag    2304
Glu Glu Val Thr Ser Val Lys Asp Met Ser Pro Ser Ala Glu Thr Glu
        755                 760                 765 gct ccc ctg gct aag aat gct gat ctg cac tca gga aca gag ctg att    2352
Ala Pro Leu Ala Lys Asn Ala Asp Leu His Ser Gly Thr Glu Leu Ile
    770                 775                 780 gtg gac aac agc atg gct cca gcc tcc gat ctt gca ctg ccc ttg gaa    2400
Val Asp Asn Ser Met Ala Pro Ala Ser Asp Leu Ala Leu Pro Leu Glu
785                 790                 795                 800 aca aaa gta gca aca gtt cca att aaa gac aaa gga tga                2439
Thr Lys Val Ala Thr Val Pro Ile Lys Asp Lys Gly
```

<210> SEQ ID NO 4
<211> LENGTH: 812
<212> TYPE: PRT
<213> ORGANISM: Artificial Sequence
<220> FEATURE:
<223> OTHER INFORMATION: Description of Artificial Sequence: EYFP-DEVD-MAPKDM construct

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Lys
225                 230                 235                 240

Gly Asp Glu Val Asp Gly Ala Asp Leu Ser Leu Val Asp Ala Leu Thr
                245                 250                 255

Glu Pro Pro Pro Glu Ile Glu Gly Glu Ile Lys Arg Asp Phe Met Ala
            260                 265                 270

Ala Leu Glu Ala Glu Pro Tyr Asp Asp Ile Val Gly Glu Thr Val Glu
        275                 280                 285

Lys Thr Glu Phe Ile Pro Leu Leu Asp Gly Asp Glu Lys Thr Gly Asn
    290                 295                 300

Ser Glu Ser Lys Lys Pro Cys Leu Asp Thr Ser Gln Val Glu Gly
305                 310                 315                 320

Ile Pro Ser Ser Lys Pro Thr Leu Leu Ala Asn Gly Asp His Gly Met
                325                 330                 335

Glu Gly Asn Asn Thr Ala Gly Ser Pro Thr Asp Phe Leu Glu Glu Arg
            340                 345                 350

-continued

```
Val Asp Tyr Pro Asp Tyr Gln Ser Ser Gln Asn Trp Pro Glu Asp Ala
    355                 360                 365
Ser Phe Cys Phe Gln Pro Gln Gln Val Leu Asp Thr Asp Gln Ala Glu
    370                 375                 380
Pro Phe Asn Glu His Arg Asp Asp Gly Leu Ala Asp Leu Leu Phe Val
385                 390                 395                 400
Ser Ser Gly Pro Thr Asn Ala Ser Ala Phe Thr Glu Arg Asp Asn Pro
                405                 410                 415
Ser Glu Asp Ser Tyr Gly Met Leu Pro Cys Asp Ser Phe Ala Ser Thr
                420                 425                 430
Ala Val Val Ser Gln Glu Trp Ser Val Gly Ala Pro Asn Ser Pro Cys
            435                 440                 445
Ser Glu Ser Cys Val Ser Pro Glu Val Thr Ile Glu Thr Leu Gln Pro
        450                 455                 460
Ala Thr Glu Leu Ser Lys Ala Ala Glu Val Glu Ser Val Lys Glu Gln
465                 470                 475                 480
Leu Pro Ala Lys Ala Leu Glu Thr Met Ala Glu Gln Thr Thr Asp Val
                485                 490                 495
Val His Ser Pro Ser Thr Asp Thr Thr Pro Gly Pro Asp Thr Glu Ala
                500                 505                 510
Ala Leu Ala Lys Asp Ile Glu Glu Ile Thr Lys Pro Asp Val Ile Leu
            515                 520                 525
Ala Asn Val Thr Gln Pro Ser Thr Glu Ser Asp Met Phe Leu Ala Gln
        530                 535                 540
Asp Met Glu Leu Leu Thr Gly Thr Glu Ala Ala His Ala Asn Asn Ile
545                 550                 555                 560
Ile Leu Pro Thr Glu Pro Asp Glu Ser Ser Thr Lys Asp Val Ala Pro
                565                 570                 575
Pro Met Glu Glu Glu Ile Val Pro Gly Asn Asp Thr Thr Ser Pro Lys
                580                 585                 590
Glu Thr Glu Thr Thr Leu Pro Ile Lys Met Asp Leu Ala Pro Pro Glu
            595                 600                 605
Asp Val Leu Leu Thr Lys Glu Thr Glu Leu Ala Pro Ala Lys Gly Met
        610                 615                 620
Val Ser Leu Ser Glu Ile Glu Glu Ala Leu Ala Lys Asn Asp Val Arg
625                 630                 635                 640
Ser Ala Glu Ile Pro Val Ala Gln Glu Thr Val Val Ser Glu Thr Glu
                645                 650                 655
Val Val Leu Ala Thr Glu Val Val Leu Pro Ser Asp Pro Ile Thr Thr
                660                 665                 670
Leu Thr Lys Asp Val Thr Leu Pro Leu Glu Ala Glu Arg Pro Leu Val
            675                 680                 685
Thr Asp Met Thr Pro Ser Leu Gly Thr Glu Met Thr Leu Gly Lys Glu
        690                 695                 700
Thr Ala Pro Pro Thr Glu Thr Asn Leu Gly Met Ala Lys Asp Met Ser
705                 710                 715                 720
Pro Leu Pro Glu Ser Glu Val Thr Leu Gly Lys Asp Val Val Ile Leu
                725                 730                 735
Pro Glu Thr Lys Val Ala Glu Phe Asn Asn Val Thr Pro Leu Ser Glu
                740                 745                 750
Glu Glu Val Thr Ser Val Lys Asp Met Ser Pro Ser Ala Glu Thr Glu
            755                 760                 765
Ala Pro Leu Ala Lys Asn Ala Asp Leu His Ser Gly Thr Glu Leu Ile
```

-continued

```
               770                 775                 780
Val Asp Asn Ser Met Ala Pro Ala Ser Asp Leu Ala Leu Pro Leu Glu
785                 790                 795                 800

Thr Lys Val Ala Thr Val Pro Ile Lys Asp Lys Gly
                805                 810

<210> SEQ ID NO 5
<211> LENGTH: 2439
<212> TYPE: DNA
<213> ORGANISM: Artificial Sequence
<220> FEATURE:
<221> NAME/KEY: CDS
<222> LOCATION: (1)..(2436)
<223> OTHER INFORMATION: Description of Artificial Sequence:
      EYFP-DEAD-MAPKDM construct

<400> SEQUENCE: 5 atg gtg agc aag ggc gag gag ctg ttc acc ggg gtg gtg ccc atc ctg     48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc     96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc    144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc    192
Cys Thr Thr Gly Lys Leu Pro Val Pro Trp Pro Thr Leu Val Thr Thr
     50                  55                  60 ttc ggc tac ggc ctg cag tgc ttc gcc cgc tac ccc gac cac atg aag    240
Phe Gly Tyr Gly Leu Gln Cys Phe Ala Arg Tyr Pro Asp His Met Lys
 65                  70                  75                  80 cag cac gac ttc ttc aag tcc gcc atg ccc gaa ggc tac gtc cag gag    288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag    336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc    384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac    432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac    480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc    528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc    576
Val Gln Leu Ala Asp His Tyr Gln Gln Asn Thr Pro Ile Gly Asp Gly
            180                 185                 190 ccc gtg ctg ctg ccc gac aac cac tac ctg agc tac cag tcc gcc ctg    624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc    672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag ccc    720
Val Thr Ala Ala Gly Ile Thr Leu Gly Met Asp Glu Leu Tyr Lys Pro
```

```
                225                 230                 235                 240
aga gac gaa gcc gac agc gcc gac ctc agt ctt gtg gat gcg ttg aca        768
Arg Asp Glu Ala Asp Ser Ala Asp Leu Ser Leu Val Asp Ala Leu Thr
                    245                 250                 255 gaa cca cct cca gaa att gag gga gaa ata aag cga gac ttc atg gct        816
Glu Pro Pro Pro Glu Ile Glu Gly Glu Ile Lys Arg Asp Phe Met Ala
            260                 265                 270 gcg ctg gag gca gag ccc tat gat gac atc gtg gga gaa act gtg gag        864
Ala Leu Glu Ala Glu Pro Tyr Asp Asp Ile Val Gly Glu Thr Val Glu
        275                 280                 285 aaa act gag ttt att cct ctc ctg gat ggt gat gag aaa acc ggg aac        912
Lys Thr Glu Phe Ile Pro Leu Leu Asp Gly Asp Glu Lys Thr Gly Asn
    290                 295                 300 tca gag tcc aaa aag aaa ccc tgc tta gac act agc cag gtt gaa ggt        960
Ser Glu Ser Lys Lys Lys Pro Cys Leu Asp Thr Ser Gln Val Glu Gly
305                 310                 315                 320 atc cca tct tct aaa cca aca ctc cta gcc aat ggt gat cat gga atg       1008
Ile Pro Ser Ser Lys Pro Thr Leu Leu Ala Asn Gly Asp His Gly Met
                    325                 330                 335 gag ggg aat aac act gca ggg tct cca act gac ttc ctt gaa gag aga       1056
Glu Gly Asn Asn Thr Ala Gly Ser Pro Thr Asp Phe Leu Glu Glu Arg
                340                 345                 350 gtg gac tat ccg gat tat cag agc agc cag aac tgg cca gaa gat gca       1104
Val Asp Tyr Pro Asp Tyr Gln Ser Ser Gln Asn Trp Pro Glu Asp Ala
            355                 360                 365 agc ttt tgt ttc cag cct cag caa gtg tta gat act gac cag gct gag       1152
Ser Phe Cys Phe Gln Pro Gln Gln Val Leu Asp Thr Asp Gln Ala Glu
        370                 375                 380 ccc ttt aac gag cac cgt gat gat ggt ttg gca gat ctg ctc ttt gtc       1200
Pro Phe Asn Glu His Arg Asp Asp Gly Leu Ala Asp Leu Leu Phe Val
385                 390                 395                 400 tcc agt gga ccc acg aac gct tct gca ttt aca gag cga gac aat cct       1248
Ser Ser Gly Pro Thr Asn Ala Ser Ala Phe Thr Glu Arg Asp Asn Pro
                    405                 410                 415 tca gaa gac agt tac ggt atg ctt ccc tgt gac tca ttt gct tcc acg       1296
Ser Glu Asp Ser Tyr Gly Met Leu Pro Cys Asp Ser Phe Ala Ser Thr
                420                 425                 430 gct gtt gta tct cag gag tgg tct gtg gga gcc cca aac tct cca tgt       1344
Ala Val Val Ser Gln Glu Trp Ser Val Gly Ala Pro Asn Ser Pro Cys
            435                 440                 445 tca gag tcc tgt gtc tcc cca gag gtt act ata gaa acc cta cag cca       1392
Ser Glu Ser Cys Val Ser Pro Glu Val Thr Ile Glu Thr Leu Gln Pro
        450                 455                 460 gca aca gag ctc tcc aag gca gca gaa gtg gaa tca gtg aaa gag cag       1440
Ala Thr Glu Leu Ser Lys Ala Ala Glu Val Glu Ser Val Lys Glu Gln
465                 470                 475                 480 ctg cca gct aaa gca ttg gaa acg atg gca gag cag acc act gat gtg       1488
Leu Pro Ala Lys Ala Leu Glu Thr Met Ala Glu Gln Thr Thr Asp Val
                    485                 490                 495 gtg cac tct cca tcc aca gac aca aca cca ggc cca gac aca gag gca       1536
Val His Ser Pro Ser Thr Asp Thr Thr Pro Gly Pro Asp Thr Glu Ala
                500                 505                 510 gca ctg gct aaa gac ata gaa gag atc acc aag cca gat gtg ata ttg       1584
Ala Leu Ala Lys Asp Ile Glu Glu Ile Thr Lys Pro Asp Val Ile Leu
            515                 520                 525 gca aat gtc acg cag cca tct act gaa tcg gat atg ttc ctg gcc cag       1632
Ala Asn Val Thr Gln Pro Ser Thr Glu Ser Asp Met Phe Leu Ala Gln
        530                 535                 540 gac atg gaa cta ctc aca gga aca gag gca gcc cac gct aac aat atc       1680
```

```
Asp Met Glu Leu Leu Thr Gly Thr Glu Ala Ala His Ala Asn Asn Ile
545                 550                 555                 560 ata ttg cct aca gaa cca gac gaa tct tca acc aag gat gta gca cca    1728
Ile Leu Pro Thr Glu Pro Asp Glu Ser Ser Thr Lys Asp Val Ala Pro
                565                 570                 575 cct atg gaa gaa gaa att gtc cca ggc aat gat acg aca tcc ccc aaa    1776
Pro Met Glu Glu Glu Ile Val Pro Gly Asn Asp Thr Thr Ser Pro Lys
            580                 585                 590 gaa aca gag aca aca ctt cca ata aaa atg gac ttg gca cca cct gag    1824
Glu Thr Glu Thr Thr Leu Pro Ile Lys Met Asp Leu Ala Pro Pro Glu
        595                 600                 605 gat gtg tta ctt acc aaa gaa aca gaa cta gcc cca gcc aag ggc atg    1872
Asp Val Leu Leu Thr Lys Glu Thr Glu Leu Ala Pro Ala Lys Gly Met
    610                 615                 620 gtt tca ctc tca gaa ata gaa gag gct ctg gca aag aat gat gtt cgc    1920
Val Ser Leu Ser Glu Ile Glu Glu Ala Leu Ala Lys Asn Asp Val Arg
625                 630                 635                 640 tct gca gaa ata cct gtg gct cag gag aca gtg gtc tca gaa aca gag    1968
Ser Ala Glu Ile Pro Val Ala Gln Glu Thr Val Val Ser Glu Thr Glu
                645                 650                 655 gtg gtc ctg gca aca gaa gtg gta ctg ccc tca gat ccc ata aca aca    2016
Val Val Leu Ala Thr Glu Val Val Leu Pro Ser Asp Pro Ile Thr Thr
            660                 665                 670 ttg aca aag gat gtg aca ctc ccc tta gaa gca gag aga ccg ttg gtg    2064
Leu Thr Lys Asp Val Thr Leu Pro Leu Glu Ala Glu Arg Pro Leu Val
        675                 680                 685 acg gac atg act cca tct ctg gaa aca gaa atg acc cta ggc aaa gag    2112
Thr Asp Met Thr Pro Ser Leu Glu Thr Glu Met Thr Leu Gly Lys Glu
    690                 695                 700 aca gct cca ccc aca gaa aca aat ttg ggc atg gcc aaa gac atg tct    2160
Thr Ala Pro Pro Thr Glu Thr Asn Leu Gly Met Ala Lys Asp Met Ser
705                 710                 715                 720 cca ctc cca gaa tca gaa gtg act ctg ggc aag gac gtg gtt ata ctt    2208
Pro Leu Pro Glu Ser Glu Val Thr Leu Gly Lys Asp Val Val Ile Leu
                725                 730                 735 cca gaa aca aag gtg gct gag ttt aac aat gtg act cca ctt tca gaa    2256
Pro Glu Thr Lys Val Ala Glu Phe Asn Asn Val Thr Pro Leu Ser Glu
            740                 745                 750 gaa gag gta acc tca gtc aag gac atg tct ccg tct gca gaa aca gag    2304
Glu Glu Val Thr Ser Val Lys Asp Met Ser Pro Ser Ala Glu Thr Glu
        755                 760                 765 gct ccc ctg gct aag aat gct gat ctg cac tca gga aca gag ctg att    2352
Ala Pro Leu Ala Lys Asn Ala Asp Leu His Ser Gly Thr Glu Leu Ile
    770                 775                 780 gtg gac aac agc atg gct cca gcc tcc gat ctt gca ctg ccc ttg gaa    2400
Val Asp Asn Ser Met Ala Pro Ala Ser Asp Leu Ala Leu Pro Leu Glu
785                 790                 795                 800 aca aaa gta gca aca gtt cca att aaa gac aaa gga tga                2439
Thr Lys Val Ala Thr Val Pro Ile Lys Asp Lys Gly
                805                 810

<210> SEQ ID NO 6
<211> LENGTH: 812
<212> TYPE: PRT
<213> ORGANISM: Artificial Sequence
<220> FEATURE:
<223> OTHER INFORMATION: Description of Artificial Sequence:
      EYFP-DEAD-MAPKDM construct

<400> SEQUENCE: 6

Met Val Ser Lys Gly Glu Glu Leu Phe Thr Gly Val Val Pro Ile Leu
```

-continued

```
  1               5               10              15
Val Glu Leu Asp Gly Asp Val Asn Gly His Lys Phe Ser Val Ser Gly
              20              25              30

Glu Gly Glu Gly Asp Ala Thr Tyr Gly Lys Leu Thr Leu Lys Phe Ile
          35              40              45

Cys Thr Thr Gly Lys Leu Pro Val Pro Trp Pro Thr Leu Val Thr Thr
          50              55              60

Phe Gly Tyr Gly Leu Gln Cys Phe Ala Arg Tyr Pro Asp His Met Lys
65              70              75              80

Gln His Asp Phe Phe Lys Ser Ala Met Pro Glu Gly Tyr Val Gln Glu
              85              90              95

Arg Thr Ile Phe Phe Lys Asp Asp Gly Asn Tyr Lys Thr Arg Ala Glu
              100             105             110

Val Lys Phe Glu Gly Asp Thr Leu Val Asn Arg Ile Glu Leu Lys Gly
          115             120             125

Ile Asp Phe Lys Glu Asp Gly Asn Ile Leu Gly His Lys Leu Glu Tyr
          130             135             140

Asn Tyr Asn Ser His Asn Val Tyr Ile Met Ala Asp Lys Gln Lys Asn
145             150             155             160

Gly Ile Lys Val Asn Phe Lys Ile Arg His Asn Ile Glu Asp Gly Ser
              165             170             175

Val Gln Leu Ala Asp His Tyr Gln Gln Asn Thr Pro Ile Gly Asp Gly
              180             185             190

Pro Val Leu Leu Pro Asp Asn His Tyr Leu Ser Tyr Gln Ser Ala Leu
              195             200             205

Ser Lys Asp Pro Asn Glu Lys Arg Asp His Met Val Leu Leu Glu Phe
210             215             220

Val Thr Ala Ala Gly Ile Thr Leu Gly Met Asp Glu Leu Tyr Lys Pro
225             230             235             240

Arg Asp Glu Ala Asp Ser Ala Asp Leu Ser Leu Val Asp Ala Leu Thr
              245             250             255

Glu Pro Pro Glu Ile Glu Gly Ile Lys Arg Asp Phe Met Ala
              260             265             270

Ala Leu Glu Ala Glu Pro Tyr Asp Asp Ile Val Gly Glu Thr Val Glu
          275             280             285

Lys Thr Glu Phe Ile Pro Leu Leu Asp Gly Asp Glu Lys Thr Gly Asn
290             295             300

Ser Glu Ser Lys Lys Lys Pro Cys Leu Asp Thr Ser Gln Val Glu Gly
305             310             315             320

Ile Pro Ser Ser Lys Pro Thr Leu Leu Ala Asn Gly Asp His Gly Met
              325             330             335

Glu Gly Asn Asn Thr Ala Gly Ser Pro Thr Asp Phe Leu Glu Glu Arg
              340             345             350

Val Asp Tyr Pro Asp Tyr Gln Ser Ser Gln Asn Trp Pro Glu Asp Ala
          355             360             365

Ser Phe Cys Phe Gln Pro Gln Val Leu Asp Thr Asp Gln Ala Glu
          370             375             380

Pro Phe Asn Glu His Arg Asp Asp Gly Leu Ala Asp Leu Leu Phe Val
385             390             395             400

Ser Ser Gly Pro Thr Asn Ala Ser Ala Phe Thr Glu Arg Asp Asn Pro
              405             410             415

Ser Glu Asp Ser Tyr Gly Met Leu Pro Cys Asp Ser Phe Ala Ser Thr
              420             425             430
```

```
Ala Val Val Ser Gln Glu Trp Ser Val Gly Ala Pro Asn Ser Pro Cys
        435                 440                 445

Ser Glu Ser Cys Val Ser Pro Glu Val Thr Ile Glu Thr Leu Gln Pro
        450                 455                 460

Ala Thr Glu Leu Ser Lys Ala Ala Glu Val Glu Ser Val Lys Glu Gln
465                 470                 475                 480

Leu Pro Ala Lys Ala Leu Glu Thr Met Ala Glu Gln Thr Thr Asp Val
                485                 490                 495

Val His Ser Pro Ser Thr Asp Thr Thr Pro Gly Pro Asp Thr Glu Ala
                500                 505                 510

Ala Leu Ala Lys Asp Ile Glu Glu Ile Thr Lys Pro Asp Val Ile Leu
                515                 520                 525

Ala Asn Val Thr Gln Pro Ser Thr Glu Ser Asp Met Phe Leu Ala Gln
                530                 535                 540

Asp Met Glu Leu Leu Thr Gly Thr Glu Ala Ala His Ala Asn Asn Ile
545                 550                 555                 560

Ile Leu Pro Thr Glu Pro Asp Glu Ser Ser Thr Lys Asp Val Ala Pro
                565                 570                 575

Pro Met Glu Glu Glu Ile Val Pro Gly Asn Asp Thr Thr Ser Pro Lys
                580                 585                 590

Glu Thr Glu Thr Thr Leu Pro Ile Lys Met Asp Leu Ala Pro Pro Glu
                595                 600                 605

Asp Val Leu Leu Thr Lys Glu Thr Glu Leu Ala Pro Ala Lys Gly Met
                610                 615                 620

Val Ser Leu Ser Glu Ile Glu Glu Ala Leu Ala Lys Asn Asp Val Arg
625                 630                 635                 640

Ser Ala Glu Ile Pro Val Ala Gln Glu Thr Val Val Ser Glu Thr Glu
                645                 650                 655

Val Val Leu Ala Thr Glu Val Val Leu Pro Ser Asp Pro Ile Thr Thr
                660                 665                 670

Leu Thr Lys Asp Val Thr Leu Pro Leu Glu Ala Glu Arg Pro Leu Val
                675                 680                 685

Thr Asp Met Thr Pro Ser Leu Glu Thr Glu Met Thr Leu Gly Lys Glu
690                 695                 700

Thr Ala Pro Pro Thr Glu Thr Asn Leu Gly Met Ala Lys Asp Met Ser
705                 710                 715                 720

Pro Leu Pro Glu Ser Glu Val Thr Leu Gly Lys Asp Val Val Ile Leu
                725                 730                 735

Pro Glu Thr Lys Val Ala Glu Phe Asn Asn Val Thr Pro Leu Ser Glu
                740                 745                 750

Glu Glu Val Thr Ser Val Lys Asp Met Ser Pro Ser Ala Glu Thr Glu
                755                 760                 765

Ala Pro Leu Ala Lys Asn Ala Asp Leu His Ser Gly Thr Glu Leu Ile
                770                 775                 780

Val Asp Asn Ser Met Ala Pro Ala Ser Asp Leu Ala Leu Pro Leu Glu
785                 790                 795                 800

Thr Lys Val Ala Thr Val Pro Ile Lys Asp Lys Gly
                805                 810

<210> SEQ ID NO 7
<211> LENGTH: 864
<212> TYPE: DNA
<213> ORGANISM: Artificial Sequence
<220> FEATURE:
```

<221> NAME/KEY: CDS
<222> LOCATION: (1)..(861)
<223> OTHER INFORMATION: Description of Artificial Sequence: F25-MEK1 construct

<400> SEQUENCE: 7

| | | | | | | | | | | | | | | | | |
|---|---|---|---|---|---|---|---|---|---|---|---|---|---|---|---|---|
| atg | gct | agc | aaa | gga | gaa | gaa | ctc | ttc | act | gga | gtt | gtc | cca | att | ctt | 48 |
| Met | Ala | Ser | Lys | Gly | Glu | Glu | Leu | Phe | Thr | Gly | Val | Val | Pro | Ile | Leu | |
| 1 | | | | 5 | | | | | 10 | | | | | 15 | | |
| gtt | gaa | tta | gat | ggt | gat | gtt | aac | ggc | cac | aag | ttc | tct | gtc | agt | gga | 96 |
| Val | Glu | Leu | Asp | Gly | Asp | Val | Asn | Gly | His | Lys | Phe | Ser | Val | Ser | Gly | |
| | | | 20 | | | | | 25 | | | | | 30 | | | |
| gag | ggt | gaa | ggt | gat | gca | aca | tac | gga | aaa | ctt | acc | ctg | aag | ttc | atc | 144 |
| Glu | Gly | Glu | Gly | Asp | Ala | Thr | Tyr | Gly | Lys | Leu | Thr | Leu | Lys | Phe | Ile | |
| | | 35 | | | | | 40 | | | | | 45 | | | | |
| tgc | act | act | ggc | aaa | ctg | cct | gtt | cca | tgg | cca | aca | cta | gtc | act | act | 192 |
| Cys | Thr | Thr | Gly | Lys | Leu | Pro | Val | Pro | Trp | Pro | Thr | Leu | Val | Thr | Thr | |
| 50 | | | | | 55 | | | | | 60 | | | | | | |
| ctg | tgc | tat | ggt | gtt | caa | tgc | ttt | tca | aga | tac | ccg | gat | cat | atg | aaa | 240 |
| Leu | Cys | Tyr | Gly | Val | Gln | Cys | Phe | Ser | Arg | Tyr | Pro | Asp | His | Met | Lys | |
| 65 | | | | 70 | | | | | 75 | | | | | 80 | | |
| cgg | cat | gac | ttt | ttc | aag | agt | gcc | atg | ccc | gaa | ggt | tat | gta | cag | gaa | 288 |
| Arg | His | Asp | Phe | Phe | Lys | Ser | Ala | Met | Pro | Glu | Gly | Tyr | Val | Gln | Glu | |
| | | | | 85 | | | | | 90 | | | | | 95 | | |
| agg | acc | atc | ttc | ttc | aaa | gat | gac | ggc | aac | tac | aag | aca | cgt | gct | gaa | 336 |
| Arg | Thr | Ile | Phe | Phe | Lys | Asp | Asp | Gly | Asn | Tyr | Lys | Thr | Arg | Ala | Glu | |
| | | | | 100 | | | | | 105 | | | | | 110 | | |
| gtc | aag | ttt | gaa | ggt | gat | acc | ctt | gtt | aat | aga | atc | gag | tta | aaa | ggt | 384 |
| Val | Lys | Phe | Glu | Gly | Asp | Thr | Leu | Val | Asn | Arg | Ile | Glu | Leu | Lys | Gly | |
| | | | 115 | | | | | 120 | | | | | 125 | | | |
| att | gac | ttc | aag | gaa | gat | ggc | aac | att | ctg | gga | cac | aaa | ttg | gaa | tac | 432 |
| Ile | Asp | Phe | Lys | Glu | Asp | Gly | Asn | Ile | Leu | Gly | His | Lys | Leu | Glu | Tyr | |
| | 130 | | | | | 135 | | | | | 140 | | | | | |
| aac | tat | aac | tca | cac | aat | gta | tac | atc | atg | gca | gac | aaa | caa | aag | aat | 480 |
| Asn | Tyr | Asn | Ser | His | Asn | Val | Tyr | Ile | Met | Ala | Asp | Lys | Gln | Lys | Asn | |
| 145 | | | | | 150 | | | | | 155 | | | | | 160 | |
| gga | atc | aaa | gtg | aac | ttc | aag | acc | cgc | cac | aac | att | gaa | gat | gga | agc | 528 |
| Gly | Ile | Lys | Val | Asn | Phe | Lys | Thr | Arg | His | Asn | Ile | Glu | Asp | Gly | Ser | |
| | | | | 165 | | | | | 170 | | | | | 175 | | |
| gtt | caa | cta | gca | gac | cat | tat | caa | caa | aat | act | cca | att | ggc | gat | ggc | 576 |
| Val | Gln | Leu | Ala | Asp | His | Tyr | Gln | Gln | Asn | Thr | Pro | Ile | Gly | Asp | Gly | |
| | | | 180 | | | | | 185 | | | | | 190 | | | |
| cct | gtc | ctt | tta | cca | gac | aac | cat | tac | ctg | tcc | aca | caa | tct | gcc | ctt | 624 |
| Pro | Val | Leu | Leu | Pro | Asp | Asn | His | Tyr | Leu | Ser | Thr | Gln | Ser | Ala | Leu | |
| | | 195 | | | | | 200 | | | | | 205 | | | | |
| tcg | aaa | gat | ccc | aac | gaa | aag | aga | gac | cac | atg | gtc | ctt | ctt | gag | ttt | 672 |
| Ser | Lys | Asp | Pro | Asn | Glu | Lys | Arg | Asp | His | Met | Val | Leu | Leu | Glu | Phe | |
| | 210 | | | | | 215 | | | | | 220 | | | | | |
| gta | aca | gct | gct | ggg | att | aca | cat | ggc | atg | gat | gaa | ctg | tac | aac | acc | 720 |
| Val | Thr | Ala | Ala | Gly | Ile | Thr | His | Gly | Met | Asp | Glu | Leu | Tyr | Asn | Thr | |
| 225 | | | | | 230 | | | | | 235 | | | | | 240 | |
| ggt | atg | ccc | aag | aag | aag | ccg | acg | ccc | atc | cag | ctg | aac | ccg | gcc | ccc | 768 |
| Gly | Met | Pro | Lys | Lys | Lys | Pro | Thr | Pro | Ile | Gln | Leu | Asn | Pro | Ala | Pro | |
| | | | 245 | | | | | 250 | | | | | 255 | | | |
| gac | ggc | tct | gca | gtt | aac | ggg | acc | agc | tct | gcg | gag | acc | aac | ttg | gag | 816 |
| Asp | Gly | Ser | Ala | Val | Asn | Gly | Thr | Ser | Ser | Ala | Glu | Thr | Asn | Leu | Glu | |
| | | 260 | | | | | 265 | | | | | 270 | | | | |
| gcc | ttg | cag | aag | aag | ctg | gag | gag | cta | gag | ctt | gat | gag | cag | cag | tga | 864 |
| Ala | Leu | Gln | Lys | Lys | Leu | Glu | Glu | Leu | Glu | Leu | Asp | Glu | Gln | Gln | | |
| | 275 | | | | | 280 | | | | | 285 | | | | | |

<210> SEQ ID NO 8
<211> LENGTH: 287
<212> TYPE: PRT
<213> ORGANISM: Artificial Sequence
<220> FEATURE:
<223> OTHER INFORMATION: Description of Artificial Sequence: F25-MEK1 construct

<400> SEQUENCE: 8

```
Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Thr
225                 230                 235                 240

Gly Met Pro Lys Lys Lys Pro Thr Pro Ile Gln Leu Asn Pro Ala Pro
                245                 250                 255

Asp Gly Ser Ala Val Asn Gly Thr Ser Ser Ala Glu Thr Asn Leu Glu
            260                 265                 270

Ala Leu Gln Lys Lys Leu Glu Glu Leu Glu Leu Asp Glu Gln Gln
        275                 280                 285
```

<210> SEQ ID NO 9
<211> LENGTH: 876
<212> TYPE: DNA
<213> ORGANISM: Artificial Sequence
<220> FEATURE:
<221> NAME/KEY: CDS
<222> LOCATION: (1)..(873)
<223> OTHER INFORMATION: Description of Artificial Sequence: F25-MEK2 construct

<400> SEQUENCE: 9 atg gct agc aaa gga gaa gaa ctc ttc act gga gtt gtc cca att ctt    48

```
Met Ala Ser Lys Gly Glu Glu Leu Phe Thr Gly Val Val Pro Ile Leu
  1               5                  10                  15 gtt gaa tta gat ggt gat gtt aac ggc cac aag ttc tct gtc agt gga     96
Val Glu Leu Asp Gly Asp Val Asn Gly His Lys Phe Ser Val Ser Gly
             20                  25                  30 gag ggt gaa ggt gat gca aca tac gga aaa ctt acc ctg aag ttc atc    144
Glu Gly Glu Gly Asp Ala Thr Tyr Gly Lys Leu Thr Leu Lys Phe Ile
         35                  40                  45 tgc act act ggc aaa ctg cct gtt cca tgg cca aca cta gtc act act    192
Cys Thr Thr Gly Lys Leu Pro Val Pro Trp Pro Thr Leu Val Thr Thr
     50                  55                  60 ctg tgc tat ggt gtt caa tgc ttt tca aga tac ccg gat cat atg aaa    240
Leu Cys Tyr Gly Val Gln Cys Phe Ser Arg Tyr Pro Asp His Met Lys
 65                  70                  75                  80 cgg cat gac ttt ttc aag agt gcc atg ccc gaa ggt tat gta cag gaa    288
Arg His Asp Phe Phe Lys Ser Ala Met Pro Glu Gly Tyr Val Gln Glu
                 85                  90                  95 agg acc atc ttc ttc aaa gat gac ggc aac tac aag aca cgt gct gaa    336
Arg Thr Ile Phe Phe Lys Asp Asp Gly Asn Tyr Lys Thr Arg Ala Glu
            100                 105                 110 gtc aag ttt gaa ggt gat acc ctt gtt aat aga atc gag tta aaa ggt    384
Val Lys Phe Glu Gly Asp Thr Leu Val Asn Arg Ile Glu Leu Lys Gly
        115                 120                 125 att gac ttc aag gaa gat ggc aac att ctg gga cac aaa ttg gaa tac    432
Ile Asp Phe Lys Glu Asp Gly Asn Ile Leu Gly His Lys Leu Glu Tyr
130                 135                 140 aac tat aac tca cac aat gta tac atc atg gca gac aaa caa aag aat    480
Asn Tyr Asn Ser His Asn Val Tyr Ile Met Ala Asp Lys Gln Lys Asn
145                 150                 155                 160 gga atc aaa gtg aac ttc aag acc cgc cac aac att gaa gat gga agc    528
Gly Ile Lys Val Asn Phe Lys Thr Arg His Asn Ile Glu Asp Gly Ser
                165                 170                 175 gtt caa cta gca gac cat tat caa caa aat act cca att ggc gat ggc    576
Val Gln Leu Ala Asp His Tyr Gln Gln Asn Thr Pro Ile Gly Asp Gly
            180                 185                 190 cct gtc ctt tta cca gac aac cat tac ctg tcc aca caa tct gcc ctt    624
Pro Val Leu Leu Pro Asp Asn His Tyr Leu Ser Thr Gln Ser Ala Leu
        195                 200                 205 tcg aaa gat ccc aac gaa aag aga gac cac atg gtc ctt ctt gag ttt    672
Ser Lys Asp Pro Asn Glu Lys Arg Asp His Met Val Leu Leu Glu Phe
210                 215                 220 gta aca gct gct ggg att aca cat ggc atg gat gaa ctg tac aac acc    720
Val Thr Ala Ala Gly Ile Thr His Gly Met Asp Glu Leu Tyr Asn Thr
225                 230                 235                 240 ggt atg ctg gcc cgg agg aag ccg gtg ctg ccg gcg ctc acc atc aac    768
Gly Met Leu Ala Arg Arg Lys Pro Val Leu Pro Ala Leu Thr Ile Asn
                245                 250                 255 cct acc atc gcc gag ggc cca tcc cct acc agc gag ggc gcc tcc gag    816
Pro Thr Ile Ala Glu Gly Pro Ser Pro Thr Ser Glu Gly Ala Ser Glu
            260                 265                 270 gca aac ctg gtg gac ctg cag aag aag ctg gag gag ctg gaa ctt gac    864
Ala Asn Leu Val Asp Leu Gln Lys Lys Leu Glu Glu Leu Glu Leu Asp
        275                 280                 285 gag cag cag taa                                                    876
Glu Gln Gln
        290

<210> SEQ ID NO 10
<211> LENGTH: 291
<212> TYPE: PRT
```

<213> ORGANISM: Artificial Sequence
<220> FEATURE:
<223> OTHER INFORMATION: Description of Artificial Sequence: F25-MEK2 construct

<400> SEQUENCE: 10

```
Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Cys Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Glu Leu Tyr Asn Thr
225                 230                 235                 240

Gly Met Leu Ala Arg Arg Lys Pro Val Leu Pro Ala Leu Thr Ile Asn
                245                 250                 255

Pro Thr Ile Ala Glu Gly Pro Ser Pro Thr Ser Glu Gly Ala Ser Glu
            260                 265                 270

Ala Asn Leu Val Asp Leu Gln Lys Lys Leu Glu Glu Leu Glu Leu Asp
        275                 280                 285

Glu Gln Gln
    290
```

<210> SEQ ID NO 11
<211> LENGTH: 889
<212> TYPE: DNA
<213> ORGANISM: Artificial Sequence
<220> FEATURE:
<221> NAME/KEY: CDS
<222> LOCATION: (1)..(888)
<223> OTHER INFORMATION: Description of Artificial Sequence: Caspase 3-DEVD-substrate construct

<400> SEQUENCE: 11

```
atg gct agc aaa gga gaa gaa ctc ttc act gga gtt gtc cca att ctt      48
Met Ala Ser Lys Gly Glu Glu Leu Phe Thr Gly Val Val Pro Ile Leu
```

```
            1               5                       10                          15
    gtt gaa tta gat ggt gat gtt aac ggc cac aag ttc tct gtc agt gga        96
    Val Glu Leu Asp Gly Asp Val Asn Gly His Lys Phe Ser Val Ser Gly
                    20                  25                  30 gag ggt gaa ggt gat gca aca tac gga aaa ctt acc ctg aag ttc atc       144
    Glu Gly Glu Gly Asp Ala Thr Tyr Gly Lys Leu Thr Leu Lys Phe Ile
                35                  40                  45 tgc act act ggc aaa ctg cct gtt cca tgg cca aca cta gtc act act       192
    Cys Thr Thr Gly Lys Leu Pro Val Pro Trp Pro Thr Leu Val Thr Thr
            50                  55                  60 ctg tgc tat ggt gtt caa tgc ttt tca aga tac ccg gat cat atg aaa       240
    Leu Cys Tyr Gly Val Gln Cys Phe Ser Arg Tyr Pro Asp His Met Lys
        65                  70                  75                  80 cgg cat gac ttt ttc aag agt gcc atg ccc gaa ggt tat gta cag gaa       288
    Arg His Asp Phe Phe Lys Ser Ala Met Pro Glu Gly Tyr Val Gln Glu
                    85                  90                  95 agg acc atc ttc ttc aaa gat gac ggc aac tac aag aca cgt gct gaa       336
    Arg Thr Ile Phe Phe Lys Asp Asp Gly Asn Tyr Lys Thr Arg Ala Glu
                100                 105                 110 gtc aag ttt gaa ggt gat acc ctt gtt aat aga atc gag tta aaa ggt       384
    Val Lys Phe Glu Gly Asp Thr Leu Val Asn Arg Ile Glu Leu Lys Gly
            115                 120                 125 att gac ttc aag gaa gat ggc aac att ctg gga cac aaa ttg gaa tac       432
    Ile Asp Phe Lys Glu Asp Gly Asn Ile Leu Gly His Lys Leu Glu Tyr
    130                 135                 140 aac tat aac tca cac aat gta tac atc atg gca gac aaa caa aag aat       480
    Asn Tyr Asn Ser His Asn Val Tyr Ile Met Ala Asp Lys Gln Lys Asn
    145                 150                 155                 160 gga atc aaa gtg aac ttc aag acc cgc cac aac att gaa gat gga agc       528
    Gly Ile Lys Val Asn Phe Lys Thr Arg His Asn Ile Glu Asp Gly Ser
                    165                 170                 175 gtt caa cta gca gac cat tat caa caa aat act cca att ggc gat ggc       576
    Val Gln Leu Ala Asp His Tyr Gln Gln Asn Thr Pro Ile Gly Asp Gly
                180                 185                 190 cct gtc ctt tta cca gac aac cat tac ctg tcc aca caa tct gcc ctt       624
    Pro Val Leu Leu Pro Asp Asn His Tyr Leu Ser Thr Gln Ser Ala Leu
            195                 200                 205 tcg aaa gat ccc aac gaa aag aga gac cac atg gtc ctt ctt gag ttt       672
    Ser Lys Asp Pro Asn Glu Lys Arg Asp His Met Val Leu Leu Glu Phe
        210                 215                 220 gta aca gct gct ggg att aca cat ggc atg gat gaa ctg tac aac tcc       720
    Val Thr Ala Ala Gly Ile Thr His Gly Met Asp Glu Leu Tyr Asn Ser
    225                 230                 235                 240 gga aga agg aaa cga caa aag cga tcg gct gtt aaa tct gaa gga aag       768
    Gly Arg Arg Lys Arg Gln Lys Arg Ser Ala Val Lys Ser Glu Gly Lys
                    245                 250                 255 aga aag tgt gac gaa gtt gat gga att gat gaa gta gca agt act atg       816
    Arg Lys Cys Asp Glu Val Asp Gly Ile Asp Glu Val Ala Ser Thr Met
                260                 265                 270 tct act gtc cac gaa atc ctg tgc aag ctc agc ttg gag ggt gtt cat       864
    Ser Thr Val His Glu Ile Leu Cys Lys Leu Ser Leu Glu Gly Val His
            275                 280                 285 tct aca ccc cca agt acc cgg atc c                                      889
    Ser Thr Pro Pro Ser Thr Arg Ile
        290                 295

<210> SEQ ID NO 12
<211> LENGTH: 296
<212> TYPE: PRT
<213> ORGANISM: Artificial Sequence
```

```
<220> FEATURE:
<223> OTHER INFORMATION: Description of Artificial Sequence: Caspase
      3-DEVD-substrate construct

<400> SEQUENCE: 12

Met Ala Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Cys Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Ser
225                 230                 235                 240

Gly Arg Arg Lys Arg Gln Lys Arg Ser Ala Val Lys Ser Glu Gly Lys
                245                 250                 255

Arg Lys Cys Asp Glu Val Asp Gly Ile Asp Glu Val Ala Ser Thr Met
            260                 265                 270

Ser Thr Val His Glu Ile Leu Cys Lys Leu Ser Leu Glu Gly Val His
        275                 280                 285

Ser Thr Pro Pro Ser Thr Arg Ile
    290                 295

<210> SEQ ID NO 13
<211> LENGTH: 846
<212> TYPE: DNA
<213> ORGANISM: Artificial Sequence
<220> FEATURE:
<221> NAME/KEY: CDS
<222> LOCATION: (1)..(846)
<223> OTHER INFORMATION: Description of Artificial Sequence: Caspase
      6-VEID-substrate construct

<400> SEQUENCE: 13 atg gct agc aaa gga gaa gaa ctc ttc act gga gtt gtc cca att ctt    48
Met Ala Ser Lys Gly Glu Glu Leu Phe Thr Gly Val Val Pro Ile Leu
  1               5                  10                  15
```

```
gtt gaa tta gat ggt gat gtt aac ggc cac aag ttc tct gtc agt gga      96
Val Glu Leu Asp Gly Asp Val Asn Gly His Lys Phe Ser Val Ser Gly
             20                  25                  30 gag ggt gaa ggt gat gca aca tac gga aaa ctt acc ctg aag ttc atc     144
Glu Gly Glu Gly Asp Ala Thr Tyr Gly Lys Leu Thr Leu Lys Phe Ile
     35                  40                  45 tgc act act ggc aaa ctg cct gtt cca tgg cca aca cta gtc act act     192
Cys Thr Thr Gly Lys Leu Pro Val Pro Trp Pro Thr Leu Val Thr Thr
 50                  55                  60 ctg tgc tat ggt gtt caa tgc ttt tca aga tac ccg gat cat atg aaa     240
Leu Cys Tyr Gly Val Gln Cys Phe Ser Arg Tyr Pro Asp His Met Lys
 65                  70                  75                  80 cgg cat gac ttt ttc aag agt gcc atg ccc gaa ggt tat gta cag gaa     288
Arg His Asp Phe Phe Lys Ser Ala Met Pro Glu Gly Tyr Val Gln Glu
                 85                  90                  95 agg acc atc ttc ttc aaa gat gac ggc aac tac aag aca cgt gct gaa     336
Arg Thr Ile Phe Phe Lys Asp Asp Gly Asn Tyr Lys Thr Arg Ala Glu
            100                 105                 110 gtc aag ttt gaa ggt gat acc ctt gtt aat aga atc gag tta aaa ggt     384
Val Lys Phe Glu Gly Asp Thr Leu Val Asn Arg Ile Glu Leu Lys Gly
        115                 120                 125 att gac ttc aag gaa gat ggc aac att ctg gga cac aaa ttg gaa tac     432
Ile Asp Phe Lys Glu Asp Gly Asn Ile Leu Gly His Lys Leu Glu Tyr
130                 135                 140 aac tat aac tca cac aat gta tac atc atg gca gac aaa caa aag aat     480
Asn Tyr Asn Ser His Asn Val Tyr Ile Met Ala Asp Lys Gln Lys Asn
145                 150                 155                 160 gga atc aaa gtg aac ttc aag acc cgc cac aac att gaa gat gga agc     528
Gly Ile Lys Val Asn Phe Lys Thr Arg His Asn Ile Glu Asp Gly Ser
                165                 170                 175 gtt caa cta gca gac cat tat caa caa aat act cca att ggc gat ggc     576
Val Gln Leu Ala Asp His Tyr Gln Gln Asn Thr Pro Ile Gly Asp Gly
            180                 185                 190 cct gtc ctt tta cca gac aac cat tac ctg tcc aca caa tct gcc ctt     624
Pro Val Leu Leu Pro Asp Asn His Tyr Leu Ser Thr Gln Ser Ala Leu
        195                 200                 205 tcg aaa gat ccc aac gaa aag aga gac cac atg gtc ctt ctt gag ttt     672
Ser Lys Asp Pro Asn Glu Lys Arg Asp His Met Val Leu Leu Glu Phe
210                 215                 220 gta aca gct gct ggg att aca cat ggc atg gat gaa ctg tac aac tcc     720
Val Thr Ala Ala Gly Ile Thr His Gly Met Asp Glu Leu Tyr Asn Ser
225                 230                 235                 240 gga aga agg aaa cga caa aag cga tcg aca aga ctt gtt gaa att gac     768
Gly Arg Arg Lys Arg Gln Lys Arg Ser Thr Arg Leu Val Glu Ile Asp
                245                 250                 255 aac agt act atg agc aca gta cac gaa att tta tgt aaa tta agc tta     816
Asn Ser Thr Met Ser Thr Val His Glu Ile Leu Cys Lys Leu Ser Leu
            260                 265                 270 gaa gga gta cac agt aca cca cca agc gca                             846
Glu Gly Val His Ser Thr Pro Pro Ser Ala
        275                 280
```

<210> SEQ ID NO 14
<211> LENGTH: 282
<212> TYPE: PRT
<213> ORGANISM: Artificial Sequence
<220> FEATURE:
<223> OTHER INFORMATION: Description of Artificial Sequence: Caspase
      6-VEID-substrate construct

<400> SEQUENCE: 14

```
Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
 50                  55                  60

Leu Cys Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Glu Leu Tyr Asn Ser
225                 230                 235                 240

Gly Arg Arg Lys Arg Gln Lys Arg Ser Thr Arg Leu Val Glu Ile Asp
                245                 250                 255

Asn Ser Thr Met Ser Thr Val His Glu Ile Leu Cys Lys Leu Ser Leu
            260                 265                 270

Glu Gly Val His Ser Thr Pro Pro Ser Ala
        275                 280

<210> SEQ ID NO 15
<211> LENGTH: 876
<212> TYPE: DNA
<213> ORGANISM: Artificial Sequence
<220> FEATURE:
<221> NAME/KEY: CDS
<222> LOCATION: (1)..(876)
<223> OTHER INFORMATION: Description of Artificial Sequence: Caspase
      8-VETD construct

<400> SEQUENCE: 15 atg gct agc aaa gga gaa gaa ctc ttc act gga gtt gtc cca att ctt      48
Met Ala Ser Lys Gly Glu Glu Leu Phe Thr Gly Val Val Pro Ile Leu
 1               5                  10                  15 gtt gaa tta gat ggt gat gtt aac ggc cac aag ttc tct gtc agt gga      96
Val Glu Leu Asp Gly Asp Val Asn Gly His Lys Phe Ser Val Ser Gly
            20                  25                  30 gag ggt gaa ggt gat gca aca tac gga aaa ctt acc ctg aag ttc atc     144
Glu Gly Glu Gly Asp Ala Thr Tyr Gly Lys Leu Thr Leu Lys Phe Ile
        35                  40                  45
```

```
tgc act act ggc aaa ctg cct gtt cca tgg cca aca cta gtc act act      192
Cys Thr Thr Gly Lys Leu Pro Val Pro Trp Pro Thr Leu Val Thr Thr
     50                  55                  60 ctg tgc tat ggt gtt caa tgc ttt tca aga tac ccg gat cat atg aaa      240
Leu Cys Tyr Gly Val Gln Cys Phe Ser Arg Tyr Pro Asp His Met Lys
 65                  70                  75                  80 cgg cat gac ttt ttc aag agt gcc atg ccc gaa ggt tat gta cag gaa      288
Arg His Asp Phe Phe Lys Ser Ala Met Pro Glu Gly Tyr Val Gln Glu
                 85                  90                  95 agg acc atc ttc ttc aaa gat gac ggc aac tac aag aca cgt gct gaa      336
Arg Thr Ile Phe Phe Lys Asp Asp Gly Asn Tyr Lys Thr Arg Ala Glu
            100                 105                 110 gtc aag ttt gaa ggt gat acc ctt gtt aat aga atc gag tta aaa ggt      384
Val Lys Phe Glu Gly Asp Thr Leu Val Asn Arg Ile Glu Leu Lys Gly
        115                 120                 125 att gac ttc aag gaa gat ggc aac att ctg gga cac aaa ttg gaa tac      432
Ile Asp Phe Lys Glu Asp Gly Asn Ile Leu Gly His Lys Leu Glu Tyr
    130                 135                 140 aac tat aac tca cac aat gta tac atc atg gca gac aaa caa aag aat      480
Asn Tyr Asn Ser His Asn Val Tyr Ile Met Ala Asp Lys Gln Lys Asn
145                 150                 155                 160 gga atc aaa gtg aac ttc aag acc cgc cac aac att gaa gat gga agc      528
Gly Ile Lys Val Asn Phe Lys Thr Arg His Asn Ile Glu Asp Gly Ser
                165                 170                 175 gtt caa cta gca gac cat tat caa caa aat act cca att ggc gat ggc      576
Val Gln Leu Ala Asp His Tyr Gln Gln Asn Thr Pro Ile Gly Asp Gly
            180                 185                 190 cct gtc ctt tta cca gac aac cat tac ctg tcc aca caa tct gcc ctt      624
Pro Val Leu Leu Pro Asp Asn His Tyr Leu Ser Thr Gln Ser Ala Leu
        195                 200                 205 tcg aaa gat ccc aac gaa aag aga gac cac atg gtc ctt ctt gag ttt      672
Ser Lys Asp Pro Asn Glu Lys Arg Asp His Met Val Leu Leu Glu Phe
    210                 215                 220 gta aca gct gct ggg att aca cat ggc atg gat gaa ctg tac aac tcc      720
Val Thr Ala Ala Gly Ile Thr His Gly Met Asp Glu Leu Tyr Asn Ser
225                 230                 235                 240 gga aga agc aaa cga caa aag cga tcg tat gaa aaa gga ata cca gtt      768
Gly Arg Ser Lys Arg Gln Lys Arg Ser Tyr Glu Lys Gly Ile Pro Val
                245                 250                 255 gaa aca gac agc gaa gag caa gct tat agt act atg tct act gtc cac      816
Glu Thr Asp Ser Glu Glu Gln Ala Tyr Ser Thr Met Ser Thr Val His
            260                 265                 270 gaa atc ctg tgc aag ctc agc ttg gag ggt gtt cat tct aca ccc cca      864
Glu Ile Leu Cys Lys Leu Ser Leu Glu Gly Val His Ser Thr Pro Pro
        275                 280                 285 agt gcc gga tcc                                                      876
Ser Ala Gly Ser
    290

<210> SEQ ID NO 16
<211> LENGTH: 292
<212> TYPE: PRT
<213> ORGANISM: Artificial Sequence
<220> FEATURE:
<223> OTHER INFORMATION: Description of Artificial Sequence: Caspase
      8-VETD construct

<400> SEQUENCE: 16

Met Ala Ser Lys Gly Glu Glu Leu Phe Thr Gly Val Val Pro Ile Leu
 1               5                  10                  15
```

-continued

```
Val Glu Leu Asp Gly Asp Val Asn Gly His Lys Phe Ser Val Ser Gly
         20                  25                  30

Glu Gly Glu Gly Asp Ala Thr Tyr Gly Lys Leu Thr Leu Lys Phe Ile
     35                  40                  45

Cys Thr Thr Gly Lys Leu Pro Val Pro Trp Pro Thr Leu Val Thr Thr
 50                  55                  60

Leu Cys Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Ser
225                 230                 235                 240

Gly Arg Ser Lys Arg Gln Lys Arg Ser Tyr Glu Lys Gly Ile Pro Val
                245                 250                 255

Glu Thr Asp Ser Glu Glu Gln Ala Tyr Ser Thr Met Ser Thr Val His
            260                 265                 270

Glu Ile Leu Cys Lys Leu Ser Leu Glu Gly Val His Ser Thr Pro Pro
        275                 280                 285

Ser Ala Gly Ser
        290
```

<210> SEQ ID NO 17
<211> LENGTH: 906
<212> TYPE: DNA
<213> ORGANISM: Artificial Sequence
<220> FEATURE:
<221> NAME/KEY: CDS
<222> LOCATION: (1)..(906)
<223> OTHER INFORMATION: Description of Artificial Sequence: Cas 3-multiple DEVD construct

<400> SEQUENCE: 17

```
atg gct agc aaa gga gaa gaa ctc ttc act gga gtt gtc cca att ctt    48
Met Ala Ser Lys Gly Glu Glu Leu Phe Thr Gly Val Val Pro Ile Leu
  1               5                  10                  15 gtt gaa tta gat ggt gat gtt aac ggc cac aag ttc tct gtc agt gga    96
Val Glu Leu Asp Gly Asp Val Asn Gly His Lys Phe Ser Val Ser Gly
             20                  25                  30 gag ggt gaa ggt gat gca aca tac gga aaa ctt acc ctg aag ttc atc   144
Glu Gly Glu Gly Asp Ala Thr Tyr Gly Lys Leu Thr Leu Lys Phe Ile
         35                  40                  45
```

```
tgc act act ggc aaa ctg cct gtt cca tgg cca aca cta gtc act act    192
Cys Thr Thr Gly Lys Leu Pro Val Pro Trp Pro Thr Leu Val Thr Thr
     50                  55                  60 ctg tgc tat ggt gtt caa tgc ttt tca aga tac ccg gat cat atg aaa    240
Leu Cys Tyr Gly Val Gln Cys Phe Ser Arg Tyr Pro Asp His Met Lys
 65                  70                  75                  80 cgg cat gac ttt ttc aag agt gcc atg ccc gaa ggt tat gta cag gaa    288
Arg His Asp Phe Phe Lys Ser Ala Met Pro Glu Gly Tyr Val Gln Glu
                 85                  90                  95 agg acc atc ttc ttc aaa gat gac ggc aac tac aag aca cgt gct gaa    336
Arg Thr Ile Phe Phe Lys Asp Asp Gly Asn Tyr Lys Thr Arg Ala Glu
            100                 105                 110 gtc aag ttt gaa ggt gat acc ctt gtt aat aga atc gag tta aaa ggt    384
Val Lys Phe Glu Gly Asp Thr Leu Val Asn Arg Ile Glu Leu Lys Gly
        115                 120                 125 att gac ttc aag gaa gat ggc aac att ctg gga cac aaa ttg gaa tac    432
Ile Asp Phe Lys Glu Asp Gly Asn Ile Leu Gly His Lys Leu Glu Tyr
130                 135                 140 aac tat aac tca cac aat gta tac atc atg gca gac aaa caa aag aat    480
Asn Tyr Asn Ser His Asn Val Tyr Ile Met Ala Asp Lys Gln Lys Asn
145                 150                 155                 160 gga atc aaa gtg aac ttc aag acc cgc cac aac att gaa gat gga agc    528
Gly Ile Lys Val Asn Phe Lys Thr Arg His Asn Ile Glu Asp Gly Ser
                165                 170                 175 gtt caa cta gca gac cat tat caa caa aat act cca att ggc gat ggc    576
Val Gln Leu Ala Asp His Tyr Gln Gln Asn Thr Pro Ile Gly Asp Gly
            180                 185                 190 cct gtc ctt tta cca gac aac cat tac ctg tcc aca caa tct gcc ctt    624
Pro Val Leu Leu Pro Asp Asn His Tyr Leu Ser Thr Gln Ser Ala Leu
        195                 200                 205 tcg aaa gat ccc aac gaa aag aga gac cac atg gtc ctt ctt gag ttt    672
Ser Lys Asp Pro Asn Glu Lys Arg Asp His Met Val Leu Leu Glu Phe
210                 215                 220 gta aca gct gct ggg att aca cat ggc atg gat gaa ctg tac aac tcc    720
Val Thr Ala Ala Gly Ile Thr His Gly Met Asp Glu Leu Tyr Asn Ser
225                 230                 235                 240 gga aga agg aaa cga caa aag cga tcg gca ggt gac gaa gtt gat gca    768
Gly Arg Arg Lys Arg Gln Lys Arg Ser Ala Gly Asp Glu Val Asp Ala
                245                 250                 255 ggt gac gaa gtt gat gca ggt gac gaa gtt gat gca ggt gac gaa gtt    816
Gly Asp Glu Val Asp Ala Gly Asp Glu Val Asp Ala Gly Asp Glu Val
            260                 265                 270 gac gca ggt agt act atg tct act gtc cac gaa atc ctg tgc aag ctc    864
Asp Ala Gly Ser Thr Met Ser Thr Val His Glu Ile Leu Cys Lys Leu
        275                 280                 285 agc ttg gag ggt gtt cat tct aca ccc cca agt gcc gga tcc            906
Ser Leu Glu Gly Val His Ser Thr Pro Pro Ser Ala Gly Ser
290                 295                 300

<210> SEQ ID NO 18
<211> LENGTH: 302
<212> TYPE: PRT
<213> ORGANISM: Artificial Sequence
<220> FEATURE:
<223> OTHER INFORMATION: Description of Artificial Sequence: Cas
      3-multiple DEVD construct

<400> SEQUENCE: 18

Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
```

```
                    20                  25                  30
Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
         50                  55                  60

Leu Cys Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Ser
225                 230                 235                 240

Gly Arg Arg Lys Arg Gln Lys Arg Ser Ala Gly Asp Glu Val Asp Ala
                245                 250                 255

Gly Asp Glu Val Asp Ala Gly Asp Glu Val Asp Ala Gly Asp Glu Val
            260                 265                 270

Asp Ala Gly Ser Thr Met Ser Thr Val His Glu Ile Leu Cys Lys Leu
        275                 280                 285

Ser Leu Glu Gly Val His Ser Thr Pro Pro Ser Ala Gly Ser
    290                 295                 300
```

<210> SEQ ID NO 19
<211> LENGTH: 906
<212> TYPE: DNA
<213> ORGANISM: Artificial Sequence
<220> FEATURE:
<221> NAME/KEY: CDS
<222> LOCATION: (1)..(885)
<223> OTHER INFORMATION: Description of Artificial Sequence: Caspase 8-multiple VETD construct

<400> SEQUENCE: 19

```
atg gct agc aaa gga gaa gaa ctc ttc act gga gtt gtc cca att ctt      48
Met Ala Ser Lys Gly Glu Glu Leu Phe Thr Gly Val Val Pro Ile Leu
  1               5                  10                  15 gtt gaa tta gat ggt gat gtt aac ggc cac aag ttc tct gtc agt gga     96
Val Glu Leu Asp Gly Asp Val Asn Gly His Lys Phe Ser Val Ser Gly
                 20                  25                  30 gag ggt gaa ggt gat gca aca tac gga aaa ctt acc ctg aag ttc atc    144
Glu Gly Glu Gly Asp Ala Thr Tyr Gly Lys Leu Thr Leu Lys Phe Ile
             35                  40                  45 tgc act act ggc aaa ctg cct gtt cca tgg cca aca cta gtc act act    192
```

| | | | | | | | | | | | | |
|---|---|---|---|---|---|---|---|---|---|---|---|---|
|Cys|Thr|Thr|Gly|Lys|Leu|Pro|Val|Pro|Trp|Pro|Thr|Leu|Val|Thr|Thr|
| |50| | | |55| | | |60| | | | | | |

```
ctg tgc tat ggt gtt caa tgc ttt tca aga tac ccg gat cat atg aaa      240
Leu Cys Tyr Gly Val Gln Cys Phe Ser Arg Tyr Pro Asp His Met Lys
 65              70                  75                  80 cgg cat gac ttt ttc aag agt gcc atg ccc gaa ggt tat gta cag gaa      288
Arg His Asp Phe Phe Lys Ser Ala Met Pro Glu Gly Tyr Val Gln Glu
                 85                  90                  95 agg acc atc ttc ttc aaa gat gac ggc aac tac aag aca cgt gct gaa      336
Arg Thr Ile Phe Phe Lys Asp Asp Gly Asn Tyr Lys Thr Arg Ala Glu
                100                 105                 110 gtc aag ttt gaa ggt gat acc ctt gtt aat aga atc gag tta aaa ggt      384
Val Lys Phe Glu Gly Asp Thr Leu Val Asn Arg Ile Glu Leu Lys Gly
            115                 120                 125 att gac ttc aag gaa gat ggc aac att ctg gga cac aaa ttg gaa tac      432
Ile Asp Phe Lys Glu Asp Gly Asn Ile Leu Gly His Lys Leu Glu Tyr
130                 135                 140 aac tat aac tca cac aat gta tac atc atg gca gac aaa caa aag aat      480
Asn Tyr Asn Ser His Asn Val Tyr Ile Met Ala Asp Lys Gln Lys Asn
145                 150                 155                 160 gga atc aaa gtg aac ttc aag acc cgc cac aac att gaa gat gga agc      528
Gly Ile Lys Val Asn Phe Lys Thr Arg His Asn Ile Glu Asp Gly Ser
                165                 170                 175 gtt caa cta gca gac cat tat caa caa aat act cca att ggc gat ggc      576
Val Gln Leu Ala Asp His Tyr Gln Gln Asn Thr Pro Ile Gly Asp Gly
            180                 185                 190 cct gtc ctt tta cca gac aac cat tac ctg tcc aca caa tct gcc ctt      624
Pro Val Leu Leu Pro Asp Asn His Tyr Leu Ser Thr Gln Ser Ala Leu
        195                 200                 205 tcg aaa gat ccc aac gaa aag aga gac cac atg gtc ctt ctt gag ttt      672
Ser Lys Asp Pro Asn Glu Lys Arg Asp His Met Val Leu Leu Glu Phe
210                 215                 220 gta aca gct gct ggg att aca cat ggc atg gat gaa ctg tac aac tcc      720
Val Thr Ala Ala Gly Ile Thr His Gly Met Asp Glu Leu Tyr Asn Ser
225                 230                 235                 240 gga aga agg aaa cga caa aag cga tcg gca ggt gtt gaa aca gac gca      768
Gly Arg Arg Lys Arg Gln Lys Arg Ser Ala Gly Val Glu Thr Asp Ala
                245                 250                 255 ggt gtt gaa aca gac gca ggt gtt gaa aca gac gca ggt gtt gaa aca      816
Gly Val Glu Thr Asp Ala Gly Val Glu Thr Asp Ala Gly Val Glu Thr
            260                 265                 270 gac gca ggt agt act atg tct act gtc cac gaa atc ctg tgc aag ctc      864
Asp Ala Gly Ser Thr Met Ser Thr Val His Glu Ile Leu Cys Lys Leu
        275                 280                 285 agc ttg gag ggt gtt cat tct acacccccaa gtgccggatc c                  906
Ser Leu Glu Gly Val His Ser
        290                 295
```

<210> SEQ ID NO 20
<211> LENGTH: 295
<212> TYPE: PRT
<213> ORGANISM: Artificial Sequence
<220> FEATURE:
<223> OTHER INFORMATION: Description of Artificial Sequence: Caspase 8-multiple VETD construct

<400> SEQUENCE: 20

```
Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30
```

```
Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
 50                  55                  60

Leu Cys Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Ser
225                 230                 235                 240

Gly Arg Arg Lys Arg Gln Lys Arg Ser Ala Gly Val Glu Thr Asp Ala
                245                 250                 255

Gly Val Glu Thr Asp Ala Gly Val Glu Thr Asp Ala Gly Val Glu Thr
            260                 265                 270

Asp Ala Gly Ser Thr Met Ser Thr Val His Glu Ile Leu Cys Lys Leu
        275                 280                 285

Ser Leu Glu Gly Val His Ser
    290                 295

<210> SEQ ID NO 21
<211> LENGTH: 4833
<212> TYPE: DNA
<213> ORGANISM: Artificial Sequence
<220> FEATURE:
<221> NAME/KEY: CDS
<222> LOCATION: (1)..(4830)
<223> OTHER INFORMATION: Description of Artificial Sequence:
      EYFP-DEVD-MAP4-EBFP construct

<400> SEQUENCE: 21 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
                 20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
 50                  55                  60
```

```
                  50                    55                    60
ttc ggc tac ggc ctg cag tgc ttc gcc cgc tac ccc gac cac atg aag        240
Phe Gly Tyr Gly Leu Gln Cys Phe Ala Arg Tyr Pro Asp His Met Lys
 65                  70                  75                  80 cag cac gac ttc ttc aag tcc gcc atg ccc gaa ggc tac gtc cag gag        288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag        336
Arg Thr Ile Phe Phe Lys Asp Asp Gly Asn Tyr Lys Thr Arg Ala Glu
                100                 105                 110 gtg aag ttc gag ggc gac acc ctg gtg aac cgc atc gag ctg aag ggc        384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac        432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac        480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc        528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc        576
Val Gln Leu Ala Asp His Tyr Gln Gln Asn Thr Pro Ile Gly Asp Gly
            180                 185                 190 ccc gtg ctg ctg ccc gac aac cac tac ctg agc tac cag tcc gcc ctg        624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc        672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag aag        720
Val Thr Ala Ala Gly Ile Thr Leu Gly Met Asp Glu Leu Tyr Lys Lys
225                 230                 235                 240 gga gac gaa gtg gac gga atg gcc gac ctc agt ctt gtg gat gcg ttg        768
Gly Asp Glu Val Asp Gly Met Ala Asp Leu Ser Leu Val Asp Ala Leu
                245                 250                 255 aca gaa cca cct cca gaa att gag gga gaa ata aag cga gac ttc atg        816
Thr Glu Pro Pro Pro Glu Ile Glu Gly Glu Ile Lys Arg Asp Phe Met
            260                 265                 270 gct gcg ctg gag gca gag ccc tat gat gac atc gtg gga gaa act gtg        864
Ala Ala Leu Glu Ala Glu Pro Tyr Asp Asp Ile Val Gly Glu Thr Val
        275                 280                 285 gag aaa act gag ttt att cct ctc ctg gat ggt gat gag aaa acc ggg        912
Glu Lys Thr Glu Phe Ile Pro Leu Leu Asp Gly Asp Glu Lys Thr Gly
    290                 295                 300 aac tca gag tcc aaa aag aaa ccc tgc tta gac act agc cag gtt gaa        960
Asn Ser Glu Ser Lys Lys Lys Pro Cys Leu Asp Thr Ser Gln Val Glu
305                 310                 315                 320 ggt atc cca tct tct aaa cca aca ctc cta gcc aat ggt gat cat gga       1008
Gly Ile Pro Ser Ser Lys Pro Thr Leu Leu Ala Asn Gly Asp His Gly
                325                 330                 335 atg gag ggg aat aac act gca ggg tct cca act gac ttc ctt gaa gag       1056
Met Glu Gly Asn Asn Thr Ala Gly Ser Pro Thr Asp Phe Leu Glu Glu
            340                 345                 350 aga gtg gac tat ccg gat tat cag agc agc cag aac tgg cca gaa gat       1104
Arg Val Asp Tyr Pro Asp Tyr Gln Ser Ser Gln Asn Trp Pro Glu Asp
        355                 360                 365 gca agc ttt tgt ttc cag cct cag caa gtg tta gat act gac cag gct       1152
```

-continued

```
Ala Ser Phe Cys Phe Gln Pro Gln Gln Val Leu Asp Thr Asp Gln Ala
    370                 375                 380 gag ccc ttt aac gag cac cgt gat gat ggt ttg gca gat ctg ctc ttt      1200
Glu Pro Phe Asn Glu His Arg Asp Asp Gly Leu Ala Asp Leu Leu Phe
385                 390                 395                 400 gtc tcc agt gga ccc acg aac gct tct gca ttt aca gag cga gac aat      1248
Val Ser Ser Gly Pro Thr Asn Ala Ser Ala Phe Thr Glu Arg Asp Asn
                405                 410                 415 cct tca gaa gac agt tac ggt atg ctt ccc tgt gac tca ttt gct tcc      1296
Pro Ser Glu Asp Ser Tyr Gly Met Leu Pro Cys Asp Ser Phe Ala Ser
            420                 425                 430 acg gct gtt gta tct cag gag tgg tct gtg gga gcc cca aac tct cca      1344
Thr Ala Val Val Ser Gln Glu Trp Ser Val Gly Ala Pro Asn Ser Pro
        435                 440                 445 tgt tca gag tcc tgt gtc tcc cca gag gtt act ata gaa acc cta cag      1392
Cys Ser Glu Ser Cys Val Ser Pro Glu Val Thr Ile Glu Thr Leu Gln
450                 455                 460 cca gca aca gag ctc tcc aag gca gca gaa gtg gaa tca gtg aaa gag      1440
Pro Ala Thr Glu Leu Ser Lys Ala Ala Glu Val Glu Ser Val Lys Glu
465                 470                 475                 480 cag ctg cca gct aaa gca ttg gaa acg atg gca gag cag acc act gat      1488
Gln Leu Pro Ala Lys Ala Leu Glu Thr Met Ala Glu Gln Thr Thr Asp
                485                 490                 495 gtg gtg cac tct cca tcc aca gac aca aca cca ggc cca gac aca gag      1536
Val Val His Ser Pro Ser Thr Asp Thr Thr Pro Gly Pro Asp Thr Glu
            500                 505                 510 gca gca ctg gct aaa gac ata gaa gag atc acc aag cca gat gtg ata      1584
Ala Ala Leu Ala Lys Asp Ile Glu Glu Ile Thr Lys Pro Asp Val Ile
        515                 520                 525 ttg gca aat gtc acg cag cca tct act gaa tcg gat atg ttc ctg gcc      1632
Leu Ala Asn Val Thr Gln Pro Ser Thr Glu Ser Asp Met Phe Leu Ala
    530                 535                 540 cag gac atg gaa cta ctc aca gga aca gag gca gcc cac gct aac aat      1680
Gln Asp Met Glu Leu Leu Thr Gly Thr Glu Ala Ala His Ala Asn Asn
545                 550                 555                 560 atc ata ttg cct aca gaa cca gac gaa tct tca acc aag gat gta gca      1728
Ile Ile Leu Pro Thr Glu Pro Asp Glu Ser Ser Thr Lys Asp Val Ala
                565                 570                 575 cca cct atg gaa gaa gaa att gtc cca ggc aat gat acg aca tcc ccc      1776
Pro Pro Met Glu Glu Glu Ile Val Pro Gly Asn Asp Thr Thr Ser Pro
            580                 585                 590 aaa gaa aca gag aca aca ctt cca ata aaa atg gac ttg gca cca cct      1824
Lys Glu Thr Glu Thr Thr Leu Pro Ile Lys Met Asp Leu Ala Pro Pro
        595                 600                 605 gag gat gtg tta ctt acc aaa gaa aca gaa cta gcc cca gcc aag ggc      1872
Glu Asp Val Leu Leu Thr Lys Glu Thr Glu Leu Ala Pro Ala Lys Gly
    610                 615                 620 atg gtt tca ctc tca gaa ata gaa gag gct ctg gca aag aat gat gtt      1920
Met Val Ser Leu Ser Glu Ile Glu Glu Ala Leu Ala Lys Asn Asp Val
625                 630                 635                 640 cgc tct gca gaa ata cct gtg gct cag gag aca gtg gtc tca gaa aca      1968
Arg Ser Ala Glu Ile Pro Val Ala Gln Glu Thr Val Val Ser Glu Thr
                645                 650                 655 gag gtg gtc ctg gca aca gaa gtg gta ctg ccc tca gat ccc ata aca      2016
Glu Val Val Leu Ala Thr Glu Val Val Leu Pro Ser Asp Pro Ile Thr
            660                 665                 670 aca ttg aca aag gat gtg aca ctc ccc tta gaa gca gag aga ccg ttg      2064
Thr Leu Thr Lys Asp Val Thr Leu Pro Leu Glu Ala Glu Arg Pro Leu
        675                 680                 685
```

```
                                                              -continued gtg acg gac atg act cca tct ctg gaa aca gaa atg acc cta ggc aaa        2112
Val Thr Asp Met Thr Pro Ser Leu Glu Thr Glu Met Thr Leu Gly Lys
        690                 695                 700 gag aca gct cca ccc aca gaa aca aat ttg ggc atg gcc aaa gac atg        2160
Glu Thr Ala Pro Pro Thr Glu Thr Asn Leu Gly Met Ala Lys Asp Met
705                 710                 715                 720 tct cca ctc cca gaa tca gaa gtg act ctg ggc aag gac gtg gtt ata        2208
Ser Pro Leu Pro Glu Ser Glu Val Thr Leu Gly Lys Asp Val Val Ile
                725                 730                 735 ctt cca gaa aca aag gtg gct gag ttt aac aat gtg act cca ctt tca        2256
Leu Pro Glu Thr Lys Val Ala Glu Phe Asn Asn Val Thr Pro Leu Ser
            740                 745                 750 gaa gaa gag gta acc tca gtc aag gac atg tct ccg tct gca gaa aca        2304
Glu Glu Glu Val Thr Ser Val Lys Asp Met Ser Pro Ser Ala Glu Thr
        755                 760                 765 gag gct ccc ctg gct aag aat gct gat ctg cac tca gga aca gag ctg        2352
Glu Ala Pro Leu Ala Lys Asn Ala Asp Leu His Ser Gly Thr Glu Leu
770                 775                 780 att gtg gac aac agc atg gct cca gcc tcc gat ctt gca ctg ccc ttg        2400
Ile Val Asp Asn Ser Met Ala Pro Ala Ser Asp Leu Ala Leu Pro Leu
785                 790                 795                 800 gaa aca aaa gta gca aca gtt cca att aaa gac aaa gga act gta cag        2448
Glu Thr Lys Val Ala Thr Val Pro Ile Lys Asp Lys Gly Thr Val Gln
                805                 810                 815 act gaa gaa aaa cca cgt gaa gac tcc cag tta gca tct atg cag cac        2496
Thr Glu Glu Lys Pro Arg Glu Asp Ser Gln Leu Ala Ser Met Gln His
            820                 825                 830 aag gga cag tca aca gta cct cct tgc acg gct tca cca gaa cca gtc        2544
Lys Gly Gln Ser Thr Val Pro Pro Cys Thr Ala Ser Pro Glu Pro Val
        835                 840                 845 aaa gct gca gaa caa atg tct acc tta cca ata gat gca cct tct cca        2592
Lys Ala Ala Glu Gln Met Ser Thr Leu Pro Ile Asp Ala Pro Ser Pro
850                 855                 860 tta gag aac tta gag cag aag gaa acg cct ggc agc cag cct tct gag        2640
Leu Glu Asn Leu Glu Gln Lys Glu Thr Pro Gly Ser Gln Pro Ser Glu
865                 870                 875                 880 cct tgc tca gga gta tcc cgg caa gaa gaa gca aag gct gct gta ggt        2688
Pro Cys Ser Gly Val Ser Arg Gln Glu Glu Ala Lys Ala Ala Val Gly
                885                 890                 895 gtg act gga aat gac atc act acc ccg cca aac aag gag cca cca cca        2736
Val Thr Gly Asn Asp Ile Thr Thr Pro Pro Asn Lys Glu Pro Pro Pro
            900                 905                 910 agc cca gaa aag aaa gca aag cct ttg gcc acc act caa cct gca aag        2784
Ser Pro Glu Lys Lys Ala Lys Pro Leu Ala Thr Thr Gln Pro Ala Lys
        915                 920                 925 act tca aca tcg aaa gcc aaa aca cag ccc act tct ctc cct aag caa        2832
Thr Ser Thr Ser Lys Ala Lys Thr Gln Pro Thr Ser Leu Pro Lys Gln
930                 935                 940 cca gct ccc acc acc tct ggt ggg ttg aat aaa aaa ccc atg agc ctc        2880
Pro Ala Pro Thr Thr Ser Gly Gly Leu Asn Lys Lys Pro Met Ser Leu
945                 950                 955                 960 gcc tca ggc tca gtg cca gct gcc cca cac aaa cgc cct gct gct gcc        2928
Ala Ser Gly Ser Val Pro Ala Ala Pro His Lys Arg Pro Ala Ala Ala
                965                 970                 975 act gct act gcc agg cct tcc acc cta cct gcc aga gac gtg aag cca        2976
Thr Ala Thr Ala Arg Pro Ser Thr Leu Pro Ala Arg Asp Val Lys Pro
            980                 985                 990 aag cca att aca gaa gct aag gtt gcc gaa aag cgg acc tct cca tcc        3024
Lys Pro Ile Thr Glu Ala Lys Val Ala Glu Lys Arg Thr Ser Pro Ser
        995                 1000                1005
```

```
aag cct tca tct gcc cca gcc ctc aaa cct gga cct aaa acc acc cca        3072
Lys Pro Ser Ser Ala Pro Ala Leu Lys Pro Gly Pro Lys Thr Thr Pro
    1010            1015                1020 acc gtt tca aaa gcc aca tct ccc tca act ctt gtt tcc act gga cca        3120
Thr Val Ser Lys Ala Thr Ser Pro Ser Thr Leu Val Ser Thr Gly Pro
1025            1030                1035                1040 agt agt aga agt cca gct aca act ctg cct aag agg cca acc agc atc        3168
Ser Ser Arg Ser Pro Ala Thr Thr Leu Pro Lys Arg Pro Thr Ser Ile
            1045                1050                1055 aag act gag ggg aaa cct gct gat gtc aaa agg atg act gct aag tct        3216
Lys Thr Glu Gly Lys Pro Ala Asp Val Lys Arg Met Thr Ala Lys Ser
        1060                1065                1070 gcc tca gct gac ttg agt cgc tca aag acc acc tct gcc agt tct gtg        3264
Ala Ser Ala Asp Leu Ser Arg Ser Lys Thr Thr Ser Ala Ser Ser Val
    1075                1080                1085 aag aga aac acc act ccc act ggg gca gca ccc cca gca ggg atg act        3312
Lys Arg Asn Thr Thr Pro Thr Gly Ala Ala Pro Pro Ala Gly Met Thr
1090                1095                1100 tcc act cga gtc aag ccc atg tct gca cct agc cgc tct tct ggg gct        3360
Ser Thr Arg Val Lys Pro Met Ser Ala Pro Ser Arg Ser Ser Gly Ala
1105            1110                1115                1120 ctt tct gtg gac aag aag ccc act tcc act aag cct agc tcc tct gct        3408
Leu Ser Val Asp Lys Lys Pro Thr Ser Thr Lys Pro Ser Ser Ser Ala
            1125                1130                1135 ccc agg gtg agc cgc ctg gcc aca act gtt tct gcc cct gac ctg aag        3456
Pro Arg Val Ser Arg Leu Ala Thr Thr Val Ser Ala Pro Asp Leu Lys
        1140                1145                1150 agt gtt cgc tcc aag gtc ggc tct aca gaa aac atc aaa cac cag cct        3504
Ser Val Arg Ser Lys Val Gly Ser Thr Glu Asn Ile Lys His Gln Pro
    1155                1160                1165 gga gga ggc cgg gcc aaa gta gag aaa aaa aca gag gca gct acc aca        3552
Gly Gly Gly Arg Ala Lys Val Glu Lys Lys Thr Glu Ala Ala Thr Thr
1170                1175                1180 gct ggg aag cct gaa cct aat gca gtc act aaa gca gcc ggc tcc att        3600
Ala Gly Lys Pro Glu Pro Asn Ala Val Thr Lys Ala Ala Gly Ser Ile
1185            1190                1195                1200 gcg agt gca cag aaa ccg cct gct ggg aaa gtc cag ata gta tcc aaa        3648
Ala Ser Ala Gln Lys Pro Pro Ala Gly Lys Val Gln Ile Val Ser Lys
            1205                1210                1215 aaa gtg agc tac agt cat att caa tcc aag tgt gtt tcc aag gac aat        3696
Lys Val Ser Tyr Ser His Ile Gln Ser Lys Cys Val Ser Lys Asp Asn
        1220                1225                1230 att aag cat gtc cct gga tgt ggc aat gtt cag att cag aac aag aaa        3744
Ile Lys His Val Pro Gly Cys Gly Asn Val Gln Ile Gln Asn Lys Lys
    1235                1240                1245 gtg gac ata tcc aag gtc tcc tcc aag tgt ggg tcc aaa gct aat atc        3792
Val Asp Ile Ser Lys Val Ser Ser Lys Cys Gly Ser Lys Ala Asn Ile
1250                1255                1260 aag cac aag cct ggt gga gga gat gtc aag att gaa agt cag aag ttg        3840
Lys His Lys Pro Gly Gly Gly Asp Val Lys Ile Glu Ser Gln Lys Leu
1265            1270                1275                1280 aac ttc aag gag aag gcc caa gcc aaa gtg gga tcc ctt gat aac gtt        3888
Asn Phe Lys Glu Lys Ala Gln Ala Lys Val Gly Ser Leu Asp Asn Val
            1285                1290                1295 ggc cac ttt cct gca gga ggt gcc gtg aag act gag ggc ggt ggc agt        3936
Gly His Phe Pro Ala Gly Gly Ala Val Lys Thr Glu Gly Gly Gly Ser
        1300                1305                1310 gag gcc ctt ccg tgt cca ggc ccc ccc gct ggg gag gag cca gtc atc        3984
Glu Ala Leu Pro Cys Pro Gly Pro Pro Ala Gly Glu Glu Pro Val Ile
```

```
                1315                1320                1325
cct gag gct gcg cct gac cgt ggc gcc cct act tca gcc agt ggc ctc      4032
Pro Glu Ala Ala Pro Asp Arg Gly Ala Pro Thr Ser Ala Ser Gly Leu
    1330                1335                1340 agt ggc cac acc acc ctg tca ggg ggt ggt gac caa agg gag ccc cag      4080
Ser Gly His Thr Thr Leu Ser Gly Gly Gly Asp Gln Arg Glu Pro Gln
1345                1350                1355                1360 acc ttg gac agc cag atc cag gag aca agc atc atg gtg agc aag ggc      4128
Thr Leu Asp Ser Gln Ile Gln Glu Thr Ser Ile Met Val Ser Lys Gly
            1365                1370                1375 gag gag ctg ttc acc ggg gtg gtg ccc atc ctg gtc gag ctg gac ggc      4176
Glu Glu Leu Phe Thr Gly Val Val Pro Ile Leu Val Glu Leu Asp Gly
        1380                1385                1390 gac gta aac ggc cac aag ttc agc gtg tcc ggc gag ggc gag ggc gat      4224
Asp Val Asn Gly His Lys Phe Ser Val Ser Gly Glu Gly Glu Gly Asp
    1395                1400                1405 gcc acc tac ggc aag ctg acc ctg aag ttc atc tgc acc acc ggc aag      4272
Ala Thr Tyr Gly Lys Leu Thr Leu Lys Phe Ile Cys Thr Thr Gly Lys
1410                1415                1420 ctg ccc gtg ccc tgg ccc acc ctc gtg acc acc ctg acc cac ggc gtg      4320
Leu Pro Val Pro Trp Pro Thr Leu Val Thr Thr Leu Thr His Gly Val
1425                1430                1435                1440 cag tgc ttc agc cgc tac ccc gac cac atg aag cag cac gac ttc ttc      4368
Gln Cys Phe Ser Arg Tyr Pro Asp His Met Lys Gln His Asp Phe Phe
            1445                1450                1455 aag tcc gcc atg ccc gaa ggc tac gtc cag gag cgc acc atc ttc ttc      4416
Lys Ser Ala Met Pro Glu Gly Tyr Val Gln Glu Arg Thr Ile Phe Phe
        1460                1465                1470 aag gac gac ggc aac tac aag acc cgc gcc gag gtg aag ttc gag ggc      4464
Lys Asp Asp Gly Asn Tyr Lys Thr Arg Ala Glu Val Lys Phe Glu Gly
    1475                1480                1485 gac acc ctg gtg aac cgc atc gag ctg aag ggc atc gac ttc aag gag      4512
Asp Thr Leu Val Asn Arg Ile Glu Leu Lys Gly Ile Asp Phe Lys Glu
    1490                1495                1500 gac ggc aac atc ctg ggg cac aag ctg gag tac aac ttc aac agc cac      4560
Asp Gly Asn Ile Leu Gly His Lys Leu Glu Tyr Asn Phe Asn Ser His
1505                1510                1515                1520 aac gtc tat atc atg gcc gac aag cag aag aac ggc atc aag gtg aac      4608
Asn Val Tyr Ile Met Ala Asp Lys Gln Lys Asn Gly Ile Lys Val Asn
            1525                1530                1535 ttc aag atc cgc cac aac atc gag gac ggc agc gtg cag ctc gcc gac      4656
Phe Lys Ile Arg His Asn Ile Glu Asp Gly Ser Val Gln Leu Ala Asp
        1540                1545                1550 cac tac cag cag aac acc ccc atc ggc gac ggc ccc gtg ctg ctg ccc      4704
His Tyr Gln Gln Asn Thr Pro Ile Gly Asp Gly Pro Val Leu Leu Pro
    1555                1560                1565 gac aac cac tac ctg agc acc cag tcc gcc ctg agc aaa gac ccc aac      4752
Asp Asn His Tyr Leu Ser Thr Gln Ser Ala Leu Ser Lys Asp Pro Asn
    1570                1575                1580 gag aag cgc gat cac atg gtc ctg ctg gag ttc gtg acc gcc gcc ggg      4800
Glu Lys Arg Asp His Met Val Leu Leu Glu Phe Val Thr Ala Ala Gly
1585                1590                1595                1600 atc act ctc ggc atg gac gag ctg tac aag tag                          4833
Ile Thr Leu Gly Met Asp Glu Leu Tyr Lys
            1605                1610

<210> SEQ ID NO 22
<211> LENGTH: 1610
<212> TYPE: PRT
<213> ORGANISM: Artificial Sequence
```

-continued

```
<220> FEATURE:
<223> OTHER INFORMATION: Description of Artificial Sequence:
      EYFP-DEVD-MAP4-EBFP construct

<400> SEQUENCE: 22

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Lys
225                 230                 235                 240

Gly Asp Glu Val Asp Gly Met Ala Asp Leu Ser Leu Val Asp Ala Leu
                245                 250                 255

Thr Glu Pro Pro Pro Glu Ile Glu Gly Glu Ile Lys Arg Asp Phe Met
            260                 265                 270

Ala Ala Leu Glu Ala Glu Pro Tyr Asp Asp Ile Val Gly Glu Thr Val
        275                 280                 285

Glu Lys Thr Glu Phe Ile Pro Leu Leu Asp Gly Asp Glu Lys Thr Gly
    290                 295                 300

Asn Ser Glu Ser Lys Lys Pro Cys Leu Asp Thr Ser Gln Val Glu
305                 310                 315                 320

Gly Ile Pro Ser Ser Lys Pro Thr Leu Leu Ala Asn Gly Asp His Gly
                325                 330                 335

Met Glu Gly Asn Asn Thr Ala Gly Ser Pro Thr Asp Phe Leu Glu Glu
            340                 345                 350

Arg Val Asp Tyr Pro Asp Tyr Gln Ser Ser Gln Asn Trp Pro Glu Asp
        355                 360                 365

Ala Ser Phe Cys Phe Gln Pro Gln Gln Val Leu Asp Thr Asp Gln Ala
    370                 375                 380

Glu Pro Phe Asn Glu His Arg Asp Asp Gly Leu Ala Asp Leu Leu Phe
```

```
                385                 390                 395                 400
Val Ser Ser Gly Pro Thr Asn Ala Ser Ala Phe Thr Glu Arg Asp Asn
                405                 410                 415

Pro Ser Glu Asp Ser Tyr Gly Met Leu Pro Cys Asp Ser Phe Ala Ser
                420                 425                 430

Thr Ala Val Val Ser Gln Glu Trp Ser Val Gly Ala Pro Asn Ser Pro
            435                 440                 445

Cys Ser Glu Ser Cys Val Ser Pro Glu Val Thr Ile Glu Thr Leu Gln
        450                 455                 460

Pro Ala Thr Glu Leu Ser Lys Ala Ala Glu Val Glu Ser Val Lys Glu
465                 470                 475                 480

Gln Leu Pro Ala Lys Ala Leu Glu Thr Met Ala Glu Gln Thr Thr Asp
                485                 490                 495

Val Val His Ser Pro Ser Thr Asp Thr Pro Gly Pro Asp Thr Glu
                500                 505                 510

Ala Ala Leu Ala Lys Asp Ile Glu Glu Ile Thr Lys Pro Asp Val Ile
            515                 520                 525

Leu Ala Asn Val Thr Gln Pro Ser Thr Glu Ser Asp Met Phe Leu Ala
        530                 535                 540

Gln Asp Met Glu Leu Leu Thr Gly Thr Glu Ala Ala His Ala Asn Asn
545                 550                 555                 560

Ile Ile Leu Pro Thr Glu Pro Asp Glu Ser Ser Thr Lys Asp Val Ala
                565                 570                 575

Pro Pro Met Glu Glu Ile Val Pro Gly Asn Asp Thr Thr Ser Pro
            580                 585                 590

Lys Glu Thr Glu Thr Thr Leu Pro Ile Lys Met Asp Leu Ala Pro Pro
        595                 600                 605

Glu Asp Val Leu Leu Thr Lys Glu Thr Glu Leu Ala Pro Ala Lys Gly
    610                 615                 620

Met Val Ser Leu Ser Glu Ile Glu Glu Ala Leu Ala Lys Asn Asp Val
625                 630                 635                 640

Arg Ser Ala Glu Ile Pro Val Ala Gln Glu Thr Val Val Ser Glu Thr
                645                 650                 655

Glu Val Val Leu Ala Thr Glu Val Val Leu Pro Ser Asp Pro Ile Thr
            660                 665                 670

Thr Leu Thr Lys Asp Val Thr Leu Pro Leu Glu Ala Glu Arg Pro Leu
        675                 680                 685

Val Thr Asp Met Thr Pro Ser Leu Glu Thr Glu Met Thr Leu Gly Lys
    690                 695                 700

Glu Thr Ala Pro Pro Thr Glu Thr Asn Leu Gly Met Ala Lys Asp Met
705                 710                 715                 720

Ser Pro Leu Pro Glu Ser Glu Val Thr Leu Gly Lys Asp Val Val Ile
                725                 730                 735

Leu Pro Glu Thr Lys Val Ala Glu Phe Asn Asn Val Thr Pro Leu Ser
            740                 745                 750

Glu Glu Glu Val Thr Ser Val Lys Asp Met Ser Pro Ser Ala Glu Thr
        755                 760                 765

Glu Ala Pro Leu Ala Lys Asn Ala Asp Leu His Ser Gly Thr Glu Leu
    770                 775                 780

Ile Val Asp Asn Ser Met Ala Pro Ala Ser Asp Leu Ala Leu Pro Leu
785                 790                 795                 800

Glu Thr Lys Val Ala Thr Val Pro Ile Lys Asp Lys Gly Thr Val Gln
                805                 810                 815
```

-continued

```
Thr Glu Glu Lys Pro Arg Glu Asp Ser Gln Leu Ala Ser Met Gln His
            820                 825                 830
Lys Gly Gln Ser Thr Val Pro Pro Cys Thr Ala Ser Pro Glu Pro Val
        835                 840                 845
Lys Ala Ala Glu Gln Met Ser Thr Leu Pro Ile Asp Ala Pro Ser Pro
    850                 855                 860
Leu Glu Asn Leu Glu Gln Lys Glu Thr Pro Gly Ser Gln Pro Ser Glu
865                 870                 875                 880
Pro Cys Ser Gly Val Ser Arg Gln Glu Glu Ala Lys Ala Ala Val Gly
                885                 890                 895
Val Thr Gly Asn Asp Ile Thr Thr Pro Pro Asn Lys Glu Pro Pro Pro
            900                 905                 910
Ser Pro Glu Lys Lys Ala Lys Pro Leu Ala Thr Thr Gln Pro Ala Lys
        915                 920                 925
Thr Ser Thr Ser Lys Ala Lys Thr Gln Pro Thr Ser Leu Pro Lys Gln
    930                 935                 940
Pro Ala Pro Thr Thr Ser Gly Gly Leu Asn Lys Lys Pro Met Ser Leu
945                 950                 955                 960
Ala Ser Gly Ser Val Pro Ala Ala Pro His Lys Arg Pro Ala Ala Ala
                965                 970                 975
Thr Ala Thr Ala Arg Pro Ser Thr Leu Pro Ala Arg Asp Val Lys Pro
            980                 985                 990
Lys Pro Ile Thr Glu Ala Lys Val Ala Glu Lys Arg Thr Ser Pro Ser
        995                 1000                1005
Lys Pro Ser Ser Ala Pro Ala Leu Lys Pro Gly Pro Lys Thr Thr Pro
    1010                1015                1020
Thr Val Ser Lys Ala Thr Ser Pro Ser Thr Leu Val Ser Thr Gly Pro
1025                1030                1035                1040
Ser Ser Arg Ser Pro Ala Thr Thr Leu Pro Lys Arg Pro Thr Ser Ile
                1045                1050                1055
Lys Thr Glu Gly Lys Pro Ala Asp Val Lys Arg Met Thr Ala Lys Ser
            1060                1065                1070
Ala Ser Ala Asp Leu Ser Arg Ser Lys Thr Thr Ser Ala Ser Ser Val
        1075                1080                1085
Lys Arg Asn Thr Thr Pro Thr Gly Ala Ala Pro Pro Ala Gly Met Thr
    1090                1095                1100
Ser Thr Arg Val Lys Pro Met Ser Ala Pro Ser Arg Ser Ser Gly Ala
1105                1110                1115                1120
Leu Ser Val Asp Lys Lys Pro Thr Ser Thr Lys Pro Ser Ser Ser Ala
                1125                1130                1135
Pro Arg Val Ser Arg Leu Ala Thr Thr Val Ser Ala Pro Asp Leu Lys
            1140                1145                1150
Ser Val Arg Ser Lys Val Gly Ser Thr Glu Asn Ile Lys His Gln Pro
        1155                1160                1165
Gly Gly Gly Arg Ala Lys Val Glu Lys Lys Thr Glu Ala Ala Thr Thr
    1170                1175                1180
Ala Gly Lys Pro Glu Pro Asn Ala Val Thr Lys Ala Ala Gly Ser Ile
1185                1190                1195                1200
Ala Ser Ala Gln Lys Pro Pro Ala Gly Lys Val Gln Ile Val Ser Lys
                1205                1210                1215
Lys Val Ser Tyr Ser His Ile Gln Ser Lys Cys Val Ser Lys Asp Asn
            1220                1225                1230
```

```
Ile Lys His Val Pro Gly Cys Gly Asn Val Gln Ile Gln Asn Lys Lys
1235                1240                1245

Val Asp Ile Ser Lys Val Ser Ser Lys Cys Gly Ser Lys Ala Asn Ile
1250                1255                1260

Lys His Lys Pro Gly Gly Gly Asp Val Lys Ile Glu Ser Gln Lys Leu
1265                1270                1275                1280

Asn Phe Lys Glu Lys Ala Gln Ala Lys Val Gly Ser Leu Asp Asn Val
                1285                1290                1295

Gly His Phe Pro Ala Gly Gly Ala Val Lys Thr Glu Gly Gly Gly Ser
                1300                1305                1310

Glu Ala Leu Pro Cys Pro Gly Pro Ala Gly Glu Glu Pro Val Ile
            1315                1320                1325

Pro Glu Ala Ala Pro Asp Arg Gly Ala Pro Thr Ser Ala Ser Gly Leu
1330                1335                1340

Ser Gly His Thr Thr Leu Ser Gly Gly Gly Asp Gln Arg Glu Pro Gln
1345                1350                1355                1360

Thr Leu Asp Ser Gln Ile Gln Glu Thr Ser Ile Met Val Ser Lys Gly
                1365                1370                1375

Glu Glu Leu Phe Thr Gly Val Val Pro Ile Leu Val Glu Leu Asp Gly
                1380                1385                1390

Asp Val Asn Gly His Lys Phe Ser Val Ser Gly Glu Gly Glu Gly Asp
            1395                1400                1405

Ala Thr Tyr Gly Lys Leu Thr Leu Lys Phe Ile Cys Thr Thr Gly Lys
            1410                1415                1420

Leu Pro Val Pro Trp Pro Thr Leu Val Thr Thr Leu Thr His Gly Val
1425                1430                1435                1440

Gln Cys Phe Ser Arg Tyr Pro Asp His Met Lys Gln His Asp Phe Phe
                1445                1450                1455

Lys Ser Ala Met Pro Glu Gly Tyr Val Gln Glu Arg Thr Ile Phe Phe
                1460                1465                1470

Lys Asp Asp Gly Asn Tyr Lys Thr Arg Ala Glu Val Lys Phe Glu Gly
            1475                1480                1485

Asp Thr Leu Val Asn Arg Ile Glu Leu Lys Gly Ile Asp Phe Lys Glu
    1490                1495                1500

Asp Gly Asn Ile Leu Gly His Lys Leu Glu Tyr Asn Phe Asn Ser His
1505                1510                1515                1520

Asn Val Tyr Ile Met Ala Asp Lys Gln Lys Asn Gly Ile Lys Val Asn
            1525                1530                1535

Phe Lys Ile Arg His Asn Ile Glu Asp Gly Ser Val Gln Leu Ala Asp
            1540                1545                1550

His Tyr Gln Gln Asn Thr Pro Ile Gly Asp Gly Pro Val Leu Leu Pro
    1555                1560                1565

Asp Asn His Tyr Leu Ser Thr Gln Ser Ala Leu Ser Lys Asp Pro Asn
    1570                1575                1580

Glu Lys Arg Asp His Met Val Leu Leu Glu Phe Val Thr Ala Ala Gly
1585                1590                1595                1600

Ile Thr Leu Gly Met Asp Glu Leu Tyr Lys
                1605                1610

<210> SEQ ID NO 23
<211> LENGTH: 978
<212> TYPE: DNA
<213> ORGANISM: Artificial Sequence
<220> FEATURE:
<221> NAME/KEY: CDS
```

<222> LOCATION: (1)..(978)
<223> OTHER INFORMATION: Description of Artificial Sequence:
       GFP-nucleolus-Caspase 8-annexin II construct

<400> SEQUENCE: 23

| atg gct agc aaa gga gaa gaa ctc ttc act gga gtt gtc cca att ctt | 48 |
|---|---|
| Met Ala Ser Lys Gly Glu Glu Leu Phe Thr Gly Val Val Pro Ile Leu | |
| 1               5                   10                  15 | |

| gtt gaa tta gat ggt gat gtt aac ggc cac aag ttc tct gtc agt gga | 96 |
|---|---|
| Val Glu Leu Asp Gly Asp Val Asn Gly His Lys Phe Ser Val Ser Gly | |
|             20                  25                  30 | |

| gag ggt gaa ggt gat gca aca tac gga aaa ctt acc ctg aag ttc atc | 144 |
|---|---|
| Glu Gly Glu Gly Asp Ala Thr Tyr Gly Lys Leu Thr Leu Lys Phe Ile | |
|         35                  40                  45 | |

| tgc act act ggc aaa ctg cct gtt cca tgg cca aca cta gtc act act | 192 |
|---|---|
| Cys Thr Thr Gly Lys Leu Pro Val Pro Trp Pro Thr Leu Val Thr Thr | |
|     50                  55                  60 | |

| ctg tgc tat ggt gtt caa tgc ttt tca aga tac ccg gat cat atg aaa | 240 |
|---|---|
| Leu Cys Tyr Gly Val Gln Cys Phe Ser Arg Tyr Pro Asp His Met Lys | |
| 65                  70                  75                  80 | |

| cgg cat gac ttt ttc aag agt gcc atg ccc gaa ggt tat gta cag gaa | 288 |
|---|---|
| Arg His Asp Phe Phe Lys Ser Ala Met Pro Glu Gly Tyr Val Gln Glu | |
|                 85                  90                  95 | |

| agg acc atc ttc ttc aaa gat gac ggc aac tac aag aca cgt gct gaa | 336 |
|---|---|
| Arg Thr Ile Phe Phe Lys Asp Asp Gly Asn Tyr Lys Thr Arg Ala Glu | |
|             100                 105                 110 | |

| gtc aag ttt gaa ggt gat acc ctt gtt aat aga atc gag tta aaa ggt | 384 |
|---|---|
| Val Lys Phe Glu Gly Asp Thr Leu Val Asn Arg Ile Glu Leu Lys Gly | |
|         115                 120                 125 | |

| att gac ttc aag gaa gat ggc aac att ctg gga cac aaa ttg gaa tac | 432 |
|---|---|
| Ile Asp Phe Lys Glu Asp Gly Asn Ile Leu Gly His Lys Leu Glu Tyr | |
| 130                 135                 140 | |

| aac tat aac tca cac aat gta tac atc atg gca gac aaa caa aag aat | 480 |
|---|---|
| Asn Tyr Asn Ser His Asn Val Tyr Ile Met Ala Asp Lys Gln Lys Asn | |
| 145                 150                 155                 160 | |

| gga atc aaa gtg aac ttc aag acc cgc cac aac att gaa gat gga agc | 528 |
|---|---|
| Gly Ile Lys Val Asn Phe Lys Thr Arg His Asn Ile Glu Asp Gly Ser | |
|                 165                 170                 175 | |

| gtt caa cta gca gac cat tat caa caa aat act cca att ggc gat ggc | 576 |
|---|---|
| Val Gln Leu Ala Asp His Tyr Gln Gln Asn Thr Pro Ile Gly Asp Gly | |
|             180                 185                 190 | |

| cct gtc ctt tta cca gac aac cat tac ctg tcc aca caa tct gcc ctt | 624 |
|---|---|
| Pro Val Leu Leu Pro Asp Asn His Tyr Leu Ser Thr Gln Ser Ala Leu | |
|         195                 200                 205 | |

| tcg aaa gat ccc aac gaa aag aga gac cac atg gtc ctt ctt gag ttt | 672 |
|---|---|
| Ser Lys Asp Pro Asn Glu Lys Arg Asp His Met Val Leu Leu Glu Phe | |
| 210                 215                 220 | |

| gta aca gct gct ggg att aca cat ggc atg gat gaa ctg tac aac tcc | 720 |
|---|---|
| Val Thr Ala Ala Gly Ile Thr His Gly Met Asp Glu Leu Tyr Asn Ser | |
| 225                 230                 235                 240 | |

| gga aga aaa cgt ata cgt act tac ctc aag tcc tgc agg cgg atg aaa | 768 |
|---|---|
| Gly Arg Lys Arg Ile Arg Thr Tyr Leu Lys Ser Cys Arg Arg Met Lys | |
|                 245                 250                 255 | |

| aga agt ggt ttt gag atg tct cga cct att cct tcc cac ctt act cga | 816 |
|---|---|
| Arg Ser Gly Phe Glu Met Ser Arg Pro Ile Pro Ser His Leu Thr Arg | |
|             260                 265                 270 | |

| tcg gca ggt gtt gaa aca gac gca ggt gtt gaa aca gac gca ggt gtt | 864 |
|---|---|
| Ser Ala Gly Val Glu Thr Asp Ala Gly Val Glu Thr Asp Ala Gly Val | |
|         275                 280                 285 | |

| gaa aca gac gca ggt gtt gaa aca gac gca ggt agt act atg tct act | 912 |

```
Glu Thr Asp Ala Gly Val Glu Thr Asp Ala Gly Ser Thr Met Ser Thr
        290                 295                 300 gtc cac gaa atc ctg tgc aag ctc agc ttg gag ggt gtt cat tct aca     960
Val His Glu Ile Leu Cys Lys Leu Ser Leu Glu Gly Val His Ser Thr
305                 310                 315                 320 ccc cca agt gcc gga tcc                                             978
Pro Pro Ser Ala Gly Ser
                325
```

<210> SEQ ID NO 24
<211> LENGTH: 326
<212> TYPE: PRT
<213> ORGANISM: Artificial Sequence
<220> FEATURE:
<223> OTHER INFORMATION: Description of Artificial Sequence: GFP-nucleolus-Caspase 8-annexin II construct

<400> SEQUENCE: 24

```
Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Cys Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Ser
225                 230                 235                 240

Gly Arg Lys Arg Ile Arg Thr Tyr Leu Lys Ser Cys Arg Arg Met Lys
                245                 250                 255

Arg Ser Gly Phe Glu Met Ser Arg Pro Ile Pro Ser His Leu Thr Arg
            260                 265                 270

Ser Ala Gly Val Glu Thr Asp Ala Gly Val Glu Thr Asp Ala Gly Val
        275                 280                 285

Glu Thr Asp Ala Gly Val Glu Thr Asp Ala Gly Ser Thr Met Ser Thr
    290                 295                 300
```

```
Val His Glu Ile Leu Cys Lys Leu Ser Leu Glu Gly Val His Ser Thr
305                 310                 315                 320

Pro Pro Ser Ala Gly Ser
                325

<210> SEQ ID NO 25
<211> LENGTH: 948
<212> TYPE: DNA
<213> ORGANISM: Artificial Sequence
<220> FEATURE:
<221> NAME/KEY: CDS
<222> LOCATION: (1)..(948)
<223> OTHER INFORMATION: Description of Artificial Sequence:
      GFP-nucleolus-Caspase 3-annexin II construct

<400> SEQUENCE: 25 atg gct agc aaa gga gaa gaa ctc ttc act gga gtt gtc cca att ctt      48
Met Ala Ser Lys Gly Glu Glu Leu Phe Thr Gly Val Val Pro Ile Leu
1               5                   10                  15 gtt gaa tta gat ggt gat gtt aac ggc cac aag ttc tct gtc agt gga      96
Val Glu Leu Asp Gly Asp Val Asn Gly His Lys Phe Ser Val Ser Gly
            20                  25                  30 gag ggt gaa ggt gat gca aca tac gga aaa ctt acc ctg aag ttc atc     144
Glu Gly Glu Gly Asp Ala Thr Tyr Gly Lys Leu Thr Leu Lys Phe Ile
        35                  40                  45 tgc act act ggc aaa ctg cct gtt cca tgg cca aca cta gtc act act     192
Cys Thr Thr Gly Lys Leu Pro Val Pro Trp Pro Thr Leu Val Thr Thr
    50                  55                  60 ctg tgc tat ggt gtt caa tgc ttt tca aga tac ccg gat cat atg aaa     240
Leu Cys Tyr Gly Val Gln Cys Phe Ser Arg Tyr Pro Asp His Met Lys
65                  70                  75                  80 cgg cat gac ttt ttc aag agt gcc atg ccc gaa ggt tat gta cag gaa     288
Arg His Asp Phe Phe Lys Ser Ala Met Pro Glu Gly Tyr Val Gln Glu
                85                  90                  95 agg acc atc ttc ttc aaa gat gac ggc aac tac aag aca cgt gct gaa     336
Arg Thr Ile Phe Phe Lys Asp Asp Gly Asn Tyr Lys Thr Arg Ala Glu
            100                 105                 110 gtc aag ttt gaa ggt gat acc ctt gtt aat aga atc gag tta aaa ggt     384
Val Lys Phe Glu Gly Asp Thr Leu Val Asn Arg Ile Glu Leu Lys Gly
        115                 120                 125 att gac ttc aag gaa gat ggc aac att ctg gga cac aaa ttg gaa tac     432
Ile Asp Phe Lys Glu Asp Gly Asn Ile Leu Gly His Lys Leu Glu Tyr
    130                 135                 140 aac tat aac tca cac aat gta tac atc atg gca gac aaa caa aag aat     480
Asn Tyr Asn Ser His Asn Val Tyr Ile Met Ala Asp Lys Gln Lys Asn
145                 150                 155                 160 gga atc aaa gtg aac ttc aag acc cgc cac aac att gaa gat gga agc     528
Gly Ile Lys Val Asn Phe Lys Thr Arg His Asn Ile Glu Asp Gly Ser
                165                 170                 175 gtt caa cta gca gac cat tat caa caa aat act cca att ggc gat ggc     576
Val Gln Leu Ala Asp His Tyr Gln Gln Asn Thr Pro Ile Gly Asp Gly
            180                 185                 190 cct gtc ctt tta cca gac aac cat tac ctg tcc aca caa tct gcc ctt     624
Pro Val Leu Leu Pro Asp Asn His Tyr Leu Ser Thr Gln Ser Ala Leu
        195                 200                 205 tcg aaa gat ccc aac gaa aag aga gac cac atg gtc ctt ctt gag ttt     672
Ser Lys Asp Pro Asn Glu Lys Arg Asp His Met Val Leu Leu Glu Phe
    210                 215                 220 gta aca gct gct ggg att aca cat ggc atg gat gaa ctg tac aac tcc     720
Val Thr Ala Ala Gly Ile Thr His Gly Met Asp Glu Leu Tyr Asn Ser
225                 230                 235                 240
```

| | | | | | | | | | | | | | | | |
|---|---|---|---|---|---|---|---|---|---|---|---|---|---|---|---|
| gga | aga | aaa | cgt | ata | cgt | act | tac | ctc | aag | tcc | tgc | agg | cgg | atg | aaa | 768 |
| Gly | Arg | Lys | Arg | Ile | Arg | Thr | Tyr | Leu | Lys | Ser | Cys | Arg | Arg | Met | Lys | |
| | | | 245 | | | | | 250 | | | | | 255 | | | |
| aga | agt | ggt | ttt | gag | atg | tct | cga | cct | att | cct | tcc | cac | ctt | act | cga | 816 |
| Arg | Ser | Gly | Phe | Glu | Met | Ser | Arg | Pro | Ile | Pro | Ser | His | Leu | Thr | Arg | |
| | | | 260 | | | | | 265 | | | | | 270 | | | |
| tcg | tat | gaa | aaa | gga | ata | cca | gtt | gaa | aca | gac | agc | gaa | gag | caa | gct | 864 |
| Ser | Tyr | Glu | Lys | Gly | Ile | Pro | Val | Glu | Thr | Asp | Ser | Glu | Glu | Gln | Ala | |
| | | | 275 | | | | | 280 | | | | | 285 | | | |
| tat | agt | act | atg | tct | act | gtc | cac | gaa | atc | ctg | tgc | aag | ctc | agc | ttg | 912 |
| Tyr | Ser | Thr | Met | Ser | Thr | Val | His | Glu | Ile | Leu | Cys | Lys | Leu | Ser | Leu | |
| | | 290 | | | | | 295 | | | | | 300 | | | | |
| gag | ggt | gtt | cat | tct | aca | ccc | cca | agt | gcc | gga | tcc | | | | | 948 |
| Glu | Gly | Val | His | Ser | Thr | Pro | Pro | Ser | Ala | Gly | Ser | | | | | |
| 305 | | | | 310 | | | | | 315 | | | | | | | |

<210> SEQ ID NO 26
<211> LENGTH: 316
<212> TYPE: PRT
<213> ORGANISM: Artificial Sequence
<220> FEATURE:
<223> OTHER INFORMATION: Description of Artificial Sequence:
    GFP-nucleolus-Caspase 3-annexin II construct

<400> SEQUENCE: 26

Met Ala Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Cys Tyr Gly Val Gln Cys Phe Ser Arg Tyr Pro Asp His Met Lys
 65                  70                  75                  80

Arg His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Thr Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Asn Ser
225                 230                 235                 240

Gly Arg Lys Arg Ile Arg Thr Tyr Leu Lys Ser Cys Arg Arg Met Lys
                245                 250                 255

```
Arg Ser Gly Phe Glu Met Ser Arg Pro Ile Pro Ser His Leu Thr Arg
            260                 265                 270
Ser Tyr Glu Lys Gly Ile Pro Val Glu Thr Asp Ser Glu Glu Gln Ala
        275                 280                 285
Tyr Ser Thr Met Ser Thr Val His Glu Ile Leu Cys Lys Leu Ser Leu
        290                 295                 300
Glu Gly Val His Ser Thr Pro Pro Ser Ala Gly Ser
305                 310                 315

<210> SEQ ID NO 27
<211> LENGTH: 2088
<212> TYPE: DNA
<213> ORGANISM: Artificial Sequence
<220> FEATURE:
<221> NAME/KEY: CDS
<222> LOCATION: (1)..(1041)
<223> OTHER INFORMATION: Description of Artificial Sequence:
      NLS-Fred25-synaptobrevin construct

<400> SEQUENCE: 27
```

| | | | | | | | | | | | | | | | | |
|---|---|---|---|---|---|---|---|---|---|---|---|---|---|---|---|---|
| atg | aga | aga | aaa | cga | caa | aag | gct | agc | aaa | gga | gaa | gaa | ctc | ttc | act | 48 |
| Met | Arg | Arg | Lys | Arg | Gln | Lys | Ala | Ser | Lys | Gly | Glu | Glu | Leu | Phe | Thr | |
| 1 | | | | 5 | | | | | 10 | | | | | 15 | | |
| gga | gtt | gtc | cca | att | ctt | gtt | gaa | tta | gat | ggt | gat | gtt | aac | ggc | cac | 96 |
| Gly | Val | Val | Pro | Ile | Leu | Val | Glu | Leu | Asp | Gly | Asp | Val | Asn | Gly | His | |
| | | | 20 | | | | | 25 | | | | | 30 | | | |
| aag | ttc | tct | gtc | agt | gga | gag | ggt | gaa | ggt | gat | gca | aca | tac | gga | aaa | 144 |
| Lys | Phe | Ser | Val | Ser | Gly | Glu | Gly | Glu | Gly | Asp | Ala | Thr | Tyr | Gly | Lys | |
| | | 35 | | | | | 40 | | | | | 45 | | | | |
| ctt | acc | ctg | aag | ttc | atc | tgc | act | act | ggc | aaa | ctg | cct | gtt | cca | tgg | 192 |
| Leu | Thr | Leu | Lys | Phe | Ile | Cys | Thr | Thr | Gly | Lys | Leu | Pro | Val | Pro | Trp | |
| 50 | | | | | 55 | | | | | 60 | | | | | | |
| cca | aca | cta | gtc | act | act | ctg | tgc | tat | ggt | gtt | caa | tgc | ttt | tca | aga | 240 |
| Pro | Thr | Leu | Val | Thr | Thr | Leu | Cys | Tyr | Gly | Val | Gln | Cys | Phe | Ser | Arg | |
| 65 | | | | | 70 | | | | | 75 | | | | | 80 | |
| tac | ccg | gat | cat | atg | aaa | cgg | cat | gac | ttt | ttc | aag | agt | gcc | atg | ccc | 288 |
| Tyr | Pro | Asp | His | Met | Lys | Arg | His | Asp | Phe | Phe | Lys | Ser | Ala | Met | Pro | |
| | | | | 85 | | | | | 90 | | | | | 95 | | |
| gaa | ggt | tat | gta | cag | gaa | agg | acc | atc | ttc | ttc | aaa | gat | gac | ggc | aac | 336 |
| Glu | Gly | Tyr | Val | Gln | Glu | Arg | Thr | Ile | Phe | Phe | Lys | Asp | Asp | Gly | Asn | |
| | | | 100 | | | | | 105 | | | | | 110 | | | |
| tac | aag | aca | cgt | gct | gaa | gtc | aag | ttt | gaa | ggt | gat | acc | ctt | gtt | aat | 384 |
| Tyr | Lys | Thr | Arg | Ala | Glu | Val | Lys | Phe | Glu | Gly | Asp | Thr | Leu | Val | Asn | |
| | | 115 | | | | | 120 | | | | | 125 | | | | |
| aga | atc | gag | tta | aaa | ggt | att | gac | ttc | aag | gaa | gat | ggc | aac | att | ctg | 432 |
| Arg | Ile | Glu | Leu | Lys | Gly | Ile | Asp | Phe | Lys | Glu | Asp | Gly | Asn | Ile | Leu | |
| | 130 | | | | | 135 | | | | | 140 | | | | | |
| gga | cac | aaa | ttg | gaa | tac | aac | tat | aac | tca | cac | aat | gta | tac | atc | atg | 480 |
| Gly | His | Lys | Leu | Glu | Tyr | Asn | Tyr | Asn | Ser | His | Asn | Val | Tyr | Ile | Met | |
| 145 | | | | | 150 | | | | | 155 | | | | | 160 | |
| gca | gac | aaa | caa | aag | aat | gga | atc | aaa | gtg | aac | ttc | aag | acc | cgc | cac | 528 |
| Ala | Asp | Lys | Gln | Lys | Asn | Gly | Ile | Lys | Val | Asn | Phe | Lys | Thr | Arg | His | |
| | | | | 165 | | | | | 170 | | | | | 175 | | |
| aac | att | gaa | gat | gga | agc | gtt | caa | cta | gca | gac | cat | tat | caa | caa | aat | 576 |
| Asn | Ile | Glu | Asp | Gly | Ser | Val | Gln | Leu | Ala | Asp | His | Tyr | Gln | Gln | Asn | |
| | | | 180 | | | | | 185 | | | | | 190 | | | |
| act | cca | att | ggc | gat | ggc | cct | gtc | ctt | tta | cca | gac | aac | cat | tac | ctg | 624 |
| Thr | Pro | Ile | Gly | Asp | Gly | Pro | Val | Leu | Leu | Pro | Asp | Asn | His | Tyr | Leu | |
| | | 195 | | | | | 200 | | | | | 205 | | | | |
| tcc | aca | caa | tct | gcc | ctt | tcg | aaa | gat | ccc | aac | gaa | aag | aga | gac | cac | 672 |
| Ser | Thr | Gln | Ser | Ala | Leu | Ser | Lys | Asp | Pro | Asn | Glu | Lys | Arg | Asp | His | |

-continued

```
atg gtc ctt ctt gag ttt gta aca gct gct ggg att aca cat ggc atg      720
Met Val Leu Leu Glu Phe Val Thr Ala Ala Gly Ile Thr His Gly Met
225                 230                 235                 240 gat gaa ctg tac aac acc ggt atg tct aca ggt cca act gct gcc act      768
Asp Glu Leu Tyr Asn Thr Gly Met Ser Thr Gly Pro Thr Ala Ala Thr
                245                 250                 255 ggc agt aat cga aga ctt cag cag aca caa aat caa gta gat gag gtg      816
Gly Ser Asn Arg Arg Leu Gln Gln Thr Gln Asn Gln Val Asp Glu Val
            260                 265                 270 gtg gac ata atg cga gtt aac gtg gac aag gtt ctg gaa aga gac cag      864
Val Asp Ile Met Arg Val Asn Val Asp Lys Val Leu Glu Arg Asp Gln
        275                 280                 285 aag ctc tct gag tta gac gac cgt gca gac gca ctg cag gca ggc gct      912
Lys Leu Ser Glu Leu Asp Asp Arg Ala Asp Ala Leu Gln Ala Gly Ala
    290                 295                 300 tct caa ttt gaa acg agc gca gcc aag ttg aag agg aaa tat tgg tgg      960
Ser Gln Phe Glu Thr Ser Ala Ala Lys Leu Lys Arg Lys Tyr Trp Trp
305                 310                 315                 320 aag aat tgc aag atg tgg gca atc ggg att act gtt ctg gtt atc ttc     1008
Lys Asn Cys Lys Met Trp Ala Ile Gly Ile Thr Val Leu Val Ile Phe
                325                 330                 335 atc atc atc atc atc gtg tgg gtt gtc tct tca tgaatgagaa gaaaacgaca   1061
Ile Ile Ile Ile Ile Val Trp Val Val Ser Ser
                340                 345 aaaggctagc aaaggagaag aactcttcac tggagttgtc ccaattcttg ttgaattaga   1121
tggtgatgtt aacggccaca agttctctgt cagtggagag ggtgaaggtg atgcaacata   1181
cggaaaactt accctgaagt tcatctgcac tactggcaaa ctgcctgttc catggccaac   1241
actagtcact actctgtgct atggtgttca atgcttttca agatacccgg atcatatgaa   1301
acggcatgac ttttcaaga gtgccatgcc cgaaggttat gtacaggaaa ggaccatctt    1361
cttcaaagat gacggcaact acaagacacg tgctgaagtc aagtttgaag gtgataccct   1421
tgttaataga atcgagttaa aagtattga cttcaaggaa gatggcaaca ttctgggaca    1481
caaattggaa tacaactata actcacacaa tgtatacatc atggcagaca acaaaagaa    1541
tggaatcaaa gtgaacttca gacccgcca caacattgaa gatggaagcg ttcaactagc    1601
agaccattat caacaaaata ctccaattgg cgatggccct gtccttttac cagacaacca   1661
ttacctgtcc acacaatctg cccttcgaa agatcccaac gaaaagagag accacatggt    1721
ccttcttgag tttgtaacag ctgctgggat tacacatggc atggatgaac tgtacaacac   1781
cggtatgtct acaggtccaa ctgctgccac tggcagtaat cgaagacttc agcagacaca   1841
aaatcaagta gatgaggtgg tggacataat gcgagttaac gtggacaagg ttctggaaag   1901
agaccagaag ctctctgagt tagacgaccg tgcagacgca ctgcaggcag gcgcttctca   1961
atttgaaacg agcgcagcca agttgaagag gaaatattgg tggaagaatt gcaagatgtg   2021
ggcaatcggg attactgttc tggttatctt catcatcatc atcatcgtgt gggttgtctc   2081
ttcatga                                                             2088
```

<210> SEQ ID NO 28
<211> LENGTH: 347
<212> TYPE: PRT
<213> ORGANISM: Artificial Sequence
<220> FEATURE:
<223> OTHER INFORMATION: Description of Artificial Sequence:
     NLS-Fred25-synaptobrevin construct

```
<400> SEQUENCE: 28

Met Arg Arg Lys Arg Gln Lys Ala Ser Lys Gly Glu Glu Leu Phe Thr
 1               5                  10                 15
Gly Val Val Pro Ile Leu Val Glu Leu Asp Gly Asp Val Asn Gly His
                20                  25                 30
Lys Phe Ser Val Ser Gly Glu Gly Glu Gly Asp Ala Thr Tyr Gly Lys
            35                  40                 45
Leu Thr Leu Lys Phe Ile Cys Thr Thr Gly Lys Leu Pro Val Pro Trp
 50                  55                  60
Pro Thr Leu Val Thr Thr Leu Cys Tyr Gly Val Gln Cys Phe Ser Arg
 65                  70                  75                 80
Tyr Pro Asp His Met Lys Arg His Asp Phe Phe Lys Ser Ala Met Pro
                85                  90                 95
Glu Gly Tyr Val Gln Glu Arg Thr Ile Phe Phe Lys Asp Asp Gly Asn
                100                 105                110
Tyr Lys Thr Arg Ala Glu Val Lys Phe Glu Gly Asp Thr Leu Val Asn
            115                 120                125
Arg Ile Glu Leu Lys Gly Ile Asp Phe Lys Glu Asp Gly Asn Ile Leu
    130                 135                 140
Gly His Lys Leu Glu Tyr Asn Tyr Asn Ser His Asn Val Tyr Ile Met
145                 150                 155                160
Ala Asp Lys Gln Lys Asn Gly Ile Lys Val Asn Phe Lys Thr Arg His
                165                 170                175
Asn Ile Glu Asp Gly Ser Val Gln Leu Ala Asp His Tyr Gln Gln Asn
            180                 185                190
Thr Pro Ile Gly Asp Gly Pro Val Leu Leu Pro Asp Asn His Tyr Leu
    195                 200                 205
Ser Thr Gln Ser Ala Leu Ser Lys Asp Pro Asn Glu Lys Arg Asp His
210                 215                 220
Met Val Leu Leu Glu Phe Val Thr Ala Ala Gly Ile Thr His Gly Met
225                 230                 235                240
Asp Glu Leu Tyr Asn Thr Gly Met Ser Thr Gly Pro Thr Ala Ala Thr
                245                 250                255
Gly Ser Asn Arg Arg Leu Gln Gln Thr Gln Asn Gln Val Asp Glu Val
            260                 265                270
Val Asp Ile Met Arg Val Asn Val Asp Lys Val Leu Glu Arg Asp Gln
    275                 280                 285
Lys Leu Ser Glu Leu Asp Asp Arg Ala Asp Ala Leu Gln Ala Gly Ala
290                 295                 300
Ser Gln Phe Glu Thr Ser Ala Ala Lys Leu Lys Arg Lys Tyr Trp Trp
305                 310                 315                320
Lys Asn Cys Lys Met Trp Ala Ile Gly Ile Thr Val Leu Val Ile Phe
                325                 330                335
Ile Ile Ile Ile Ile Val Trp Val Val Ser Ser
            340                 345

<210> SEQ ID NO 29
<211> LENGTH: 2106
<212> TYPE: DNA
<213> ORGANISM: Artificial Sequence
<220> FEATURE:
<221> NAME/KEY: CDS
<222> LOCATION: (1)..(1050)
<223> OTHER INFORMATION: Description of Artificial Sequence:
      NLS-Fred25-cellubrevin construct
```

```
<400> SEQUENCE: 29 atg aga aga aaa cga caa aag gct agc aaa gga gaa gaa ctc ttc act        48
Met Arg Arg Lys Arg Gln Lys Ala Ser Lys Gly Glu Glu Leu Phe Thr
 1               5                  10                  15 gga gtt gtc cca att ctt gtt gaa tta gat ggt gat gtt aac ggc cac        96
Gly Val Val Pro Ile Leu Val Glu Leu Asp Gly Asp Val Asn Gly His
             20                  25                  30 aag ttc tct gtc agt gga gag ggt gaa ggt gat gca aca tac gga aaa       144
Lys Phe Ser Val Ser Gly Glu Gly Glu Gly Asp Ala Thr Tyr Gly Lys
         35                  40                  45 ctt acc ctg aag ttc atc tgc act act ggc aaa ctg cct gtt cca tgg       192
Leu Thr Leu Lys Phe Ile Cys Thr Thr Gly Lys Leu Pro Val Pro Trp
     50                  55                  60 cca aca cta gtc act act ctg tgc tat ggt gtt caa tgc ttt tca aga       240
Pro Thr Leu Val Thr Thr Leu Cys Tyr Gly Val Gln Cys Phe Ser Arg
 65                  70                  75                  80 tac ccg gat cat atg aaa cgg cat gac ttt ttc aag agt gcc atg ccc       288
Tyr Pro Asp His Met Lys Arg His Asp Phe Phe Lys Ser Ala Met Pro
                 85                  90                  95 gaa ggt tat gta cag gaa agg acc atc ttc ttc aaa gat gac ggc aac       336
Glu Gly Tyr Val Gln Glu Arg Thr Ile Phe Phe Lys Asp Asp Gly Asn
            100                 105                 110 tac aag aca cgt gct gaa gtc aag ttt gaa ggt gat acc ctt gtt aat       384
Tyr Lys Thr Arg Ala Glu Val Lys Phe Glu Gly Asp Thr Leu Val Asn
        115                 120                 125 aga atc gag tta aaa ggt att gac ttc aag gaa gat ggc aac att ctg       432
Arg Ile Glu Leu Lys Gly Ile Asp Phe Lys Glu Asp Gly Asn Ile Leu
    130                 135                 140 gga cac aaa ttg gaa tac aac tat aac tca cac aat gta tac atc atg       480
Gly His Lys Leu Glu Tyr Asn Tyr Asn Ser His Asn Val Tyr Ile Met
145                 150                 155                 160 gca gac aaa caa aag aat gga atc aaa gtg aac ttc aag acc cgc cac       528
Ala Asp Lys Gln Lys Asn Gly Ile Lys Val Asn Phe Lys Thr Arg His
                165                 170                 175 aac att gaa gat gga agc gtt caa cta gca gac cat tat caa caa aat       576
Asn Ile Glu Asp Gly Ser Val Gln Leu Ala Asp His Tyr Gln Gln Asn
            180                 185                 190 act cca att ggc gat ggc cct gtc ctt tta cca gac aac cat tac ctg       624
Thr Pro Ile Gly Asp Gly Pro Val Leu Leu Pro Asp Asn His Tyr Leu
        195                 200                 205 tcc aca caa tct gcc ctt tcg aaa gat ccc aac gaa aag aga gac cac       672
Ser Thr Gln Ser Ala Leu Ser Lys Asp Pro Asn Glu Lys Arg Asp His
    210                 215                 220 atg gtc ctt ctt gag ttt gta aca gct gct ggg att aca cat ggc atg       720
Met Val Leu Leu Glu Phe Val Thr Ala Ala Gly Ile Thr His Gly Met
225                 230                 235                 240 gat gaa ctg tac aac acc ggt atg tct aca ggt gtg cct tcg ggg tca       768
Asp Glu Leu Tyr Asn Thr Gly Met Ser Thr Gly Val Pro Ser Gly Ser
                245                 250                 255 agt gct gcc act ggc agt aat cga aga ctc cag cag aca caa aat caa       816
Ser Ala Ala Thr Gly Ser Asn Arg Arg Leu Gln Gln Thr Gln Asn Gln
            260                 265                 270 gta gat gag gtg gtt gac atc atg aga gtc aat gtg gat aag gtg tta       864
Val Asp Glu Val Val Asp Ile Met Arg Val Asn Val Asp Lys Val Leu
        275                 280                 285 gaa aga gac cag aag ctc tcg gag cta gat gac cgc gca gat gca ctg       912
Glu Arg Asp Gln Lys Leu Ser Glu Leu Asp Asp Arg Ala Asp Ala Leu
    290                 295                 300 cag gca ggt gcc tcg cag ttt gaa aca agt gct gcc aag ttg aag aga       960
Gln Ala Gly Ala Ser Gln Phe Glu Thr Ser Ala Ala Lys Leu Lys Arg
```

```
Gln Ala Gly Ala Ser Gln Phe Glu Thr Ser Ala Ala Lys Leu Lys Arg
305                 310                 315                 320 aag tat tgg tgg aag aac tgc aag atg tgg gcg ata ggg atc agt gtc      1008
Lys Tyr Trp Trp Lys Asn Cys Lys Met Trp Ala Ile Gly Ile Ser Val
                325                 330                 335 ctg gtg atc att gtc atc atc atc gtg tgg tgt gtc tct                  1050
Leu Val Ile Ile Val Ile Ile Ile Val Trp Cys Val Ser
                340                 345                 350 taaatgagaa gaaaacgaca aaaggctagc aaaggagaag aactcttcac tggagttgtc    1110
ccaattcttg ttgaattaga tggtgatgtt aacggccaca agttctctgt cagtggagag    1170
ggtgaaggtg atgcaacata cggaaaactt accctgaagt tcatctgcac tactggcaaa    1230
ctgcctgttc catggccaac actagtcact actctgtgct atggtgttca atgcttttca    1290
agatacccgg atcatatgaa acggcatgac tttttcaaga gtgccatgcc cgaaggttat    1350
gtacaggaaa ggaccatctt cttcaaagat gacggcaact acaagacacg tgctgaagtc    1410
aagtttgaag gtgataccct tgttaataga atcgagttaa aaggtattga cttcaaggaa    1470
gatggcaaca ttctgggaca caaattggaa tacaactata actcacacaa tgtatacatc    1530
atggcagaca acaaaagaa tggaatcaaa gtgaacttca gacccgcca caacattgaa      1590 gatggaagcg ttcaactagc agaccattat caacaaaata ctccaattgg cgatggccct    1650 gtcccttttac cagacaacca ttacctgtcc acacaatctg ccctttcgaa agatcccaac    1710
gaaaagagag accacatggt ccttcttgag tttgtaacag ctgctgggat tacacatggc    1770
atggatgaac tgtacaacac cggtatgtct acaggtgtgc cttcgggtc aagtgctgcc     1830 actggcagta atcgaagact ccagcagaca caaaatcaag tagatgaggt ggttgacatc    1890
atgagagtca atgtggataa ggtgttagaa agagaccaga agctctcgga gctagatgac    1950
cgcgcagatg cactgcaggc aggtgcctcg cagtttgaaa caagtgctgc caagttgaag    2010
agaaagtatt ggtggaagaa ctgcaagatg tgggcgatag ggatcagtgt cctggtgatc    2070
attgtcatca tcatcatcgt gtggtgtgtc tcttaa                              2106
```

<210> SEQ ID NO 30
<211> LENGTH: 350
<212> TYPE: PRT
<213> ORGANISM: Artificial Sequence
<220> FEATURE:
<223> OTHER INFORMATION: Description of Artificial Sequence:
      NLS-Fred25-cellubrevin construct

<400> SEQUENCE: 30

```
Met Arg Arg Lys Arg Gln Lys Ala Ser Lys Gly Glu Glu Leu Phe Thr
1               5                   10                  15

Gly Val Val Pro Ile Leu Val Glu Leu Asp Gly Asp Val Asn Gly His
                20                  25                  30

Lys Phe Ser Val Ser Gly Glu Gly Glu Gly Asp Ala Thr Tyr Gly Lys
            35                  40                  45

Leu Thr Leu Lys Phe Ile Cys Thr Thr Gly Lys Leu Pro Val Pro Trp
    50                  55                  60

Pro Thr Leu Val Thr Thr Leu Cys Tyr Gly Val Gln Cys Phe Ser Arg
65                  70                  75                  80

Tyr Pro Asp His Met Lys Arg His Asp Phe Phe Lys Ser Ala Met Pro
                85                  90                  95

Glu Gly Tyr Val Gln Glu Arg Thr Ile Phe Phe Lys Asp Asp Gly Asn
            100                 105                 110
```

```
Tyr Lys Thr Arg Ala Glu Val Lys Phe Glu Gly Asp Thr Leu Val Asn
            115                 120                 125

Arg Ile Glu Leu Lys Gly Ile Asp Phe Lys Glu Asp Gly Asn Ile Leu
        130                 135                 140

Gly His Lys Leu Glu Tyr Asn Tyr Asn Ser His Asn Val Tyr Ile Met
145                 150                 155                 160

Ala Asp Lys Gln Lys Asn Gly Ile Lys Val Asn Phe Lys Thr Arg His
                165                 170                 175

Asn Ile Glu Asp Gly Ser Val Gln Leu Ala Asp His Tyr Gln Gln Asn
            180                 185                 190

Thr Pro Ile Gly Asp Gly Pro Val Leu Leu Pro Asp Asn His Tyr Leu
        195                 200                 205

Ser Thr Gln Ser Ala Leu Ser Lys Asp Pro Asn Glu Lys Arg Asp His
    210                 215                 220

Met Val Leu Leu Glu Phe Val Thr Ala Ala Gly Ile Thr His Gly Met
225                 230                 235                 240

Asp Glu Leu Tyr Asn Thr Gly Met Ser Thr Gly Val Pro Ser Gly Ser
                245                 250                 255

Ser Ala Ala Thr Gly Ser Asn Arg Arg Leu Gln Gln Thr Gln Asn Gln
            260                 265                 270

Val Asp Glu Val Val Asp Ile Met Arg Val Asn Val Asp Lys Val Leu
        275                 280                 285

Glu Arg Asp Gln Lys Leu Ser Glu Leu Asp Asp Arg Ala Asp Ala Leu
    290                 295                 300

Gln Ala Gly Ala Ser Gln Phe Glu Thr Ser Ala Ala Lys Leu Lys Arg
305                 310                 315                 320

Lys Tyr Trp Trp Lys Asn Cys Lys Met Trp Ala Ile Gly Ile Ser Val
                325                 330                 335

Leu Val Ile Ile Val Ile Ile Ile Ile Val Trp Cys Val Ser
            340                 345                 350

<210> SEQ ID NO 31
<211> LENGTH: 3171
<212> TYPE: DNA
<213> ORGANISM: Artificial Sequence
<220> FEATURE:
<221> NAME/KEY: CDS
<222> LOCATION: (1)..(3168)
<223> OTHER INFORMATION: Description of Artificial Sequence:
      NLS-EYFP-MAPKDM-EBFP construct

<400> SEQUENCE: 31 atg agg ccc aga aga aag gtg agc aag ggc gag gag ctg ttc acc ggg      48
Met Arg Pro Arg Arg Lys Val Ser Lys Gly Glu Glu Leu Phe Thr Gly
 1               5                  10                  15 gtg gtg ccc atc ctg gtc gag ctg gac ggc gac gta aac ggc cac aag      96
Val Val Pro Ile Leu Val Glu Leu Asp Gly Asp Val Asn Gly His Lys
            20                  25                  30 ttc agc gtg tcc ggc gag ggc gag ggc gat gcc acc tac ggc aag ctg     144
Phe Ser Val Ser Gly Glu Gly Glu Gly Asp Ala Thr Tyr Gly Lys Leu
        35                  40                  45 acc ctg aag ttc atc tgc acc acc ggc aag ctg ccc gtg ccc tgg ccc     192
Thr Leu Lys Phe Ile Cys Thr Thr Gly Lys Leu Pro Val Pro Trp Pro
    50                  55                  60 acc ctc gtg acc acc ttc ggc tac ggc ctg cag tgc ttc gcc cgc tac     240
Thr Leu Val Thr Thr Phe Gly Tyr Gly Leu Gln Cys Phe Ala Arg Tyr
65                  70                  75                  80 ccc gac cac atg aag cag cac gac ttc ttc aag tcc gcc atg ccc gaa     288
```

-continued

```
                Pro Asp His Met Lys Gln His Asp Phe Phe Lys Ser Ala Met Pro Glu
                             85                  90                  95 ggc tac gtc cag gag cgc acc atc ttc ttc aag gac gac ggc aac tac        336
Gly Tyr Val Gln Glu Arg Thr Ile Phe Phe Lys Asp Asp Gly Asn Tyr
            100                 105                 110 aag acc cgc gcc gag gtg aag ttc gag ggc gac acc ctg gtg aac cgc        384
Lys Thr Arg Ala Glu Val Lys Phe Glu Gly Asp Thr Leu Val Asn Arg
        115                 120                 125 atc gag ctg aag ggc atc gac ttc aag gag gac ggc aac atc ctg ggg        432
Ile Glu Leu Lys Gly Ile Asp Phe Lys Glu Asp Gly Asn Ile Leu Gly
    130                 135                 140 cac aag ctg gag tac aac tac aac agc cac aac gtc tat atc atg gcc        480
His Lys Leu Glu Tyr Asn Tyr Asn Ser His Asn Val Tyr Ile Met Ala
145                 150                 155                 160 gac aag cag aag aac ggc atc aag gtg aac ttc aag atc cgc cac aac        528
Asp Lys Gln Lys Asn Gly Ile Lys Val Asn Phe Lys Ile Arg His Asn
                165                 170                 175 atc gag gac ggc agc gtg cag ctc gcc gac cac tac cag cag aac acc        576
Ile Glu Asp Gly Ser Val Gln Leu Ala Asp His Tyr Gln Gln Asn Thr
            180                 185                 190 ccc atc ggc gac ggc ccc gtg ctg ctg ccc gac aac cac tac ctg agc        624
Pro Ile Gly Asp Gly Pro Val Leu Leu Pro Asp Asn His Tyr Leu Ser
        195                 200                 205 tac cag tcc gcc ctg agc aaa gac ccc aac gag aag cgc gat cac atg        672
Tyr Gln Ser Ala Leu Ser Lys Asp Pro Asn Glu Lys Arg Asp His Met
    210                 215                 220 gtc ctg ctg gag ttc gtg acc gcc gcc ggg atc act ctc ggc atg gac        720
Val Leu Leu Glu Phe Val Thr Ala Ala Gly Ile Thr Leu Gly Met Asp
225                 230                 235                 240 gag ctg tac aag aag gga gac gaa gtg gac gga gcc gac ctc agt ctt        768
Glu Leu Tyr Lys Lys Gly Asp Glu Val Asp Gly Ala Asp Leu Ser Leu
                245                 250                 255 gtg gat gcg ttg aca gaa cca cct cca gaa att gag gga gaa ata aag        816
Val Asp Ala Leu Thr Glu Pro Pro Pro Glu Ile Glu Gly Glu Ile Lys
            260                 265                 270 cga gac ttc atg gct gcg ctg gag gca gag ccc tat gat gac atc gtg        864
Arg Asp Phe Met Ala Ala Leu Glu Ala Glu Pro Tyr Asp Asp Ile Val
        275                 280                 285 gga gaa act gtg gag aaa act gag ttt att cct ctc ctg gat ggt gat        912
Gly Glu Thr Val Glu Lys Thr Glu Phe Ile Pro Leu Leu Asp Gly Asp
    290                 295                 300 gag aaa acc ggg aac tca gag tcc aaa aag aaa ccc tgc tta gac act        960
Glu Lys Thr Gly Asn Ser Glu Ser Lys Lys Lys Pro Cys Leu Asp Thr
305                 310                 315                 320 agc cag gtt gaa ggt atc cca tct tct aaa cca aca ctc cta gcc aat       1008
Ser Gln Val Glu Gly Ile Pro Ser Ser Lys Pro Thr Leu Leu Ala Asn
                325                 330                 335 ggt gat cat gga atg gag ggg aat aac act gca ggg tct cca act gac       1056
Gly Asp His Gly Met Glu Gly Asn Asn Thr Ala Gly Ser Pro Thr Asp
            340                 345                 350 ttc ctt gaa gag aga gtg gac tat ccg gat tat cag agc agc cag aac       1104
Phe Leu Glu Glu Arg Val Asp Tyr Pro Asp Tyr Gln Ser Ser Gln Asn
        355                 360                 365 tgg cca gaa gat gca agc ttt tgt ttc cag cct cag caa gtg tta gat       1152
Trp Pro Glu Asp Ala Ser Phe Cys Phe Gln Pro Gln Gln Val Leu Asp
    370                 375                 380 act gac cag gct gag ccc ttt aac gag cac cgt gat gat ggt ttg gca       1200
Thr Asp Gln Ala Glu Pro Phe Asn Glu His Arg Asp Asp Gly Leu Ala
385                 390                 395                 400
```

```
gat ctg ctc ttt gtc tcc agt gga ccc acg aac gct tct gca ttt aca    1248
Asp Leu Leu Phe Val Ser Ser Gly Pro Thr Asn Ala Ser Ala Phe Thr
                405                 410                 415 gag cga gac aat cct tca gaa gac agt tac ggt atg ctt ccc tgt gac    1296
Glu Arg Asp Asn Pro Ser Glu Asp Ser Tyr Gly Met Leu Pro Cys Asp
                420                 425                 430 tca ttt gct tcc acg gct gtt gta tct cag gag tgg tct gtg gga gcc    1344
Ser Phe Ala Ser Thr Ala Val Val Ser Gln Glu Trp Ser Val Gly Ala
                435                 440                 445 cca aac tct cca tgt tca gag tcc tgt gtc tcc cca gag gtt act ata    1392
Pro Asn Ser Pro Cys Ser Glu Ser Cys Val Ser Pro Glu Val Thr Ile
    450                 455                 460 gaa acc cta cag cca gca aca gag ctc tcc aag gca gca gaa gtg gaa    1440
Glu Thr Leu Gln Pro Ala Thr Glu Leu Ser Lys Ala Ala Glu Val Glu
465                 470                 475                 480 tca gtg aaa gag cag ctg cca gct aaa gca ttg gaa acg atg gca gag    1488
Ser Val Lys Glu Gln Leu Pro Ala Lys Ala Leu Glu Thr Met Ala Glu
                485                 490                 495 cag acc act gat gtg gtg cac tct cca tcc aca gac aca aca cca ggc    1536
Gln Thr Thr Asp Val Val His Ser Pro Ser Thr Asp Thr Thr Pro Gly
                500                 505                 510 cca gac aca gag gca gca ctg gct aaa gac ata gaa gag atc acc aag    1584
Pro Asp Thr Glu Ala Ala Leu Ala Lys Asp Ile Glu Glu Ile Thr Lys
                515                 520                 525 cca gat gtg ata ttg gca aat gtc acg cag cca tct act gaa tcg gat    1632
Pro Asp Val Ile Leu Ala Asn Val Thr Gln Pro Ser Thr Glu Ser Asp
    530                 535                 540 atg ttc ctg gcc cag gac atg gaa cta ctc aca gga aca gag gca gcc    1680
Met Phe Leu Ala Gln Asp Met Glu Leu Leu Thr Gly Thr Glu Ala Ala
545                 550                 555                 560 cac gct aac aat atc ata ttg cct aca gaa cca gac gaa tct tca acc    1728
His Ala Asn Asn Ile Ile Leu Pro Thr Glu Pro Asp Glu Ser Ser Thr
                565                 570                 575 aag gat gta gca cca cct atg gaa gaa gaa att gtc cca ggc aat gat    1776
Lys Asp Val Ala Pro Pro Met Glu Glu Glu Ile Val Pro Gly Asn Asp
                580                 585                 590 acg aca tcc ccc aaa gaa aca gag aca aca ctt cca ata aaa atg gac    1824
Thr Thr Ser Pro Lys Glu Thr Glu Thr Thr Leu Pro Ile Lys Met Asp
                595                 600                 605 ttg gca cca cct gag gat gtg tta ctt acc aaa gaa aca gaa cta gcc    1872
Leu Ala Pro Pro Glu Asp Val Leu Leu Thr Lys Glu Thr Glu Leu Ala
610                 615                 620 cca gcc aag ggc atg gtt tca ctc tca gaa ata gaa gag gct ctg gca    1920
Pro Ala Lys Gly Met Val Ser Leu Ser Glu Ile Glu Glu Ala Leu Ala
625                 630                 635                 640 aag aat gat gtt cgc tct gca gaa ata cct gtg gct cag gag aca gtg    1968
Lys Asn Asp Val Arg Ser Ala Glu Ile Pro Val Ala Gln Glu Thr Val
                645                 650                 655 gtc tca gaa aca gag gtg gtc ctg gca aca gaa gtg gta ctg ccc tca    2016
Val Ser Glu Thr Glu Val Val Leu Ala Thr Glu Val Val Leu Pro Ser
                660                 665                 670 gat ccc ata aca aca ttg aca aag gat gtg aca ctc ccc tta gaa gca    2064
Asp Pro Ile Thr Thr Leu Thr Lys Asp Val Thr Leu Pro Leu Glu Ala
    675                 680                 685 gag aga ccg ttg gtg acg gac atg act cca tct ctg gaa aca gaa atg    2112
Glu Arg Pro Leu Val Thr Asp Met Thr Pro Ser Leu Glu Thr Glu Met
    690                 695                 700 acc cta ggc aaa gag aca gct cca ccc aca gaa aca aat ttg ggc atg    2160
Thr Leu Gly Lys Glu Thr Ala Pro Pro Thr Glu Thr Asn Leu Gly Met
705                 710                 715                 720
```

```
gcc aaa gac atg tct cca ctc cca gaa tca gaa gtg act ctg ggc aag        2208
Ala Lys Asp Met Ser Pro Leu Pro Glu Ser Glu Val Thr Leu Gly Lys
            725                 730                 735 gac gtg gtt ata ctt cca gaa aca aag gtg gct gag ttt aac aat gtg        2256
Asp Val Val Ile Leu Pro Glu Thr Lys Val Ala Glu Phe Asn Asn Val
            740                 745                 750 act cca ctt tca gaa gaa gag gta acc tca gtc aag gac atg tct ccg        2304
Thr Pro Leu Ser Glu Glu Glu Val Thr Ser Val Lys Asp Met Ser Pro
            755                 760                 765 tct gca gaa aca gag gct ccc ctg gct aag aat gct gat ctg cac tca        2352
Ser Ala Glu Thr Glu Ala Pro Leu Ala Lys Asn Ala Asp Leu His Ser
770                 775                 780 gga aca gag ctg att gtg gac aac agc atg gct cca gcc tcc gat ctt        2400
Gly Thr Glu Leu Ile Val Asp Asn Ser Met Ala Pro Ala Ser Asp Leu
785                 790                 795                 800 gca ctg ccc ttg gaa aca aaa gta gca aca gtt cca att aaa gac aaa        2448
Ala Leu Pro Leu Glu Thr Lys Val Ala Thr Val Pro Ile Lys Asp Lys
            805                 810                 815 gga atg gtg agc aag ggc gag gag ctg ttc acc ggg gtg gtg ccc atc        2496
Gly Met Val Ser Lys Gly Glu Glu Leu Phe Thr Gly Val Val Pro Ile
            820                 825                 830 ctg gtc gag ctg gac ggc gac gta aac ggc cac aag ttc agc gtg tcc        2544
Leu Val Glu Leu Asp Gly Asp Val Asn Gly His Lys Phe Ser Val Ser
            835                 840                 845 ggc gag ggc gag ggc gat gcc acc tac ggc aag ctg acc ctg aag ttc        2592
Gly Glu Gly Glu Gly Asp Ala Thr Tyr Gly Lys Leu Thr Leu Lys Phe
850                 855                 860 atc tgc acc acc ggc aag ctg ccc gtg ccc tgg ccc acc ctc gtg acc        2640
Ile Cys Thr Thr Gly Lys Leu Pro Val Pro Trp Pro Thr Leu Val Thr
865                 870                 875                 880 acc ctg acc cac ggc gtg cag tgc ttc agc cgc tac ccc gac cac atg        2688
Thr Leu Thr His Gly Val Gln Cys Phe Ser Arg Tyr Pro Asp His Met
            885                 890                 895 aag cag cac gac ttc ttc aag tcc gcc atg ccc gaa ggc tac gtc cag        2736
Lys Gln His Asp Phe Phe Lys Ser Ala Met Pro Glu Gly Tyr Val Gln
            900                 905                 910 gag cgc acc atc ttc ttc aag gac gac ggc aac tac aag acc cgc gcc        2784
Glu Arg Thr Ile Phe Phe Lys Asp Asp Gly Asn Tyr Lys Thr Arg Ala
            915                 920                 925 gag gtg aag ttc gag ggc gac acc ctg gtg aac cgc atc gag ctg aag        2832
Glu Val Lys Phe Glu Gly Asp Thr Leu Val Asn Arg Ile Glu Leu Lys
930                 935                 940 ggc atc gac ttc aag gag gac ggc aac atc ctg ggg cac aag ctg gag        2880
Gly Ile Asp Phe Lys Glu Asp Gly Asn Ile Leu Gly His Lys Leu Glu
945                 950                 955                 960 tac aac ttc aac agc cac aac gtc tat atc atg gcc gac aag cag aag        2928
Tyr Asn Phe Asn Ser His Asn Val Tyr Ile Met Ala Asp Lys Gln Lys
            965                 970                 975 aac ggc atc aag gtg aac ttc aag atc cgc cac aac atc gag gac ggc        2976
Asn Gly Ile Lys Val Asn Phe Lys Ile Arg His Asn Ile Glu Asp Gly
            980                 985                 990 agc gtg cag ctc gcc gac cac tac cag cag aac acc ccc atc ggc gac        3024
Ser Val Gln Leu Ala Asp His Tyr Gln Gln Asn Thr Pro Ile Gly Asp
            995                 1000                1005 ggc ccc gtg ctg ctg ccc gac aac cac tac ctg agc acc cag tcc gcc        3072
Gly Pro Val Leu Leu Pro Asp Asn His Tyr Leu Ser Thr Gln Ser Ala
    1010                1015                1020 ctg agc aaa gac ccc aac gag aag cgc gat cac atg gtc ctg ctg gag        3120
Leu Ser Lys Asp Pro Asn Glu Lys Arg Asp His Met Val Leu Leu Glu
```

|  |  |  |  |  |  |  |  |  |  |  |  |  |  | 1025 | | | | 1030 | | | | 1035 | | | | 1040 | | | |
|---|---|---|---|---|---|---|---|---|---|---|---|---|---|---|---|---|---|---|---|---|---|---|---|---|---|---|---|---|---|

```
                        1025                1030                1035                1040
ttc gtg acc gcc gcc ggg atc act ctc ggc atg gac gag ctg tac aag              3168
Phe Val Thr Ala Ala Gly Ile Thr Leu Gly Met Asp Glu Leu Tyr Lys
                        1045                1050                1055 tag                                                                          3171

<210> SEQ ID NO 32
<211> LENGTH: 1056
<212> TYPE: PRT
<213> ORGANISM: Artificial Sequence
<220> FEATURE:
<223> OTHER INFORMATION: Description of Artificial Sequence:
      NLS-EYFP-MAPKDM-EBFP construct

<400> SEQUENCE: 32

Met Arg Pro Arg Lys Val Ser Lys Gly Glu Leu Phe Thr Gly
 1               5                  10                  15

Val Val Pro Ile Leu Val Glu Leu Asp Gly Asp Val Asn Gly His Lys
                20                  25                  30

Phe Ser Val Ser Gly Glu Gly Glu Gly Asp Ala Thr Tyr Gly Lys Leu
            35                  40                  45

Thr Leu Lys Phe Ile Cys Thr Thr Gly Lys Leu Pro Val Pro Trp Pro
 50                  55                  60

Thr Leu Val Thr Thr Phe Gly Tyr Gly Leu Gln Cys Phe Ala Arg Tyr
 65                  70                  75                  80

Pro Asp His Met Lys Gln His Asp Phe Lys Ser Ala Met Pro Glu
                85                  90                  95

Gly Tyr Val Gln Glu Arg Thr Ile Phe Phe Lys Asp Asp Gly Asn Tyr
                100                 105                 110

Lys Thr Arg Ala Glu Val Lys Phe Glu Gly Asp Thr Leu Val Asn Arg
            115                 120                 125

Ile Glu Leu Lys Gly Ile Asp Phe Lys Glu Asp Gly Asn Ile Leu Gly
        130                 135                 140

His Lys Leu Glu Tyr Asn Tyr Asn Ser His Asn Val Tyr Ile Met Ala
145                 150                 155                 160

Asp Lys Gln Lys Asn Gly Ile Lys Val Asn Phe Lys Ile Arg His Asn
                165                 170                 175

Ile Glu Asp Gly Ser Val Gln Leu Ala Asp His Tyr Gln Gln Asn Thr
                180                 185                 190

Pro Ile Gly Asp Gly Pro Val Leu Leu Pro Asp Asn His Tyr Leu Ser
            195                 200                 205

Tyr Gln Ser Ala Leu Ser Lys Asp Pro Asn Glu Lys Arg Asp His Met
        210                 215                 220

Val Leu Leu Glu Phe Val Thr Ala Ala Gly Ile Thr Leu Gly Met Asp
225                 230                 235                 240

Glu Leu Tyr Lys Lys Gly Asp Glu Val Asp Gly Ala Asp Leu Ser Leu
                245                 250                 255

Val Asp Ala Leu Thr Glu Pro Pro Glu Ile Glu Gly Glu Ile Lys
                260                 265                 270

Arg Asp Phe Met Ala Ala Leu Glu Ala Glu Pro Tyr Asp Asp Ile Val
            275                 280                 285

Gly Glu Thr Val Glu Lys Thr Glu Phe Ile Pro Leu Leu Asp Gly Asp
        290                 295                 300

Glu Lys Thr Gly Asn Ser Glu Ser Lys Lys Pro Cys Leu Asp Thr
305                 310                 315                 320
```

-continued

```
Ser Gln Val Glu Gly Ile Pro Ser Ser Lys Pro Thr Leu Leu Ala Asn
            325                 330                 335

Gly Asp His Gly Met Glu Gly Asn Asn Thr Ala Gly Ser Pro Thr Asp
            340                 345                 350

Phe Leu Glu Glu Arg Val Asp Tyr Pro Asp Tyr Gln Ser Ser Gln Asn
            355                 360                 365

Trp Pro Glu Asp Ala Ser Phe Cys Phe Gln Pro Gln Gln Val Leu Asp
            370                 375                 380

Thr Asp Gln Ala Glu Pro Phe Asn Glu His Arg Asp Asp Gly Leu Ala
385                 390                 395                 400

Asp Leu Leu Phe Val Ser Ser Gly Pro Thr Asn Ala Ser Ala Phe Thr
            405                 410                 415

Glu Arg Asp Asn Pro Ser Glu Asp Ser Tyr Gly Met Leu Pro Cys Asp
            420                 425                 430

Ser Phe Ala Ser Thr Ala Val Val Ser Gln Glu Trp Ser Val Gly Ala
            435                 440                 445

Pro Asn Ser Pro Cys Ser Glu Ser Cys Val Ser Pro Glu Val Thr Ile
            450                 455                 460

Glu Thr Leu Gln Pro Ala Thr Glu Leu Ser Lys Ala Ala Glu Val Glu
465                 470                 475                 480

Ser Val Lys Glu Gln Leu Pro Ala Lys Ala Leu Glu Thr Met Ala Glu
            485                 490                 495

Gln Thr Thr Asp Val Val His Ser Pro Ser Thr Asp Thr Thr Pro Gly
            500                 505                 510

Pro Asp Thr Glu Ala Ala Leu Ala Lys Asp Ile Glu Glu Ile Thr Lys
            515                 520                 525

Pro Asp Val Ile Leu Ala Asn Val Thr Gln Pro Ser Thr Glu Ser Asp
            530                 535                 540

Met Phe Leu Ala Gln Asp Met Glu Leu Leu Thr Gly Thr Glu Ala Ala
545                 550                 555                 560

His Ala Asn Asn Ile Ile Leu Pro Thr Glu Pro Asp Glu Ser Ser Thr
            565                 570                 575

Lys Asp Val Ala Pro Pro Met Glu Glu Glu Ile Val Pro Gly Asn Asp
            580                 585                 590

Thr Thr Ser Pro Lys Glu Thr Glu Thr Thr Leu Pro Ile Lys Met Asp
            595                 600                 605

Leu Ala Pro Pro Glu Asp Val Leu Leu Thr Lys Glu Thr Glu Leu Ala
            610                 615                 620

Pro Ala Lys Gly Met Val Ser Leu Ser Glu Ile Glu Glu Ala Leu Ala
625                 630                 635                 640

Lys Asn Asp Val Arg Ser Ala Glu Ile Pro Val Ala Gln Glu Thr Val
            645                 650                 655

Val Ser Glu Thr Glu Val Val Leu Ala Thr Glu Val Val Leu Pro Ser
            660                 665                 670

Asp Pro Ile Thr Thr Leu Thr Lys Asp Val Thr Leu Pro Leu Glu Ala
            675                 680                 685

Glu Arg Pro Leu Val Thr Asp Met Thr Pro Ser Leu Glu Thr Glu Met
            690                 695                 700

Thr Leu Gly Lys Glu Thr Ala Pro Pro Thr Glu Thr Asn Leu Gly Met
705                 710                 715                 720

Ala Lys Asp Met Ser Pro Leu Pro Glu Ser Glu Val Thr Leu Gly Lys
            725                 730                 735

Asp Val Val Ile Leu Pro Glu Thr Lys Val Ala Glu Phe Asn Asn Val
```

```
                    740                 745                 750
Thr Pro Leu Ser Glu Glu Val Thr Ser Val Lys Asp Met Ser Pro
        755                 760                 765

Ser Ala Glu Thr Glu Ala Pro Leu Ala Lys Asn Ala Asp Leu His Ser
    770                 775                 780

Gly Thr Glu Leu Ile Val Asp Asn Ser Met Ala Pro Ala Ser Asp Leu
785                 790                 795                 800

Ala Leu Pro Leu Glu Thr Lys Val Ala Thr Val Pro Ile Lys Asp Lys
                805                 810                 815

Gly Met Val Ser Lys Gly Glu Glu Leu Phe Thr Gly Val Val Pro Ile
            820                 825                 830

Leu Val Glu Leu Asp Gly Asp Val Asn Gly His Lys Phe Ser Val Ser
        835                 840                 845

Gly Glu Gly Glu Gly Asp Ala Thr Tyr Gly Lys Leu Thr Leu Lys Phe
    850                 855                 860

Ile Cys Thr Thr Gly Lys Leu Pro Val Pro Trp Pro Thr Leu Val Thr
865                 870                 875                 880

Thr Leu Thr His Gly Val Gln Cys Phe Ser Arg Tyr Pro Asp His Met
                885                 890                 895

Lys Gln His Asp Phe Phe Lys Ser Ala Met Pro Glu Gly Tyr Val Gln
            900                 905                 910

Glu Arg Thr Ile Phe Phe Lys Asp Asp Gly Asn Tyr Lys Thr Arg Ala
        915                 920                 925

Glu Val Lys Phe Glu Gly Asp Thr Leu Val Asn Arg Ile Glu Leu Lys
    930                 935                 940

Gly Ile Asp Phe Lys Glu Asp Gly Asn Ile Leu Gly His Lys Leu Glu
945                 950                 955                 960

Tyr Asn Phe Asn Ser His Asn Val Tyr Ile Met Ala Asp Lys Gln Lys
                965                 970                 975

Asn Gly Ile Lys Val Asn Phe Lys Ile Arg His Asn Ile Glu Asp Gly
            980                 985                 990

Ser Val Gln Leu Ala Asp His Tyr Gln Gln Asn Thr Pro Ile Gly Asp
        995                 1000                1005

Gly Pro Val Leu Leu Pro Asp Asn His Tyr Leu Ser Thr Gln Ser Ala
    1010                1015                1020

Leu Ser Lys Asp Pro Asn Glu Lys Arg Asp His Met Val Leu Leu Glu
1025                1030                1035                1040

Phe Val Thr Ala Ala Gly Ile Thr Leu Gly Met Asp Glu Leu Tyr Lys
                1045                1050                1055

<210> SEQ ID NO 33
<211> LENGTH: 1623
<212> TYPE: DNA
<213> ORGANISM: Artificial Sequence
<220> FEATURE:
<221> NAME/KEY: CDS
<222> LOCATION: (1)..(1623)
<223> OTHER INFORMATION: Description of Artificial Sequence:
      YFP-NLS-CP3-multiple DEVD-CFP-Annexin II construct

<400> SEQUENCE: 33 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30
```

```
gag ggc gag ggc gat gcc acc tac ggc aag ctg acc ctg aag ttc atc      144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc      192
Cys Thr Thr Gly Lys Leu Pro Val Pro Trp Pro Thr Leu Val Thr Thr
 50                  55                  60 ttc ggc tac ggc ctg cag tgc ttc gcc cgc tac ccc gac cac atg aag      240
Phe Gly Tyr Gly Leu Gln Cys Phe Ala Arg Tyr Pro Asp His Met Lys
 65                  70                  75                  80 cag cac gac ttc ttc aag tcc gcc atg ccc gaa ggc tac gtc cag gag      288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
    130                 135                 140 aac tac aac agc cac aac gtc tat atc atg gcc gac aag cag aag aac      480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190 ccc gtg ctg ctg ccc gac aac cac tac ctg agc tac cag tcc gcc ctg      624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc      720
Val Thr Ala Ala Gly Ile Thr Leu Gly Met Asp Glu Leu Tyr Lys Ser
225                 230                 235                 240 gga aga agg aaa cga caa aag cga tcg gca ggt gac gaa gtt gat gca      768
Gly Arg Arg Lys Arg Gln Lys Arg Ser Ala Gly Asp Glu Val Asp Ala
                245                 250                 255 ggt gac gaa gtt gat gca ggt gac gaa gtt gat gca ggt gac gaa gtt      816
Gly Asp Glu Val Asp Ala Gly Asp Glu Val Asp Ala Gly Asp Glu Val
            260                 265                 270 gac gca ggt agt act atg gtg agc aag ggc gag gag ctg ttc acc ggg      864
Asp Ala Gly Ser Thr Met Val Ser Lys Gly Glu Glu Leu Phe Thr Gly
        275                 280                 285 gtg gtg ccc atc ctg gtc gag ctg gac ggc gac gta aac ggc cac aag      912
Val Val Pro Ile Leu Val Glu Leu Asp Gly Asp Val Asn Gly His Lys
    290                 295                 300 ttc agc gtg tcc ggc gag ggc gag ggc gat gcc acc tac ggc aag ctg      960
Phe Ser Val Ser Gly Glu Gly Glu Gly Asp Ala Thr Tyr Gly Lys Leu
305                 310                 315                 320 acc ctg aag ttc atc tgc acc acc ggc aag ctg ccc gtg ccc tgg ccc     1008
Thr Leu Lys Phe Ile Cys Thr Thr Gly Lys Leu Pro Val Pro Trp Pro
                325                 330                 335 acc ctc gtg acc acc ctg acc tgg ggc gtg cag tgc ttc agc cgc tac     1056
Thr Leu Val Thr Thr Leu Thr Trp Gly Val Gln Cys Phe Ser Arg Tyr
```

```
                340                 345                 350
ccc gac cac atg aag cag cac gac ttc ttc aag tcc gcc atg ccc gaa     1104
Pro Asp His Met Lys Gln His Asp Phe Phe Lys Ser Ala Met Pro Glu
        355                 360                 365 ggc tac gtc cag gag cgc acc atc ttc ttc aag gac gac ggc aac tac     1152
Gly Tyr Val Gln Glu Arg Thr Ile Phe Phe Lys Asp Asp Gly Asn Tyr
    370                 375                 380 aag acc cgc gcc gag gtg aag ttc gag ggc gac acc ctg gtg aac cgc     1200
Lys Thr Arg Ala Glu Val Lys Phe Glu Gly Asp Thr Leu Val Asn Arg
385                 390                 395                 400 atc gag ctg aag ggc atc gac ttc aag gag gac ggc aac atc ctg ggg     1248
Ile Glu Leu Lys Gly Ile Asp Phe Lys Glu Asp Gly Asn Ile Leu Gly
                405                 410                 415 cac aag ctg gag tac aac tac atc agc cac aac gtc tat atc acc gcc     1296
His Lys Leu Glu Tyr Asn Tyr Ile Ser His Asn Val Tyr Ile Thr Ala
            420                 425                 430 gac aag cag aag aac ggc atc aag gcc aac ttc aag atc cgc cac aac     1344
Asp Lys Gln Lys Asn Gly Ile Lys Ala Asn Phe Lys Ile Arg His Asn
        435                 440                 445 atc gag gac ggc agc gtg cag ctc gcc gac cac tac cag cag aac acc     1392
Ile Glu Asp Gly Ser Val Gln Leu Ala Asp His Tyr Gln Gln Asn Thr
    450                 455                 460 ccc atc ggc gac ggc ccc gtg ctg ctg ccc gac aac cac tac ctg agc     1440
Pro Ile Gly Asp Gly Pro Val Leu Leu Pro Asp Asn His Tyr Leu Ser
465                 470                 475                 480 acc cag tcc gcc ctg agc aaa gac ccc aac gag aag cgc gat cac atg     1488
Thr Gln Ser Ala Leu Ser Lys Asp Pro Asn Glu Lys Arg Asp His Met
                485                 490                 495 gtc ctg ctg gag ttc gtg acc gcc gcc ggg atc act ctc ggc atg gac     1536
Val Leu Leu Glu Phe Val Thr Ala Ala Gly Ile Thr Leu Gly Met Asp
            500                 505                 510 gag ctg tac aag atg tct act gtc cac gaa atc ctg tgc aag ctc agc     1584
Glu Leu Tyr Lys Met Ser Thr Val His Glu Ile Leu Cys Lys Leu Ser
        515                 520                 525 ttg gag ggt gtt cat tct aca ccc cca agt gcc gga tcc                 1623
Leu Glu Gly Val His Ser Thr Pro Pro Ser Ala Gly Ser
    530                 535                 540

<210> SEQ ID NO 34
<211> LENGTH: 541
<212> TYPE: PRT
<213> ORGANISM: Artificial Sequence
<220> FEATURE:
<223> OTHER INFORMATION: Description of Artificial Sequence:
      YFP-NLS-CP3-multiple DEVD-CFP-Annexin II construct

<400> SEQUENCE: 34

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
         50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95
```

```
Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys Ser
225                 230                 235                 240

Gly Arg Arg Lys Arg Gln Lys Arg Ser Ala Gly Asp Glu Val Asp Ala
                245                 250                 255

Gly Asp Glu Val Asp Ala Gly Asp Glu Val Asp Ala Gly Asp Glu Val
            260                 265                 270

Asp Ala Gly Ser Thr Met Val Ser Lys Gly Glu Glu Leu Phe Thr Gly
            275                 280                 285

Val Val Pro Ile Leu Val Glu Leu Asp Gly Asp Val Asn Gly His Lys
            290                 295                 300

Phe Ser Val Ser Gly Glu Gly Glu Gly Asp Ala Thr Tyr Gly Lys Leu
305                 310                 315                 320

Thr Leu Lys Phe Ile Cys Thr Thr Gly Lys Leu Pro Val Pro Trp Pro
                325                 330                 335

Thr Leu Val Thr Thr Leu Thr Trp Gly Val Gln Cys Phe Ser Arg Tyr
            340                 345                 350

Pro Asp His Met Lys Gln His Asp Phe Phe Lys Ser Ala Met Pro Glu
            355                 360                 365

Gly Tyr Val Gln Glu Arg Thr Ile Phe Phe Lys Asp Asp Gly Asn Tyr
            370                 375                 380

Lys Thr Arg Ala Glu Val Lys Phe Glu Gly Asp Thr Leu Val Asn Arg
385                 390                 395                 400

Ile Glu Leu Lys Gly Ile Asp Phe Lys Glu Asp Gly Asn Ile Leu Gly
                405                 410                 415

His Lys Leu Glu Tyr Asn Tyr Ile Ser His Asn Val Tyr Ile Thr Ala
            420                 425                 430

Asp Lys Gln Lys Asn Gly Ile Lys Ala Asn Phe Lys Ile Arg His Asn
            435                 440                 445

Ile Glu Asp Gly Ser Val Gln Leu Ala Asp His Tyr Gln Gln Asn Thr
            450                 455                 460

Pro Ile Gly Asp Gly Pro Val Leu Leu Pro Asp Asn His Tyr Leu Ser
465                 470                 475                 480

Thr Gln Ser Ala Leu Ser Lys Asp Pro Asn Glu Lys Arg Asp His Met
                485                 490                 495

Val Leu Leu Glu Phe Val Thr Ala Ala Gly Ile Thr Leu Gly Met Asp
            500                 505                 510

Glu Leu Tyr Lys Met Ser Thr Val His Glu Ile Leu Cys Lys Leu Ser
```

```
                515                 520                 525
Leu Glu Gly Val His Ser Thr Pro Pro Ser Ala Gly Ser
    530                 535                 540

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: FLAG
      epitope
<400> SEQUENCE: 35
gactacaaag acgacgacga caaa                                          24

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: FLAG
      epitope

<400> SEQUENCE: 36

Asp Tyr Lys Asp Asp Asp Asp Lys
  1               5

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: HA epitope

<400> SEQUENCE: 37
tacccatacg acgtaccaga ctacgca                                       27

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: HA epitope

<400> SEQUENCE: 38

Tyr Pro Tyr Asp Val Pro Asp Tyr Ala
  1               5

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: KT3 epitope

<400> SEQUENCE: 39
ccaccagaac cagaaaca                                                 18

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: KT3 epitope

<400> SEQUENCE: 40

Pro Pro Glu Pro Glu Thr
```

```
<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Myc epitope

<400> SEQUENCE: 41
gcagaagaac aaaaattaat aagcgaagaa gactta                              36

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Myc epitope

<400> SEQUENCE: 42

Ala Glu Glu Gln Lys Leu Ile Ser Glu Glu Asp Leu
 1               5                  10

<210> SEQ ID NO 43
<211> LENGTH: 717
<212> TYPE: DNA
<213> ORGANISM: Artificial Sequence
<220> FEATURE:
<221> NAME/KEY: CDS
<222> LOCATION: (1)..(717)
<223> OTHER INFORMATION: Description of Artificial Sequence: EYFP

<400> SEQUENCE: 43 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
                 20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
             35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
         50                  55                  60 ttc ggc tac ggc ctg cag tgc ttc gcc cgc tac ccc gac cac atg aag     240
Phe Gly Tyr Gly Leu Gln Cys Phe Ala Arg Tyr Pro Asp His Met Lys
 65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
        130                 135                 140 aac tac aac agc cac aac gtc tat atc atg gcc gac aag cag aag aac     480
Asn Tyr Asn Ser His Asn Val Tyr Ile Met Ala Asp Lys Gln Lys Asn
145                 150                 155                 160
```

```
ggc atc aag gtg aac ttc aag atc cgc cac aac atc gag gac ggc agc      528
Gly Ile Lys Val Asn Phe Lys Ile Arg His Asn Ile Glu Asp Gly Ser
            165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
        180                 185                 190 ccc gtg ctg ctg ccc gac aac cac tac ctg agc tac cag tcc gcc ctg      624
Pro Val Leu Leu Pro Asp Asn His Tyr Leu Ser Tyr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
        210                 215                 220 gtg acc gcc gcc ggg atc act ctc ggc atg gac gag ctg tac aag          717
Val Thr Ala Ala Gly Ile Thr Leu Gly Met Asp Glu Leu Tyr Lys
225                 230                 235
```

<210> SEQ ID NO 44
<211> LENGTH: 239
<212> TYPE: PRT
<213> ORGANISM: Artificial Sequence
<220> FEATURE:
<223> OTHER INFORMATION: Description of Artificial Sequence: EYFP

<400> SEQUENCE: 44

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 45
<211> LENGTH: 717
<212> TYPE: DNA

<213> ORGANISM: Artificial Sequence
<220> FEATURE:
<221> NAME/KEY: CDS
<222> LOCATION: (1)..(717)
<223> OTHER INFORMATION: Description of Artificial Sequence: EGFP

<400> SEQUENCE: 45

| | | | | | | | | | | | | | | | | |
|---|---|---|---|---|---|---|---|---|---|---|---|---|---|---|---|---|
| atg | gtg | agc | aag | ggc | gag | gag | ctg | ttc | acc | ggg | gtg | gtg | ccc | atc | ctg | 48 |
| Met | Val | Ser | Lys | Gly | Glu | Glu | Leu | Phe | Thr | Gly | Val | Val | Pro | Ile | Leu | |
| 1 | | | | 5 | | | | | 10 | | | | | 15 | | |
| gtc | gag | ctg | gac | ggc | gac | gta | aac | ggc | cac | aag | ttc | agc | gtg | tcc | ggc | 96 |
| Val | Glu | Leu | Asp | Gly | Asp | Val | Asn | Gly | His | Lys | Phe | Ser | Val | Ser | Gly | |
| | | | 20 | | | | | 25 | | | | | 30 | | | |
| gag | ggc | gag | ggc | gat | gcc | acc | tac | ggc | aag | ctg | acc | ctg | aag | ttc | atc | 144 |
| Glu | Gly | Glu | Gly | Asp | Ala | Thr | Tyr | Gly | Lys | Leu | Thr | Leu | Lys | Phe | Ile | |
| | 35 | | | | | 40 | | | | | 45 | | | | | |
| tgc | acc | acc | ggc | aag | ctg | ccc | gtg | ccc | tgg | ccc | acc | ctc | gtg | acc | acc | 192 |
| Cys | Thr | Thr | Gly | Lys | Leu | Pro | Val | Pro | Trp | Pro | Thr | Leu | Val | Thr | Thr | |
| 50 | | | | | 55 | | | | | 60 | | | | | | |
| ctg | acc | tac | ggc | gtg | cag | tgc | ttc | agc | cgc | tac | ccc | gac | cac | atg | aag | 240 |
| Leu | Thr | Tyr | Gly | Val | Gln | Cys | Phe | Ser | Arg | Tyr | Pro | Asp | His | Met | Lys | |
| 65 | | | | | 70 | | | | | 75 | | | | | 80 | |
| cag | cac | gac | ttc | ttc | aag | tcc | gcc | atg | ccc | gaa | ggc | tac | gtc | cag | gag | 288 |
| Gln | His | Asp | Phe | Phe | Lys | Ser | Ala | Met | Pro | Glu | Gly | Tyr | Val | Gln | Glu | |
| | | | | 85 | | | | | 90 | | | | | 95 | | |
| cgc | acc | atc | ttc | ttc | aag | gac | gac | ggc | aac | tac | aag | acc | cgc | gcc | gag | 336 |
| Arg | Thr | Ile | Phe | Phe | Lys | Asp | Asp | Gly | Asn | Tyr | Lys | Thr | Arg | Ala | Glu | |
| | | | 100 | | | | | 105 | | | | | 110 | | | |
| gtg | aag | ttc | gag | ggc | gac | acc | ctg | gtg | aac | cgc | atc | gag | ctg | aag | ggc | 384 |
| Val | Lys | Phe | Glu | Gly | Asp | Thr | Leu | Val | Asn | Arg | Ile | Glu | Leu | Lys | Gly | |
| | | 115 | | | | | 120 | | | | | 125 | | | | |
| atc | gac | ttc | aag | gag | gac | ggc | aac | atc | ctg | ggg | cac | aag | ctg | gag | tac | 432 |
| Ile | Asp | Phe | Lys | Glu | Asp | Gly | Asn | Ile | Leu | Gly | His | Lys | Leu | Glu | Tyr | |
| | 130 | | | | | 135 | | | | | 140 | | | | | |
| aac | tac | aac | agc | cac | aac | gtc | tat | atc | atg | gcc | gac | aag | cag | aag | aac | 480 |
| Asn | Tyr | Asn | Ser | His | Asn | Val | Tyr | Ile | Met | Ala | Asp | Lys | Gln | Lys | Asn | |
| 145 | | | | | 150 | | | | | 155 | | | | | 160 | |
| ggc | atc | aag | gtg | aac | ttc | aag | atc | cgc | cac | aac | atc | gag | gac | ggc | agc | 528 |
| Gly | Ile | Lys | Val | Asn | Phe | Lys | Ile | Arg | His | Asn | Ile | Glu | Asp | Gly | Ser | |
| | | | | 165 | | | | | 170 | | | | | 175 | | |
| gtg | cag | ctc | gcc | gac | cac | tac | cag | cag | aac | acc | ccc | atc | ggc | gac | ggc | 576 |
| Val | Gln | Leu | Ala | Asp | His | Tyr | Gln | Gln | Asn | Thr | Pro | Ile | Gly | Asp | Gly | |
| | | | 180 | | | | | 185 | | | | | 190 | | | |
| ccc | gtg | ctg | ctg | ccc | gac | aac | cac | tac | ctg | agc | acc | cag | tcc | gcc | ctg | 624 |
| Pro | Val | Leu | Leu | Pro | Asp | Asn | His | Tyr | Leu | Ser | Thr | Gln | Ser | Ala | Leu | |
| | | 195 | | | | | 200 | | | | | 205 | | | | |
| agc | aaa | gac | ccc | aac | gag | aag | cgc | gat | cac | atg | gtc | ctg | ctg | gag | ttc | 672 |
| Ser | Lys | Asp | Pro | Asn | Glu | Lys | Arg | Asp | His | Met | Val | Leu | Leu | Glu | Phe | |
| | 210 | | | | | 215 | | | | | 220 | | | | | |
| gtg | acc | gcc | gcc | ggg | atc | act | ctc | ggc | atg | gac | gag | ctg | tac | aag | | 717 |
| Val | Thr | Ala | Ala | Gly | Ile | Thr | Leu | Gly | Met | Asp | Glu | Leu | Tyr | Lys | | |
| 225 | | | | | 230 | | | | | 235 | | | | | | |

<210> SEQ ID NO 46
<211> LENGTH: 239
<212> TYPE: PRT
<213> ORGANISM: Artificial Sequence
<220> FEATURE:
<223> OTHER INFORMATION: Description of Artificial Sequence: EGFP

<400> SEQUENCE: 46

Met Val Ser Lys Gly Glu Glu Leu Phe Thr Gly Val Val Pro Ile Leu

```
                1               5              10              15
              Val Glu Leu Asp Gly Asp Val Asn Gly His Lys Phe Ser Val Ser Gly
                             20              25              30

Glu Gly Glu Gly Asp Ala Thr Tyr Gly Lys Leu Thr Leu Lys Phe Ile
                         35              40              45

Cys Thr Thr Gly Lys Leu Pro Val Pro Trp Pro Thr Leu Val Thr Thr
                     50              55              60

Leu Thr Tyr Gly Val Gln Cys Phe Ser Arg Tyr Pro Asp His Met Lys
                 65              70              75              80

Gln His Asp Phe Phe Lys Ser Ala Met Pro Glu Gly Tyr Val Gln Glu
                             85              90              95

Arg Thr Ile Phe Phe Lys Asp Asp Gly Asn Tyr Lys Thr Arg Ala Glu
                         100             105             110

Val Lys Phe Glu Gly Asp Thr Leu Val Asn Arg Ile Glu Leu Lys Gly
                         115             120             125

Ile Asp Phe Lys Glu Asp Gly Asn Ile Leu Gly His Lys Leu Glu Tyr
                     130             135             140

Asn Tyr Asn Ser His Asn Val Tyr Ile Met Ala Asp Lys Gln Lys Asn
              145             150             155             160

Gly Ile Lys Val Asn Phe Lys Ile Arg His Asn Ile Glu Asp Gly Ser
                             165             170             175

Val Gln Leu Ala Asp His Tyr Gln Gln Asn Thr Pro Ile Gly Asp Gly
                         180             185             190

Pro Val Leu Leu Pro Asp Asn His Tyr Leu Ser Thr Gln Ser Ala Leu
                         195             200             205

Ser Lys Asp Pro Asn Glu Lys Arg Asp His Met Val Leu Leu Glu Phe
                     210             215             220

Val Thr Ala Ala Gly Ile Thr Leu Gly Met Asp Glu Leu Tyr Lys
              225             230             235

<210> SEQ ID NO 47
<211> LENGTH: 717
<212> TYPE: DNA
<213> ORGANISM: Artificial Sequence
<220> FEATURE:
<221> NAME/KEY: CDS
<222> LOCATION: (1)..(717)
<223> OTHER INFORMATION: Description of Artificial Sequence: EBFP

<400> SEQUENCE: 47 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
  1               5              10              15 gtc gag ctg gac ggc gac gta aac ggc cac aag ttc agc gtg tcc ggc      96
Val Glu Leu Asp Gly Asp Val Asn Gly His Lys Phe Ser Val Ser Gly
             20              25              30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35              40              45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
     50              55              60 ctg acc cac ggc gtg cag tgc ttc agc cgc tac ccc gac cac atg aag     240
Leu Thr His Gly Val Gln Cys Phe Ser Arg Tyr Pro Asp His Met Lys
 65              70              75              80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
             85              90              95
```

```
cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
        100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
    115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
130                 135                 140 aac ttc aac agc cac aac gtc tat atc atg gcc gac aag cag aag aac     480
Asn Phe Asn Ser His Asn Val Tyr Ile Met Ala Asp Lys Gln Lys Asn
145                 150                 155                 160 ggc atc aag gtg aac ttc aag atc cgc cac aac atc gag gac ggc agc     528
Gly Ile Lys Val Asn Phe Lys Ile Arg His Asn Ile Glu Asp Gly Ser
            165                 170                 175 gtg cag ctc gcc gac cac tac cag cag aac acc ccc atc ggc gac ggc     576
Val Gln Leu Ala Asp His Tyr Gln Gln Asn Thr Pro Ile Gly Asp Gly
        180                 185                 190 ccc gtg ctg ctg ccc gac aac cac tac ctg agc acc cag tcc gcc ctg     624
Pro Val Leu Leu Pro Asp Asn His Tyr Leu Ser Thr Gln Ser Ala Leu
    195                 200                 205 agc aaa gac ccc aac gag aag cgc gat cac atg gtc ctg ctg gag ttc     672
Ser Lys Asp Pro Asn Glu Lys Arg Asp His Met Val Leu Leu Glu Phe
210                 215                 220 gtg acc gcc gcc ggg atc act ctc ggc atg gac gag ctg tac aag         717
Val Thr Ala Ala Gly Ile Thr Leu Gly Met Asp Glu Leu Tyr Lys
225                 230                 235

<210> SEQ ID NO 48
<211> LENGTH: 239
<212> TYPE: PRT
<213> ORGANISM: Artificial Sequence
<220> FEATURE:
<223> OTHER INFORMATION: Description of Artificial Sequence: EBFP

<400> SEQUENCE: 48

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Phe Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175
```

```
Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 49
<211> LENGTH: 717
<212> TYPE: DNA
<213> ORGANISM: Artificial Sequence
<220> FEATURE:
<221> NAME/KEY: CDS
<222> LOCATION: (1)..(717)
<223> OTHER INFORMATION: Description of Artificial Sequence: ECFP

<400> SEQUENCE: 49 atg gtg agc aag ggc gag gag ctg ttc acc ggg gtg gtg ccc atc ctg        48
Met Val Ser Lys Gly Glu Glu Leu Phe Thr Gly Val Val Pro Ile Leu
 1               5                  10                  15 gtc gag ctg gac ggc gac gta aac ggc cac aag ttc agc gtg tcc ggc        96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc       144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc       192
Cys Thr Thr Gly Lys Leu Pro Val Pro Trp Pro Thr Leu Val Thr Thr
     50                  55                  60 ctg acc tgg ggc gtg cag tgc ttc agc cgc tac ccc gac cac atg aag       240
Leu Thr Trp Gly Val Gln Cys Phe Ser Arg Tyr Pro Asp His Met Lys
 65                  70                  75                  80 cag cac gac ttc ttc aag tcc gcc atg ccc gaa ggc tac gtc cag gag       288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag       336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc       384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac       432
Ile Asp Phe Lys Glu Asp Gly Asn Ile Leu Gly His Lys Leu Glu Tyr
    130                 135                 140 aac tac atc agc cac aac gtc tat atc acc gcc gac aag cag aag aac       480
Asn Tyr Ile Ser His Asn Val Tyr Ile Thr Ala Asp Lys Gln Lys Asn
145                 150                 155                 160 ggc atc aag gcc aac ttc aag atc cgc cac aac atc gag gac ggc agc       528
Gly Ile Lys Ala Asn Phe Lys Ile Arg His Asn Ile Glu Asp Gly Ser
                165                 170                 175 gtg cag ctc gcc gac cac tac cag cag aac acc ccc atc ggc gac ggc       576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg       624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc       672
Ser Lys Asp Pro Asn Glu Lys Arg Asp His Met Val Leu Leu Glu Phe
```

-continued

```
              210                 215                 220
gtg acc gcc gcc ggg atc act ctc ggc atg gac gag ctg tac aag        717
Val Thr Ala Ala Gly Ile Thr Leu Gly Met Asp Glu Leu Tyr Lys
225                 230                 235

<210> SEQ ID NO 50
<211> LENGTH: 239
<212> TYPE: PRT
<213> ORGANISM: Artificial Sequence
<220> FEATURE:
<223> OTHER INFORMATION: Description of Artificial Sequence: ECFP

<400> SEQUENCE: 50

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 51
<211> LENGTH: 720
<212> TYPE: DNA
<213> ORGANISM: Artificial Sequence
<220> FEATURE:
<221> NAME/KEY: CDS
<222> LOCATION: (1)..(717)
<223> OTHER INFORMATION: Description of Artificial Sequence: Fred25

<400> SEQUENCE: 51 atg gct agc aaa gga gaa gaa ctc ttc act gga gtt gtc cca att ctt         48
Met Ala Ser Lys Gly Glu Glu Leu Phe Thr Gly Val Val Pro Ile Leu
 1               5                  10                  15 gtt gaa tta gat ggt gat gtt aac ggc cac aag ttc tct gtc agt gga         96
Val Glu Leu Asp Gly Asp Val Asn Gly His Lys Phe Ser Val Ser Gly
```

|  |  |  |  |  |  |  |  |  |  |  |  |  |  |  |  |
|---|---|---|---|---|---|---|---|---|---|---|---|---|---|---|---|

```
                  20                       25                       30 gag ggt gaa ggt gat gca aca tac gga aaa ctt acc ctg aag ttc atc       144
Glu Gly Glu Gly Asp Ala Thr Tyr Gly Lys Leu Thr Leu Lys Phe Ile
         35                      40                      45 tgc act act ggc aaa ctg cct gtt cca tgg cca aca cta gtc act act       192
Cys Thr Thr Gly Lys Leu Pro Val Pro Trp Pro Thr Leu Val Thr Thr
 50                      55                      60 ctg tgc tat ggt gtt caa tgc ttt tca aga tac ccg gat cat atg aaa       240
Leu Cys Tyr Gly Val Gln Cys Phe Ser Arg Tyr Pro Asp His Met Lys
 65                      70                      75                  80 cgg cat gac ttt ttc aag agt gcc atg ccc gaa ggt tat gta cag gaa       288
Arg His Asp Phe Phe Lys Ser Ala Met Pro Glu Gly Tyr Val Gln Glu
                         85                      90                      95 agg acc atc ttc ttc aaa gat gac ggc aac tac aag aca cgt gct gaa       336
Arg Thr Ile Phe Phe Lys Asp Asp Gly Asn Tyr Lys Thr Arg Ala Glu
                 100                     105                     110 gtc aag ttt gaa ggt gat acc ctt gtt aat aga atc gag tta aaa ggt       384
Val Lys Phe Glu Gly Asp Thr Leu Val Asn Arg Ile Glu Leu Lys Gly
             115                     120                     125 att gac ttc aag gaa gat ggc aac att ctg gga cac aaa ttg gaa tac       432
Ile Asp Phe Lys Glu Asp Gly Asn Ile Leu Gly His Lys Leu Glu Tyr
 130                     135                     140 aac tat aac tca cac aat gta tac atc atg gca gac aaa caa aag aat       480
Asn Tyr Asn Ser His Asn Val Tyr Ile Met Ala Asp Lys Gln Lys Asn
145                     150                     155                 160 gga atc aaa gtg aac ttc aag acc cgc cac aac att gaa gat gga agc       528
Gly Ile Lys Val Asn Phe Lys Thr Arg His Asn Ile Glu Asp Gly Ser
                 165                     170                     175 gtt caa cta gca gac cat tat caa caa aat act cca att ggc gat ggc       576
Val Gln Leu Ala Asp His Tyr Gln Gln Asn Thr Pro Ile Gly Asp Gly
             180                     185                     190 cct gtc ctt tta cca gac aac cat tac ctg tcc aca caa tct gcc ctt       624
Pro Val Leu Leu Pro Asp Asn His Tyr Leu Ser Thr Gln Ser Ala Leu
         195                     200                     205 tcg aaa gat ccc aac gaa aag aga gac cac atg gtc ctt ctt gag ttt       672
Ser Lys Asp Pro Asn Glu Lys Arg Asp His Met Val Leu Leu Glu Phe
 210                     215                     220 gta aca gct gct ggg att aca cat ggc atg gat gaa ctg tac aac tag       720
Val Thr Ala Ala Gly Ile Thr His Gly Met Asp Glu Leu Tyr Asn
225                     230                     235

<210> SEQ ID NO 52
<211> LENGTH: 239
<212> TYPE: PRT
<213> ORGANISM: Artificial Sequence
<220> FEATURE:
<223> OTHER INFORMATION: Description of Artificial Sequence: Fred25

<400> SEQUENCE: 52

Met Ala Ser Lys Gly Glu Glu Leu Phe Thr Gly Val Val Pro Ile Leu
 1               5                   10                      15

Val Glu Leu Asp Gly Asp Val Asn Gly His Lys Phe Ser Val Ser Gly
                 20                      25                      30

Glu Gly Glu Gly Asp Ala Thr Tyr Gly Lys Leu Thr Leu Lys Phe Ile
             35                      40                      45

Cys Thr Thr Gly Lys Leu Pro Val Pro Trp Pro Thr Leu Val Thr Thr
         50                      55                      60

Leu Cys Tyr Gly Val Gln Cys Phe Ser Arg Tyr Pro Asp His Met Lys
 65                      70                      75                  80
```

```
Arg His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Phe Lys Glu Asp Gly Asn Ile Leu Gly His Lys Leu Glu Tyr
    130                 135                 140
Asn Tyr Asn Ser His Asn Val Tyr Ile Met Ala Asp Lys Gln Lys Asn
145                 150                 155                 160
Gly Ile Lys Val Asn Phe Lys Thr Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
    210                 215                 220
Val Thr Ala Ala Gly Ile Thr His Gly Met Asp Glu Leu Tyr Asn
225                 230                 235

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence:
      Caspase-1,4,5 substrate recognition sequence

<400> SEQUENCE: 53
tgggaacatg acaa                                                      14

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence:
      Caspase-1,4,5 substrate recognition sequence

<400> SEQUENCE: 54

Trp Glu His Asp
  1

<210> SEQ ID NO 55
<211> LENGTH: 12
<212> TYPE: DNA
<213> ORGANISM: Artificial Sequence
<220> FEATURE:
<223> OTHER INFORMATION: Description of Artificial Sequence:
      proCaspase-1 substrate recognition sequence

<400> SEQUENCE: 55
tggtttaaag ac                                                        12

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence:
      proCaspase-1 substrate recognition sequence
```

```
<400> SEQUENCE: 56

Trp Phe Lys Asp
 1

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence:
      Caspase-2 substrate recognition sequence

<400> SEQUENCE: 57
gacgaacacg ac                                                          12

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence:
      Caspase-2 substrate recognition sequence

<400> SEQUENCE: 58

Asp Glu His Asp
 1

<210> SEQ ID NO 59
<211> LENGTH: 12
<212> TYPE: DNA
<213> ORGANISM: Artificial Sequence
<220> FEATURE:
<223> OTHER INFORMATION: Description of Artificial Sequence:
      Caspase-3,7 substrate recognition sequence

<400> SEQUENCE: 59
gacgaagttg ac                                                          12

<210> SEQ ID NO 60
<211> LENGTH: 4
<212> TYPE: PRT
<213> ORGANISM: Artificial Sequence
<220> FEATURE:
<223> OTHER INFORMATION: Description of Artificial Sequence:
      Caspase-3,7 substrate recognition sequence

<400> SEQUENCE: 60

Asp Glu Val Asp
 1

<210> SEQ ID NO 61
<211> LENGTH: 12
<212> TYPE: DNA
<213> ORGANISM: Artificial Sequence
<220> FEATURE:
<223> OTHER INFORMATION: Description of Artificial Sequence:
      proCaspase-3 substrate recognition sequence

<400> SEQUENCE: 61
atagaaacag ac                                                          12

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence:
``` proCaspase-3 substrate recognition sequence

<400> SEQUENCE: 62

Ile Glu Thr Asp
 1

<210> SEQ ID NO 63
<211> LENGTH: 12
<212> TYPE: DNA
<213> ORGANISM: Artificial Sequence
<220> FEATURE:
<223> OTHER INFORMATION: Description of Artificial Sequence:
      proCaspase-4,5 substrate recognition sequence

<400> SEQUENCE: 63
tgggtaagag ac                                                          12

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence:
      proCaspase-4,5 substrate recognition sequence

<400> SEQUENCE: 64

Trp Val Arg Asp
 1

<210> SEQ ID NO 65
<211> LENGTH: 12
<212> TYPE: DNA
<213> ORGANISM: Artificial Sequence
<220> FEATURE:
<223> OTHER INFORMATION: Description of Artificial Sequence: Caspase-6
      substrate recognition sequence

<400> SEQUENCE: 65
gtagaaatag ac                                                          12

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Caspase-6
      substrate recognition sequence

<400> SEQUENCE: 66

Val Glu Ile Asp
 1

<210> SEQ ID NO 67
<211> LENGTH: 12
<212> TYPE: DNA
<213> ORGANISM: Artificial Sequence
<220> FEATURE:
<223> OTHER INFORMATION: Description of Artificial Sequence: Caspase-6
      substrate recognition sequence

<400> SEQUENCE: 67
gtagaacacg ac                                                          12

<210> SEQ ID NO 68
<211> LENGTH: 4
<212> TYPE: PRT
<213> ORGANISM: Artificial Sequence

```
<220> FEATURE:
<223> OTHER INFORMATION: Description of Artificial Sequence: Caspase-6
      substrate recognition sequence

<400> SEQUENCE: 68

Val Glu His Asp
  1

<210> SEQ ID NO 69
<211> LENGTH: 12
<212> TYPE: DNA
<213> ORGANISM: Artificial Sequence
<220> FEATURE:
<223> OTHER INFORMATION: Description of Artificial Sequence:
      proCaspase-6 substrate recognition sequence

<400> SEQUENCE: 69
acagaagtag ac                                                          12

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence:
      proCaspase-6 substrate recognition sequence

<400> SEQUENCE: 70

Thr Glu Val Asp
  1

<210> SEQ ID NO 71
<211> LENGTH: 12
<212> TYPE: DNA
<213> ORGANISM: Artificial Sequence
<220> FEATURE:
<223> OTHER INFORMATION: Description of Artificial Sequence:
      proCaspase-7 substrate recognition sequence

<400> SEQUENCE: 71
atacaagcag ac                                                          12

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence:
      proCaspase-7 substrate recognition sequence

<400> SEQUENCE: 72

Ile Gln Ala Asp
  1

<210> SEQ ID NO 73
<211> LENGTH: 12
<212> TYPE: DNA
<213> ORGANISM: Artificial Sequence
<220> FEATURE:
<223> OTHER INFORMATION: Description of Artificial Sequence: Caspase-8
      substrate recognition sequence

<400> SEQUENCE: 73
gtagaaacag ac                                                          12

<210> SEQ ID NO 74
<211> LENGTH: 4
```

```
<212> TYPE: PRT
<213> ORGANISM: Artificial Sequence
<220> FEATURE:
<223> OTHER INFORMATION: Description of Artificial Sequence: Caspase-8
      substrate recognition sequence

<400> SEQUENCE: 74

Val Glu Thr Asp
  1

<210> SEQ ID NO 75
<211> LENGTH: 12
<212> TYPE: DNA
<213> ORGANISM: Artificial Sequence
<220> FEATURE:
<223> OTHER INFORMATION: Description of Artificial Sequence:
      proCaspase-8 substrate recognition sequence

<400> SEQUENCE: 75
ttagaaacag ac                                                            12

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence:
      proCaspase-8 substrate recognition sequence

<400> SEQUENCE: 76

Leu Glu Thr Asp
  1

<210> SEQ ID NO 77
<211> LENGTH: 12
<212> TYPE: DNA
<213> ORGANISM: Artificial Sequence
<220> FEATURE:
<223> OTHER INFORMATION: Description of Artificial Sequence: Caspase-9
      substrate recognition sequence

<400> SEQUENCE: 77
ttagaacacg ac                                                            12

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Caspase-9
      substrate recognition sequence

<400> SEQUENCE: 78

Leu Glu His Asp
  1

<210> SEQ ID NO 79
<211> LENGTH: 12
<212> TYPE: DNA
<213> ORGANISM: Artificial Sequence
<220> FEATURE:
<223> OTHER INFORMATION: Description of Artificial Sequence:
      proCaspase-9 substrate recognition sequence

<400> SEQUENCE: 79
ttagaacacg ac                                                            12
```

```
<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence:
      proCaspase-9 substrate recognition sequence

<400> SEQUENCE: 80

Leu Glu His Asp
 1

<210> SEQ ID NO 81
<211> LENGTH: 12
<212> TYPE: DNA
<213> ORGANISM: Artificial Sequence
<220> FEATURE:
<223> OTHER INFORMATION: Description of Artificial Sequence: HIV
      protease substrate recognition sequence

<400> SEQUENCE: 81
agccaaaatt ac                                                          12

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: HIV
      protease substrate recognition sequence

<400> SEQUENCE: 82

Ser Gln Asn Tyr
 1

<210> SEQ ID NO 83
<211> LENGTH: 12
<212> TYPE: DNA
<213> ORGANISM: Artificial Sequence
<220> FEATURE:
<223> OTHER INFORMATION: Description of Artificial Sequence: HIV
      protease substrate recognition sequence

<400> SEQUENCE: 83
ccaatagtac aa                                                          12

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: HIV
      protease substrate recognition sequence

<400> SEQUENCE: 84

Pro Ile Val Gln
 1

<210> SEQ ID NO 85
<211> LENGTH: 12
<212> TYPE: DNA
<213> ORGANISM: Artificial Sequence
<220> FEATURE:
<223> OTHER INFORMATION: Description of Artificial Sequence:
      Adenovirus endopeptidase substrate recognition sequence

<400> SEQUENCE: 85
atgtttggag ga                                                          12
```

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence:
    Adenovirus endopeptidase substrate recognition sequence

<400> SEQUENCE: 86

Met Phe Gly Gly
 1

<210> SEQ ID NO 87
<211> LENGTH: 12
<212> TYPE: DNA
<213> ORGANISM: Artificial Sequence
<220> FEATURE:
<223> OTHER INFORMATION: Description of Artificial Sequence: Adenovirus
    endopeptidase substrate recognition sequence

<400> SEQUENCE: 87
gcaaaaaaaa ga                                                          12

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Adenovirus
    endopeptidase substrate recognition sequence

<400> SEQUENCE: 88

Ala Lys Lys Arg
 1

<210> SEQ ID NO 89
<211> LENGTH: 9
<212> TYPE: DNA
<213> ORGANISM: Artificial Sequence
<220> FEATURE:
<223> OTHER INFORMATION: Description of Artificial Sequence: b-Secretase
    substrate recognition sequence

<400> SEQUENCE: 89 gtgaaaatg                                                               9

<210> SEQ ID NO 90
<211> LENGTH: 3
<212> TYPE: PRT
<213> ORGANISM: Artificial Sequence
<220> FEATURE:
<223> OTHER INFORMATION: Description of Artificial Sequence: b-Secretase
    substrate recognition sequence

<400> SEQUENCE: 90

Val Lys Met
 1

<210> SEQ ID NO 91
<211> LENGTH: 12
<212> TYPE: DNA
<213> ORGANISM: Artificial Sequence
<220> FEATURE:
<223> OTHER INFORMATION: Description of Artificial Sequence: b-Secretase
    substrate recognition sequence

<400> SEQUENCE: 91

```
gacgcagaat tc                                                            12

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: b-Secretase
      substrate recognition sequence

<400> SEQUENCE: 92

Asp Ala Glu Phe
  1

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Cathepsin D
      substrate recognition sequence

<400> SEQUENCE: 93
aaaccagcat tattc                                                         15

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Cathepsin D
      substrate recognition sequence

<400> SEQUENCE: 94

Lys Pro Ala Leu Phe
  1               5

<210> SEQ ID NO 95
<211> LENGTH: 9
<212> TYPE: DNA
<213> ORGANISM: Artificial Sequence
<220> FEATURE:
<223> OTHER INFORMATION: Description of Artificial Sequence: Cathepsin D
      substrate recognition sequence

<400> SEQUENCE: 95 ttcagatta                                                                 9

<210> SEQ ID NO 96
<211> LENGTH: 3
<212> TYPE: PRT
<213> ORGANISM: Artificial Sequence
<220> FEATURE:
<223> OTHER INFORMATION: Description of Artificial Sequence: Cathepsin D
      substrate recognition sequence

<400> SEQUENCE: 96

Phe Arg Leu
  1

<210> SEQ ID NO 97
<211> LENGTH: 15
<212> TYPE: DNA
<213> ORGANISM: Artificial Sequence
<220> FEATURE:
<223> OTHER INFORMATION: Description of Artificial Sequence: Matrix
      Metalloprotease substrate recognition sequence
```

```
<400> SEQUENCE: 97
ggaccattag gacca                                                          15

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Matrix
      Metalloprotease substrate recognition sequence

<400> SEQUENCE: 98

Gly Pro Leu Gly Pro
  1               5

<210> SEQ ID NO 99
<211> LENGTH: 12
<212> TYPE: DNA
<213> ORGANISM: Artificial Sequence
<220> FEATURE:
<223> OTHER INFORMATION: Description of Artificial Sequence: Granzyme B
      substrate recognition sequence

<400> SEQUENCE: 99
atagaaccag ac                                                             12

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Granzyme B
      substrate recognition sequence

<400> SEQUENCE: 100

Ile Glu Pro Asp
  1

<210> SEQ ID NO 101
<211> LENGTH: 36
<212> TYPE: DNA
<213> ORGANISM: Artificial Sequence
<220> FEATURE:
<223> OTHER INFORMATION: Description of Artificial Sequence: Anthrax
      protease substrate recognition sequence

<400> SEQUENCE: 101
atgcccaaga agaagccgac gcccatccag ctgaac                                   36

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Anthrax
      protease substrate recognition sequence

<400> SEQUENCE: 102

Met Pro Lys Lys Lys Pro Thr Pro Ile Gln Leu Asn
  1               5                  10

<210> SEQ ID NO 103
<211> LENGTH: 45
<212> TYPE: DNA
<213> ORGANISM: Artificial Sequence
<220> FEATURE:
```

<223> OTHER INFORMATION: Description of Artificial Sequence: Anthrax
      protease substrate recognition sequence

<400> SEQUENCE: 103
atgctggccc ggaggaagcc ggtgctgccg gcgctcacca tcaac                      45

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Anthrax
      protease substrate recognition sequence

<400> SEQUENCE: 104

Met Leu Ala Arg Arg Lys Pro Val Leu Pro Ala Leu Thr Ile Asn
 1               5                  10                  15

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence:
      tetanus/botulium substrate recognition sequence

<400> SEQUENCE: 105
gcctcgcagt ttgaaaca                                                    18

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence:
      tetanus/botulium substrate recognition sequence

<400> SEQUENCE: 106

Ala Ser Gln Phe Glu Thr
 1               5

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence:
      tetanus/botulium substrate recognition sequence

<400> SEQUENCE: 107
gcttctcaat ttgaaacg                                                    18

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence:
      tetanus/botulium substrate recognition sequence

<400> SEQUENCE: 108

Ala Ser Gln Phe Glu Thr
 1               5

<210> SEQ ID NO 109
<211> LENGTH: 18
<212> TYPE: DNA

<213> ORGANISM: Artificial Sequence
<220> FEATURE:
<223> OTHER INFORMATION: Description of Artificial Sequence: Botulinum
      neurotoxin A substrate recognition sequence

<400> SEQUENCE: 109
gccaaccaac gtgcaaca                                                18

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Botulinum
      neurotoxin A substrate recognition sequence

<400> SEQUENCE: 110

Ala Asn Gln Arg Ala Thr
 1               5

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Botulinum
      neurotoxin B substrate recognition sequence

<400> SEQUENCE: 111
gcttctcaat ttgaaacg                                                18

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Botulinum
      neurotoxin B substrate recognition sequence

<400> SEQUENCE: 112

Ala Ser Gln Phe Glu Thr
 1               5

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Botulinum
      neurotoxin C substrate recognition sequence

<400> SEQUENCE: 113
acgaaaaaag ctgtgaaa                                                18

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Botulinum
      neurotoxin C substrate recognition sequence

<400> SEQUENCE: 114

Thr Lys Lys Ala Val Lys
 1               5

<210> SEQ ID NO 115

```
<211> LENGTH: 18
<212> TYPE: DNA
<213> ORGANISM: Artificial Sequence
<220> FEATURE:
<223> OTHER INFORMATION: Description of Artificial Sequence: Botulinum
      neurotoxin D substrate recognition sequence

<400> SEQUENCE: 115
gaccagaagc tctctgag                                                    18

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Botulinum
      neurotoxin D substrate recognition sequence

<400> SEQUENCE: 116

Asp Gln Lys Leu Ser Glu
  1               5

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Botulinum
      neurotoxin E substrate recognition sequence

<400> SEQUENCE: 117
atcgacagga tcatggag                                                    18

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Botulinum
      neurotoxin E substrate recognition sequence

<400> SEQUENCE: 118

Ile Asp Arg Ile Met Glu
  1               5

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Botulinum
      neurotoxin F substrate recognition sequence

<400> SEQUENCE: 119
agagaccaga agctctct                                                    18

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Botulinum
      neurotoxin F substrate recognition sequence

<400> SEQUENCE: 120

Arg Asp Gln Lys Leu Ser
  1               5
```

```
<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Botulinum
      neurotoxin G substrate recognition sequence

<400> SEQUENCE: 121
acgagcgcag ccaagttg                                                    18

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Botulinum
      neurotoxin G substrate recognition sequence

<400> SEQUENCE: 122

Thr Ser Ala Ala Lys Leu
 1               5

<210> SEQ ID NO 123
<211> LENGTH: 69
<212> TYPE: DNA
<213> ORGANISM: Artificial Sequence
<220> FEATURE:
<223> OTHER INFORMATION: Description of Artificial Sequence:
      Cytoplasm/cytoskeleton target sequence

<400> SEQUENCE: 123
atgtctactg tccacgaaat cctgtgcaag ctcagcttgg agggtgttca ttctacaccc      60
ccaagtgcc                                                              69

<210> SEQ ID NO 124
<211> LENGTH: 23
<212> TYPE: PRT
<213> ORGANISM: Artificial Sequence
<220> FEATURE:
<223> OTHER INFORMATION: Description of Artificial Sequence:
      Cytoplasm/cytoskeleton target sequence

<400> SEQUENCE: 124

Met Ser Thr Val His Glu Ile Leu Cys Lys Leu Ser Leu Glu Gly Val
 1               5                  10                  15

His Ser Thr Pro Pro Ser Ala
            20

<210> SEQ ID NO 125
<211> LENGTH: 96
<212> TYPE: DNA
<213> ORGANISM: Artificial Sequence
<220> FEATURE:
<223> OTHER INFORMATION: Description of Artificial Sequence: Inner
      surface of plasma membrane target sequence

<400> SEQUENCE: 125
atgggatgta cattaagcgc agaagacaaa gcagcagtag aaagaagcaa aatgatagac      60
agaaacttaa gagaagacgg agaaaaagct gctaga                                96

<210> SEQ ID NO 126
<211> LENGTH: 32
<212> TYPE: PRT
<213> ORGANISM: Artificial Sequence
```

```
<220> FEATURE:
<223> OTHER INFORMATION: Description of Artificial Sequence: Inner
      surface of plasma membrane target sequence

<400> SEQUENCE: 126

Met Gly Cys Thr Leu Ser Ala Glu Asp Lys Ala Ala Val Glu Arg Ser
  1               5                  10                  15

Lys Met Ile Asp Arg Asn Leu Arg Glu Asp Gly Glu Lys Ala Ala Arg
             20                  25                  30

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Nucleus
      target sequence

<400> SEQUENCE: 127
agaaggaaac gacaaaag                                                    18

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Nucleus
      target sequence

<400> SEQUENCE: 128

Arg Arg Lys Arg Gln Lys
  1               5

<210> SEQ ID NO 129
<211> LENGTH: 90
<212> TYPE: DNA
<213> ORGANISM: Artificial Sequence
<220> FEATURE:
<223> OTHER INFORMATION: Description of Artificial Sequence: Nucleolus
      target sequence

<400> SEQUENCE: 129
agaaaacgta tacgtactta cctcaagtcc tgcaggcgga tgaaagaag tggttttgag        60 atgtctcgac ctattccttc ccaccttact                                       90

<210> SEQ ID NO 130
<211> LENGTH: 30
<212> TYPE: PRT
<213> ORGANISM: Artificial Sequence
<220> FEATURE:
<223> OTHER INFORMATION: Description of Artificial Sequence: Nucleolus
      target sequence

<400> SEQUENCE: 130

Arg Lys Arg Ile Arg Thr Tyr Leu Lys Ser Cys Arg Arg Met Lys Arg
  1               5                  10                  15

Ser Gly Phe Glu Met Ser Arg Pro Ile Pro Ser His Leu Thr
             20                  25                  30

<210> SEQ ID NO 131
<211> LENGTH: 87
<212> TYPE: DNA
<213> ORGANISM: Artificial Sequence
<220> FEATURE:
<223> OTHER INFORMATION: Description of Artificial Sequence:
      Mitochondria target sequence
```

<400> SEQUENCE: 131

```
atgtccgtcc tgacgccgct gctgctgcgg ggcttgacag gctcggcccg gcggctccca      60
gtgccgcgcg ccaagatcca ttcgttg                                          87
```

<210> SEQ ID NO 132
<211> LENGTH: 29
<212> TYPE: PRT
<213> ORGANISM: Artificial Sequence
<220> FEATURE:
<223> OTHER INFORMATION: Description of Artificial Sequence: Mitochondria target sequence

<400> SEQUENCE: 132

```
Met Ser Val Leu Thr Pro Leu Leu Leu Arg Gly Leu Thr Gly Ser Ala
  1               5                  10                  15

Arg Arg Leu Pro Val Pro Arg Ala Leu Ile His Ser Leu
             20                  25
```

<210> SEQ ID NO 133
<211> LENGTH: 99
<212> TYPE: DNA
<213> ORGANISM: Artificial Sequence
<220> FEATURE:
<223> OTHER INFORMATION: Description of Artificial Sequence: Nuclear Envelope target sequence

<400> SEQUENCE: 133

```
atgagcattg ttttaataat tgttattgtg gtgattttt taatatgttt tttatattta      60
agcaacagca aagatcccag agtaccagtt gaattaatg                             99
```

<210> SEQ ID NO 134
<211> LENGTH: 33
<212> TYPE: PRT
<213> ORGANISM: Artificial Sequence
<220> FEATURE:
<223> OTHER INFORMATION: Description of Artificial Sequence: Nuclear Envelope target sequence

<400> SEQUENCE: 134

```
Met Ser Ile Val Leu Ile Ile Val Ile Val Val Ile Phe Leu Ile Cys
  1               5                  10                  15

Phe Leu Tyr Leu Ser Asn Ser Lys Asp Pro Arg Val Pro Val Glu Leu
             20                  25                  30

Met
```

<210> SEQ ID NO 135
<211> LENGTH: 246
<212> TYPE: DNA
<213> ORGANISM: Artificial Sequence
<220> FEATURE:
<223> OTHER INFORMATION: Description of Artificial Sequence: Golgi target sequence

<400> SEQUENCE: 135

```
atgaggcttc gggagccgct cctgagcggc agcgccgcga tgccaggcgc gtccctacag      60
cgggcctgcc gcctgctcgt ggccgtctgc gctctgcacc ttggcgtcac cctcgtttac     120
tacctggctg gccgcgacct gagccgcctg ccccaactgg tcggagtctc cacaccgctg     180
cagggcggct cgaacagtgc cgccgccatc gggcagtcct ccggggagct ccggaccgga     240
ggggcc                                                                246
```

<210> SEQ ID NO 136
<211> LENGTH: 82
<212> TYPE: PRT
<213> ORGANISM: Artificial Sequence
<220> FEATURE:
<223> OTHER INFORMATION: Description of Artificial Sequence: Golgi
      target sequence

<400> SEQUENCE: 136

Met Arg Leu Arg Glu Pro Leu Leu Ser Gly Ser Ala Ala Met Pro Gly
 1               5                  10                  15

Ala Ser Leu Gln Arg Ala Cys Arg Leu Leu Val Ala Val Cys Ala Leu
            20                  25                  30

His Leu Gly Val Thr Leu Val Tyr Tyr Leu Ala Gly Arg Asp Leu Ser
        35                  40                  45

Arg Leu Pro Gln Leu Val Gly Val Ser Thr Pro Leu Gln Gly Gly Ser
    50                  55                  60

Asn Ser Ala Ala Ala Ile Gly Gln Ser Ser Gly Glu Leu Arg Thr Gly
65                  70                  75                  80

Gly Ala

<210> SEQ ID NO 137
<211> LENGTH: 150
<212> TYPE: DNA
<213> ORGANISM: Artificial Sequence
<220> FEATURE:
<223> OTHER INFORMATION: Description of Artificial Sequence:
      Endoplasmic reticulum target sequence

<400> SEQUENCE: 137
gaaacaataa gacctataag aataagaaga tgttcttatt ttacatctac agacagcaaa      60
atggcaattc aattaagatc tccctttcca ttagcattac caggaatgtt agctttatta     120
ggatggtggt ggttttcag tagaaaaaaa                                       150

<210> SEQ ID NO 138
<211> LENGTH: 50
<212> TYPE: PRT
<213> ORGANISM: Artificial Sequence
<220> FEATURE:
<223> OTHER INFORMATION: Description of Artificial Sequence: Endoplasmic
      reticulum target sequence

<400> SEQUENCE: 138

Glu Thr Ile Arg Pro Ile Arg Ile Arg Arg Cys Ser Tyr Phe Thr Ser
 1               5                  10                  15

Thr Asp Ser Lys Met Ala Ile Gln Leu Arg Ser Pro Phe Pro Leu Ala
            20                  25                  30

Leu Pro Gly Met Leu Ala Leu Leu Gly Trp Trp Trp Phe Phe Ser Arg
        35                  40                  45

Lys Lys
    50

<210> SEQ ID NO 139
<211> LENGTH: 39
<212> TYPE: DNA
<213> ORGANISM: Artificial Sequence
<220> FEATURE:
<223> OTHER INFORMATION: Description of Artificial Sequence: Nuclear
      Export target sequence

<400> SEQUENCE: 139

```
gccttgcaga agaagctgga ggagctagag cttgatgag                              39
```

<210> SEQ ID NO 140
<211> LENGTH: 13
<212> TYPE: PRT
<213> ORGANISM: Artificial Sequence
<220> FEATURE:
<223> OTHER INFORMATION: Description of Artificial Sequence: Nuclear
      Export target sequence

<400> SEQUENCE: 140

```
Ala Leu Gln Lys Lys Leu Glu Glu Leu Glu Leu Asp Glu
 1               5                  10
```

<210> SEQ ID NO 141
<211> LENGTH: 1024
<212> TYPE: DNA
<213> ORGANISM: Artificial Sequence
<220> FEATURE:
<223> OTHER INFORMATION: Description of Artificial Sequence: Size
      exclusion target sequence

<400> SEQUENCE: 141

```
gccgacctca gtcttgtgga tgcgttgaca gaaccacctc cagaaattga gggagaaata     60
aagcgagact tcatggctgc gctggaggca gagccctatg atgacatcgt gggagaaact   120
gtggagaaaa ctgagtttat tcctctcctg gatggtgatg agaaaaccgg gaactcagag   180
tccaaaaaga aaccctgctt agacactagc caggttgaag gtatcccatc ttctaaacca   240
acactcctag ccaatggtga tcatggaatg gaggggaata acactgcagg gtctccaact   300
gacttccttg aagagagagt ggactatccg gattatcaga gcagccagaa ctggccagaa   360
gatgcaagct tttgtttcca gcctcagcaa gtgttagata ctgaccaggc tgagcccttt   420
aacgagcacc gtgatgatgg tttggcagat ctgctctttg tctccagtgg acccacgaac   480
gcttctgcat ttacagagcg agacaatcct tcagaagaca gttacggtat gcttccctgt   540
gactcatttg cttccacggc tgttgtatct caggagtggt ctgtgggagc cccaaactct   600
ccatgttcag agtcctgtgt ctccccagag gttactatag aaaccctaca gccagcaaca   660
gagctctcca aggcagcaga agtggaatca gtgaaagagc agctgccagc taaagcattg   720
gaaacgatgg cagagcagac cactgatgtg gtgcactctc catccacaga cacaacacca   780
ggcccagaca cagaggcagc actggctaaa gacatagaag agatcaccaa gccagatgtg   840
atattggcaa atgtcacgca gccatctact gaatcggata tgttcctggc ccaggacatg   900
gaactactca caggaacaga ggcagcccac gctaacaata tcatattgcc tacagaacca   960
gacgaatctt caaccaagga tgtagcacca cctatggaag aagaaattgt cccaggcaat  1020
gata                                                               1024
```

<210> SEQ ID NO 142
<211> LENGTH: 566
<212> TYPE: PRT
<213> ORGANISM: Artificial Sequence
<220> FEATURE:
<223> OTHER INFORMATION: Description of Artificial Sequence: Size
      exclusion target sequence

<400> SEQUENCE: 142

```
Ala Asp Leu Ser Leu Val Asp Ala Leu Thr Glu Pro Pro Pro Glu Ile
 1               5                  10                  15

Glu Gly Glu Ile Lys Arg Asp Phe Met Ala Ala Leu Glu Ala Glu Pro
             20                  25                  30
```

-continued

```
Tyr Asp Asp Ile Val Gly Glu Thr Val Glu Lys Thr Glu Phe Ile Pro
         35                  40                  45
Leu Leu Asp Gly Asp Glu Lys Thr Gly Asn Ser Glu Ser Lys Lys Lys
 50                  55                  60
Pro Cys Leu Asp Thr Ser Gln Val Glu Gly Ile Pro Ser Ser Lys Pro
 65                  70                  75                  80
Thr Leu Leu Ala Asn Gly Asp His Gly Met Glu Gly Asn Asn Thr Ala
                 85                  90                  95
Gly Ser Pro Thr Asp Phe Leu Glu Glu Arg Val Asp Tyr Pro Asp Tyr
             100                 105                 110
Gln Ser Ser Gln Asn Trp Pro Glu Asp Ala Ser Phe Cys Phe Gln Pro
         115                 120                 125
Gln Gln Val Leu Asp Thr Asp Gln Ala Glu Pro Phe Asn Glu His Arg
 130                 135                 140
Asp Asp Gly Leu Ala Asp Leu Leu Phe Val Ser Ser Gly Pro Thr Asn
145                 150                 155                 160
Ala Ser Ala Phe Thr Glu Arg Asp Asn Pro Ser Glu Asp Ser Tyr Gly
                165                 170                 175
Met Leu Pro Cys Asp Ser Phe Ala Ser Thr Ala Val Val Ser Gln Glu
            180                 185                 190
Trp Ser Val Gly Ala Pro Asn Ser Pro Cys Ser Glu Ser Cys Val Ser
        195                 200                 205
Pro Glu Val Thr Ile Glu Thr Leu Gln Pro Ala Thr Glu Leu Ser Lys
    210                 215                 220
Ala Ala Glu Val Glu Ser Val Lys Glu Gln Leu Pro Ala Lys Ala Leu
225                 230                 235                 240
Glu Thr Met Ala Glu Gln Thr Thr Asp Val Val His Ser Pro Ser Thr
                245                 250                 255
Asp Thr Thr Pro Gly Pro Asp Thr Glu Ala Ala Leu Ala Lys Asp Ile
            260                 265                 270
Glu Glu Ile Thr Lys Pro Asp Val Ile Leu Ala Asn Val Thr Gln Pro
        275                 280                 285
Ser Thr Glu Ser Asp Met Phe Leu Ala Gln Asp Met Glu Leu Leu Thr
    290                 295                 300
Gly Thr Glu Ala Ala His Ala Asn Asn Ile Ile Leu Pro Thr Glu Pro
305                 310                 315                 320
Asp Glu Ser Ser Thr Lys Asp Val Ala Pro Pro Met Glu Glu Glu Ile
                325                 330                 335
Val Pro Gly Asn Asp Thr Thr Ser Pro Lys Glu Thr Thr Thr Leu
            340                 345                 350
Pro Ile Lys Met Asp Leu Ala Pro Pro Glu Asp Val Leu Leu Thr Lys
        355                 360                 365
Glu Thr Glu Leu Ala Pro Ala Lys Gly Met Val Ser Leu Ser Glu Ile
    370                 375                 380
Glu Glu Ala Leu Ala Lys Asn Asp Val Arg Ser Ala Glu Ile Pro Val
385                 390                 395                 400
Ala Gln Glu Thr Val Val Ser Glu Thr Glu Val Val Leu Ala Thr Glu
                405                 410                 415
Val Val Leu Pro Ser Asp Pro Ile Thr Thr Leu Thr Lys Asp Val Thr
            420                 425                 430
Leu Pro Leu Glu Ala Glu Arg Pro Leu Val Thr Asp Met Thr Pro Ser
        435                 440                 445
```

```
Leu Glu Thr Glu Met Thr Leu Gly Lys Glu Thr Ala Pro Pro Thr Glu
    450                 455                 460

Thr Asn Leu Gly Met Ala Lys Asp Met Ser Pro Leu Pro Glu Ser Glu
465                 470                 475                 480

Val Thr Leu Gly Lys Asp Val Val Ile Leu Pro Glu Thr Lys Val Ala
                485                 490                 495

Glu Phe Asn Asn Val Thr Pro Leu Ser Glu Glu Glu Val Thr Ser Val
            500                 505                 510

Lys Asp Met Ser Pro Ser Ala Glu Thr Glu Ala Pro Leu Ala Lys Asn
        515                 520                 525

Ala Asp Leu His Ser Gly Thr Glu Leu Ile Val Asp Asn Ser Met Ala
    530                 535                 540

Pro Ala Ser Asp Leu Ala Leu Pro Leu Glu Thr Lys Val Ala Thr Val
545                 550                 555                 560

Pro Ile Lys Asp Lys Gly
                565
```

<210> SEQ ID NO 143
<211> LENGTH: 63
<212> TYPE: DNA
<213> ORGANISM: Artificial Sequence
<220> FEATURE:
<223> OTHER INFORMATION: Description of Artificial Sequence: Vesicle
      membrane target sequence

<400> SEQUENCE: 143
atgtgggcaa tcgggattac tgttctggtt atcttcatca tcatcatcat cgtgtgggtt    60
gtc                                                                  63

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Vesicle
      membrane target sequence

<400> SEQUENCE: 144

```
Met Trp Ala Ile Gly Ile Thr Val Leu Val Ile Phe Ile Ile Ile Ile
  1               5                  10                  15

Ile Val Trp Val Val
            20
```

<210> SEQ ID NO 145
<211> LENGTH: 61
<212> TYPE: DNA
<213> ORGANISM: Artificial Sequence
<220> FEATURE:
<223> OTHER INFORMATION: Description of Artificial Sequence: Vesicle
      membrane target sequence

<400> SEQUENCE: 145
atgtgggcga tagggatcag tgtcctggtg atcattgtca tcatcatcat cgtgtggtgt    60
g                                                                   61

<210> SEQ ID NO 146
<211> LENGTH: 20
<212> TYPE: PRT
<213> ORGANISM: Artificial Sequence
<220> FEATURE:
<223> OTHER INFORMATION: Description of Artificial Sequence: Vesicle
      membrane target sequence

<400> SEQUENCE: 146

Met Trp Ala Ile Gly Ile Ser Val Leu Val Ile Ile Val Ile Ile
 1               5                  10                  15

Ile Val Trp Cys
            20

<210> SEQ ID NO 147
<211> LENGTH: 39
<212> TYPE: DNA
<213> ORGANISM: Artificial Sequence
<220> FEATURE:
<223> OTHER INFORMATION: Description of Artificial Sequence: Nuclear
      Export target sequence

<400> SEQUENCE: 147
gacctgcaga agaagctgga ggagctggaa cttgacgag                              39

<210> SEQ ID NO 148
<211> LENGTH: 13
<212> TYPE: PRT
<213> ORGANISM: Artificial Sequence
<220> FEATURE:
<223> OTHER INFORMATION: Description of Artificial Sequence: Nuclear
      Export target sequence

<400> SEQUENCE: 148

Asp Leu Gln Lys Lys Leu Glu Glu Leu Glu Leu Asp Glu
 1               5                  10

<210> SEQ ID NO 149
<211> LENGTH: 9
<212> TYPE: DNA
<213> ORGANISM: Artificial Sequence
<220> FEATURE:
<223> OTHER INFORMATION: Description of Artificial Sequence:
      Peroxisome target sequence

<400> SEQUENCE: 149 tctaaactg                                                               9

<210> SEQ ID NO 150
<211> LENGTH: 3
<212> TYPE: PRT
<213> ORGANISM: Artificial Sequence
<220> FEATURE:
<223> OTHER INFORMATION: Description of Artificial Sequence: Peroxisome
      target sequence

<400> SEQUENCE: 150

Ser Lys Leu
 1

<210> SEQ ID NO 151
<211> LENGTH: 3378
<212> TYPE: DNA
<213> ORGANISM: Mus musculus
<220> FEATURE:
<221> NAME/KEY: CDS
<222> LOCATION: (1)..(3375)

<400> SEQUENCE: 151 atg gcc gac ctc agt ctt gtg gat gcg ttg aca gaa cca cct cca gaa        48
Met Ala Asp Leu Ser Leu Val Asp Ala Leu Thr Glu Pro Pro Pro Glu
 1               5                  10                  15 att gag gga gaa ata aag cga gac ttc atg gct gcg ctg gag gca gag        96

```
Ile Glu Gly Glu Ile Lys Arg Asp Phe Met Ala Ala Leu Glu Ala Glu
             20                  25                  30 ccc tat gat gac atc gtg gga gaa act gtg gag aaa act gag ttt att    144
Pro Tyr Asp Asp Ile Val Gly Glu Thr Val Glu Lys Thr Glu Phe Ile
         35                  40                  45 cct ctc ctg gat ggt gat gag aaa acc ggg aac tca gag tcc aaa aag    192
Pro Leu Leu Asp Gly Asp Glu Lys Thr Gly Asn Ser Glu Ser Lys Lys
 50                  55                  60 aaa ccc tgc tta gac act agc cag gtt gaa ggt atc cca tct tct aaa    240
Lys Pro Cys Leu Asp Thr Ser Gln Val Glu Gly Ile Pro Ser Ser Lys
 65                  70                  75                  80 cca aca ctc cta gcc aat ggt gat cat gga atg gag ggg aat aac act    288
Pro Thr Leu Leu Ala Asn Gly Asp His Gly Met Glu Gly Asn Asn Thr
                 85                  90                  95 gca ggg tct cca act gac ttc ctt gaa gag aga gtg gac tat ccg gat    336
Ala Gly Ser Pro Thr Asp Phe Leu Glu Glu Arg Val Asp Tyr Pro Asp
            100                 105                 110 tat cag agc agc cag aac tgg cca gaa gat gca agc ttt tgt ttc cag    384
Tyr Gln Ser Ser Gln Asn Trp Pro Glu Asp Ala Ser Phe Cys Phe Gln
        115                 120                 125 cct cag caa gtg tta gat act gac cag gct gag ccc ttt aac gag cac    432
Pro Gln Gln Val Leu Asp Thr Asp Gln Ala Glu Pro Phe Asn Glu His
130                 135                 140 cgt gat gat ggt ttg gca gat ctg ctc ttt gtc tcc agt gga ccc acg    480
Arg Asp Asp Gly Leu Ala Asp Leu Leu Phe Val Ser Ser Gly Pro Thr
145                 150                 155                 160 aac gct tct gca ttt aca gag cga gac aat cct tca gaa gac agt tac    528
Asn Ala Ser Ala Phe Thr Glu Arg Asp Asn Pro Ser Glu Asp Ser Tyr
                165                 170                 175 ggt atg ctt ccc tgt gac tca ttt gct tcc acg gct gtt gta tct cag    576
Gly Met Leu Pro Cys Asp Ser Phe Ala Ser Thr Ala Val Val Ser Gln
            180                 185                 190 gag tgg tct gtg gga gcc cca aac tct cca tgt tca gag tcc tgt gtc    624
Glu Trp Ser Val Gly Ala Pro Asn Ser Pro Cys Ser Glu Ser Cys Val
        195                 200                 205 tcc cca gag gtt act ata gaa acc cta cag cca gca aca gag ctc tcc    672
Ser Pro Glu Val Thr Ile Glu Thr Leu Gln Pro Ala Thr Glu Leu Ser
210                 215                 220 aag gca gca gaa gtg gaa tca gtg aaa gag cag ctg cca gct aaa gca    720
Lys Ala Ala Glu Val Glu Ser Val Lys Glu Gln Leu Pro Ala Lys Ala
225                 230                 235                 240 ttg gaa acg atg gca gag cag acc act gat gtg gtg cac tct cca tcc    768
Leu Glu Thr Met Ala Glu Gln Thr Thr Asp Val Val His Ser Pro Ser
                245                 250                 255 aca gac aca aca cca ggc cca gac aca gag gca gca ctg gct aaa gac    816
Thr Asp Thr Thr Pro Gly Pro Asp Thr Glu Ala Ala Leu Ala Lys Asp
            260                 265                 270 ata gaa gag atc acc aag cca gat gtg ata ttg gca aat gtc acg cag    864
Ile Glu Glu Ile Thr Lys Pro Asp Val Ile Leu Ala Asn Val Thr Gln
        275                 280                 285 cca tct act gaa tcg gat atg ttc ctg gcc cag gac atg gaa cta ctc    912
Pro Ser Thr Glu Ser Asp Met Phe Leu Ala Gln Asp Met Glu Leu Leu
290                 295                 300 aca gga aca gag gca gcc cac gct aac aat atc ata ttg cct aca gaa    960
Thr Gly Thr Glu Ala Ala His Ala Asn Asn Ile Ile Leu Pro Thr Glu
305                 310                 315                 320 cca gac gaa tct tca acc aag gat gta gca cca cct atg gaa gaa gaa   1008
Pro Asp Glu Ser Ser Thr Lys Asp Val Ala Pro Pro Met Glu Glu Glu
                325                 330                 335
```

```
att gtc cca ggc aat gat acg aca tcc ccc aaa gaa aca gag aca aca      1056
Ile Val Pro Gly Asn Asp Thr Thr Ser Pro Lys Glu Thr Glu Thr Thr
            340                 345                 350 ctt cca ata aaa atg gac ttg gca cca cct gag gat gtg tta ctt acc      1104
Leu Pro Ile Lys Met Asp Leu Ala Pro Pro Glu Asp Val Leu Leu Thr
            355                 360                 365 aaa gaa aca gaa cta gcc cca gcc aag ggc atg gtt tca ctc tca gaa      1152
Lys Glu Thr Glu Leu Ala Pro Ala Lys Gly Met Val Ser Leu Ser Glu
370                 375                 380 ata gaa gag gct ctg gca aag aat gat gtt cgc tct gca gaa ata cct      1200
Ile Glu Glu Ala Leu Ala Lys Asn Asp Val Arg Ser Ala Glu Ile Pro
385                 390                 395                 400 gtg gct cag gag aca gtg gtc tca gaa aca gag gtg gtc ctg gca aca      1248
Val Ala Gln Glu Thr Val Val Ser Glu Thr Glu Val Val Leu Ala Thr
                405                 410                 415 gaa gtg gta ctg ccc tca gat ccc ata aca aca ttg aca aag gat gtg      1296
Glu Val Val Leu Pro Ser Asp Pro Ile Thr Thr Leu Thr Lys Asp Val
                420                 425                 430 aca ctc ccc tta gaa gca gag aga ccg ttg gtg acg gac atg act cca      1344
Thr Leu Pro Leu Glu Ala Glu Arg Pro Leu Val Thr Asp Met Thr Pro
            435                 440                 445 tct ctg gaa aca gaa atg acc cta ggc aaa gag aca gct cca ccc aca      1392
Ser Leu Glu Thr Glu Met Thr Leu Gly Lys Glu Thr Ala Pro Pro Thr
450                 455                 460 gaa aca aat ttg ggc atg gcc aaa gac atg tct cca ctc cca gaa tca      1440
Glu Thr Asn Leu Gly Met Ala Lys Asp Met Ser Pro Leu Pro Glu Ser
465                 470                 475                 480 gaa gtg act ctg ggc aag gac gtg gtt ata ctt cca gaa aca aag gtg      1488
Glu Val Thr Leu Gly Lys Asp Val Val Ile Leu Pro Glu Thr Lys Val
                485                 490                 495 gct gag ttt aac aat gtg act cca ctt tca gaa gaa gag gta acc tca      1536
Ala Glu Phe Asn Asn Val Thr Pro Leu Ser Glu Glu Glu Val Thr Ser
                500                 505                 510 gtc aag gac atg tct ccg tct gca gaa aca gag gct ccc ctg gct aag      1584
Val Lys Asp Met Ser Pro Ser Ala Glu Thr Glu Ala Pro Leu Ala Lys
            515                 520                 525 aat gct gat ctg cac tca gga aca gag ctg att gtg gac aac agc atg      1632
Asn Ala Asp Leu His Ser Gly Thr Glu Leu Ile Val Asp Asn Ser Met
530                 535                 540 gct cca gcc tcc gat ctt gca ctg ccc ttg gaa aca aaa gta gca aca      1680
Ala Pro Ala Ser Asp Leu Ala Leu Pro Leu Glu Thr Lys Val Ala Thr
545                 550                 555                 560 gtt cca att aaa gac aaa gga act gta cag act gaa gaa aaa cca cgt      1728
Val Pro Ile Lys Asp Lys Gly Thr Val Gln Thr Glu Glu Lys Pro Arg
                565                 570                 575 gaa gac tcc cag tta gca tct atg cag cac aag gga cag tca aca gta      1776
Glu Asp Ser Gln Leu Ala Ser Met Gln His Lys Gly Gln Ser Thr Val
                580                 585                 590 cct cct tgc acg gct tca cca gaa cca gtc aaa gct gca gaa caa atg      1824
Pro Pro Cys Thr Ala Ser Pro Glu Pro Val Lys Ala Ala Glu Gln Met
            595                 600                 605 tct acc tta cca ata gat gca cct tct cca tta gag aac tta gag cag      1872
Ser Thr Leu Pro Ile Asp Ala Pro Ser Pro Leu Glu Asn Leu Glu Gln
610                 615                 620 aag gaa acg cct ggc agc cag cct tct gag cct tgc tca gga gta tcc      1920
Lys Glu Thr Pro Gly Ser Gln Pro Ser Glu Pro Cys Ser Gly Val Ser
625                 630                 635                 640 cgg caa gaa gaa gca aag gct gct gta ggt gtg act gga aat gac atc      1968
Arg Gln Glu Glu Ala Lys Ala Ala Val Gly Val Thr Gly Asn Asp Ile
                645                 650                 655
```

```
act acc ccg cca aac aag gag cca cca cca agc cca gaa aag aaa gca    2016
Thr Thr Pro Pro Asn Lys Glu Pro Pro Pro Ser Pro Glu Lys Lys Ala
            660                 665                 670 aag cct ttg gcc acc act caa cct gca aag act tca aca tcg aaa gcc    2064
Lys Pro Leu Ala Thr Thr Gln Pro Ala Lys Thr Ser Thr Ser Lys Ala
            675                 680                 685 aaa aca cag ccc act tct ctc cct aag caa cca gct ccc acc acc tct    2112
Lys Thr Gln Pro Thr Ser Leu Pro Lys Gln Pro Ala Pro Thr Thr Ser
            690                 695                 700 ggt ggg ttg aat aaa aaa ccc atg agc ctc gcc tca ggc tca gtg cca    2160
Gly Gly Leu Asn Lys Lys Pro Met Ser Leu Ala Ser Gly Ser Val Pro
705                 710                 715                 720 gct gcc cca cac aaa cgc cct gct gct gcc act gct act gcc agg cct    2208
Ala Ala Pro His Lys Arg Pro Ala Ala Ala Thr Ala Thr Ala Arg Pro
                725                 730                 735 tcc acc cta cct gcc aga gac gtg aag cca aag cca att aca gaa gct    2256
Ser Thr Leu Pro Ala Arg Asp Val Lys Pro Lys Pro Ile Thr Glu Ala
            740                 745                 750 aag gtt gcc gaa aag cgg acc tct cca tcc aag cct tca tct gcc cca    2304
Lys Val Ala Glu Lys Arg Thr Ser Pro Ser Lys Pro Ser Ser Ala Pro
            755                 760                 765 gcc ctc aaa cct gga cct aaa acc acc cca acc gtt tca aaa gcc aca    2352
Ala Leu Lys Pro Gly Pro Lys Thr Thr Pro Thr Val Ser Lys Ala Thr
770                 775                 780 tct ccc tca act ctt gtt tcc act gga cca agt agt aga agt cca gct    2400
Ser Pro Ser Thr Leu Val Ser Thr Gly Pro Ser Ser Arg Ser Pro Ala
785                 790                 795                 800 aca act ctg cct aag agg cca acc agc atc aag act gag ggg aaa cct    2448
Thr Thr Leu Pro Lys Arg Pro Thr Ser Ile Lys Thr Glu Gly Lys Pro
            805                 810                 815 gct gat gtc aaa agg atg act gct aag tct gcc tca gct gac ttg agt    2496
Ala Asp Val Lys Arg Met Thr Ala Lys Ser Ala Ser Ala Asp Leu Ser
            820                 825                 830 cgc tca aag acc acc tct gcc agt tct gtg aag aga aac acc act ccc    2544
Arg Ser Lys Thr Thr Ser Ala Ser Ser Val Lys Arg Asn Thr Thr Pro
            835                 840                 845 act ggg gca gca ccc cca gca ggg atg act tcc act cga gtc aag ccc    2592
Thr Gly Ala Ala Pro Pro Ala Gly Met Thr Ser Thr Arg Val Lys Pro
850                 855                 860 atg tct gca cct agc cgc tct tct ggg gct ctt tct gtg gac aag aag    2640
Met Ser Ala Pro Ser Arg Ser Ser Gly Ala Leu Ser Val Asp Lys Lys
865                 870                 875                 880 ccc act tcc act aag cct agc tcc tct gct ccc agg gtg agc cgc ctg    2688
Pro Thr Ser Thr Lys Pro Ser Ser Ser Ala Pro Arg Val Ser Arg Leu
            885                 890                 895 gcc aca act gtt tct gcc cct gac ctg aag agt gtt cgc tcc aag gtc    2736
Ala Thr Thr Val Ser Ala Pro Asp Leu Lys Ser Val Arg Ser Lys Val
            900                 905                 910 ggc tct aca gaa aac atc aaa cac cag cct gga gga ggc cgg gcc aaa    2784
Gly Ser Thr Glu Asn Ile Lys His Gln Pro Gly Gly Gly Arg Ala Lys
            915                 920                 925 gta gag aaa aaa aca gag gca gct acc aca gct ggg aag cct gaa cct    2832
Val Glu Lys Lys Thr Glu Ala Ala Thr Thr Ala Gly Lys Pro Glu Pro
930                 935                 940 aat gca gtc act aaa gca gcc ggc tcc att gcg agt gca cag aaa ccg    2880
Asn Ala Val Thr Lys Ala Ala Gly Ser Ile Ala Ser Ala Gln Lys Pro
945                 950                 955                 960 cct gct ggg aaa gtc cag ata gta tcc aaa aaa gtg agc tac agt cat    2928
Pro Ala Gly Lys Val Gln Ile Val Ser Lys Lys Val Ser Tyr Ser His
```

```
                    965                 970                 975
att caa tcc aag tgt gtt tcc aag gac aat att aag cat gtc cct gga          2976
Ile Gln Ser Lys Cys Val Ser Lys Asp Asn Ile Lys His Val Pro Gly
            980                 985                 990 tgt ggc aat gtt cag att cag aac aag aaa gtg gac ata tcc aag gtc          3024
Cys Gly Asn Val Gln Ile Gln Asn Lys Lys Val Asp Ile Ser Lys Val
        995                1000                1005 tcc tcc aag tgt ggg tcc aaa gct aat atc aag cac aag cct ggt gga          3072
Ser Ser Lys Cys Gly Ser Lys Ala Asn Ile Lys His Lys Pro Gly Gly
   1010                1015                1020 gga gat gtc aag att gaa agt cag aag ttg aac ttc aag gag aag gcc          3120
Gly Asp Val Lys Ile Glu Ser Gln Lys Leu Asn Phe Lys Glu Lys Ala
1025                1030                1035                1040 caa gcc aaa gtg gga tcc ctt gat aac gtt ggc cac ttt cct gca gga          3168
Gln Ala Lys Val Gly Ser Leu Asp Asn Val Gly His Phe Pro Ala Gly
                1045                1050                1055 ggt gcc gtg aag act gag ggc ggt ggc agt gag gcc ctt ccg tgt cca          3216
Gly Ala Val Lys Thr Glu Gly Gly Gly Ser Glu Ala Leu Pro Cys Pro
            1060                1065                1070 ggc ccc ccc gct ggg gag gag cca gtc atc cct gag gct gcg cct gac          3264
Gly Pro Pro Ala Gly Glu Glu Pro Val Ile Pro Glu Ala Ala Pro Asp
        1075                1080                1085 cgt ggc gcc cct act tca gcc agt ggc ctc agt ggc cac acc acc ctg          3312
Arg Gly Ala Pro Thr Ser Ala Ser Gly Leu Ser Gly His Thr Thr Leu
   1090                1095                1100 tca ggg ggt ggt gac caa agg gag ccc cag acc ttg gac agc cag atc          3360
Ser Gly Gly Gly Asp Gln Arg Glu Pro Gln Thr Leu Asp Ser Gln Ile
1105                1110                1115                1120 cag gag aca agc atc taa                                                   3378
Gln Glu Thr Ser Ile
                1125

<210> SEQ ID NO 152
<211> LENGTH: 1125
<212> TYPE: PRT
<213> ORGANISM: Mus musculus

<400> SEQUENCE: 152

Met Ala Asp Leu Ser Leu Val Asp Ala Leu Thr Glu Pro Pro Glu
  1               5                  10                  15

Ile Glu Gly Glu Ile Lys Arg Asp Phe Met Ala Ala Leu Glu Ala Glu
             20                  25                  30

Pro Tyr Asp Asp Ile Val Gly Glu Thr Val Glu Lys Thr Glu Phe Ile
         35                  40                  45

Pro Leu Leu Asp Gly Asp Glu Lys Thr Gly Asn Ser Glu Ser Lys Lys
     50                  55                  60

Lys Pro Cys Leu Asp Thr Ser Gln Val Glu Gly Ile Pro Ser Ser Lys
 65                  70                  75                  80

Pro Thr Leu Leu Ala Asn Gly Asp His Gly Met Glu Gly Asn Asn Thr
                 85                  90                  95

Ala Gly Ser Pro Thr Asp Phe Leu Glu Glu Arg Val Asp Tyr Pro Asp
            100                 105                 110

Tyr Gln Ser Ser Gln Asn Trp Pro Glu Asp Ala Ser Phe Cys Phe Gln
        115                 120                 125

Pro Gln Gln Val Leu Asp Thr Asp Gln Ala Glu Pro Phe Asn Glu His
    130                 135                 140

Arg Asp Asp Gly Leu Ala Asp Leu Leu Phe Val Ser Ser Gly Pro Thr
145                 150                 155                 160
```

```
Asn Ala Ser Ala Phe Thr Glu Arg Asp Asn Pro Ser Glu Asp Ser Tyr
                165                 170                 175
Gly Met Leu Pro Cys Asp Ser Phe Ala Ser Thr Ala Val Val Ser Gln
                180                 185                 190
Glu Trp Ser Val Gly Ala Pro Asn Ser Pro Cys Ser Glu Ser Cys Val
            195                 200                 205
Ser Pro Glu Val Thr Ile Glu Thr Leu Gln Pro Ala Thr Glu Leu Ser
        210                 215                 220
Lys Ala Ala Glu Val Glu Ser Val Lys Glu Gln Leu Pro Ala Lys Ala
225                 230                 235                 240
Leu Glu Thr Met Ala Glu Gln Thr Thr Asp Val Val His Ser Pro Ser
                245                 250                 255
Thr Asp Thr Thr Pro Gly Pro Asp Thr Glu Ala Ala Leu Ala Lys Asp
                260                 265                 270
Ile Glu Glu Ile Thr Lys Pro Asp Val Ile Leu Ala Asn Val Thr Gln
                275                 280                 285
Pro Ser Thr Glu Ser Asp Met Phe Leu Ala Gln Asp Met Glu Leu Leu
        290                 295                 300
Thr Gly Thr Glu Ala Ala His Ala Asn Asn Ile Ile Leu Pro Thr Glu
305                 310                 315                 320
Pro Asp Glu Ser Ser Thr Lys Asp Val Ala Pro Met Glu Glu Glu
                325                 330                 335
Ile Val Pro Gly Asn Asp Thr Thr Ser Pro Lys Glu Thr Glu Thr Thr
                340                 345                 350
Leu Pro Ile Lys Met Asp Leu Ala Pro Pro Glu Asp Val Leu Leu Thr
            355                 360                 365
Lys Glu Thr Glu Leu Ala Pro Ala Lys Gly Met Val Ser Leu Ser Glu
370                 375                 380
Ile Glu Glu Ala Leu Ala Lys Asn Asp Val Arg Ser Ala Glu Ile Pro
385                 390                 395                 400
Val Ala Gln Glu Thr Val Val Ser Glu Thr Glu Val Val Leu Ala Thr
                405                 410                 415
Glu Val Val Leu Pro Ser Asp Pro Ile Thr Thr Leu Thr Lys Asp Val
            420                 425                 430
Thr Leu Pro Leu Glu Ala Glu Arg Pro Leu Val Thr Asp Met Thr Pro
        435                 440                 445
Ser Leu Glu Thr Glu Met Thr Leu Gly Lys Glu Thr Ala Pro Pro Thr
        450                 455                 460
Glu Thr Asn Leu Gly Met Ala Lys Asp Met Ser Pro Leu Pro Glu Ser
465                 470                 475                 480
Glu Val Thr Leu Gly Lys Asp Val Val Ile Leu Pro Glu Thr Lys Val
                485                 490                 495
Ala Glu Phe Asn Asn Val Thr Pro Leu Ser Glu Glu Val Thr Ser
                500                 505                 510
Val Lys Asp Met Ser Pro Ser Ala Glu Thr Glu Ala Pro Leu Ala Lys
            515                 520                 525
Asn Ala Asp Leu His Ser Gly Thr Glu Leu Ile Val Asp Asn Ser Met
            530                 535                 540
Ala Pro Ala Ser Asp Leu Ala Leu Pro Leu Glu Thr Lys Val Ala Thr
545                 550                 555                 560
Val Pro Ile Lys Asp Lys Gly Thr Val Gln Thr Glu Glu Lys Pro Arg
                565                 570                 575
```

-continued

Glu Asp Ser Gln Leu Ala Ser Met Gln His Lys Gly Gln Ser Thr Val
            580                 585                 590

Pro Pro Cys Thr Ala Ser Pro Glu Pro Val Lys Ala Ala Glu Gln Met
            595                 600                 605

Ser Thr Leu Pro Ile Asp Ala Pro Ser Pro Leu Glu Asn Leu Glu Gln
            610                 615                 620

Lys Glu Thr Pro Gly Ser Gln Pro Ser Glu Pro Cys Ser Gly Val Ser
625                 630                 635                 640

Arg Gln Glu Glu Ala Lys Ala Ala Val Gly Val Thr Gly Asn Asp Ile
                645                 650                 655

Thr Thr Pro Pro Asn Lys Glu Pro Pro Ser Pro Glu Lys Lys Ala
            660                 665                 670

Lys Pro Leu Ala Thr Thr Gln Pro Ala Lys Thr Ser Thr Ser Lys Ala
            675                 680                 685

Lys Thr Gln Pro Thr Ser Leu Pro Lys Gln Pro Ala Pro Thr Thr Ser
            690                 695                 700

Gly Gly Leu Asn Lys Lys Pro Met Ser Leu Ala Ser Gly Ser Val Pro
705                 710                 715                 720

Ala Ala Pro His Lys Arg Pro Ala Ala Thr Ala Thr Ala Arg Pro
                725                 730                 735

Ser Thr Leu Pro Ala Arg Asp Val Lys Pro Lys Pro Ile Thr Glu Ala
            740                 745                 750

Lys Val Ala Glu Lys Arg Thr Ser Pro Ser Lys Pro Ser Ser Ala Pro
            755                 760                 765

Ala Leu Lys Pro Gly Pro Lys Thr Thr Pro Thr Val Ser Lys Ala Thr
770                 775                 780

Ser Pro Ser Thr Leu Val Ser Thr Gly Pro Ser Ser Arg Ser Pro Ala
785                 790                 795                 800

Thr Thr Leu Pro Lys Arg Pro Thr Ser Ile Lys Thr Glu Gly Lys Pro
            805                 810                 815

Ala Asp Val Lys Arg Met Thr Ala Lys Ser Ala Ser Ala Asp Leu Ser
            820                 825                 830

Arg Ser Lys Thr Thr Ser Ala Ser Ser Val Lys Arg Asn Thr Thr Pro
            835                 840                 845

Thr Gly Ala Ala Pro Pro Ala Gly Met Thr Ser Thr Arg Val Lys Pro
            850                 855                 860

Met Ser Ala Pro Ser Arg Ser Ser Gly Ala Leu Ser Val Asp Lys Lys
865                 870                 875                 880

Pro Thr Ser Thr Lys Pro Ser Ser Ala Pro Arg Val Ser Arg Leu
                885                 890                 895

Ala Thr Thr Val Ser Ala Pro Asp Leu Lys Ser Val Arg Ser Lys Val
            900                 905                 910

Gly Ser Thr Glu Asn Ile Lys His Gln Pro Gly Gly Gly Arg Ala Lys
            915                 920                 925

Val Glu Lys Lys Thr Glu Ala Ala Thr Thr Ala Gly Lys Pro Glu Pro
            930                 935                 940

Asn Ala Val Thr Lys Ala Ala Gly Ser Ile Ala Ser Ala Gln Lys Pro
945                 950                 955                 960

Pro Ala Gly Lys Val Gln Ile Val Ser Lys Val Ser Tyr Ser His
                965                 970                 975

Ile Gln Ser Lys Cys Val Ser Lys Asp Asn Ile Lys His Val Pro Gly
            980                 985                 990

Cys Gly Asn Val Gln Ile Gln Asn Lys Lys Val Asp Ile Ser Lys Val

```
                995              1000           1005
Ser Ser Lys Cys Gly Ser Lys Ala Asn Ile Lys His Lys Pro Gly Gly
    1010            1015             1020

Gly Asp Val Lys Ile Glu Ser Gln Lys Leu Asn Phe Lys Glu Lys Ala
1025            1030            1035            1040

Gln Ala Lys Val Gly Ser Leu Asp Asn Val Gly His Phe Pro Ala Gly
            1045            1050            1055

Gly Ala Val Lys Thr Glu Gly Gly Ser Glu Ala Leu Pro Cys Pro
            1060            1065            1070

Gly Pro Pro Ala Gly Glu Glu Pro Val Ile Pro Glu Ala Ala Pro Asp
        1075            1080            1085

Arg Gly Ala Pro Thr Ser Ala Ser Gly Leu Ser Gly His Thr Thr Leu
    1090            1095            1100

Ser Gly Gly Gly Asp Gln Arg Glu Pro Gln Thr Leu Asp Ser Gln Ile
1105            1110            1115            1120

Gln Glu Thr Ser Ile
            1125
```

<210> SEQ ID NO 153
<211> LENGTH: 96
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 153
tcatcatccg agctggagc cggagctggc cgatcggctg ttaaatctga aggaaagaga    60
aagtgtgacg aagttgatgg aattgatgaa gtagca                             96

<210> SEQ ID NO 154
<211> LENGTH: 99
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 154
gaagaaggat ccggcacttg ggggtgtaga atgaacaccc tccaagctga gcttgcacag    60
gatttcgtgg acagtagaca tagtacttgc tacttcatc                           99

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 155
tcatcatccg agctgga                                                    18

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 156
gaagaaggat ccggcact                                              18

<210> SEQ ID NO 157
<211> LENGTH: 96
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 157
tcatcatccg gaagaaggaa acgacaaaag cgatcggctg ttaaatctga aggaaagaga      60
aagtgtgacg aagttgatgg aattgatgaa gtagca                               96

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 158
tcatcatccg gaagaagg                                              18

<210> SEQ ID NO 159
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 159
tcatcatccg gaagaaggaa acgacaaaag cgatcgacaa gacttgttga aattgacaac      60

<210> SEQ ID NO 160
<211> LENGTH: 99
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 160
gaagaaggat ccggcacttg ggggtgtaga atgaacaccc tccaagctga gcttgcacag      60
gatttcgtgg acagtagaca tagtactgtt gtcaatttc                            99

<210> SEQ ID NO 161
<211> LENGTH: 84
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 161
tcatcatccg gaagaaggaa acgacaaaag cgatcgtatc aaaaaggaat accagttgaa      60
acagacagcg aagagcaacc ttat                                            84

<210> SEQ ID NO 162
<211> LENGTH: 99
<212> TYPE: DNA
<213> ORGANISM: Artificial Sequence

```
<220> FEATURE:
<223> OTHER INFORMATION: Description of Artificial Sequence:
      oligonucleotide

<400> SEQUENCE: 162
gaagaaggat ccggcacttg ggggtgtaga atgaacaccc tccaagctga gcttgcacag    60
gatttcgtgg acagtagaca tagtactata aggttgctc                           99

<210> SEQ ID NO 163
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 163
tcatcatccg aagaaaacg tatacgtact tacctcaagt cctgcaggcg gatgaaaaga    60

<210> SEQ ID NO 164
<211> LENGTH: 63
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 164
gaagaacgat cgagtaaggt gggaaggaat aggtcgagac atctcaaaac cacttctttt    60
cat                                                                   63

<210> SEQ ID NO 165
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 165
tcatcatccg aagaaaa                                                    18

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 166
gaagaacgat cgagtaag                                                   18

<210> SEQ ID NO 167
<211> LENGTH: 14
<212> TYPE: DNA
<213> ORGANISM: Artificial Sequence
<220> FEATURE:
<223> OTHER INFORMATION: Description of Artificial Sequence:
      Caspase-1,4,5 substrate recognition sequence

<400> SEQUENCE: 167
ttagaacatg acaa                                                       14

<210> SEQ ID NO 168
```

```
<211> LENGTH: 4
<212> TYPE: PRT
<213> ORGANISM: Artificial Sequence
<220> FEATURE:
<223> OTHER INFORMATION: Description of Artificial Sequence:
      Caspase-1,4,5 substrate recognition sequence

<400> SEQUENCE: 168

Leu Glu His Asp
  1

<210> SEQ ID NO 169
<211> LENGTH: 1380
<212> TYPE: DNA
<213> ORGANISM: Artificial Sequence
<220> FEATURE:
<223> OTHER INFORMATION: Description of Artificial Sequence: GFP-HSP27
<221> NAME/KEY: CDS
<222> LOCATION: (1)..(1380)

<400> SEQUENCE: 169
```

| | | | | | | | | | | | | | | | | |
|---|---|---|---|---|---|---|---|---|---|---|---|---|---|---|---|---|
| atg | gtg | agc | aag | ggc | gag | gag | ctg | ttc | acc | ggg | gtg | gtg | ccc | atc | ctg | 48 |
| Met | Val | Ser | Lys | Gly | Glu | Glu | Leu | Phe | Thr | Gly | Val | Val | Pro | Ile | Leu | |
|  1  |     |     |     |  5  |     |     |     |     | 10  |     |     |     |     | 15  |     | |
| gtc | gag | ctg | gac | ggc | gac | gta | aac | ggc | cac | aag | ttc | agc | gtg | tcc | ggc | 96 |
| Val | Glu | Leu | Asp | Gly | Asp | Val | Asn | Gly | His | Lys | Phe | Ser | Val | Ser | Gly | |
|     |     |     | 20  |     |     |     |     | 25  |     |     |     |     | 30  |     |     | |
| gag | ggc | gag | ggc | gat | gcc | acc | tac | ggc | aag | ctg | acc | ctg | aag | ttc | atc | 144 |
| Glu | Gly | Glu | Gly | Asp | Ala | Thr | Tyr | Gly | Lys | Leu | Thr | Leu | Lys | Phe | Ile | |
|     | 35  |     |     |     |     | 40  |     |     |     |     | 45  |     |     |     |     | |
| tgc | acc | acc | ggc | aag | ctg | ccc | gtg | ccc | tgg | ccc | acc | ctc | gtg | acc | acc | 192 |
| Cys | Thr | Thr | Gly | Lys | Leu | Pro | Val | Pro | Trp | Pro | Thr | Leu | Val | Thr | Thr | |
| 50  |     |     |     |     | 55  |     |     |     |     | 60  |     |     |     |     |     | |
| ctg | acc | tac | ggc | gtg | cag | tgc | ttc | agc | cgc | tac | ccc | gac | cac | atg | aag | 240 |
| Leu | Thr | Tyr | Gly | Val | Gln | Cys | Phe | Ser | Arg | Tyr | Pro | Asp | His | Met | Lys | |
| 65  |     |     |     | 70  |     |     |     |     | 75  |     |     |     |     | 80  |     | |
| cag | cac | gac | ttc | ttc | aag | tcc | gcc | atg | ccc | gaa | ggc | tac | gtc | cag | gag | 288 |
| Gln | His | Asp | Phe | Phe | Lys | Ser | Ala | Met | Pro | Glu | Gly | Tyr | Val | Gln | Glu | |
|     |     |     |     | 85  |     |     |     |     | 90  |     |     |     |     | 95  |     | |
| cgc | acc | atc | ttc | ttc | aag | gac | gac | ggc | aac | tac | aag | acc | cgc | gcc | gag | 336 |
| Arg | Thr | Ile | Phe | Phe | Lys | Asp | Asp | Gly | Asn | Tyr | Lys | Thr | Arg | Ala | Glu | |
|     |     |     |     | 100 |     |     |     |     | 105 |     |     |     |     | 110 |     | |
| gtg | aag | ttc | gag | ggc | gac | acc | ctg | gtg | aac | cgc | atc | gag | ctg | aag | ggc | 384 |
| Val | Lys | Phe | Glu | Gly | Asp | Thr | Leu | Val | Asn | Arg | Ile | Glu | Leu | Lys | Gly | |
|     |     |     | 115 |     |     |     |     | 120 |     |     |     |     | 125 |     |     | |
| atc | gac | ttc | aag | gag | gac | ggc | aac | atc | ctg | ggg | cac | aag | ctg | gag | tac | 432 |
| Ile | Asp | Phe | Lys | Glu | Asp | Gly | Asn | Ile | Leu | Gly | His | Lys | Leu | Glu | Tyr | |
|     | 130 |     |     |     |     | 135 |     |     |     |     | 140 |     |     |     |     | |
| aac | tac | aac | agc | cac | aac | gtc | tat | atc | atg | gcc | gac | aag | cag | aag | aac | 480 |
| Asn | Tyr | Asn | Ser | His | Asn | Val | Tyr | Ile | Met | Ala | Asp | Lys | Gln | Lys | Asn | |
| 145 |     |     |     |     | 150 |     |     |     |     | 155 |     |     |     |     | 160 | |
| ggc | atc | aag | gtg | aac | ttc | aag | atc | cgc | cac | aac | atc | gag | gac | ggc | agc | 528 |
| Gly | Ile | Lys | Val | Asn | Phe | Lys | Ile | Arg | His | Asn | Ile | Glu | Asp | Gly | Ser | |
|     |     |     |     | 165 |     |     |     |     | 170 |     |     |     |     | 175 |     | |
| gtg | cag | ctc | gcc | gac | cac | tac | cag | cag | aac | acc | ccc | atc | ggc | gac | ggc | 576 |
| Val | Gln | Leu | Ala | Asp | His | Tyr | Gln | Gln | Asn | Thr | Pro | Ile | Gly | Asp | Gly | |
|     |     |     | 180 |     |     |     |     | 185 |     |     |     |     | 190 |     |     | |
| ccc | gtg | ctg | ctg | ccc | gac | aac | cac | tac | ctg | agc | acc | cag | tcc | gcc | ctg | 624 |
| Pro | Val | Leu | Leu | Pro | Asp | Asn | His | Tyr | Leu | Ser | Thr | Gln | Ser | Ala | Leu | |
|     | 195 |     |     |     |     | 200 |     |     |     |     | 205 |     |     |     |     | |
| agc | aaa | gac | ccc | aac | gag | aag | cgc | gat | cac | atg | gtc | ctg | ctg | gag | ttc | 672 |
| Ser | Lys | Asp | Pro | Asn | Glu | Lys | Arg | Asp | His | Met | Val | Leu | Leu | Glu | Phe | |
| 210 |     |     |     |     | 215 |     |     |     |     | 220 |     |     |     |     |     | |

```
gtg acc gcc gcc ggg atc act ctc ggc atg gac gag ctg tac aag tcc      720
Val Thr Ala Ala Gly Ile Thr Leu Gly Met Asp Glu Leu Tyr Lys Ser
225                 230                 235                 240 gga ctc aga tct cga gcg gcg tcc aga gca gag tca gcc agc atg acc      768
Gly Leu Arg Ser Arg Ala Ala Ser Arg Ala Glu Ser Ala Ser Met Thr
                245                 250                 255 gag cgc cgc gtc ccc ttc tcg ctc ctg cgg ggc ccc agc tgg gac ccc      816
Glu Arg Arg Val Pro Phe Ser Leu Leu Arg Gly Pro Ser Trp Asp Pro
            260                 265                 270 ttc cgc gac tgg tac ccg cat agc cgc ctc ttc gac cag gcc ttc ggg      864
Phe Arg Asp Trp Tyr Pro His Ser Arg Leu Phe Asp Gln Ala Phe Gly
        275                 280                 285 ctg ccc cgg ctg ccg gag gag tgg tcg cag tgg tta ggc ggc agc agc      912
Leu Pro Arg Leu Pro Glu Glu Trp Ser Gln Trp Leu Gly Gly Ser Ser
    290                 295                 300 tgg cca ggc tac gtg cgc ccc ctg ccc ccc gcc gcc atc gag agc ccc      960
Trp Pro Gly Tyr Val Arg Pro Leu Pro Pro Ala Ala Ile Glu Ser Pro
305                 310                 315                 320 gca gtg gcc gcg ccc gcc tac agc cgc gcg ctc agc cgg caa ctc agc     1008
Ala Val Ala Ala Pro Ala Tyr Ser Arg Ala Leu Ser Arg Gln Leu Ser
                325                 330                 335 agc ggg gtc tcg gag atc cgg cac act gcg gac cgc tgg cgc gtg tcc     1056
Ser Gly Val Ser Glu Ile Arg His Thr Ala Asp Arg Trp Arg Val Ser
            340                 345                 350 ctg gat gtc aac cac ttc gcc ccg gac gag ctg acg gtc aag acc aag     1104
Leu Asp Val Asn His Phe Ala Pro Asp Glu Leu Thr Val Lys Thr Lys
        355                 360                 365 gat ggc gtg gtg gag atc acc ggc aag cac gag gag cgg cag gac gag     1152
Asp Gly Val Val Glu Ile Thr Gly Lys His Glu Glu Arg Gln Asp Glu
    370                 375                 380 cat ggc tac atc tcc cgg tgc ttc acg cgg aaa tac acg ctg ccc ccc     1200
His Gly Tyr Ile Ser Arg Cys Phe Thr Arg Lys Tyr Thr Leu Pro Pro
385                 390                 395                 400 ggt gtg gac ccc acc caa gtt tcc tcc tcc ctg tcc cct gag ggc aca     1248
Gly Val Asp Pro Thr Gln Val Ser Ser Ser Leu Ser Pro Glu Gly Thr
                405                 410                 415 ctg acc gtg gag gcc ccc atg ccc aag cta gcc acg cag tcc aac gag     1296
Leu Thr Val Glu Ala Pro Met Pro Lys Leu Ala Thr Gln Ser Asn Glu
            420                 425                 430 atc acc atc cca gtc acc ttc gag tcg cgg gcc cag ctt ggg ggc cca     1344
Ile Thr Ile Pro Val Thr Phe Glu Ser Arg Ala Gln Leu Gly Gly Pro
        435                 440                 445 gaa gct gca aaa tcc gat gag act gcc gcc aag taa                     1380
Glu Ala Ala Lys Ser Asp Glu Thr Ala Ala Lys
    450                 455                 460

<210> SEQ ID NO 170
<211> LENGTH: 459
<212> TYPE: PRT
<213> ORGANISM: Artificial Sequence
<220> FEATURE:
<223> OTHER INFORMATION: Description of Artificial Sequence: GFP-HSP27

<400> SEQUENCE: 170

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45
```

```
Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Ala Ala Ser Arg Ala Glu Ser Ala Ser Met Thr
                245                 250                 255

Glu Arg Arg Val Pro Phe Ser Leu Leu Arg Gly Pro Ser Trp Asp Pro
            260                 265                 270

Phe Arg Asp Trp Tyr Pro His Ser Arg Leu Phe Asp Gln Ala Phe Gly
        275                 280                 285

Leu Pro Arg Leu Pro Glu Glu Trp Ser Gln Trp Leu Gly Gly Ser Ser
    290                 295                 300

Trp Pro Gly Tyr Val Arg Pro Leu Pro Pro Ala Ala Ile Glu Ser Pro
305                 310                 315                 320

Ala Val Ala Ala Pro Ala Tyr Ser Arg Ala Leu Ser Arg Gln Leu Ser
                325                 330                 335

Ser Gly Val Ser Glu Ile Arg His Thr Ala Asp Arg Trp Arg Val Ser
            340                 345                 350

Leu Asp Val Asn His Phe Ala Pro Asp Glu Leu Thr Val Lys Thr Lys
        355                 360                 365

Asp Gly Val Val Glu Ile Thr Gly Lys His Glu Glu Arg Gln Asp Glu
    370                 375                 380

His Gly Tyr Ile Ser Arg Cys Phe Thr Arg Lys Tyr Thr Leu Pro Pro
385                 390                 395                 400

Gly Val Asp Pro Thr Gln Val Ser Ser Ser Leu Ser Pro Glu Gly Thr
                405                 410                 415

Leu Thr Val Glu Ala Pro Met Pro Lys Leu Ala Thr Gln Ser Asn Glu
            420                 425                 430

Ile Thr Ile Pro Val Thr Phe Glu Ser Arg Ala Gln Leu Gly Gly Pro
        435                 440                 445

Glu Ala Ala Lys Ser Asp Glu Thr Ala Ala Lys
    450                 455
```

-continued

<210> SEQ ID NO 171
<211> LENGTH: 2823
<212> TYPE: DNA
<213> ORGANISM: Artificial Sequence
<220> FEATURE:
<223> OTHER INFORMATION: Description of Artificial Sequence: GFP-HSP70
<221> NAME/KEY: CDS
<222> LOCATION: (1)..(2823)

<400> SEQUENCE: 171

| | | | | | | | | | | | | | | | | |
|---|---|---|---|---|---|---|---|---|---|---|---|---|---|---|---|---|
| atg | gtg | agc | aag | ggc | gag | gag | ctg | ttc | acc | ggg | gtg | gtg | ccc | atc | ctg | 48 |
| Met | Val | Ser | Lys | Gly | Glu | Glu | Leu | Phe | Thr | Gly | Val | Val | Pro | Ile | Leu | |
| 1 | | | | 5 | | | | | 10 | | | | | 15 | | |
| gtc | gag | ctg | gac | ggc | gac | gta | aac | ggc | cac | aag | ttc | agc | gtg | tcc | ggc | 96 |
| Val | Glu | Leu | Asp | Gly | Asp | Val | Asn | Gly | His | Lys | Phe | Ser | Val | Ser | Gly | |
| | | | 20 | | | | | 25 | | | | | 30 | | | |
| gag | ggc | gag | ggc | gat | gcc | acc | tac | ggc | aag | ctg | acc | ctg | aag | ttc | atc | 144 |
| Glu | Gly | Glu | Gly | Asp | Ala | Thr | Tyr | Gly | Lys | Leu | Thr | Leu | Lys | Phe | Ile | |
| | 35 | | | | | 40 | | | | | 45 | | | | | |
| tgc | acc | acc | ggc | aag | ctg | ccc | gtg | ccc | tgg | ccc | acc | ctc | gtg | acc | acc | 192 |
| Cys | Thr | Thr | Gly | Lys | Leu | Pro | Val | Pro | Trp | Pro | Thr | Leu | Val | Thr | Thr | |
| 50 | | | | | 55 | | | | | 60 | | | | | | |
| ctg | acc | tac | ggc | gtg | cag | tgc | ttc | agc | cgc | tac | ccc | gac | cac | atg | aag | 240 |
| Leu | Thr | Tyr | Gly | Val | Gln | Cys | Phe | Ser | Arg | Tyr | Pro | Asp | His | Met | Lys | |
| 65 | | | | | 70 | | | | | 75 | | | | | 80 | |
| cag | cac | gac | ttc | ttc | aag | tcc | gcc | atg | ccc | gaa | ggc | tac | gtc | cag | gag | 288 |
| Gln | His | Asp | Phe | Phe | Lys | Ser | Ala | Met | Pro | Glu | Gly | Tyr | Val | Gln | Glu | |
| | | | | 85 | | | | | 90 | | | | | 95 | | |
| cgc | acc | atc | ttc | ttc | aag | gac | gac | ggc | aac | tac | aag | acc | cgc | gcc | gag | 336 |
| Arg | Thr | Ile | Phe | Phe | Lys | Asp | Asp | Gly | Asn | Tyr | Lys | Thr | Arg | Ala | Glu | |
| | | | | 100 | | | | | 105 | | | | | 110 | | |
| gtg | aag | ttc | gag | ggc | gac | acc | ctg | gtg | aac | cgc | atc | gag | ctg | aag | ggc | 384 |
| Val | Lys | Phe | Glu | Gly | Asp | Thr | Leu | Val | Asn | Arg | Ile | Glu | Leu | Lys | Gly | |
| | | | 115 | | | | | 120 | | | | | 125 | | | |
| atc | gac | ttc | aag | gag | gac | ggc | aac | atc | ctg | ggg | cac | aag | ctg | gag | tac | 432 |
| Ile | Asp | Phe | Lys | Glu | Asp | Gly | Asn | Ile | Leu | Gly | His | Lys | Leu | Glu | Tyr | |
| | 130 | | | | | 135 | | | | | 140 | | | | | |
| aac | tac | aac | agc | cac | aac | gtc | tat | atc | atg | gcc | gac | aag | cag | aag | aac | 480 |
| Asn | Tyr | Asn | Ser | His | Asn | Val | Tyr | Ile | Met | Ala | Asp | Lys | Gln | Lys | Asn | |
| 145 | | | | | 150 | | | | | 155 | | | | | 160 | |
| ggc | atc | aag | gtg | aac | ttc | aag | atc | cgc | cac | aac | atc | gag | gac | ggc | agc | 528 |
| Gly | Ile | Lys | Val | Asn | Phe | Lys | Ile | Arg | His | Asn | Ile | Glu | Asp | Gly | Ser | |
| | | | | 165 | | | | | 170 | | | | | 175 | | |
| gtg | cag | ctc | gcc | gac | cac | tac | cag | cag | aac | acc | ccc | atc | ggc | gac | ggc | 576 |
| Val | Gln | Leu | Ala | Asp | His | Tyr | Gln | Gln | Asn | Thr | Pro | Ile | Gly | Asp | Gly | |
| | | | 180 | | | | | 185 | | | | | 190 | | | |
| ccc | gtg | ctg | ctg | ccc | gac | aac | cac | tac | ctg | agc | acc | cag | tcc | gcc | ctg | 624 |
| Pro | Val | Leu | Leu | Pro | Asp | Asn | His | Tyr | Leu | Ser | Thr | Gln | Ser | Ala | Leu | |
| | | 195 | | | | | 200 | | | | | 205 | | | | |
| agc | aaa | gac | ccc | aac | gag | aag | cgc | gat | cac | atg | gtc | ctg | ctg | gag | ttc | 672 |
| Ser | Lys | Asp | Pro | Asn | Glu | Lys | Arg | Asp | His | Met | Val | Leu | Leu | Glu | Phe | |
| | 210 | | | | | 215 | | | | | 220 | | | | | |
| gtg | acc | gcc | gcc | ggg | atc | act | ctc | ggc | atg | gac | gag | ctg | tac | aag | tcc | 720 |
| Val | Thr | Ala | Ala | Gly | Ile | Thr | Leu | Gly | Met | Asp | Glu | Leu | Tyr | Lys | Ser | |
| 225 | | | | | 230 | | | | | 235 | | | | | 240 | |
| gga | atg | tcg | gtg | gtg | gga | ata | gac | ctg | ggc | ttc | cag | agc | tgc | tac | gtc | 768 |
| Gly | Met | Ser | Val | Val | Gly | Ile | Asp | Leu | Gly | Phe | Gln | Ser | Cys | Tyr | Val | |
| | | | | 245 | | | | | 250 | | | | | 255 | | |
| gct | gtg | gcc | cgc | gcc | ggc | ggc | atc | gag | act | atc | gct | aat | gag | tat | agc | 816 |
| Ala | Val | Ala | Arg | Ala | Gly | Gly | Ile | Glu | Thr | Ile | Ala | Asn | Glu | Tyr | Ser | |
| | | | 260 | | | | | 265 | | | | | 270 | | | |

```
gac cgc tgc acg ccg gct tgc att tct ttt ggt cct aag aat cgt tca      864
Asp Arg Cys Thr Pro Ala Cys Ile Ser Phe Gly Pro Lys Asn Arg Ser
        275                 280                 285 att gga gca gca gct aaa agc cag gta att tct aat gca aag aac aca      912
Ile Gly Ala Ala Ala Lys Ser Gln Val Ile Ser Asn Ala Lys Asn Thr
        290                 295                 300 gtc caa gga ttt aaa aga ttc cat ggc cga gca ttc tct gat cca ttt      960
Val Gln Gly Phe Lys Arg Phe His Gly Arg Ala Phe Ser Asp Pro Phe
305                 310                 315                 320 gtg gag gca gaa aaa tct aac ctt gca tat gat att gtg cag tgg cct     1008
Val Glu Ala Glu Lys Ser Asn Leu Ala Tyr Asp Ile Val Gln Trp Pro
                325                 330                 335 aca gga tta aca ggt ata aag gtg aca tat atg gag gaa gag cga aat     1056
Thr Gly Leu Thr Gly Ile Lys Val Thr Tyr Met Glu Glu Glu Arg Asn
                340                 345                 350 ttt acc act gag caa gtg act gcc atg ctt ttg tcc aaa ctg aag gag     1104
Phe Thr Thr Glu Gln Val Thr Ala Met Leu Leu Ser Lys Leu Lys Glu
                355                 360                 365 acc gcc gaa agt gtt ctt aag aag cct gta gtt gac tgt gtt gtt tcg     1152
Thr Ala Glu Ser Val Leu Lys Lys Pro Val Val Asp Cys Val Val Ser
370                 375                 380 gtt cct tgt ttc tat act gat gca gaa aga cga tca gtg atg gat gca     1200
Val Pro Cys Phe Tyr Thr Asp Ala Glu Arg Arg Ser Val Met Asp Ala
385                 390                 395                 400 aca cag att gct ggt ctt aat tgc ttg cga tta atg aat gaa acc act     1248
Thr Gln Ile Ala Gly Leu Asn Cys Leu Arg Leu Met Asn Glu Thr Thr
                405                 410                 415 gca gtt gct ctt gca tat gga atc tat aag cag gat ctt cct cgc tta     1296
Ala Val Ala Leu Ala Tyr Gly Ile Tyr Lys Gln Asp Leu Pro Arg Leu
                420                 425                 430 gaa gag aaa cca aga aat gta gtt ttt gta gac atg ggc cac tct gct     1344
Glu Glu Lys Pro Arg Asn Val Val Phe Val Asp Met Gly His Ser Ala
                435                 440                 445 tat caa gtt tct gta tgt gca ttt aat aga gga aaa ctg aaa gtt ctg     1392
Tyr Gln Val Ser Val Cys Ala Phe Asn Arg Gly Lys Leu Lys Val Leu
                450                 455                 460 gcc act gca ttt gac acg aca ttg gga ggt aga aaa ttt gat gaa gtg     1440
Ala Thr Ala Phe Asp Thr Thr Leu Gly Gly Arg Lys Phe Asp Glu Val
465                 470                 475                 480 tta gta aat cac ttc tgt gaa gaa ttt ggg aag aaa tac aag cta gac     1488
Leu Val Asn His Phe Cys Glu Glu Phe Gly Lys Lys Tyr Lys Leu Asp
                485                 490                 495 att aag tcc aaa atc cgt gca tta tta cga ctc tct cag gag tgt gag     1536
Ile Lys Ser Lys Ile Arg Ala Leu Leu Arg Leu Ser Gln Glu Cys Glu
                500                 505                 510 aaa ctc aag aaa ttg atg agt gca aat gct tca gat ctc cct ttg agc     1584
Lys Leu Lys Lys Leu Met Ser Ala Asn Ala Ser Asp Leu Pro Leu Ser
                515                 520                 525 att gaa tgt ttt atg aat gat gtt gat gta tct gga act atg aat aga     1632
Ile Glu Cys Phe Met Asn Asp Val Asp Val Ser Gly Thr Met Asn Arg
                530                 535                 540 ggc aaa ttt ctg gag atg tgc aat gat ctc tta gct aga gtg gag cca     1680
Gly Lys Phe Leu Glu Met Cys Asn Asp Leu Leu Ala Arg Val Glu Pro
545                 550                 555                 560 cca ctt cgt agt gtt ttg gaa caa acc aag tta aag aaa gaa gat att     1728
Pro Leu Arg Ser Val Leu Glu Gln Thr Lys Leu Lys Lys Glu Asp Ile
                565                 570                 575 tat gca gtg gag ata gtt ggt ggt gct aca cga atc cct gcg gta aaa     1776
Tyr Ala Val Glu Ile Val Gly Gly Ala Thr Arg Ile Pro Ala Val Lys
```

```
                580                    585                    590
gag aag atc agc aaa ttt ttc ggt aaa gaa ctt agt aca aca tta aat    1824
Glu Lys Ile Ser Lys Phe Phe Gly Lys Glu Leu Ser Thr Thr Leu Asn
            595                    600                605 gct gat gaa gct gtc act cga ggc tgt gca ttg cag tgt gcc atc tta    1872
Ala Asp Glu Ala Val Thr Arg Gly Cys Ala Leu Gln Cys Ala Ile Leu
        610                    615                620 tcg cct gct ttc aaa gtc aga gaa ttt tct atc act gat gta gta cca    1920
Ser Pro Ala Phe Lys Val Arg Glu Phe Ser Ile Thr Asp Val Val Pro
625                    630                    635                640 tat cca ata tct ctg aga tgg aat tct cca gct gaa gaa ggg tca agt    1968
Tyr Pro Ile Ser Leu Arg Trp Asn Ser Pro Ala Glu Glu Gly Ser Ser
                645                    650                655 gac tgt gaa gtc ttt tcc aaa aat cat gct gct cct ttc tct aaa gtt    2016
Asp Cys Glu Val Phe Ser Lys Asn His Ala Ala Pro Phe Ser Lys Val
            660                    665                670 ctt aca ttt tat aga aag gaa cct ttc act ctt gag gcc tac tac agc    2064
Leu Thr Phe Tyr Arg Lys Glu Pro Phe Thr Leu Glu Ala Tyr Tyr Ser
        675                    680                685 tct cct cag gat ttg ccc tat cca gat cct gct ata gct cag ttt tca    2112
Ser Pro Gln Asp Leu Pro Tyr Pro Asp Pro Ala Ile Ala Gln Phe Ser
    690                    695                700 gtt cag aaa gtc act cct cag tct gat ggc tcc agt tca aaa gtg aaa    2160
Val Gln Lys Val Thr Pro Gln Ser Asp Gly Ser Ser Ser Lys Val Lys
705                    710                    715                720 gtc aaa gtt cga gta aat gtc cat ggc att ttc agt gtg tcc agt gca    2208
Val Lys Val Arg Val Asn Val His Gly Ile Phe Ser Val Ser Ser Ala
                725                    730                735 tct tta gtg gag gtt cac aag tct gag gaa aat gag gag cca atg gaa    2256
Ser Leu Val Glu Val His Lys Ser Glu Glu Asn Glu Glu Pro Met Glu
            740                    745                750 aca gat cag aat gca aag gag gaa gag aag atg caa gtg gac cag gag    2304
Thr Asp Gln Asn Ala Lys Glu Glu Glu Lys Met Gln Val Asp Gln Glu
        755                    760                765 gaa cca cat gtt gaa gag caa cag cag cag aca cca gca gaa aat aag    2352
Glu Pro His Val Glu Glu Gln Gln Gln Gln Thr Pro Ala Glu Asn Lys
    770                    775                780 gca gag tct gaa gaa atg gag acc tct caa gct gga tcc aag gat aaa    2400
Ala Glu Ser Glu Glu Met Glu Thr Ser Gln Ala Gly Ser Lys Asp Lys
785                    790                    795                800 aag atg gac caa cca ccc caa tgc caa gaa ggc aaa agt gaa gac cag    2448
Lys Met Asp Gln Pro Pro Gln Cys Gln Glu Gly Lys Ser Glu Asp Gln
                805                    810                815 tac tgt gga cct gcc aat cga gaa tca gct ata tgg cag ata gac aga    2496
Tyr Cys Gly Pro Ala Asn Arg Glu Ser Ala Ile Trp Gln Ile Asp Arg
            820                    825                830 gag atg ctc aac ttg tac att gaa aat gag ggt aag atg atc atg cag    2544
Glu Met Leu Asn Leu Tyr Ile Glu Asn Glu Gly Lys Met Ile Met Gln
        835                    840                845 gat aaa ctg gag aag gag cgg aat gat gct aag aac gca gtg gag gaa    2592
Asp Lys Leu Glu Lys Glu Arg Asn Asp Ala Lys Asn Ala Val Glu Glu
    850                    855                860 tat gtg tat gaa atg aga gac aag ctt agt ggt gaa tat gag aag ttt    2640
Tyr Val Tyr Glu Met Arg Asp Lys Leu Ser Gly Glu Tyr Glu Lys Phe
865                    870                    875                880 gtg agt gaa gat gat cgt aac agt ttt act ttg aaa ctg gaa gat act    2688
Val Ser Glu Asp Asp Arg Asn Ser Phe Thr Leu Lys Leu Glu Asp Thr
                885                    890                895 gaa aat tgg ttg tat gag gat gga gaa gac cag cca aag caa gtt tat    2736
Glu Asn Trp Leu Tyr Glu Asp Gly Glu Asp Gln Pro Lys Gln Val Tyr
```

```
                Glu Asn Trp Leu Tyr Glu Asp Gly Asp Gln Pro Lys Gln Val Tyr
                            900                 905                 910 gtt gat aag ttg gct gaa tta aaa aat cta ggt caa cct att aag ata        2784
Val Asp Lys Leu Ala Glu Leu Lys Asn Leu Gly Gln Pro Ile Lys Ile
            915                 920                 925 cgt ttc cag gaa tct gaa gaa cga cca aat tat ttg aag                    2823
Arg Phe Gln Glu Ser Glu Glu Arg Pro Asn Tyr Leu Lys
        930                 935                 940

<210> SEQ ID NO 172
<211> LENGTH: 941
<212> TYPE: PRT
<213> ORGANISM: Artificial Sequence
<220> FEATURE:
<223> OTHER INFORMATION: Description of Artificial Sequence: GFP-HSP70

<400> SEQUENCE: 172

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Met Ser Val Val Gly Ile Asp Leu Gly Phe Gln Ser Cys Tyr Val
                245                 250                 255

Ala Val Ala Arg Ala Gly Gly Ile Glu Thr Ile Ala Asn Glu Tyr Ser
            260                 265                 270

Asp Arg Cys Thr Pro Ala Cys Ile Ser Phe Gly Pro Lys Asn Arg Ser
        275                 280                 285

Ile Gly Ala Ala Ala Lys Ser Gln Val Ile Ser Asn Ala Lys Asn Thr
    290                 295                 300

Val Gln Gly Phe Lys Arg Phe His Gly Arg Ala Phe Ser Asp Pro Phe
```

-continued

```
305                 310                 315                 320
Val Glu Ala Glu Lys Ser Asn Leu Ala Tyr Asp Ile Val Gln Trp Pro
                325                 330                 335
Thr Gly Leu Thr Gly Ile Lys Val Thr Tyr Met Glu Glu Arg Asn
            340                 345                 350
Phe Thr Thr Glu Gln Val Thr Ala Met Leu Leu Ser Lys Leu Lys Glu
                355                 360                 365
Thr Ala Glu Ser Val Leu Lys Lys Pro Val Val Asp Cys Val Val Ser
            370                 375                 380
Val Pro Cys Phe Tyr Thr Asp Ala Glu Arg Arg Ser Val Met Asp Ala
385                 390                 395                 400
Thr Gln Ile Ala Gly Leu Asn Cys Leu Arg Leu Met Asn Glu Thr Thr
                405                 410                 415
Ala Val Ala Leu Ala Tyr Gly Ile Tyr Lys Gln Asp Leu Pro Arg Leu
                420                 425                 430
Glu Glu Lys Pro Arg Asn Val Val Phe Val Asp Met Gly His Ser Ala
            435                 440                 445
Tyr Gln Val Ser Val Cys Ala Phe Asn Arg Gly Lys Leu Lys Val Leu
        450                 455                 460
Ala Thr Ala Phe Asp Thr Thr Leu Gly Gly Arg Lys Phe Asp Glu Val
465                 470                 475                 480
Leu Val Asn His Phe Cys Glu Glu Phe Gly Lys Lys Tyr Lys Leu Asp
                485                 490                 495
Ile Lys Ser Lys Ile Arg Ala Leu Leu Arg Leu Ser Gln Glu Cys Glu
            500                 505                 510
Lys Leu Lys Lys Leu Met Ser Ala Asn Ala Ser Asp Leu Pro Leu Ser
            515                 520                 525
Ile Glu Cys Phe Met Asn Asp Val Asp Val Ser Gly Thr Met Asn Arg
        530                 535                 540
Gly Lys Phe Leu Glu Met Cys Asn Asp Leu Leu Ala Arg Val Glu Pro
545                 550                 555                 560
Pro Leu Arg Ser Val Leu Glu Gln Thr Lys Leu Lys Lys Glu Asp Ile
                565                 570                 575
Tyr Ala Val Glu Ile Val Gly Gly Ala Thr Arg Ile Pro Ala Val Lys
            580                 585                 590
Glu Lys Ile Ser Lys Phe Phe Gly Lys Glu Leu Ser Thr Thr Leu Asn
            595                 600                 605
Ala Asp Glu Ala Val Thr Arg Gly Cys Ala Leu Gln Cys Ala Ile Leu
        610                 615                 620
Ser Pro Ala Phe Lys Val Arg Glu Phe Ser Ile Thr Asp Val Val Pro
625                 630                 635                 640
Tyr Pro Ile Ser Leu Arg Trp Asn Ser Pro Ala Glu Glu Gly Ser Ser
                645                 650                 655
Asp Cys Glu Val Phe Ser Lys Asn His Ala Ala Pro Phe Ser Lys Val
            660                 665                 670
Leu Thr Phe Tyr Arg Lys Glu Pro Phe Thr Leu Glu Ala Tyr Tyr Ser
        675                 680                 685
Ser Pro Gln Asp Leu Pro Tyr Pro Asp Pro Ala Ile Ala Gln Phe Ser
        690                 695                 700
Val Gln Lys Val Thr Pro Gln Ser Asp Gly Ser Ser Ser Lys Val Lys
705                 710                 715                 720
Val Lys Val Arg Val Asn Val His Gly Ile Phe Ser Val Ser Ser Ala
            725                 730                 735
```

```
Ser Leu Val Glu Val His Lys Ser Glu Asn Glu Pro Met Glu
            740                 745                 750

Thr Asp Gln Asn Ala Lys Glu Glu Lys Met Gln Val Asp Gln Glu
            755                 760                 765

Glu Pro His Val Glu Glu Gln Gln Gln Thr Pro Ala Glu Asn Lys
            770                 775                 780

Ala Glu Ser Glu Glu Met Glu Thr Ser Gln Ala Gly Ser Lys Asp Lys
785                 790                 795                 800

Lys Met Asp Gln Pro Pro Gln Cys Gln Glu Gly Lys Ser Glu Asp Gln
                    805                 810                 815

Tyr Cys Gly Pro Ala Asn Arg Glu Ser Ala Ile Trp Gln Ile Asp Arg
                820                 825                 830

Glu Met Leu Asn Leu Tyr Ile Glu Asn Glu Gly Lys Met Ile Met Gln
            835                 840                 845

Asp Lys Leu Glu Lys Glu Arg Asn Asp Ala Lys Asn Ala Val Glu Glu
            850                 855                 860

Tyr Val Tyr Glu Met Arg Asp Lys Leu Ser Gly Glu Tyr Glu Lys Phe
865                 870                 875                 880

Val Ser Glu Asp Asp Arg Asn Ser Phe Thr Leu Lys Leu Glu Asp Thr
                    885                 890                 895

Glu Asn Trp Leu Tyr Glu Asp Gly Glu Asp Gln Pro Lys Gln Val Tyr
                900                 905                 910

Val Asp Lys Leu Ala Glu Leu Lys Asn Leu Gly Gln Pro Ile Lys Ile
            915                 920                 925

Arg Phe Gln Glu Ser Glu Arg Pro Asn Tyr Leu Lys
    930                 935                 940

<210> SEQ ID NO 173
<211> LENGTH: 2674
<212> TYPE: DNA
<213> ORGANISM: Artificial Sequence
<220> FEATURE:
<223> OTHER INFORMATION: Description of Artificial Sequence: GFP-HSC70
<221> NAME/KEY: CDS
<222> LOCATION: (1)..(2673)

<400> SEQUENCE: 173 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
  1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
     50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
 65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110
```

```
gtg aag ttc gag ggc gac acc ctg gtg aac cgc atc gag ctg aag ggc        384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac        432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac        480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc        528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc        576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg        624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc        672
Ser Lys Asp Pro Asn Glu Lys Arg Asp His Met Val Leu Leu Glu Phe
    210                 215                 220 gtg acc gcc gcc ggg atc act ctc ggc atg gac gag ctg tac aag tcc        720
Val Thr Ala Ala Gly Ile Thr Leu Gly Met Asp Glu Leu Tyr Lys Ser
225                 230                 235                 240 gga ctc aga tct atg tcc aag gga cct gca gtt ggt att gat ctt ggc        768
Gly Leu Arg Ser Met Ser Lys Gly Pro Ala Val Gly Ile Asp Leu Gly
                245                 250                 255 acc acc tac tct tgt gtg ggt gtt ttc cag cac gga aaa gtc gag ata        816
Thr Thr Tyr Ser Cys Val Gly Val Phe Gln His Gly Lys Val Glu Ile
            260                 265                 270 att gcc aat gat cag gga aac cga acc act cca agc tat gtc gcc ttt        864
Ile Ala Asn Asp Gln Gly Asn Arg Thr Thr Pro Ser Tyr Val Ala Phe
        275                 280                 285 acg gac act gaa cgg ttg atc ggt gat gcc gca aag aat caa gtt gca        912
Thr Asp Thr Glu Arg Leu Ile Gly Asp Ala Ala Lys Asn Gln Val Ala
    290                 295                 300 atg aac ccc acc aac aca gtt ttt gat gcc aaa cgt ctg att gga cgc        960
Met Asn Pro Thr Asn Thr Val Phe Asp Ala Lys Arg Leu Ile Gly Arg
305                 310                 315                 320 aga ttt gat gat gct gtt gtc cag tct gat atg aaa cat tgg ccc ttt       1008
Arg Phe Asp Asp Ala Val Val Gln Ser Asp Met Lys His Trp Pro Phe
                325                 330                 335 atg gtg gtg aat gat gct ggc agg ccc aag gtc caa gta gaa tac aag       1056
Met Val Val Asn Asp Ala Gly Arg Pro Lys Val Gln Val Glu Tyr Lys
            340                 345                 350 gga gag acc aaa agc ttc tat cca gag gag gtg tct tct atg gtt ctg       1104
Gly Glu Thr Lys Ser Phe Tyr Pro Glu Glu Val Ser Ser Met Val Leu
        355                 360                 365 aca aag atg aag gaa att gca gaa gcc tac ctt ggg aag act gtt acc       1152
Thr Lys Met Lys Glu Ile Ala Glu Ala Tyr Leu Gly Lys Thr Val Thr
    370                 375                 380 aat gct gtg gtc aca gtg cca gct tac ttt aat gac tct cag cgt cag       1200
Asn Ala Val Val Thr Val Pro Ala Tyr Phe Asn Asp Ser Gln Arg Gln
385                 390                 395                 400 gct acc aaa gat gct gga act att gct ggt ctc aat gta ctt aga att       1248
Ala Thr Lys Asp Ala Gly Thr Ile Ala Gly Leu Asn Val Leu Arg Ile
                405                 410                 415 att aat gag cca act gct gct gct att gct tac ggc tta gac aaa aag       1296
Ile Asn Glu Pro Thr Ala Ala Ala Ile Ala Tyr Gly Leu Asp Lys Lys
```

-continued

| | | | |
|---|---|---|---|
| gtt gga gca gaa aga aac gtg ctc atc ttt gac ctg gga ggt ggc act<br>Val Gly Ala Glu Arg Asn Val Leu Ile Phe Asp Leu Gly Gly Gly Thr<br>435                    440                    445 | 1344 |
| ttt gat gtg tca atc ctc act att gag gat gga atc ttt gag gtc aag<br>Phe Asp Val Ser Ile Leu Thr Ile Glu Asp Gly Ile Phe Glu Val Lys<br>450                    455                    460 | 1392 |
| tct aca gct gga gac acc cac ttg ggt gga gaa gat ttt gac aac cga<br>Ser Thr Ala Gly Asp Thr His Leu Gly Gly Glu Asp Phe Asp Asn Arg<br>465                    470                    475                    480 | 1440 |
| atg gtc aac cat ttt att gct gag ttt aag cgc aag cat aag aag gac<br>Met Val Asn His Phe Ile Ala Glu Phe Lys Arg Lys His Lys Lys Asp<br>                    485                    490                    495 | 1488 |
| atc agt gag aac aag aga gct gta aga cgc ctc cgt act gct tgt gaa<br>Ile Ser Glu Asn Lys Arg Ala Val Arg Arg Leu Arg Thr Ala Cys Glu<br>                    500                    505                    510 | 1536 |
| cgt gct aag cgt acc ctc tct tcc agc acc cag gcc agt att gag atc<br>Arg Ala Lys Arg Thr Leu Ser Ser Ser Thr Gln Ala Ser Ile Glu Ile<br>                    515                    520                    525 | 1584 |
| gat tct ctc tat gaa gga atc gac ttc tat acc tcc att acc cgt gcc<br>Asp Ser Leu Tyr Glu Gly Ile Asp Phe Tyr Thr Ser Ile Thr Arg Ala<br>530                    535                    540 | 1632 |
| cga ttt gaa gaa ctg aat gct gac ctg ttc cgt ggc acc ctg gac cca<br>Arg Phe Glu Glu Leu Asn Ala Asp Leu Phe Arg Gly Thr Leu Asp Pro<br>545                    550                    555                    560 | 1680 |
| gta gag aaa gcc ctt cga gat gcc aaa cta gac aag tca cag att cat<br>Val Glu Lys Ala Leu Arg Asp Ala Lys Leu Asp Lys Ser Gln Ile His<br>                    565                    570                    575 | 1728 |
| gat att gtc ctg gtt ggt ggt tct act cgt atc ccc aag att cag aag<br>Asp Ile Val Leu Val Gly Gly Ser Thr Arg Ile Pro Lys Ile Gln Lys<br>                    580                    585                    590 | 1776 |
| ctt ctc caa gac ttc ttc aat gga aaa gaa ctg aat aag agc atc aac<br>Leu Leu Gln Asp Phe Phe Asn Gly Lys Glu Leu Asn Lys Ser Ile Asn<br>                    595                    600                    605 | 1824 |
| cct gat gaa gct gtt gct tat ggt gca gct gtc cag gca gcc atc ttg<br>Pro Asp Glu Ala Val Ala Tyr Gly Ala Ala Val Gln Ala Ala Ile Leu<br>610                    615                    620 | 1872 |
| tct gga gac aag tct gag aat gtt caa gat ttg ctg ctc ttg gat gtc<br>Ser Gly Asp Lys Ser Glu Asn Val Gln Asp Leu Leu Leu Leu Asp Val<br>625                    630                    635                    640 | 1920 |
| act cct ctt tcc ctt ggt att gaa act gct ggt gga gtc atg act gtc<br>Thr Pro Leu Ser Leu Gly Ile Glu Thr Ala Gly Gly Val Met Thr Val<br>                    645                    650                    655 | 1968 |
| ctc atc aag cgt aat acc acc att cct acc aag cag aca cag acc ttc<br>Leu Ile Lys Arg Asn Thr Thr Ile Pro Thr Lys Gln Thr Gln Thr Phe<br>                    660                    665                    670 | 2016 |
| act acc tat tct gac aac cag cct ggt gtg ctt att cag gtt tat gaa<br>Thr Thr Tyr Ser Asp Asn Gln Pro Gly Val Leu Ile Gln Val Tyr Glu<br>                    675                    680                    685 | 2064 |
| ggc gag cgt gcc atg aca aag gat aac aac ctg ctt ggc aag ttt gaa<br>Gly Glu Arg Ala Met Thr Lys Asp Asn Asn Leu Leu Gly Lys Phe Glu<br>                    690                    695                    700 | 2112 |
| ctc aca ggc ata cct cct gca ccc cga ggt gtt cct cag att gaa gtc<br>Leu Thr Gly Ile Pro Pro Ala Pro Arg Gly Val Pro Gln Ile Glu Val<br>705                    710                    715                    720 | 2160 |
| act ttt gac att gat gcc aat ggt ata ctc aat gtc tct gct gtg gac<br>Thr Phe Asp Ile Asp Ala Asn Gly Ile Leu Asn Val Ser Ala Val Asp<br>                    725                    730                    735 | 2208 |
| aag agt acg gga aaa gag aac aag att act atc act aat gac aag ggc | 2256 |

-continued

```
Lys Ser Thr Gly Lys Glu Asn Lys Ile Thr Ile Thr Asn Asp Lys Gly
            740                 745                 750 cgt ttg agc aag gaa gac att gaa cgt atg gtc cag gaa gct gag aag      2304
Arg Leu Ser Lys Glu Asp Ile Glu Arg Met Val Gln Glu Ala Glu Lys
            755                 760                 765 tac aaa gct gaa gat gag aag cag agg gac aag gtg tca tcc aag aat      2352
Tyr Lys Ala Glu Asp Glu Lys Gln Arg Asp Lys Val Ser Ser Lys Asn
        770                 775                 780 tca ctt gag tcc tat gcc ttc aac atg aaa gca act gtt gaa gat gag      2400
Ser Leu Glu Ser Tyr Ala Phe Asn Met Lys Ala Thr Val Glu Asp Glu
785                 790                 795                 800 aaa ctt caa ggc aag att aac gat gag gac aaa cag aag att ctg gac      2448
Lys Leu Gln Gly Lys Ile Asn Asp Glu Asp Lys Gln Lys Ile Leu Asp
                805                 810                 815 aag tgt aat gaa att atc aac tgg ctt gat aag aat cag act gct gag      2496
Lys Cys Asn Glu Ile Ile Asn Trp Leu Asp Lys Asn Gln Thr Ala Glu
            820                 825                 830 aag gaa gaa ttt gaa cat caa cag aaa gag ctg gag aaa gtt tgc aac      2544
Lys Glu Glu Phe Glu His Gln Gln Lys Glu Leu Glu Lys Val Cys Asn
        835                 840                 845 ccc atc atc acc aag ctg tac cag agt gca gga ggc atg cca gga gga      2592
Pro Ile Ile Thr Lys Leu Tyr Gln Ser Ala Gly Gly Met Pro Gly Gly
    850                 855                 860 atg cct ggg gga ttt cct ggt ggt gga gct cct ccc tct ggt ggt gct      2640
Met Pro Gly Gly Phe Pro Gly Gly Gly Ala Pro Pro Ser Gly Gly Ala
865                 870                 875                 880 tcc tca ggg ccc acc att gaa gag gtt gat taa g                        2674
Ser Ser Gly Pro Thr Ile Glu Glu Val Asp
                885                 890
```

<210> SEQ ID NO 174
<211> LENGTH: 890
<212> TYPE: PRT
<213> ORGANISM: Artificial Sequence
<220> FEATURE:
<223> OTHER INFORMATION: Description of Artificial Sequence: GFP-HSC70

<400> SEQUENCE: 174

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

-continued

```
Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Met Ser Lys Gly Pro Ala Val Gly Ile Asp Leu Gly
                245                 250                 255

Thr Thr Tyr Ser Cys Val Gly Val Phe Gln His Gly Lys Val Glu Ile
                260                 265                 270

Ile Ala Asn Asp Gln Gly Asn Arg Thr Thr Pro Ser Tyr Val Ala Phe
                275                 280                 285

Thr Asp Thr Glu Arg Leu Ile Gly Asp Ala Ala Lys Asn Gln Val Ala
            290                 295                 300

Met Asn Pro Thr Asn Thr Val Phe Asp Ala Lys Arg Leu Ile Gly Arg
305                 310                 315                 320

Arg Phe Asp Asp Ala Val Val Gln Ser Asp Met Lys His Trp Pro Phe
                325                 330                 335

Met Val Val Asn Asp Ala Gly Arg Pro Lys Val Gln Val Glu Tyr Lys
                340                 345                 350

Gly Glu Thr Lys Ser Phe Tyr Pro Glu Glu Val Ser Ser Met Val Leu
                355                 360                 365

Thr Lys Met Lys Glu Ile Ala Glu Ala Tyr Leu Gly Lys Thr Val Thr
            370                 375                 380

Asn Ala Val Val Thr Val Pro Ala Tyr Phe Asn Asp Ser Gln Arg Gln
385                 390                 395                 400

Ala Thr Lys Asp Ala Gly Thr Ile Ala Gly Leu Asn Val Leu Arg Ile
                405                 410                 415

Ile Asn Glu Pro Thr Ala Ala Ile Ala Tyr Gly Leu Asp Lys Lys
                420                 425                 430

Val Gly Ala Glu Arg Asn Val Leu Ile Phe Asp Leu Gly Gly Gly Thr
                435                 440                 445

Phe Asp Val Ser Ile Leu Thr Ile Glu Asp Gly Ile Phe Glu Val Lys
    450                 455                 460

Ser Thr Ala Gly Asp Thr His Leu Gly Gly Glu Asp Phe Asp Asn Arg
465                 470                 475                 480

Met Val Asn His Phe Ile Ala Glu Phe Lys Arg Lys His Lys Lys Asp
                485                 490                 495

Ile Ser Glu Asn Lys Arg Ala Val Arg Arg Leu Arg Thr Ala Cys Glu
                500                 505                 510

Arg Ala Lys Arg Thr Leu Ser Ser Ser Thr Gln Ala Ser Ile Glu Ile
            515                 520                 525

Asp Ser Leu Tyr Glu Gly Ile Asp Phe Tyr Thr Ser Ile Thr Arg Ala
    530                 535                 540

Arg Phe Glu Glu Leu Asn Ala Asp Leu Phe Arg Gly Thr Leu Asp Pro
545                 550                 555                 560

Val Glu Lys Ala Leu Arg Asp Ala Lys Leu Asp Lys Ser Gln Ile His
                565                 570                 575

Asp Ile Val Leu Val Gly Gly Ser Thr Arg Ile Pro Lys Ile Gln Lys
```

```
              580                 585                 590
Leu Leu Gln Asp Phe Phe Asn Gly Lys Glu Leu Asn Lys Ser Ile Asn
        595                 600                 605

Pro Asp Glu Ala Val Ala Tyr Gly Ala Val Gln Ala Ala Ile Leu
    610                 615                 620

Ser Gly Asp Lys Ser Glu Asn Val Gln Asp Leu Leu Leu Asp Val
625                 630                 635                 640

Thr Pro Leu Ser Leu Gly Ile Glu Thr Ala Gly Val Met Thr Val
                645                 650                 655

Leu Ile Lys Arg Asn Thr Thr Ile Pro Thr Lys Gln Thr Gln Thr Phe
                660                 665                 670

Thr Thr Tyr Ser Asp Asn Gln Pro Gly Val Leu Ile Gln Val Tyr Glu
            675                 680                 685

Gly Glu Arg Ala Met Thr Lys Asp Asn Asn Leu Leu Gly Lys Phe Glu
            690                 695                 700

Leu Thr Gly Ile Pro Pro Ala Pro Arg Gly Val Pro Gln Ile Glu Val
705                 710                 715                 720

Thr Phe Asp Ile Asp Ala Asn Gly Ile Leu Asn Val Ser Ala Val Asp
                725                 730                 735

Lys Ser Thr Gly Lys Glu Asn Lys Ile Thr Ile Thr Asn Asp Lys Gly
                740                 745                 750

Arg Leu Ser Lys Glu Asp Ile Glu Arg Met Val Gln Glu Ala Glu Lys
            755                 760                 765

Tyr Lys Ala Glu Asp Glu Lys Gln Arg Asp Lys Val Ser Ser Lys Asn
    770                 775                 780

Ser Leu Glu Ser Tyr Ala Phe Asn Met Lys Ala Thr Val Glu Asp Glu
785                 790                 795                 800

Lys Leu Gln Gly Lys Ile Asn Asp Glu Asp Lys Gln Lys Ile Leu Asp
                805                 810                 815

Lys Cys Asn Glu Ile Ile Asn Trp Leu Asp Lys Asn Gln Thr Ala Glu
                820                 825                 830

Lys Glu Glu Phe Glu His Gln Gln Lys Glu Leu Glu Lys Val Cys Asn
            835                 840                 845

Pro Ile Ile Thr Lys Leu Tyr Gln Ser Ala Gly Gly Met Pro Gly Gly
    850                 855                 860

Met Pro Gly Gly Phe Pro Gly Gly Ala Pro Ser Gly Gly Ala
865                 870                 875                 880

Ser Ser Gly Pro Thr Ile Glu Glu Val Asp
                885                 890

<210> SEQ ID NO 175
<211> LENGTH: 2458
<212> TYPE: DNA
<213> ORGANISM: Artificial Sequence
<220> FEATURE:
<223> OTHER INFORMATION: Description of Artificial Sequence: GFP-HSF1
<221> NAME/KEY: CDS
<222> LOCATION: (1)..(2349)

<400> SEQUENCE: 175 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30
```

```
gag ggc gag ggc gat gcc acc tac ggc aag ctg acc ctg aag ttc atc      144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc      192
Cys Thr Thr Gly Lys Leu Pro Val Pro Trp Pro Thr Leu Val Thr Thr
 50                  55                  60 ctg acc tac ggc gtg cag tgc ttc agc cgc tac ccc gac cac atg aag      240
Leu Thr Tyr Gly Val Gln Cys Phe Ser Arg Tyr Pro Asp His Met Lys
 65                  70                  75                  80 cag cac gac ttc ttc aag tcc gcc atg ccc gaa ggc tac gtc cag gag      288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag      336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc      384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac      432
Ile Asp Phe Lys Glu Asp Gly Asn Ile Leu Gly His Lys Leu Glu Tyr
130                 135                 140 aac tac aac agc cac aac gtc tat atc atg gcc gac aag cag aag aac      480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc      528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc      576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg      624
Pro Val Leu Leu Pro Asp Asn His Tyr Leu Ser Thr Gln Ser Ala Leu
        195                 200                 205 agc aaa gac ccc aac gag aag cgc gat cac atg gtc ctg ctg gag ttc      672
Ser Lys Asp Pro Asn Glu Lys Arg Asp His Met Val Leu Leu Glu Phe
210                 215                 220 gtg acc gcc gcc ggg atc act ctc ggc atg gac gag ctg tac aag tcc      720
Val Thr Ala Ala Gly Ile Thr Leu Gly Met Asp Glu Leu Tyr Lys Ser
225                 230                 235                 240 gga ctc aga tct cga gct caa gct tcg aat tct gca gtc gag atg gat      768
Gly Leu Arg Ser Arg Ala Gln Ala Ser Asn Ser Ala Val Glu Met Asp
                245                 250                 255 ctg ccc gtg ggc ccc ggc gcg gcg ggg ccc agc aac gtc ccg gcc ttc      816
Leu Pro Val Gly Pro Gly Ala Ala Gly Pro Ser Asn Val Pro Ala Phe
            260                 265                 270 ctg acc aag ctg tgg acc ctc gtg agc gac ccg gac acc gac gcg ctc      864
Leu Thr Lys Leu Trp Thr Leu Val Ser Asp Pro Asp Thr Asp Ala Leu
        275                 280                 285 atc tgc tgg agc ccg agc ggg aac agc ttc cac gtg ttc gac cag ggc      912
Ile Cys Trp Ser Pro Ser Gly Asn Ser Phe His Val Phe Asp Gln Gly
290                 295                 300 cag ttt gcc aag gag gtg ctg ccc aag tac ttc aag cac aac aac atg      960
Gln Phe Ala Lys Glu Val Leu Pro Lys Tyr Phe Lys His Asn Asn Met
305                 310                 315                 320 gcc agc ttc gtg cgg cag ctc aac atg tat ggc ttc cgg aaa gtg gtc     1008
Ala Ser Phe Val Arg Gln Leu Asn Met Tyr Gly Phe Arg Lys Val Val
                325                 330                 335 cac atc gag cag ggc ggc ctg gtc aag cca gag aga gac gac acg gag     1056
His Ile Glu Gln Gly Gly Leu Val Lys Pro Glu Arg Asp Asp Thr Glu
            340                 345                 350
```

```
ttc cag cac cca tgc ttc ctg cgt ggc cag gag cag ctc ctt gag aac    1104
Phe Gln His Pro Cys Phe Leu Arg Gly Gln Glu Gln Leu Leu Glu Asn
        355                 360                 365 atc aag agg aaa gtg acc agt gtg tcc acc ctg aag agt gaa gac ata    1152
Ile Lys Arg Lys Val Thr Ser Val Ser Thr Leu Lys Ser Glu Asp Ile
370                 375                 380 aag atc cgc cag gac agc gtc acc aag ctg ctg acg gac gtg cag ctg    1200
Lys Ile Arg Gln Asp Ser Val Thr Lys Leu Leu Thr Asp Val Gln Leu
385                 390                 395                 400 atg aag ggg aag cag gag tgc atg gac tcc aag ctc ctg gcc atg aag    1248
Met Lys Gly Lys Gln Glu Cys Met Asp Ser Lys Leu Leu Ala Met Lys
                405                 410                 415 cat gag aat gag gct ctg tgg cgg gag gtg gcc agc ctt cgg cag aag    1296
His Glu Asn Glu Ala Leu Trp Arg Glu Val Ala Ser Leu Arg Gln Lys
                420                 425                 430 cat gcc cag caa cag aaa gtc gtc aac aag ctc att cag ttc ctg atc    1344
His Ala Gln Gln Gln Lys Val Val Asn Lys Leu Ile Gln Phe Leu Ile
                435                 440                 445 tca ctg gtg cag tca aac cgg atc ctg ggg gtg aag aga aag atc ccc    1392
Ser Leu Val Gln Ser Asn Arg Ile Leu Gly Val Lys Arg Lys Ile Pro
        450                 455                 460 ctg atg ctg aac gac agt ggc tca gca cat tcc atg ccc aag tat agc    1440
Leu Met Leu Asn Asp Ser Gly Ser Ala His Ser Met Pro Lys Tyr Ser
465                 470                 475                 480 cgg cag ttc tcc ctg gag cac gtc cac ggc tcg ggc ccc tac tcg gcc    1488
Arg Gln Phe Ser Leu Glu His Val His Gly Ser Gly Pro Tyr Ser Ala
                485                 490                 495 ccc tcc cca gcc tac agc agc tcc agc ctc tac gcc cct gat gct gtg    1536
Pro Ser Pro Ala Tyr Ser Ser Ser Ser Leu Tyr Ala Pro Asp Ala Val
                500                 505                 510 gcc agc tct gga ccc atc atc tcc gac atc acc gag ctg gct cct gcc    1584
Ala Ser Ser Gly Pro Ile Ile Ser Asp Ile Thr Glu Leu Ala Pro Ala
                515                 520                 525 agc ccc atg gcc tcc ccc ggc ggg agc ata gac gag agg ccc cta tcc    1632
Ser Pro Met Ala Ser Pro Gly Gly Ser Ile Asp Glu Arg Pro Leu Ser
                530                 535                 540 agc agc ccc ctg gtg cgt gtc aag gag gag ccc ccc agc ccg cct cag    1680
Ser Ser Pro Leu Val Arg Val Lys Glu Glu Pro Pro Ser Pro Pro Gln
545                 550                 555                 560 agc ccc cgg gta gag gag gcg agt ccc ggg cgc cca tct tcc gtg gac    1728
Ser Pro Arg Val Glu Glu Ala Ser Pro Gly Arg Pro Ser Ser Val Asp
                565                 570                 575 acc ctc ttg tcc ccg acc gcc ctc att gac tcc atc ctg cgg gag agt    1776
Thr Leu Leu Ser Pro Thr Ala Leu Ile Asp Ser Ile Leu Arg Glu Ser
                580                 585                 590 gaa cct gcc ccc gcc tcc gtc aca gcc ctc acg gac gcc agg ggc cac    1824
Glu Pro Ala Pro Ala Ser Val Thr Ala Leu Thr Asp Ala Arg Gly His
                595                 600                 605 acg gac acc gag ggc cgg cct ccc tcc ccc ccg ccc acc tcc acc cct    1872
Thr Asp Thr Glu Gly Arg Pro Pro Ser Pro Pro Pro Thr Ser Thr Pro
610                 615                 620 gaa aag tgc ctc agc gta gcc tgc ctg gac aag aat gag ctc agt gac    1920
Glu Lys Cys Leu Ser Val Ala Cys Leu Asp Lys Asn Glu Leu Ser Asp
625                 630                 635                 640 cac ttg gat gct atg gac tcc aac ctg gat aac ctg cag acc atg ctg    1968
His Leu Asp Ala Met Asp Ser Asn Leu Asp Asn Leu Gln Thr Met Leu
                645                 650                 655 agc agc cac ggc ttc agc gtg gac acc agt gcc ctg ctg gac ctg ttc    2016
Ser Ser His Gly Phe Ser Val Asp Thr Ser Ala Leu Leu Asp Leu Phe
```

-continued

```
                   660                     665                      670
agc ccc tcg gtg acc gtg ccc gac atg agc ctg cct gac ctt gac agc    2064
Ser Pro Ser Val Thr Val Pro Asp Met Ser Leu Pro Asp Leu Asp Ser
        675                     680                     685 agc ctg gcc agt atc caa gag ctc ctg tct ccc cag gag ccc ccc agg    2112
Ser Leu Ala Ser Ile Gln Glu Leu Leu Ser Pro Gln Glu Pro Pro Arg
    690                     695                     700 cct ccc gag gca gag aac agc agc ccg gat tca ggg aag cag ctg gtg    2160
Pro Pro Glu Ala Glu Asn Ser Ser Pro Asp Ser Gly Lys Gln Leu Val
705                     710                     715                     720 cac tac aca gcg cag ccg ctg ttc ctg ctg gac ccc ggc tcc gtg gac    2208
His Tyr Thr Ala Gln Pro Leu Phe Leu Leu Asp Pro Gly Ser Val Asp
                725                     730                     735 acc ggg agc aac gac ctg ccg gtg ctg ttt gag ctg gga gag ggc tcc    2256
Thr Gly Ser Asn Asp Leu Pro Val Leu Phe Glu Leu Gly Glu Gly Ser
            740                     745                     750 tac ttc tcc gaa ggg gac ggc ttc gcc gag gac ccc acc atc tcc ctg    2304
Tyr Phe Ser Glu Gly Asp Gly Phe Ala Glu Asp Pro Thr Ile Ser Leu
        755                     760                     765 ctg aca ggc tcg gag cct ccc aaa gcc aag gac ccc act gtc tcc        2349
Leu Thr Gly Ser Glu Pro Pro Lys Ala Lys Asp Pro Thr Val Ser
    770                     775                     780 tagaggcccc ggaggagctg ggccagccgc ccacccccac ccccagtgca gggctggtct  2409
tggggaggca gggcagcctc gcggtcttgg gcactggtgg gtcggccgg              2458

<210> SEQ ID NO 176
<211> LENGTH: 783
<212> TYPE: PRT
<213> ORGANISM: Artificial Sequence
<220> FEATURE:
<223> OTHER INFORMATION: Description of Artificial Sequence: GFP-HSF1

<400> SEQUENCE: 176

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys Ser
225                 230                 235                 240

Gly Leu Arg Ser Arg Ala Gln Ala Ser Asn Ser Ala Val Glu Met Asp
                245                 250                 255

Leu Pro Val Gly Pro Gly Ala Ala Gly Pro Ser Asn Val Pro Ala Phe
            260                 265                 270

Leu Thr Lys Leu Trp Thr Leu Val Ser Asp Pro Asp Thr Asp Ala Leu
        275                 280                 285

Ile Cys Trp Ser Pro Ser Gly Asn Ser Phe His Val Phe Asp Gln Gly
290                 295                 300

Gln Phe Ala Lys Glu Val Leu Pro Lys Tyr Phe Lys His Asn Asn Met
305                 310                 315                 320

Ala Ser Phe Val Arg Gln Leu Asn Met Tyr Gly Phe Arg Lys Val Val
                325                 330                 335

His Ile Glu Gln Gly Gly Leu Val Lys Pro Glu Arg Asp Asp Thr Glu
            340                 345                 350

Phe Gln His Pro Cys Phe Leu Arg Gly Gln Glu Gln Leu Leu Glu Asn
        355                 360                 365

Ile Lys Arg Lys Val Thr Ser Val Ser Thr Leu Lys Ser Glu Asp Ile
        370                 375                 380

Lys Ile Arg Gln Asp Ser Val Thr Lys Leu Leu Thr Asp Val Gln Leu
385                 390                 395                 400

Met Lys Gly Lys Gln Glu Cys Met Asp Ser Lys Leu Leu Ala Met Lys
                405                 410                 415

His Glu Asn Glu Ala Leu Trp Arg Glu Val Ala Ser Leu Arg Gln Lys
            420                 425                 430

His Ala Gln Gln Gln Lys Val Val Asn Lys Leu Ile Gln Phe Leu Ile
        435                 440                 445

Ser Leu Val Gln Ser Asn Arg Ile Leu Gly Val Lys Arg Lys Ile Pro
450                 455                 460

Leu Met Leu Asn Asp Ser Gly Ser Ala His Ser Met Pro Lys Tyr Ser
465                 470                 475                 480

Arg Gln Phe Ser Leu Glu His Val His Gly Ser Gly Pro Tyr Ser Ala
                485                 490                 495

Pro Ser Pro Ala Tyr Ser Ser Ser Leu Tyr Ala Pro Asp Ala Val
            500                 505                 510

Ala Ser Ser Gly Pro Ile Ile Ser Asp Ile Thr Glu Leu Ala Pro Ala
        515                 520                 525

Ser Pro Met Ala Ser Pro Gly Gly Ser Ile Asp Glu Arg Pro Leu Ser
        530                 535                 540

Ser Ser Pro Leu Val Arg Val Lys Glu Glu Pro Ser Pro Pro Gln
545                 550                 555                 560

Ser Pro Arg Val Glu Glu Ala Ser Pro Gly Arg Pro Ser Ser Val Asp
                565                 570                 575

Thr Leu Leu Ser Pro Thr Ala Leu Ile Asp Ser Ile Leu Arg Glu Ser
            580                 585                 590

Glu Pro Ala Pro Ala Ser Val Thr Ala Leu Thr Asp Ala Arg Gly His
        595                 600                 605
```

```
Thr Asp Thr Glu Gly Arg Pro Pro Ser Pro Pro Thr Ser Thr Pro
    610                 615                 620

Glu Lys Cys Leu Ser Val Ala Cys Leu Asp Lys Asn Glu Leu Ser Asp
625                 630                 635                 640

His Leu Asp Ala Met Asp Ser Asn Leu Asp Asn Leu Gln Thr Met Leu
                645                 650                 655

Ser Ser His Gly Phe Ser Val Asp Thr Ser Ala Leu Leu Asp Leu Phe
            660                 665                 670

Ser Pro Ser Val Thr Val Pro Asp Met Ser Leu Pro Asp Leu Asp Ser
        675                 680                 685

Ser Leu Ala Ser Ile Gln Glu Leu Leu Ser Pro Gln Glu Pro Pro Arg
690                 695                 700

Pro Pro Glu Ala Glu Asn Ser Ser Pro Asp Ser Gly Lys Gln Leu Val
705                 710                 715                 720

His Tyr Thr Ala Gln Pro Leu Phe Leu Leu Asp Pro Gly Ser Val Asp
                725                 730                 735

Thr Gly Ser Asn Asp Leu Pro Val Leu Phe Glu Leu Gly Glu Gly Ser
            740                 745                 750

Tyr Phe Ser Glu Gly Asp Gly Phe Ala Glu Asp Pro Thr Ile Ser Leu
            755                 760                 765

Leu Thr Gly Ser Glu Pro Pro Lys Ala Lys Asp Pro Thr Val Ser
770                 775                 780

<210> SEQ ID NO 177
<211> LENGTH: 2416
<212> TYPE: DNA
<213> ORGANISM: Artificial Sequence
<220> FEATURE:
<223> OTHER INFORMATION: Description of Artificial Sequence: GFP-NFKB
<221> NAME/KEY: CDS
<222> LOCATION: (1)..(2415)

<400> SEQUENCE: 177 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
  1               5                  10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
             20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
         35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
     50                  55                  60 ctg acc tac ggc gtg cag tgc ttc agc cgc tac ccc gac cac atg aag     240
Leu Thr Tyr Gly Val Gln Cys Phe Ser Arg Tyr Pro Asp His Met Lys
 65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
            100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
        115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
```

```
            130                 135                 140
aac tac aac agc cac aac gtc tat atc atg gcc gac aag cag aag aac         480
Asn Tyr Asn Ser His Asn Val Tyr Ile Met Ala Asp Lys Gln Lys Asn
145                 150                 155                 160 ggc atc aag gtg aac ttc aag atc cgc cac aac atc gag gac ggc agc         528
Gly Ile Lys Val Asn Phe Lys Ile Arg His Asn Ile Glu Asp Gly Ser
                165                 170                 175 gtg cag ctc gcc gac cac tac cag cag aac acc ccc atc ggc gac ggc         576
Val Gln Leu Ala Asp His Tyr Gln Gln Asn Thr Pro Ile Gly Asp Gly
            180                 185                 190 ccc gtg ctg ctg ccc gac aac cac tac ctg agc acc cag tcc gcc ctg         624
Pro Val Leu Leu Pro Asp Asn His Tyr Leu Ser Thr Gln Ser Ala Leu
            195                 200                 205 agc aaa gac ccc aac gag aag cgc gat cac atg gtc ctg ctg gag ttc         672
Ser Lys Asp Pro Asn Glu Lys Arg Asp His Met Val Leu Leu Glu Phe
        210                 215                 220 gtg acc gcc gcc ggg atc act ctc ggc atg gac gag ctg tac aag tcc         720
Val Thr Ala Ala Gly Ile Thr Leu Gly Met Asp Glu Leu Tyr Lys Ser
225                 230                 235                 240 gga ctc aga tct cga gat ccg ccc ttc atg gac gaa ctg ttc ccc ctc         768
Gly Leu Arg Ser Arg Asp Pro Pro Phe Met Asp Glu Leu Phe Pro Leu
                245                 250                 255 atc ttc ccg gca gag cca gcc cag gcc tct ggc ccc tat gtg gag atc         816
Ile Phe Pro Ala Glu Pro Ala Gln Ala Ser Gly Pro Tyr Val Glu Ile
            260                 265                 270 att gag cag ccc aag cag cgg ggc atg cgc ttc cgc tac aag tgc gag         864
Ile Glu Gln Pro Lys Gln Arg Gly Met Arg Phe Arg Tyr Lys Cys Glu
        275                 280                 285 ggg cgc tcc gcg ggc agc atc cca ggc gag agg agc aca gat acc acc         912
Gly Arg Ser Ala Gly Ser Ile Pro Gly Glu Arg Ser Thr Asp Thr Thr
290                 295                 300 aag acc cac ccc acc atc aag atc aat ggc tac aca gga cca ggg aca         960
Lys Thr His Pro Thr Ile Lys Ile Asn Gly Tyr Thr Gly Pro Gly Thr
305                 310                 315                 320 gtg cgc atc tcc ctg gtc acc aag gac cct cct cac cgg cct cac ccc        1008
Val Arg Ile Ser Leu Val Thr Lys Asp Pro Pro His Arg Pro His Pro
                325                 330                 335 cac gag ctt gta gga aag gac tgc cgg gat ggc ttc tat gag gct gag        1056
His Glu Leu Val Gly Lys Asp Cys Arg Asp Gly Phe Tyr Glu Ala Glu
            340                 345                 350 ctc tgc ccg gac cgc tgc atc cac agt ttc cag aac ctg gga atc cag        1104
Leu Cys Pro Asp Arg Cys Ile His Ser Phe Gln Asn Leu Gly Ile Gln
            355                 360                 365 tgt gtg aag aag cgg gac ctg gag cag gct atc agt cag cgc atc cag        1152
Cys Val Lys Lys Arg Asp Leu Glu Gln Ala Ile Ser Gln Arg Ile Gln
        370                 375                 380 acc aac aac aac ccc ttc caa gtt cct ata gaa gag cag cgt ggg gac        1200
Thr Asn Asn Asn Pro Phe Gln Val Pro Ile Glu Glu Gln Arg Gly Asp
385                 390                 395                 400 tac gac ctg aat gct gtg cgg ctc tgc ttc cag gtg aca gtg cgg gac        1248
Tyr Asp Leu Asn Ala Val Arg Leu Cys Phe Gln Val Thr Val Arg Asp
                405                 410                 415 cca tca ggc agg ccc ctc cgc ctg ccg cct gtc ctt tct cat ccc atc        1296
Pro Ser Gly Arg Pro Leu Arg Leu Pro Pro Val Leu Ser His Pro Ile
            420                 425                 430 ttt gac aat cgt gcc ccc aac act gcc gag ctc aag atc tgc cga gtg        1344
Phe Asp Asn Arg Ala Pro Asn Thr Ala Glu Leu Lys Ile Cys Arg Val
            435                 440                 445 aac cga aac tct ggc agc tgc ctc ggt ggg gat gag atc ttc cta ctg        1392
```

```
                                        -continued

Asn Arg Asn Ser Gly Ser Cys Leu Gly Gly Asp Glu Ile Phe Leu Leu
    450                 455                 460 tgt gac aag gtg cag aaa gag gac att gag gtg tat ttc acg gga cca      1440
Cys Asp Lys Val Gln Lys Glu Asp Ile Glu Val Tyr Phe Thr Gly Pro
465                 470                 475                 480 ggc tgg gag gcc cga ggc tcc ttt tcg caa gct gat gtg cac cga caa      1488
Gly Trp Glu Ala Arg Gly Ser Phe Ser Gln Ala Asp Val His Arg Gln
                485                 490                 495 gtg gcc att gtg ttc cgg acc cct ccc tac gca gac ccc agc ctg cag      1536
Val Ala Ile Val Phe Arg Thr Pro Pro Tyr Ala Asp Pro Ser Leu Gln
            500                 505                 510 gct cct gtg cgt gtc tcc atg cag ctg cgg cgg cct tcc gac cgg gag      1584
Ala Pro Val Arg Val Ser Met Gln Leu Arg Arg Pro Ser Asp Arg Glu
        515                 520                 525 ctc agt gag ccc atg gaa ttc cag tac ctg cca gat aca gac gat cgt      1632
Leu Ser Glu Pro Met Glu Phe Gln Tyr Leu Pro Asp Thr Asp Asp Arg
    530                 535                 540 cac cgg att gag gag aaa cgt aaa agg aca tat gag acc ttc aag agc      1680
His Arg Ile Glu Glu Lys Arg Lys Arg Thr Tyr Glu Thr Phe Lys Ser
545                 550                 555                 560 atc atg aag aag agt cct ttc agc gga ccc acc gac ccc cgg cct cca      1728
Ile Met Lys Lys Ser Pro Phe Ser Gly Pro Thr Asp Pro Arg Pro Pro
                565                 570                 575 cct cga cgc att gct gtg cct tcc cgc agc tca gct tct gtc ccc aag      1776
Pro Arg Arg Ile Ala Val Pro Ser Arg Ser Ser Ala Ser Val Pro Lys
            580                 585                 590 cca gca ccc cag ccc tat ccc ttt acg tca tcc ctg agc acc atc aac      1824
Pro Ala Pro Gln Pro Tyr Pro Phe Thr Ser Ser Leu Ser Thr Ile Asn
        595                 600                 605 tat gat gag ttt ccc acc atg gtg ttt cct tct ggg cag atc agc cag      1872
Tyr Asp Glu Phe Pro Thr Met Val Phe Pro Ser Gly Gln Ile Ser Gln
    610                 615                 620 gcc tcg gcc ttg gcc ccg gcc cct ccc caa gtc ctg ccc cag gct cca      1920
Ala Ser Ala Leu Ala Pro Ala Pro Pro Gln Val Leu Pro Gln Ala Pro
625                 630                 635                 640 gcc cct gcc cct gct cca gcc atg gta tca gct ctg gcc cag gcc cca      1968
Ala Pro Ala Pro Ala Pro Ala Met Val Ser Ala Leu Ala Gln Ala Pro
                645                 650                 655 gcc cct gtc cca gtc cta gcc cca ggc cct cct cag gct gtg gcc cca      2016
Ala Pro Val Pro Val Leu Ala Pro Gly Pro Pro Gln Ala Val Ala Pro
            660                 665                 670 cct gcc ccc aag ccc acc cag gct ggg gaa gga acg ctg tca gag gcc      2064
Pro Ala Pro Lys Pro Thr Gln Ala Gly Glu Gly Thr Leu Ser Glu Ala
        675                 680                 685 ctg ctg cag ctg cag ttt gat gat gaa gac ctg ggg gcc ttg ctt ggc      2112
Leu Leu Gln Leu Gln Phe Asp Asp Glu Asp Leu Gly Ala Leu Leu Gly
    690                 695                 700 aac agc aca gac cca gct gtg ttc aca gac ctg gca tcc gtc gac aac      2160
Asn Ser Thr Asp Pro Ala Val Phe Thr Asp Leu Ala Ser Val Asp Asn
705                 710                 715                 720 tcc gag ttt cag cag ctg ctg aac cag ggc ata cct gtg gcc ccc cac      2208
Ser Glu Phe Gln Gln Leu Leu Asn Gln Gly Ile Pro Val Ala Pro His
                725                 730                 735 aca act gag ccc atg ctg atg gag tac cct gag gct ata act cgc cta      2256
Thr Thr Glu Pro Met Leu Met Glu Tyr Pro Glu Ala Ile Thr Arg Leu
            740                 745                 750 gtg aca gcc cag agg ccc ccc gac cca gct cct gct cca ctg ggg gcc      2304
Val Thr Ala Gln Arg Pro Pro Asp Pro Ala Pro Ala Pro Leu Gly Ala
        755                 760                 765
```

```
ccg ggg ctc ccc aat ggc ctc ctt tca gga gat gaa gac ttc tcc tcc    2352
Pro Gly Leu Pro Asn Gly Leu Leu Ser Gly Asp Glu Asp Phe Ser Ser
    770             775             780 att gcg gac atg gac ttc tca gcc ctg ctg agt cag atc agc tcc aag    2400
Ile Ala Asp Met Asp Phe Ser Ala Leu Leu Ser Gln Ile Ser Ser Lys
785             790             795             800 ggc gaa ttc gaa gct t                                              2416
Gly Glu Phe Glu Ala
            805
```

<210> SEQ ID NO 178
<211> LENGTH: 805
<212> TYPE: PRT
<213> ORGANISM: Artificial Sequence
<220> FEATURE:
<223> OTHER INFORMATION: Description of Artificial Sequence: GFP-NFKB

<400> SEQUENCE: 178

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Ser
225                 230                 235                 240

Gly Leu Arg Ser Arg Asp Pro Pro Phe Met Asp Glu Leu Phe Pro Leu
                245                 250                 255

Ile Phe Pro Ala Glu Pro Ala Gln Ala Ser Gly Pro Tyr Val Glu Ile
            260                 265                 270

Ile Glu Gln Pro Lys Gln Arg Gly Met Arg Phe Arg Tyr Lys Cys Glu
        275                 280                 285

Gly Arg Ser Ala Gly Ser Ile Pro Gly Glu Arg Ser Thr Asp Thr Thr
    290                 295                 300
```

-continued

```
Lys Thr His Pro Thr Ile Lys Ile Asn Gly Tyr Thr Gly Pro Gly Thr
305                 310                 315                 320

Val Arg Ile Ser Leu Val Thr Lys Asp Pro His Arg Pro His Pro
            325                 330                 335

His Glu Leu Val Gly Lys Asp Cys Arg Asp Gly Phe Tyr Glu Ala Glu
            340                 345                 350

Leu Cys Pro Asp Arg Cys Ile His Ser Phe Gln Asn Leu Gly Ile Gln
            355                 360                 365

Cys Val Lys Lys Arg Asp Leu Glu Gln Ala Ile Ser Gln Arg Ile Gln
370                 375                 380

Thr Asn Asn Asn Pro Phe Gln Val Pro Ile Glu Glu Gln Arg Gly Asp
385                 390                 395                 400

Tyr Asp Leu Asn Ala Val Arg Leu Cys Phe Gln Val Thr Val Arg Asp
                405                 410                 415

Pro Ser Gly Arg Pro Leu Arg Leu Pro Pro Val Leu Ser His Pro Ile
            420                 425                 430

Phe Asp Asn Arg Ala Pro Asn Thr Ala Glu Leu Lys Ile Cys Arg Val
            435                 440                 445

Asn Arg Asn Ser Gly Ser Cys Leu Gly Gly Asp Glu Ile Phe Leu Leu
450                 455                 460

Cys Asp Lys Val Gln Lys Glu Asp Ile Glu Val Tyr Phe Thr Gly Pro
465                 470                 475                 480

Gly Trp Glu Ala Arg Gly Ser Phe Ser Gln Ala Asp Val His Arg Gln
            485                 490                 495

Val Ala Ile Val Phe Arg Thr Pro Pro Tyr Ala Asp Pro Ser Leu Gln
            500                 505                 510

Ala Pro Val Arg Val Ser Met Gln Leu Arg Arg Pro Ser Asp Arg Glu
            515                 520                 525

Leu Ser Glu Pro Met Glu Phe Gln Tyr Leu Pro Asp Thr Asp Asp Arg
530                 535                 540

His Arg Ile Glu Glu Lys Arg Lys Arg Thr Tyr Glu Thr Phe Lys Ser
545                 550                 555                 560

Ile Met Lys Lys Ser Pro Phe Ser Gly Pro Thr Asp Pro Arg Pro Pro
            565                 570                 575

Pro Arg Arg Ile Ala Val Pro Ser Arg Ser Ser Ala Ser Val Pro Lys
            580                 585                 590

Pro Ala Pro Gln Pro Tyr Pro Phe Thr Ser Ser Leu Ser Thr Ile Asn
            595                 600                 605

Tyr Asp Glu Phe Pro Thr Met Val Phe Pro Ser Gly Gln Ile Ser Gln
610                 615                 620

Ala Ser Ala Leu Ala Pro Ala Pro Pro Gln Val Leu Pro Gln Ala Pro
625                 630                 635                 640

Ala Pro Ala Pro Ala Pro Ala Met Val Ser Ala Leu Ala Gln Ala Pro
            645                 650                 655

Ala Pro Val Pro Val Leu Ala Pro Gly Pro Pro Gln Ala Val Ala Pro
            660                 665                 670

Pro Ala Pro Lys Pro Thr Gln Ala Gly Glu Gly Thr Leu Ser Glu Ala
            675                 680                 685

Leu Leu Gln Leu Gln Phe Asp Asp Glu Asp Leu Gly Ala Leu Leu Gly
            690                 695                 700

Asn Ser Thr Asp Pro Ala Val Phe Thr Asp Leu Ala Ser Val Asp Asn
705                 710                 715                 720

Ser Glu Phe Gln Gln Leu Leu Asn Gln Gly Ile Pro Val Ala Pro His
```

```
                    725                 730                 735
Thr Thr Glu Pro Met Leu Met Glu Tyr Pro Glu Ala Ile Thr Arg Leu
                740                 745                 750

Val Thr Ala Gln Arg Pro Pro Asp Pro Ala Pro Ala Pro Leu Gly Ala
            755                 760                 765

Pro Gly Leu Pro Asn Gly Leu Leu Ser Gly Asp Glu Asp Phe Ser Ser
        770                 775                 780

Ile Ala Asp Met Asp Phe Ser Ala Leu Leu Ser Gln Ile Ser Ser Lys
785                 790                 795                 800

Gly Glu Phe Glu Ala
                805

<210> SEQ ID NO 179
<211> LENGTH: 1677
<212> TYPE: DNA
<213> ORGANISM: Artificial Sequence
<220> FEATURE:
<223> OTHER INFORMATION: Description of Artificial Sequence: GFP-IKB
<221> NAME/KEY: CDS
<222> LOCATION: (1)..(1674)

<400> SEQUENCE: 179 atg ttc cag gcg gct gag cgc ccc cag gag tgg gcc atg gag ggc ccc       48
Met Phe Gln Ala Ala Glu Arg Pro Gln Glu Trp Ala Met Glu Gly Pro
 1               5                  10                  15 cgc gac ggg ctg aag aag gag cgg cta ctg gac gac cgc cac gac agc       96
Arg Asp Gly Leu Lys Lys Glu Arg Leu Leu Asp Asp Arg His Asp Ser
            20                  25                  30 ggc ctg gac tcc atg aaa gac gag gag tac gag cag atg gtc aag gag      144
Gly Leu Asp Ser Met Lys Asp Glu Glu Tyr Glu Gln Met Val Lys Glu
        35                  40                  45 ctg cag gag atc cgc ctc gag ccg cag gag gtg ccg cgc ggc tcg gag      192
Leu Gln Glu Ile Arg Leu Glu Pro Gln Glu Val Pro Arg Gly Ser Glu
    50                  55                  60 ccc tgg aag cag cag ctc acc gag gac ggg gac tcg ttc ctg cac ttg      240
Pro Trp Lys Gln Gln Leu Thr Glu Asp Gly Asp Ser Phe Leu His Leu
65                  70                  75                  80 gcc atc atc cat gaa gaa aag gca ctg acc atg gaa gtg atc cgc cag      288
Ala Ile Ile His Glu Glu Lys Ala Leu Thr Met Glu Val Ile Arg Gln
                85                  90                  95 gtg aag gga gac ctg gcc ttc ctc aac ctc cag aac aac ctg cag cag      336
Val Lys Gly Asp Leu Ala Phe Leu Asn Leu Gln Asn Asn Leu Gln Gln
            100                 105                 110 act cca ctc cac ttg gct gtg atc acc aac cag cca gaa att gct gag      384
Thr Pro Leu His Leu Ala Val Ile Thr Asn Gln Pro Glu Ile Ala Glu
        115                 120                 125 gca ctt ctg gga gct ggc tgt gat cct gag ctc cga gac ttt cga gga      432
Ala Leu Leu Gly Ala Gly Cys Asp Pro Glu Leu Arg Asp Phe Arg Gly
    130                 135                 140 aat acc ccc cta cac ctt gcc tgt gag cag ggc tgc ctg gcc agc gtg      480
Asn Thr Pro Leu His Leu Ala Cys Glu Gln Gly Cys Leu Ala Ser Val
145                 150                 155                 160 gga gtc ctg act cag tcc tgc acc acc ccg cac ctc cac tcc atc ttg      528
Gly Val Leu Thr Gln Ser Cys Thr Thr Pro His Leu His Ser Ile Leu
                165                 170                 175 aag gct acc aac tac aat ggc cac acg tgt cta cac tta gcc tct atc      576
Lys Ala Thr Asn Tyr Asn Gly His Thr Cys Leu His Leu Ala Ser Ile
            180                 185                 190 cat ggc tac ctg ggc atc gtg gag ctt ttg gtg tcc ttg ggt gct gat      624
His Gly Tyr Leu Gly Ile Val Glu Leu Leu Val Ser Leu Gly Ala Asp
```

-continued

```
                 195                 200                 205
gtc aat gct cag gag ccc tgt aat ggc cgg act gcc ctt cac ctc gca      672
Val Asn Ala Gln Glu Pro Cys Asn Gly Arg Thr Ala Leu His Leu Ala
    210                 215                 220 gtg gac ctg caa aat cct gac ctg gtg tca ctc ctg ttg aag tgt ggg      720
Val Asp Leu Gln Asn Pro Asp Leu Val Ser Leu Leu Leu Lys Cys Gly
225                 230                 235                 240 gct gat gtc aac aga gtt acc tac cag ggc tat tct ccc tac cag ctc      768
Ala Asp Val Asn Arg Val Thr Tyr Gln Gly Tyr Ser Pro Tyr Gln Leu
                245                 250                 255 acc tgg ggc cgc cca agc acc cgg ata cag cag cag ctg ggc cag ctg      816
Thr Trp Gly Arg Pro Ser Thr Arg Ile Gln Gln Gln Leu Gly Gln Leu
                260                 265                 270 aca cta gaa aac ctt cag atg ctg cca gag agt gag gat gag gag agc      864
Thr Leu Glu Asn Leu Gln Met Leu Pro Glu Ser Glu Asp Glu Glu Ser
            275                 280                 285 tat gac aca gag tca gag ttc acg gag ttc aca gag gac gag ctg ccc      912
Tyr Asp Thr Glu Ser Glu Phe Thr Glu Phe Thr Glu Asp Glu Leu Pro
        290                 295                 300 tat gat gac tgt gtg ttt gga ggc cag cgt ctg acg tta acc ggt atg      960
Tyr Asp Asp Cys Val Phe Gly Gly Gln Arg Leu Thr Leu Thr Gly Met
305                 310                 315                 320 gct agc aaa gga gaa gaa ctc ttc act gga gtt gtc cca att ctt gtt     1008
Ala Ser Lys Gly Glu Glu Leu Phe Thr Gly Val Val Pro Ile Leu Val
                325                 330                 335 gaa tta gat ggt gat gtt aac ggc cac aag ttc tct gtc agt gga gag     1056
Glu Leu Asp Gly Asp Val Asn Gly His Lys Phe Ser Val Ser Gly Glu
                340                 345                 350 ggt gaa ggt gat gca aca tac gga aaa ctt acc ctg aag ttc atc tgc     1104
Gly Glu Gly Asp Ala Thr Tyr Gly Lys Leu Thr Leu Lys Phe Ile Cys
            355                 360                 365 act act ggc aaa ctg cct gtt cca tgg cca aca cta gtc act act ctg     1152
Thr Thr Gly Lys Leu Pro Val Pro Trp Pro Thr Leu Val Thr Thr Leu
        370                 375                 380 tgc tat ggt gtt caa tgc ttt tca aga tac ccg gat cat atg aaa cgg     1200
Cys Tyr Gly Val Gln Cys Phe Ser Arg Tyr Pro Asp His Met Lys Arg
385                 390                 395                 400 cat gac ttt ttc aag agt gcc atg ccc gaa ggt tat gta cag gaa agg     1248
His Asp Phe Phe Lys Ser Ala Met Pro Glu Gly Tyr Val Gln Glu Arg
                405                 410                 415 acc atc ttc ttc aaa gat gac ggc aac tac aag aca cgt gct gaa gtc     1296
Thr Ile Phe Phe Lys Asp Asp Gly Asn Tyr Lys Thr Arg Ala Glu Val
                420                 425                 430 aag ttt gaa ggt gat acc ctt gtt aat aga atc gag tta aaa ggt att     1344
Lys Phe Glu Gly Asp Thr Leu Val Asn Arg Ile Glu Leu Lys Gly Ile
            435                 440                 445 gac ttc aag gaa gat ggc aac att ctg gga cac aaa ttg gaa tac aac     1392
Asp Phe Lys Glu Asp Gly Asn Ile Leu Gly His Lys Leu Glu Tyr Asn
        450                 455                 460 tat aac tca cac aat gta tac atc atg gca gac aaa caa aag aat gga     1440
Tyr Asn Ser His Asn Val Tyr Ile Met Ala Asp Lys Gln Lys Asn Gly
465                 470                 475                 480 atc aaa gtg aac ttc aag acc cgc cac aac att gaa gat gga agc gtt     1488
Ile Lys Val Asn Phe Lys Thr Arg His Asn Ile Glu Asp Gly Ser Val
                485                 490                 495 caa cta gca gac cat tat caa caa aat act cca att ggc gat ggc cct     1536
Gln Leu Ala Asp His Tyr Gln Gln Asn Thr Pro Ile Gly Asp Gly Pro
                500                 505                 510 gtc ctt tta cca gac aac cat tac ctg tcc aca caa tct gcc ctt tcg     1584
```

```
Val Leu Leu Pro Asp Asn His Tyr Leu Ser Thr Gln Ser Ala Leu Ser
            515                 520                 525 aaa gat ccc aac gaa aag aga gac cac atg gtc ctt ctt gag ttt gta      1632
Lys Asp Pro Asn Glu Lys Arg Asp His Met Val Leu Leu Glu Phe Val
            530                 535                 540 aca gct gct ggg att aca cat ggc atg gat gaa ctg tac aac tag          1677
Thr Ala Ala Gly Ile Thr His Gly Met Asp Glu Leu Tyr Asn
545                 550                 555

<210> SEQ ID NO 180
<211> LENGTH: 558
<212> TYPE: PRT
<213> ORGANISM: Artificial Sequence
<220> FEATURE:
<223> OTHER INFORMATION: Description of Artificial Sequence: GFP-IKB

<400> SEQUENCE: 180

Met Phe Gln Ala Ala Glu Arg Pro Gln Glu Trp Ala Met Glu Gly Pro
 1               5                  10                  15

Arg Asp Gly Leu Lys Lys Glu Arg Leu Leu Asp Asp Arg His Asp Ser
                20                  25                  30

Gly Leu Asp Ser Met Lys Asp Glu Glu Tyr Glu Gln Met Val Lys Glu
            35                  40                  45

Leu Gln Glu Ile Arg Leu Glu Pro Gln Glu Val Pro Arg Gly Ser Glu
        50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Ile Arg Gln
                85                  90                  95

Val Lys Gly Asp Leu Ala Phe Leu Asn Leu Gln Asn Asn Leu Gln Gln
               100                 105                 110

Thr Pro Leu His Leu Ala Val Ile Thr Asn Gln Pro Glu Ile Ala Glu
            115                 120                 125

Ala Leu Leu Gly Ala Gly Cys Asp Pro Glu Leu Arg Asp Phe Arg Gly
        130                 135                 140

Asn Thr Pro Leu His Leu Ala Cys Glu Gln Gly Cys Leu Ala Ser Val
145                 150                 155                 160

Gly Val Leu Thr Gln Ser Cys Thr Thr Pro His Leu His Ser Ile Leu
                165                 170                 175

Lys Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
        195                 200                 205

Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Met Leu Pro Glu Ser Glu Asp Glu Glu Ser
        275                 280                 285

Tyr Asp Thr Glu Ser Glu Phe Thr Glu Phe Thr Glu Asp Glu Leu Pro
    290                 295                 300

Tyr Asp Asp Cys Val Phe Gly Gly Gln Arg Leu Thr Leu Thr Gly Met
```

-continued

```
305                 310                 315                 320
Ala Ser Lys Gly Glu Glu Leu Phe Thr Gly Val Val Pro Ile Leu Val
                325                 330                 335
Glu Leu Asp Gly Asp Val Asn Gly His Lys Phe Ser Val Ser Gly Glu
                340                 345                 350
Gly Glu Gly Asp Ala Thr Tyr Gly Lys Leu Thr Leu Lys Phe Ile Cys
                355                 360                 365
Thr Thr Gly Lys Leu Pro Val Pro Trp Pro Thr Leu Val Thr Thr Leu
            370                 375                 380
Cys Tyr Gly Val Gln Cys Phe Ser Arg Tyr Pro Asp His Met Lys Arg
385                 390                 395                 400
His Asp Phe Phe Lys Ser Ala Met Pro Glu Gly Tyr Val Gln Glu Arg
                405                 410                 415
Thr Ile Phe Phe Lys Asp Asp Gly Asn Tyr Lys Thr Arg Ala Glu Val
                420                 425                 430
Lys Phe Glu Gly Asp Thr Leu Val Asn Arg Ile Glu Leu Lys Gly Ile
                435                 440                 445
Asp Phe Lys Glu Asp Gly Asn Ile Leu Gly His Lys Leu Glu Tyr Asn
            450                 455                 460
Tyr Asn Ser His Asn Val Tyr Ile Met Ala Asp Lys Gln Lys Asn Gly
465                 470                 475                 480
Ile Lys Val Asn Phe Lys Thr Arg His Asn Ile Glu Asp Gly Ser Val
                485                 490                 495
Gln Leu Ala Asp His Tyr Gln Gln Asn Thr Pro Ile Gly Asp Gly Pro
                500                 505                 510
Val Leu Leu Pro Asp Asn His Tyr Leu Ser Thr Gln Ser Ala Leu Ser
            515                 520                 525
Lys Asp Pro Asn Glu Lys Arg Asp His Met Val Leu Leu Glu Phe Val
            530                 535                 540
Thr Ala Ala Gly Ile Thr His Gly Met Asp Glu Leu Tyr Asn
545                 550                 555
```

We claim:

1. An automated method for cell based toxin detection, classification, and/or identification comprising:

providing an array of locations containing multiple cells to be treated with a test substance, wherein the cells possess at least a first luminescent reporter molecule comprising a detector, wherein the detector detects a toxin present in the test substance, and a second luminescent reporter molecule selected from the group consisting of a classifier or an identifier, wherein the classifier detects a toxin present in the test substance and identifies a cell pathway affected by a toxin present in the test substance, and the identifier detects a toxin present in the test substance and identifies a specific toxin or group of toxins present in the test substance;

contacting the cells with the test substance either before or after possession of the first and second luminescent reporter molecules by the cells; wherein the localization, distribution, structure, or activity of the first and second luminescent reporter molecule is modified when the cell is contacted with a toxin present in the test substance, imaging or scanning multiple cells in each of the locations containing multiple cells to obtain luminescent signals from the detector;

converting the luminescent signals from the detector into digital data;

utilizing the digital data from the detector to automatically measure the localization, distribution, structure or activity of the detector on or in the cell, wherein a change in the localization, distribution, structure or activity of the detector indicates the presence of a toxin in the test substance;

selectively imaging or scanning the locations containing cells that were contacted with test sample indicated to have a toxin in it to obtain luminescent signals from the second reporter molecule;

converting the luminescent signals from the second luminescent reporter molecule into digital data;

utilizing the digital data from the second luminescent reporter molecule to automatically measure the localization, distribution, structure, or activity of the classifier or the identifier on or in the cell, wherein a change in the localization, distribution, structure or activity of the classifier identifies a cell pathway that is perturbed by the toxin present in the test substance, or wherein a change in the localization, distribution, structure or activity of the identifier identifies the a specific toxin or group of toxins that are present in the test substance.

2. The method of claim 1 wherein the second luminescent reporter molecule is a classifier, and the digital data derived from the classifier is used to select an identifier for identification of the specific toxin or group of toxins.

3. An automated method for cell based toxin detection, classification, and/or identification comprising:

provided an array of locations containing multiple cells to be treated with a test substance, wherein the cells possess at least a first luminescent reporter molecule comprising a detector, wherein the detector detects toxin present in the test substance, a second luminescent reporter molecule comprising a classifier, wherein the classifier detects a toxin present in the test substance and identifies a cell pathway affected by a toxin present in the test substance, and a third luminescent reporter molecule comprising an identifier, wherein the identifier detects a toxin present in the test substance and identifies a specific toxin or ground of toxins present in the test substance;

contacting the cells with the test substance either before or after possession of the first second, and third luminescent reporter molecules by the cells; wherein the localization, distribution, structure, or activity of the first, second, and third luminescent reporter molecules is modified when the cell is contacted with a toxin present in the test substance;

imaging or scanning multiple cells in each of the locations containing multiple cells to obtain luminescent signals from the detector;

converting the luminescent signals from the detector into digital data;

utilizing the digital data from the detector to automatically measure the localization, distribution, structure or activity of the detector on or in the cell, wherein a change in the localization, distribution, structure or activity of the detector indicates the presence of a toxin in the test substance;

selectively imaging or scanning the locations containing cells that were contacted with test substance indicated to have a toxin in it to obtain luminescent signals from the classifier;

converting the luminescent signals from the classifier into digital data;

utilizing the digital data from the classifier to automatically measure the localization, distribution, structure, or activity of the classifier on or in the cell, wherein a change in the localization, distribution, structure or activity of the classifier identifies a cell pathway that is perturbed by the toxin present in the test substance;

selectively imaging or scanning the locations containing cells that were contacted with test substance indicated to have a toxin in it to obtain luminescent signals from the identifier;

converting the luminescent signals from the identifier into digital data; and utilizing the digital data from the identifier to automatically measure the localization, distribution, structure, or activity of the identifier on or in the cell, wherein a change in the localization, distribution, structure or activity of the identifier identifies the specific toxin or group of toxins that is present in the test substance.

4. The method of claim 3 wherein the digital data derived from the classifier is used to select an identifier for identification of the specific toxin or group of toxins.

5. The method of any one of claims 1–4 wherein the detector comprises a molecule selected to from the group consisting of heat shock proteins and compounds that respond to changes in mitochondrial membrane potential, intracellular free ion concentration, cytoskeletal organization, general metabolic status, cell cycle timing events, and organellar structure and function.

6. The method of claim 5 wherein the classifier comprises a molecule selected from the group consisting of tubulin, microtubule-associated proteins, actin, actin-binding proteins, NF-κB, IκB, and stress-activated kinases.

7. The method of claim 6 wherein the cell pathway is selected from the group consisting of cell stress pathways, cell metabolic pathways, cell signaling pathways, cell growth pathways, and cell division pathways.

8. The method of claim 1, wherein the second luminescent reporter molecule is an identifier, and the identifier identifies a toxin or group of toxins selected from the group consisting of proteases, ADP-ribosylating toxins, cytotoxic phospholipases, and exfoliative toxins.

9. The method of claim 5, wherein the identifier identifies a toxin or group of toxins selected from the group consisting of proteases, ADP-ribosylating toxins, cytotoxic phospholipases, and exfoliative toxins.

10. The method of any of claims 1–4 wherein the change in the localization, distribution, structure or activity of the first, second, or third luminescent reporter molecules is selected from the group consisting of cytoplasm to nucleus translocation, nucleus or nucleolus to cytoplasm translocation, receptor internalization, mitochondrial membrane potential, loss of signal, the spectral response of the reporter molecule, phosphorylation, intracellular free ion concentration, cell size, cell shape, cytoskeleton organization, metabolic processes, cell motility, cell substrate attachment, cell cycle events, and organellar structure and function.

11. The method of any one of claims 1–4, wherein the imaging or scanning multiple cells in each of the locations containing multiple cells to obtain luminescent signals from the detector is carried out in a high throughput mode.

12. The method of any one of claims 1–4, wherein the imaging or scanning multiple cells in each of the locations containing multiple cells to obtain luminescent signals from the detector is carried out in a high content mode.

13. The method of any one of claims 1–4 wherein the selective imaging or scanning of the locations containing cells that were contacted with test sample indicated to have a toxin in it to obtain luminescent signals from the second or third reporter molecule is carried out in a high throughput mode.

14. The method of any one of claims 1–4 wherein the selective imaging or scanning of the locations containing cells that were contacted with test sample indicated to have a toxin in it to obtain luminescent signals from the second or third reporter molecule is carried out in a high content mode.

15. The method of any one of claims 1–4 further comprising providing a digital storage media for data storage and archiving.

16. The method of claim 15 further comprising a means for automated control, acquisition, processing and display of results.

17. An automated method for cell based toxin detection, classification, and/or identification comprising providing a first array of locations containing multiple cells to be treated with a test substance, wherein the cells possess a least a first luminescent reporter molecule comprising a detector, wherein the detector detects toxin present in the test substance;

contacting the cells with the test substance either before or after possession of the first luminescent reporter molecule by the cells; wherein the localization, distribution, structure, or activity of the first luminescent reporter molecule is modified when the cell is contacted with the toxin present in the test substance, imaging or scanning multiple cells in each of the locations containing multiple cells to obtain luminescent signals from the detector;

converting the luminescent signals from the detector into digital data;

utilizing the digital data from the detector to automatically measure the localization, distribution, structure or activity of the detector on or in the cell, wherein a change in the localization, distribution, structure or activity of the detector indicates the presence of a toxin in the test substance, providing a second array of locations containing cells to be treated with the test substance, wherein the cells possess a least a second luminescent reporter molecule comprising a reporter molecule selected from the group consisting of classifiers and identifiers, wherein the classifier detects a toxin present in the test substance and identifies a cell pathway affected by a toxin present in the test substance, and wherein the identifier detects a toxin present in the test substance and identifies a specific toxin or group of toxins present in the test substance, and wherein the second array of locations containing cells can comprise either the same or a different cell type as the first array of locations containing cells;

contacting the second array of locations containing cells with the test substance either before or after possession of the second luminescent reporter molecule by the cells; wherein the localization, distribution, structure, or activity of the second luminescent reporter molecule is modified when the cell is contacted with the toxin;

utilizing the digital data from the second luminescent reporter molecule to automatically measure the localization, distribution, structure, or activity of the classifier or identifier on or in the cell, wherein a change in the localization, distribution, structure or activity of the classifier identifies a cell pathway that is perturbed by the toxin present in the test substance, or wherein a change in the localization, distribution, structure or activity of the identifier identifies the specific toxin or group of toxins that are present in the test substance.

* * * * *